US007285405B2

(12) United States Patent
Reeves et al.

(10) Patent No.: US 7,285,405 B2
(45) Date of Patent: Oct. 23, 2007

(54) BIOSYNTHETIC GENE CLUSTER FOR JERANGOLIDS

(75) Inventors: Christopher D. Reeves, Orinda, CA (US); Ralph C. Reid, San Rafael, CA (US)

(73) Assignee: Kosan Biosciences Incorporated, Hayward, CA (US)

(*) Notice: Subject to any disclaimer, the term of this patent is extended or adjusted under 35 U.S.C. 154(b) by 56 days.

(21) Appl. No.: 11/109,593

(22) Filed: Apr. 18, 2005

(65) Prior Publication Data

US 2005/0233369 A1 Oct. 20, 2005

Related U.S. Application Data

(60) Provisional application No. 60/563,843, filed on Apr. 19, 2004.

(51) Int. Cl.
*C12N 9/00* (2006.01)

(52) U.S. Cl. ..................... 435/183; 435/193; 435/189; 435/232; 435/197

(58) Field of Classification Search ..................... None
See application file for complete search history.

(56) References Cited

OTHER PUBLICATIONS

No Prior Art.*

* cited by examiner

*Primary Examiner*—Nashaat T. Nashed
(74) *Attorney, Agent, or Firm*—Robin C. Chiang; Gary W. Ashley

(57) ABSTRACT

Domains of jerangolid polyketide synthase and modification enzymes and polynucleotides encoding them are provided. Methods to prepare jerangolid in pharmaceutically useful quantities are described, as are methods to prepare jerangolid analogs and other polyketides using the polynucleotides encoding jerangolid synthase domains or modifying enzymes.

2 Claims, 4 Drawing Sheets

Jerangolid A (1)

BIOSYNTHETIC GENE CLUSTER FOR JERANGOLIDS

Polyketides are complex natural products that are produced by microorganisms such as fungi and mycelial bacteria. There are about 10,000 known polyketides, from which numerous pharmaceutical products in many therapeutic areas have been derived, including: adriamycin, epothilone, erythromycin, mevacor, rapamycin, tacrolimus, tetracycline, rapamycin, and many others. However, polyketides are made in very small amounts in microorganisms and are difficult to make or modify chemically. For this and other reasons, biosynthetic methods are preferred for production of therapeutically active polyketides. See PCT publication Nos. WO 93/13663; WO 95/08548; WO 96/40968; WO 97/02358; and WO 98/27203; U.S. Pat. Nos. 4,874,748; 5,063,155; 5,098,837; 5,149,639; 5,672,491; 5,712,146 and 6,410,301; Fu et al., 1994, *Biochemistry* 33:9321-26; McDaniel et al., 1993, *Science* 262: 1546-1550; Kao et al., 1994, *Science*, 265:509-12, and Rohr, 1995, *Angew. Chem. Int. Ed. Engl*. 34: 881-88, each of which is incorporated herein by reference.

Biosynthesis of polyketides may be accomplished by heterologous expression of Type I or modular polyketide synthase enzymes (PKSs). Type I PKSs are large multifunctional protein complexes, the protein components of which are encoded by multiple open reading frames (ORF) of PKS gene clusters. Each ORF of a Type I PKS gene cluster can encode one, two, or more modules of ketosynthase activity. Each module activates and incorporates a two-carbon (ketide) unit into the polyketide backbone. Each module also contains multiple ketide-modifying enzymatic activities, or domains. In classical Type I PKSs, the number and order of modules, and the types of ketide-modifying domains within each module, determine the structure of the resulting product. Recently, variants of Type I PKSs have been found in which single modules may be used in an iterative fashion to add more than one two-carbon unit to the growing polyketide chain (see, for example, Müller 2004). Polyketide synthesis may also involve the activity of non-ribosomal peptide synthetases (NRPSs) to catalyze incorporation of an amino acid-derived building block into the polyketide, as well as post-synthesis modification, or tailoring enzymes. The modification enzymes modify the polyketide by oxidation or reduction, addition of carbohydrate groups or methyl groups, or other modifications.

In PKS polypeptides, the regions that encode enzymatic activities (domains) are separated by linker regions. These regions collectively can be considered to define boundaries of the various domains. Generally, this organization permits PKS domains of different or identical substrate specificities to be substituted (usually at the level of encoding DNA) from other PKSs by various available methodologies. Using this method, new polyketide synthases (which produce novel polyketides) can be produced. It will be recognized from the foregoing that genetic manipulation of PKS genes and heterologous expression of PKSs can be used for the efficient production of known polyketides, and for production of novel polyketides structurally related to, but distinct from, known polyketides (see references above, and Hutchinson, 1998, *Curr. Opin. Microbiol*. 1:319-29; Carreras and Santi, 1998, *Curr. Opin. Biotech*. 9:403-11; and U.S. Pat. Nos. 5,712,146 and 5,672,491, each of which is incorporated herein by reference).

One valuable class of polyketides includes the jerangolids and their analogs (FIG. 1), produced by various strains of the myxobacterium *Sorangium cellulosum*. Jerangolid A (1) as produced by *Sorangium cellulosum* strain So ce 307 was described by Gerth et al. "The Jerangolids: A Family of New Antifungal Compounds from *Sorangium cellulosum* (Myxobacteria); Production, Pysico-chemical and Biological Properties of Jerangolid A," *J. Antibiotics* 49: 71-75 (1996), along with four closely related analogs, jerangolids B, C, D, and E.

The jerangolids are anti-fungal agents showing partial structural resemblance with the ambruticins.

Given the promise of jerangolids in the treatment of fungal infections, there exists an unmet need for a production system that can provide large quantities of these polyketides. The present invention meets this need by providing the biosynthetic genes responsible for the production of jerangolids and providing for their expression in heterologous hosts.

SUMMARY OF THE INVENTION

The present invention provides recombinant nucleic acids encoding polyketide synthases and polyketide modification enzymes. The recombinant nucleic acids of the invention are useful in the production of polyketides, including but not limited to jerangolids and jerangolid analogs and derivatives in recombinant host cells. The biosynthesis of the jerangolids is performed by a modular polyketide synthase (PKS) together with polyketide modification enzymes. The jerangolid PKS is made up of several proteins, each having one or more modules. The modules have domains with specific synthetic functions.

The present invention also provides domains and modules of the jerangolid PKS and corresponding nucleic acid sequences encoding them and/or parts thereof. Such compounds are useful in the production of hybrid PKS enzymes and the recombinant genes that encode them.

The present invention also provides modifying genes of the jerangolid biosynthetic gene cluster, including but not limited to isolated and recombinant forms and forms incorporated into a vector or the chromosomal DNA of a host cell.

The present invention also provides recombinant host cells that contain the nucleic acids of the invention. In one embodiment, the host cell provided by the invention is a *Streptomyces* host cell that produces a jerangolid modification enzyme and/or a domain, module, or protein of the jerangolid PKS. Methods for the genetic manipulation of *Streptomyces* are described in Kieser et al, "Practical *Streptomyces* Genetics," The John Innes Foundation, Norwich (2000), which is incorporated herein by reference in its entirety. In other embodiments, the host cells provided by the invention are eubacterial cells such as *Escherichia coli*, yeast cells such as *Saccharomyces cerevisiae*, or myxobacterial cells such as *Myxococcus xanthus*.

Accordingly, there is provided a recombinant PKS wherein at least 10, 15, 20, or more consecutive amino acids in one or more domains of one or more modules thereof are derived from one or more domains of one or more modules of the jerangolid polyketide synthase. Preferably at least an entire domain of a module of the jerangolid synthase is included. Representative jerangolid PKS domains useful in this aspect of the invention include, for example, KR, DH, ER, AT, ACP and KS domains. In one embodiment of the invention, the PKS is assembled from polypeptides encoded by DNA molecules that comprise coding sequences for PKS domains, wherein at least one encoded domain corresponds to a domain of jerangolid PKS. In such DNA molecules, the coding sequences are operably linked to control sequences so that expression therefrom in host cells is effective. In this manner, jerangolid PKS coding sequences or modules and/or domains can be made to encode PKS to biosynthesize compounds having antibiotic or other useful bioactivity other than jerangolid.

These and other aspects of the present invention are described in more detail in the Detailed Description of the Invention, below.

BRIEF DESCRIPTION OF THE DRAWINGS

FIG. 2 shows the organization of the jerangolid biosynthetic cluster as deduced from SEQ ID NO:1.

DETAILED DESCRIPTION OF THE INVENTION

The present invention provides recombinant materials for the production of polyketides. In an aspect, the invention provides recombinant nucleic acids encoding at least one domain of a polyketide synthase required for jerangolid biosynthesis. Methods and host cells for using these genes to produce a polyketide in recombinant host cells are also provided.

The nucleotide sequences encoding jerangolid PKS domains, modules and polypeptides of the present invention were isolated from *Sorangium cellulosum* So ce 307 as described in Example 1. Given the valuable properties of jerangolid and its derivatives and analogs, means to produce useful quantities of these molecules in a highly pure form is of great potential value. The compounds produced may be used as antitumor agents or for other therapeutic uses, and/or intermediates for further enzymatic or chemical modification. The nucleotide sequences of the jerangolid biosynthetic gene cluster encoding domains, modules and polypeptides of jerangolid synthase, and modifying enzymes, and other polypeptides can be used, for example, to make both known and novel polyketides.

In one aspect of the invention, purified and isolated DNA molecules are provided that comprise one or more coding sequences for one or more domains or modules of jerangolid synthase. Examples of such encoded domains include jerangolid synthase KR, DH, ER, AT, ACP, and KS domains. Domains will herein be referred to according to the module in which they are found as "domain(module)"; for example, the module 1 AT domain will be referred to as "AT(1)." In one aspect, the invention provides DNA molecules in which sequences encoding one or more polypeptides of jerangolid synthase are operably linked to expression control sequences that are effective in suitable host cells to produce jerangolid, its analogs or derivatives, or novel polyketides.

Figure 1:
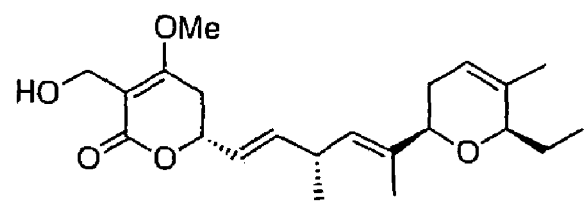
FIG. 1 shows the chemical structure of Jerangolid A
Figure 2A:
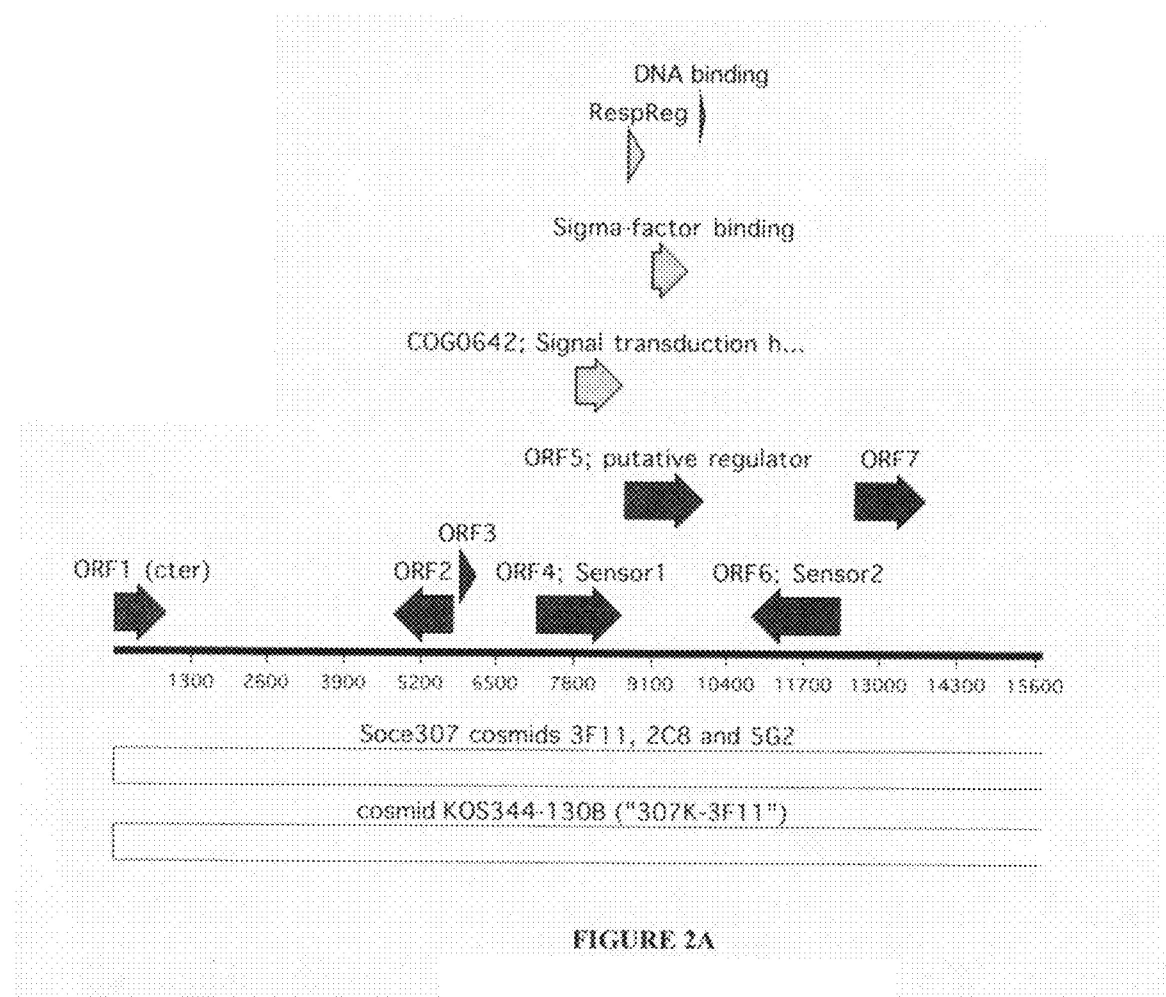
FIG. 2*A* shows the organization of the portion of the gene cluster upstream of the polyketide synthase genes.
Figure 2B:
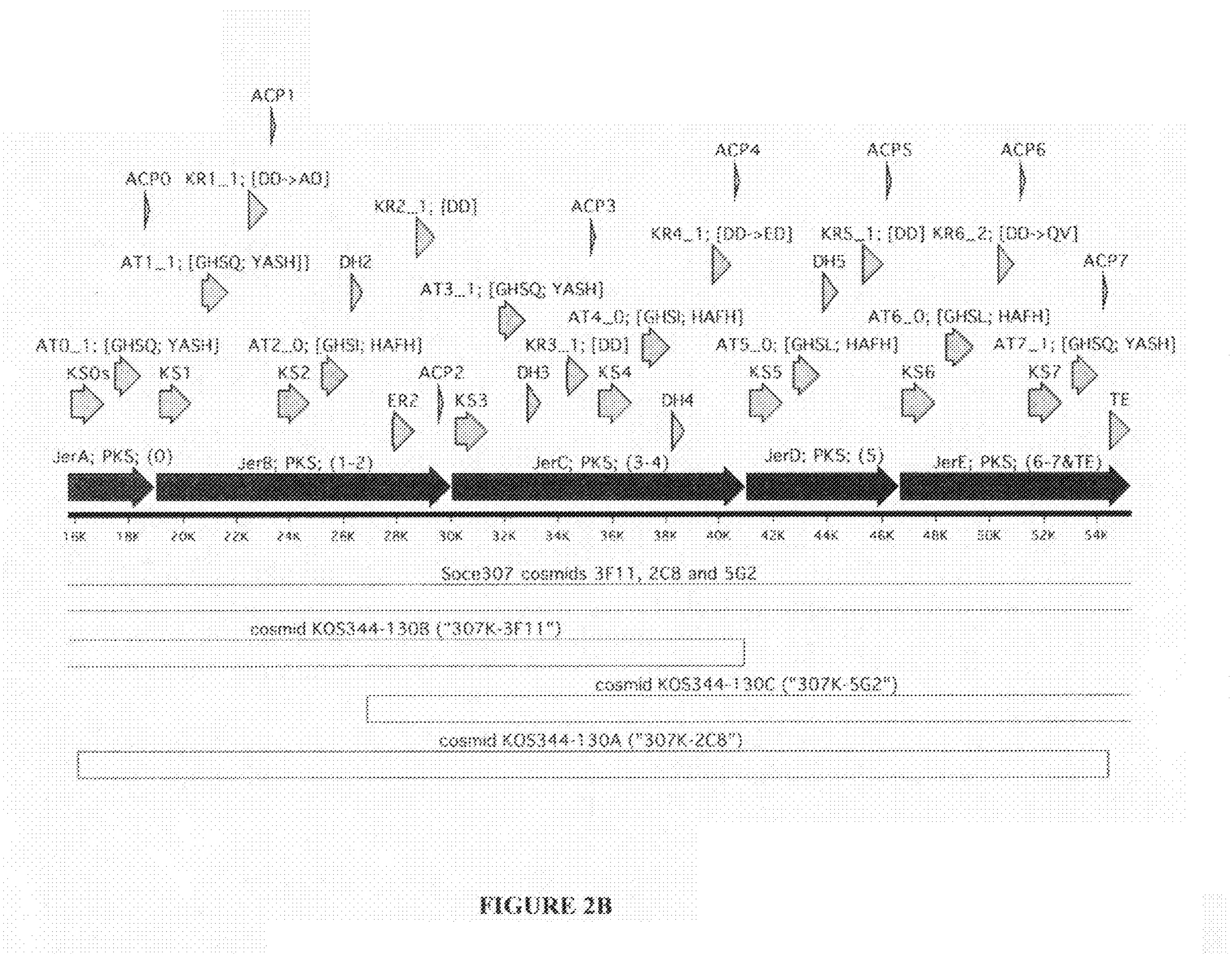
FIG. 2*B* shows the organization of the portion of the gene cluster containing the polyketide synthase genes.
Figure 2C:
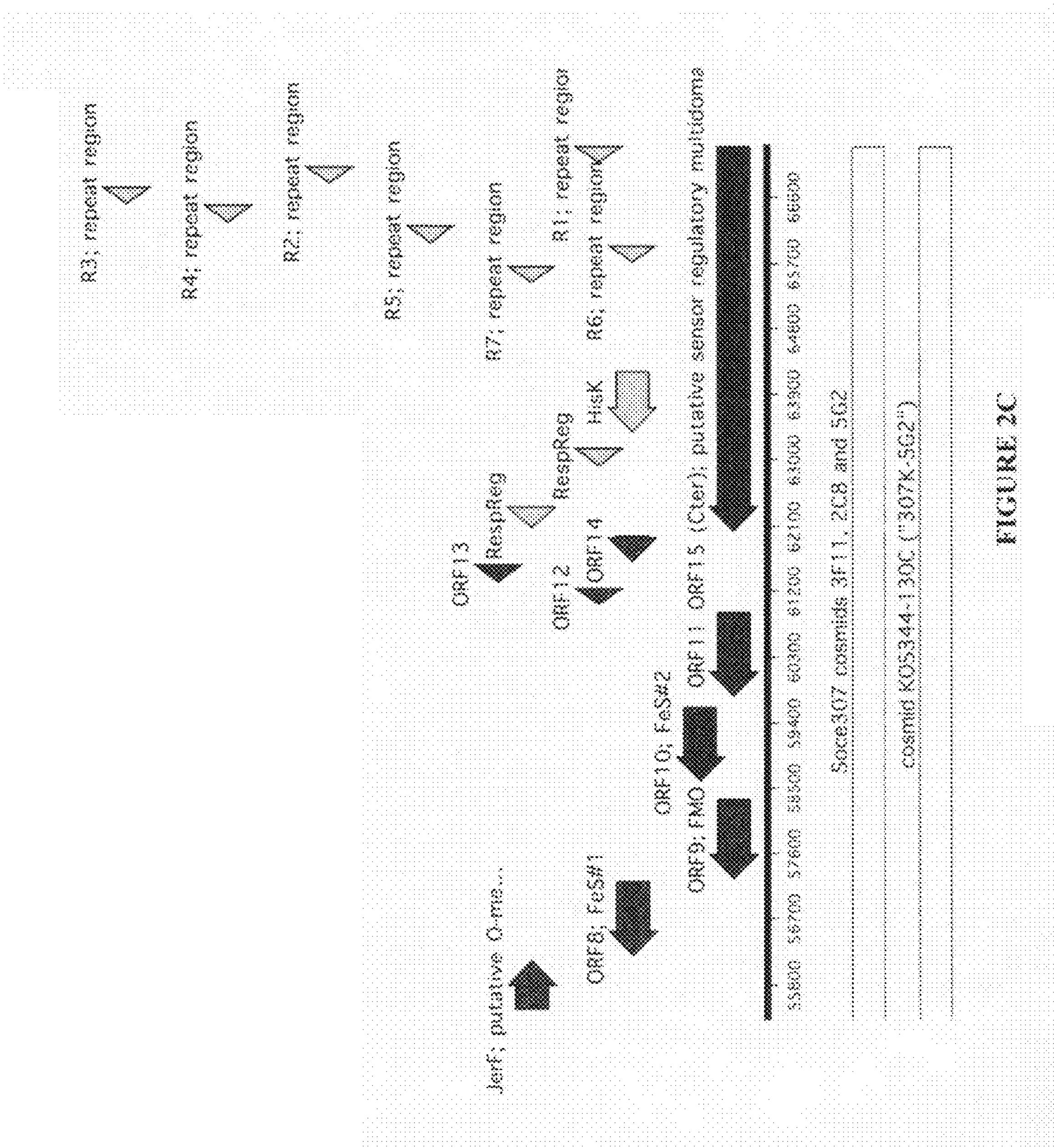
FIG. 2*C* shows the organization of the portion of the gene cluster downstream of the polyketide synthase genes.

The sequence of the beginning of the jerangolid PKS gene cluster was assembled from sequences deduced from the cosmid 10K10B3 (FIG. 2) and is shown as SEQ ID NO:1. This partial PKS gene cluster is found to comprise five open reading frames (ORFs), named jerA, jerB, jerc, jerD, and jerE. The jerA gene encodes the loading module of the jerangolid PKS, also referred to herein as "module 0," and comprises KS and AT domains. The KS(0) domain is apparently inactive as a ketosynthase, having the active site cysteine residue replaced with a serine, and is thought to act as a decarboxylase to prime the PKS with a propionate group derived from methylmalonate. The AT(0) domain comprises the signature amino acid sequences (GHSQ and YASH) of a methylmalonyl-specific AT domain. The jerB gene encodes modules 1 and 2 of the jerangolid PKS, the jerC gene encodes modules 3 and 4, the jerD gene encodes module 5, and the jerE gene encodes modules 6 and 7 along with a chain terminating thioesterase (TE) domain. Table 1 provides a description of the genes, modules, and domains of the five jerangolid PKS proteins. A further gene, jerF, encodes an O-methyltransferase thought to be involved in addition of the methyl group to O-3 of jerangolide.

TABLE 1

Genes, modules, and domains of the five proteins of the jerangolid PKS determined from the nucleotide sequence given in SEQ ID NO: 1.

| Gene | Module | Domain | boundaries |
|---|---|---|---|
| JerA | | | 15751-18978 |
| | module 0 | | 15859-18831 |
| | | KS(0) | 15859-17133 |
| | | AT(0) | 17461-18513 |
| | | ACP(0) | 18577-18831 |
| JerB | | | 19013-30074 |
| | module 1 | | 19134-23507 |
| | | KS(1) | 19134-20408 |
| | | AT(1) | 20715-21767 |
| | | KR(1) | 22398-23219 |
| | | ACP(1) | 23250-23507 |
| | module 2 | | 23559-29816 |
| | | KS(2) | 23559-24836 |
| | | AT(2) | 25167-26234 |
| | | DH(2) | 26268-26819 |
| | | ER(2) | 27822-28697 |
| | | KR(2) | 28707-29522 |
| | | ACP(2) | 29559-29816 |
| JerC | | | 30071-41035 |
| | module 3 | | 30170-35440 |
| | | KS(3) | 30170-31447 |
| | | AT(3) | 31772-32824 |
| | | DH(3) | 32858-33409 |
| | | KR(3) | 34322-35161 |
| | | ACP(3) | 35183-35440 |
| | module 4 | | 35507-40789 |
| | | KS(4) | 35507-36784 |
| | | AT(4) | 37115-38182 |
| | | DH(4) | 38216-38776 |
| | | KR(4) | 39695-40519 |
| | | ACP(4) | 40532-40789 |
| JerD | | | 41032-46674 |
| | module 5 | | 41131-46416 |
| | | KS(5) | 41131-42408 |
| | | AT(5) | 42733-43800 |
| | | DH(5) | 43834-44430 |
| | | KR(5) | 45307-46125 |
| | | ACP(5) | 46159-46416 |
| JerE | | | 46671-55280 |
| | module 6 | | 46773-51383 |
| | | KS(6) | 46773-48050 |
| | | AT(6) | 48381-49448 |
| | | KR(6) | 50295-50960 |
| | | ACP(6) | 51126-51383 |
| | module 7 | | 51462-54443 |
| | | KS(7) | 51462-52742 |
| | | AT(7) | 53052-54098 |
| | | ACP(7) | 54189-54443 |
| | | TE | 54444-55280 |

In one aspect, the invention provides an isolated or recombinant DNA molecule comprising a nucleotide sequence that encodes at least one domain, alternatively at least one module, alternatively at least one polypeptide, involved in the biosynthesis of an jerangolid.

In one aspect, the invention provides an isolated or recombinant DNA molecule comprising a sequence identical or substantially similar to SEQ ID NO: 1 or its complement. Hereinafter, each reference to a nucleic acid sequence is also intended to refer to and include the complementary sequence, unless otherwise stated or apparent from context. In an embodiment the subsequence comprises a sequence encoding a complete jerangolid PKS domain, module or polypeptide.

In one aspect, the present invention provides an isolated or recombinant DNA molecule comprising a nucleotide sequence that encodes an open reading frame, module or domain having an amino acid sequence identical or substantially similar to an ORF, module or domain encoded by SEQ ID NO: 1. Generally, a polypeptide, module or domain having a sequence substantially similar to a reference sequence has substantially the same activity as the reference protein, module or domain (e.g., when integrated into an appropriate PKS framework using methods known in the art). In certain embodiments, one or more activities of a substantially similar polypeptide, module or domain are modified or inactivated as described below.

In one aspect, the invention provides an isolated or recombinant DNA molecule comprising a nucleotide sequence that encodes at least one polypeptide, module or domain encoded by SEQ ID NO:1, e.g., a polypeptide, module or domain involved in the biosynthesis of an jerangolid, wherein said nucleotide sequence comprises at least 10, 20, 25, 30, 35, 40, 45, or 50 contiguous base pairs identical to a sequence of SEQ ID NO: 1. In one aspect, the invention provides an isolated or recombinant DNA molecule comprising a nucleotide sequence that encodes at least one polypeptide, module or domain encoded by SEQ ID NO: 1, e.g., a polypeptide, module or domain involved in the biosynthesis of a jerangolid, wherein said polypeptide, module or domain comprises at least 10, 15, 20, 30, or 40 contiguous residues of a corresponding polypeptide, module or domain comprising a sequence of SEQ ID NO: 1.

It will be understood that SEQ ID NO: 1 was determined using the inserts of cosmids 307K-3F11, 307K-5G2, and 307K-2C8. Accordingly, the invention provides an isolated or recombinant DNA molecule comprising a sequence identical or substantially similar to an ORF encoding sequence of the insert of cosmids 307K-3F11, 307K-5G2, or 307K-2C8.

Those of skill will recognize that, due to the degeneracy of the genetic code, a large number of DNA sequences encode the amino acid sequences of the domains, modules, and proteins of the jerangolid PKS, the enzymes involved in jerangolid modification and other polypeptides encoded by the genes of the jerangolid biosynthetic gene cluster. The present invention contemplates all such DNAs. For example, it may be advantageous to optimize sequence to account for the codon preference of a host organism. The invention also contemplates naturally occurring genes encoding the jerangolid PKS that are polymorphic or other variants.

As used herein, the terms “substantial identity,” “substantial sequence identity,” or “substantial similarity” in the context of nucleic acids, refers to a measure of sequence similarity between two polynucleotides. Substantial sequence identity can be determined by hybridization under stringent conditions, by direct comparison, or other means. For example, two polynucleotides can be identified as having substantial sequence identity if they are capable of specifically hybridizing to each other under stringent hybridization conditions. Other degrees of sequence identity (e.g., less than “substantial”) can be characterized by hybridization under different conditions of stringency. “Stringent hybridization conditions” refers to conditions in a range from about 5° C. to about 20° C. or 25° C. below the melting temperature (Tm) of the target sequence and a probe with exact or nearly exact complementarity to the target. As used herein, the melting temperature is the temperature at which a population of double-stranded nucleic acid molecules becomes half-dissociated into single strands. Methods for calculating the Tm of nucleic acids are well known in the art (see, e.g., Berger and Kimmel, 1987, Methods In Enzymology, Vol. 152: Guide To Molecular Cloning Techniques, San Diego: Academic Press, Inc. and Sambrook et al., 1989, Molecular Cloning: A Laboratory Manual, 2nd Ed., Vols. 1-3, Cold Spring Harbor Laboratory). Typically, stringent hybridization conditions for probes greater than 50 nucleotides are salt concentrations less than about 1.0 M sodium ion, typically about 0.01 to 1.0 M sodium ion at pH 7.0 to 8.3, and temperatures at least about 50° C., preferably at least about 60° C. As noted, stringent conditions may also be achieved with the addition of destabilizing agents such as formamide, in which case lower temperatures may be employed. Exemplary conditions include hybridization at 7% sodium dodecyl sulfate (SDS), 0.5 M $NaPO_4$ pH 7.0, 1 mM EDTA at 65° C.; wash with 2×SSC, 1% SDS, at 50° C.

Alternatively, substantial sequence identity can be described as a percentage identity between two nucleotide or amino acid sequences. Two nucleic acid sequences are considered substantially identical when they are at least about 70% identical, or at least about 80% identical, or at least about 90% identical, or at least about 95% or 98% identical. Two amino acid sequences are considered substantially identical when they are at least about 60%, sequence identical, more often at least about 70%, at least about 80%, or at least about 90% sequence identity to the reference sequence. Percentage sequence (nucleotide or amino acid) identity is typically calculated using art known means to determine the optimal alignment between two sequences and comparing the two sequences. Optimal alignment of sequences may be conducted using the local homology algorithm of Smith and Waterman (1981) *Adv. Appl. Math*. 2: 482, by the homology alignment algorithm of Needleman and Wunsch (1970) *J. Mol. Biol*. 48: 443, by the search for similarity method of Pearson and Lipman (1988) *Proc. Natl. Acad. Sci*. U.S.A. 85: 2444, by the BLAST algorithm of Altschul (1990) *J. Mol. Biol*. 215: 403-410; and Shpaer (1996) *Genomics* 38:179-191, or by the Needleham et al. (1970) *J. Mol. Biol*. 48: 443-453; and Sankoffet al., 1983, *Time Warps, String Edits, and Macromolecules, The Theory and Practice of Sequence Comparison*, Chapter One, Addison-Wesley, Reading, Mass.; generally by computerized implementations of these algorithms (GAP, BESTFIT, FASTA, and TFASTA in the Wisconsin Genetics Software Package, Genetics Computer Group, 575 Science Dr., Madison, Wis.; BLAST from the National Center for Biotechnology Information (http://www.ncbi.nlm.nih.gov/). In each case default parameters are used (for example the BLAST program uses as defaults a wordlength (W) of 11, the BLOSUM62 scoring matrix (see Henikoff (1992) *Proc. Natl. Acad. Sci*. USA 89: 10915-10919) alignments (B) of 50, expectation (E) of 10, M=5, N=−4, and a comparison of both strands).

The invention methods may be directed to the preparation of an individual polyketide. The polyketide may or may not be novel, but the method of preparation permits a more convenient or alternative method of preparing it. The resulting polyketides may be further modified to convert them to other useful compounds. Examples of chemical structures of that can be made using the materials and methods of the present invention include known analogs, such as those described in Kalesse & Christmann, 2002, "The Chemistry and Biology of the Jerangolid Family" *Synthesis* (8):981-1003 and the refereneces cited therein, and novel molecules produced by modified or chimeric PKSs comprising a portion of the jerangolid PKS sequence, molecules produced by the action of polyketide modifying enzymes from the jerangolid PKS cluster on products of other PKSs, molecules produced by the action on products of the jerangolid PKS of polyketide modifying enzymes from other PKSs, and the like. As noted, in one aspect the invention provides recombinant PKS wherein at least 10, 15, 20, or more consecutive amino acids in one or more domains of one or more modules thereof are derived from one or more domains of one or more modules of the jerangolid polyketide synthase. A polyketide synthase "derived from" a naturally occurring PKS contains the scaffolding encoded by all the portion employed of the naturally occurring synthase gene, contains at least two modules that are functional, and contains mutations, deletions, or replacements of one or more of the activities of these functional modules so that the nature of the resulting polyketide is altered. This definition applies both at the protein and genetic levels. Particular embodiments include those wherein a KS, AT, KR, DH, or ER has been deleted or replaced by a version of the activity from a different PKS or from another location within the same PKS, and derivatives where at least one noncondensation cycle enzymatic activity (KR, DH, or ER) has been deleted or wherein any of these activities has been added or mutated so as to change the ultimate polyketide synthesized. There are at least five degrees of freedom for constructing a polyketide synthase in terms of the polyketide that will be produced. See, U.S. Pat. No. 6,509,455 for a discussion.

As can be appreciated by those skilled in the art, polyketide biosynthesis can be manipulated to make a product other than the product of a naturally occurring PKS biosynthetic cluster. For example, AT domains can be altered or replaced to change specificity. The variable domains within a module can be deleted and or inactivated or replaced with other variable domains found in other modules of the same PKS or from another PKS. See e.g., Katz & McDaniel, *Med Res Rev* 19: 543-558 (1999) and WO 98/49315. Similarly, entire modules can be deleted and/or replaced with other modules from the same PKS or another PKS. See e.g., Gokhale et al., Science 284: 482 (1999) and WO 00/47724 each of which are incorporated herein by reference. Protein subunits of different PKSs also can be mixed and matched to make compounds having the desired backbone and modifications. For example, subunits of 1 and 2 (encoding modules 1-4) of the pikromycin PKS were combined with the DEBS3 subunit to make a hybrid PKS product (see Tang et al., Science, 287: 640 (2001), WO 00/26349 and WO 99/6159). Mutations can be introduced into PKS genes such that polypeptides with altered activity are encoded. Polypeptides with "altered activity" include those in which one or more domains are inactivated or deleted, or in which a mutation changes the substrate specificity of a domain, as well as other alterations in activity. Mutations can be made to the native sequences using conventional techniques. The substrates for mutation can be an entire cluster of genes or only one or two of them; the substrate for mutation may also be portions of one or more of these genes. Techniques for mutation include preparing synthetic oligonucleotides including the mutations and inserting the mutated sequence into the gene encoding a PKS subunit using restriction endonuclease digestion. (See, e.g., Kunkel, T. A. *Proc Natl Acad Sci* USA (1985) 82:448; Geisselsoder et al. *BioTechniques* (1987) 5:786.) Alternatively, the mutations can be effected using a mismatched primer (generally 10-20 nucleotides in length) that hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. (See Zoller and Smith, *Methods in Enzymology* (1983) 100:468). Primer extension is effected using DNA polymerase. The product of the extension reaction is cloned, and those clones containing the mutated DNA are selected. Selection can be accomplished using the mutant primer as a hybridization probe. The technique is also applicable for generating multiple point mutations. (See, e.g., Dalbie-McFarland et al. *Proc Natl Acad Sci* USA (1982) 79:6409). PCR mutagenesis can also be used for effecting the desired mutations. Random mutagenesis of selected portions of the nucleotide sequences encoding enzymatic activities can be accomplished by several different techniques known in the art, e.g., by inserting an oligonucleotide linker randomly into a plasmid, In addition to providing mutated forms of regions encoding enzymatic activity, regions encoding corresponding activities from different PKS synthases or from different locations in the same PKS synthase can be recovered, for example, using PCR techniques with appropriate primers. By "corresponding" activity encoding regions is meant those regions encoding the same general type of activity—e.g., a ketoreductase activity in one location of a gene cluster would "correspond" to a ketoreductase-encoding activity in another location in the gene cluster or in a different gene cluster; similarly, a complete reductase cycle could be considered corresponding—e.g., KR/DH/ER could correspond to KR alone.

If replacement of a particular target region in a host polyketide synthase is to be made, this replacement can be conducted in vitro using suitable restriction enzymes or can be effected in vivo using recombinant techniques involving homologous sequences framing the replacement gene. One such system involving plasmids of differing temperature sensitivities is described in PCT application WO 96/40968. Another useful method for modifying a PKS gene (e.g., making domain substitutions or "swaps") is a RED/ET cloning procedure developed for constructing domain swaps or modifications in an expression plasmid without first introducing restriction sites. The method is related to ET cloning methods (see, Datansko & Wanner, 2000, Proc. Natl. Acad. Sci. U.S.A. 97, 6640-45; Muyrers et al, 2000, Genetic Engineering 22:77-98). The RED/ET cloning procedure is used to introduce a unique restriction site in the recipient plasmid at the location of the targeted domain. This restriction site is used to subsequently linearize the recipient plasmid in a subsequent ET cloning step to introduce the modification. This linearization step is necessary in the absence of a selectable marker, which cannot be used for domain substitutions. An advantage of using this method for PKS engineering is that restriction sites do not have to be introduced in the recipient plasmid in order to construct the swap, which makes it faster and more powerful because boundary junctions can be altered more easily.

In a further aspect, the invention provides methods for expressing chimeric or hybrid PKSs and products of such PKSs. For example, the invention provides (1) encoding DNA for a chimeric PKS that is substantially patterned on a non-jerangolid producing enzyme, but which includes one or more functional domains, modules or polypeptides of jerangolid PKS; and (2) encoding DNA for a chimeric PKS that is substantially patterned on the jerangolid PKS, but which includes one or more functional domains, modules, or polypeptides of another PKS or NRPS.

With respect to item (1) above, in one embodiment, the invention provides chimeric PKS enzymes in which the genes for a non-jerangolid PKS function as accepting genes, and one or more of the above-identified coding sequences for jerangolid domains or modules are inserted as replacements for one or more domains or modules of comparable function. Construction of chimeric molecules is most effectively achieved by construction of appropriate encoding polynucleotides. In making a chimeric molecule, it is not necessary to replace an entire domain or module accepting of the PKS with an entire domain or module of jerangolid PKS: subsequences of a PKS domain or module that correspond to a peptide subsequence in an accepting domain or module, or which otherwise provide useful function, may be used as replacements. Accordingly, appropriate encoding DNAs for construction of such chimeric PKS include those that encode at least 10, 15, 20 or more amino acids of a selected jerangolid domain or module.

Recombinant methods for manipulating modular PKS genes to make chimeric PKS enzymes are described in U.S. Pat. Nos. 5,672,491; 5,843,718; 5,830,750; and 5,712,146; and in PCT publication Nos. 98/49315 and 97/02358. A number of genetic engineering strategies have been used with DEBS to demonstrate that the structures of polyketides can be manipulated to produce novel natural products, primarily analogs of the erythromycins (see the patent publications referenced supra and Hutchinson, 1998, *Curr Opin Microbiol*. 1:319-329, and Baltz, 1998, *Trends Microbiol*. 6:76-83). In one embodiment, the components of the chimeric PKS are arranged onto polypeptides having interpolypeptide linkers that direct the assembly of the polypeptides into the functional PKS protein, such that it is not required that the PKS have the same arrangement of modules in the polypeptides as observed in natural PKSs. Suitable interpolypeptide linkers to join polypeptides and intrapolypeptide linkers to join modules within a polypeptide are described in PCT publication WO 00/47724.

A partial list of sources of PKS sequences for use in making chimeric molecules, for illustration and not limitation, includes Avermectin (U.S. Pat. No. 5,252,474; MacNeil et al., 1993, Industrial Microorganisms: Basic and Applied Molecular Genetics, Baltz, Hegeman, & Skatrud, eds. (ASM), pp. 245-256; MacNeil et al., 1992, Gene 115: 119-25); Candicidin (FRO008) (Hu et al., 1994, *Mol. Microbiol*. 14: 163-72); Epothilone (U.S. Pat. No. 6,303,342); Erythromycin (WO 93/13663; U.S. Pat. No. 5,824,513; Donadio et al., 1991, *Science* 252:675-79; Cortes et al., 1990, *Nature* 348:176-8); FK-506 (Motamedi et al., 1998, *Eur. J. Biochem*. 256:528-34; Motamedi et al., 1997, *Eur. J. Biochem*. 244:74-80); FK-520 (U.S. Pat. No. 6,503,737; see also Nielsen et al., 1991, *Biochem*. 30:5789-96); Lovastatin (U.S. Pat. No. 5,744,350); Nemadectin (MacNeil et al., 1993, supra); Niddamycin (Kakavas et al., 1997, *J. Bacteriol*. 179:7515-22); Oleandomycin (Swan et al., 1994, *Mol. Gen. Genet*. 242:358-62; U.S. Pat. No. 6,388,099; Olano et al., 1998, *Mol. Gen. Genet*. 259:299-308); Platenolide (EP Pat. App. 791,656); Rapamycin (Schwecke et al., 1995, *Proc. Natl. Acad. Sci*. USA 92:7839-43); Aparicio et al., 1996, *Gene* 169:9-16); Rifamycin (August et al., 1998, *Chemistry & Biology,* 5: 69-79); Soraphen (U.S. Pat. No. 5,716,849; Schupp et al., 1995, *J. Bacteriology* 177: 3673-79); Spiramycin (U.S. Pat. No. 5,098,837); Tylosin (EP 0 791,655; Kuhstoss et al., 1996, Gene 183:231-36; U.S. Pat. No. 5,876,991). Additional suitable PKS coding sequences remain to be discovered and characterized, but will be available to those of skill (e.g., by reference to GenBank).

The jerangolid PKS-encoding polynucleotides of the invention may also be used in the production of libraries of PKSs (i.e., modified and chimeric PKSs comprising at least a portion of the jerangolid PKS sequence. The invention provides libraries of polyketides by generating modifications in, or using a portion of, the jerangolid PKS so that the protein complexes produced by the cluster have altered activities in one or more respects, and thus produce polyketides other than the natural jerangolid product of the PKS. Novel polyketides may thus be prepared, or polyketides in general prepared more readily, using this method. By providing a large number of different genes or gene clusters derived from a naturally occurring PKS gene cluster, each of which has been modified in a different way from the native PKS cluster, an effectively combinatorial library of polyketides can be produced as a result of the multiple variations in these activities. Expression vectors containing nucleotide sequences encoding a variety of PKS systems for the production of different polyketides can be transformed into the appropriate host cells to construct a polyketide library. In one approach, a mixture of such vectors is transformed into the selected host cells and the resulting cells plated into individual colonies and selected for successful transformants. Each individual colony has the ability to produce a particular PKS synthase and ultimately a particular polyketide. A variety of strategies can be devised to obtain a multiplicity of colonies each containing a PKS gene cluster derived from the naturally occurring host gene cluster so that each colony in the library produces a different PKS and ultimately a different polyketide. The number of different polyketides that are produced by the library is typically at least four, more typically at least ten, and preferably at least 20, more preferably at least 50, reflecting similar numbers of different altered PKS gene clusters and PKS gene products. The number of members in the library is arbitrarily chosen; however, the degrees of freedom outlined above with respect to the variation of starter, extender units, stereochemistry, oxidation state, and chain length is quite large. The polyketide producing colonies can be identified and isolated using known techniques and the produced polyketides further characterized. The polyketides produced by these colonies can be used collectively in a panel to represent a library or may be assessed individually for activity.

Colonies in the library are induced to produce the relevant synthases and thus to produce the relevant polyketides to obtain a library of candidate polyketides. The polyketides secreted into the media can be screened for binding to desired targets, such as receptors, signaling proteins, and the like. The supernatants per se can be used for screening, or partial or complete purification of the polyketides can first be effected. Typically, such screening methods involve detecting the binding of each member of the library to receptor or other target ligand. Binding can be detected either directly or through a competition assay. Means to screen such libraries for binding are well known in the art. Alternatively, individual polyketide members of the library can be tested against a desired target. In this event, screens wherein the biological response of the target is measured can be included.

As noted above, the DNA compounds of the invention can be expressed in host cells for production of proteins and of known and novel compounds. Preferred hosts include fungal systems such as yeast and procaryotic hosts, but single cell cultures of, for example, mammalian cells could also be used. A variety of methods for heterologous expression of PKS genes and host cells suitable for expression of these genes and production of polyketides are described, for example, in U.S. Pat. Nos. 5,843,718 and 5,830,750; WO 01/31035, WO 01/27306, and WO 02/068613; and U.S. patent application Ser. Nos. 10/087,451 (published as US2002000087451); 60/355,211; and 60/396,513 (corresponding to published application 20020045220).

Appropriate host cells for the expression of the hybrid PKS genes include those organisms capable of producing the needed precursors, such as malonyl-CoA, methylmalonyl-CoA, ethylmalonyl-CoA, and methoxymalonyl-ACP, and having phosphopantotheinylation systems capable of activating the ACP domains of modular PKSs. See, for example, U.S. Pat. No. 6,579,695. However, as disclosed in U.S. Pat. No. 6,033,883, a wide variety of hosts can be used, even though some hosts natively do not contain the appropriate post-translational mechanisms to activate the acyl carrier proteins of the synthases. Also see WO 97/13845 and WO 98/27203. The host cell may natively produce none, some, or all of the required polyketide precursors, and may be genetically engineered so as to produce the required polyketide precursors. Such hosts can be modified with the appropriate recombinant enzymes to effect these modifications. Suitable host cells include *Streptomyces, E. coli*, yeast, and other procaryotic hosts which use control sequences compatible with *Streptomyces* spp. Examples of suitable hosts that either natively produce modular polyketides or have been engineered so as to produce modular polyketides include but are not limited to actinomyctes such as *Streptomyces coelicolor, Streptomyces venezuelae, Streptomyces fradiae, Streptomyces ambofaciens*, and *Saccharopolyspora erythraea*, eubacteria such as *Escherichia coli*, myxobacteria such as *Myxococcus xanthus*, and yeasts such as *Saccharomyces cerevisiae.*

In one embodiment, any native modular PKS genes in the host cell have been deleted to produce a "clean host," as described in U.S. Pat. No. 5,672,491, incorporated herein by reference.

In some embodiments, the host cell expresses, or is engineered to express, a polyketide "tailoring" or "modifying" enzyme. Once a PKS product is released, it is subject to post-PKS tailoring reactions. These reactions are important for biological activity and for the diversity seen among polyketides. Tailoring enzymes normally associated with polyketide biosynthesis include oxygenases, glycosyl- and methyl-transferases, acyltransferases, halogenases, cyclases, aminotransferases, and hydroxylases. In addition to biosynthetic accessory activities, secondary metabolite clusters often code for activities such as transport.

Tailoring enzymes for modification of a product of the jerangolid PKS, a non-jerangolid PKS, or a chimeric PKS, can be those normally associated with jerangolid biosynthesis or "heterologous" tailoring enzymes. Tailoring enzymes can be expressed in the organism in which they are naturally produced, or as recombinant proteins in heterologous hosts. In some cases, the structure produced by the heterologous or hybrid PKS may be modified with different efficiencies by post-PKS tailoring enzymes from different sources. In such cases, post-PKS tailoring enzymes can be recruited from other pathways to obtain the desired compound. For example, the tailoring enzymes of the jerangolid PKS gene cluster can be expressed heterologously to modify polyketides produced by non-jerangolid synthases or can be inactivated in the Jerangolid producer. Alternatively, the unmodified polyketide compounds can be produced in the recombinant host cell, and the desired modification (e.g., oxidation) steps carried out in vitro (e.g., using purified enzymes, isolated from native sources or recombinantly produced) or in vivo in a converting cell different from the host cell (e.g., by supplying the converting cell with the unmodified polyketide).

It will be apparent to one of skill in the art that a variety of recombinant vectors can be utilized in the practice of aspects of the invention. As used herein, "vector" refers to polynucleotide elements that are used to introduce recombinant nucleic acid into cells for either expression or replication. Selection and use of such vehicles is routine in the art. An "expression vector" includes vectors capable of expressing DNAs that are operatively linked with regulatory sequences, such as promoter regions. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those that integrate into the host cell genome.

The vectors used to perform the various operations to replace the enzymatic activity in the host PKS genes or to support mutations in these regions of the host PKS genes may be chosen to contain control sequences operably linked to the resulting coding sequences in a manner that expression of the coding sequences may be effected in an appropriate host. Suitable control sequences include those that function in eucaryotic and procaryotic host cells. If the cloning vectors employed to obtain PKS genes encoding derived PKS lack control sequences for expression operably linked to the encoding nucleotide sequences, the nucleotide sequences are inserted into appropriate expression vectors. This can be done individually, or using a pool of isolated encoding nucleotide sequences, which can be inserted into host vectors, the resulting vectors transformed or transfected into host cells, and the resulting cells plated out into individual colonies. Suitable control sequences for single cell cultures of various types of organisms are well known in the art. Control systems for expression in yeast are widely available and are routinely used. Control elements include promoters, optionally containing operator sequences, and other elements depending on the nature of the host, such as ribosome binding sites. Particularly useful promoters for procaryotic hosts include those from PKS gene clusters that result in the production of polyketides as secondary metabolites, including those from Type I or aromatic (Type II) PKS gene clusters. Examples are act promoters, tcm promoters, spiramycin promoters, and the like. However, other bacterial promoters, such as those derived from sugar metabolizing enzymes, such as galactose, lactose (lac) and maltose, are also useful. Additional examples include promoters derived from biosynthetic enzymes such as for tryptophan (trp), the β-lactamase (bla), bacteriophage lambda PL, and T5. In addition, synthetic promoters, such as the tac promoter (U.S. Pat. No. 4,551,433), can be used.

As noted, particularly useful control sequences are those which themselves, or with suitable regulatory systems, activate expression during transition from growth to stationary phase in the vegetative mycelium. The system contained in the plasmid identified as pCK7, i.e., the actI/actIII promoter pair and the actII-ORF4 (an activator gene), is particularly preferred. Particularly preferred hosts are those that lack their own means for producing polyketides so that a cleaner result is obtained. Illustrative control sequences, vectors, and host cells of these types include the modified *S. coelicolor* CH999 and vectors described in PCT publication WO 96/40968 and similar strains of *S. lividans*. See U.S. Pat. Nos. 5,672,491; 5,830,750, 5,843,718; and 6,177,262, each of which is incorporated herein by reference.

Other regulatory sequences may also be desirable which allow for regulation of expression of the PKS sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences. Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid. Alternatively, several polyketides are naturally colored, and this characteristic provides a built-in marker for screening cells successfully transformed by the present constructs.

The various PKS nucleotide sequences, or a mixture of such sequences, can be cloned into one or more recombinant vectors as individual cassettes, with separate control elements or under the control of a single promoter. The PKS subunits or components can include flanking restriction sites to allow for the easy deletion and insertion of other PKS subunits so that hybrid or chimeric PKSs can be generated. The design of such restriction sites is known to those of skill in the art and can be accomplished using the techniques described above, such as site-directed mutagenesis and PCR. Methods for introducing the recombinant vectors of the present invention into suitable hosts are known to those of skill in the art and typically include the use of $CaCl_2$ or other agents, such as divalent cations, lipofection, DMSO, protoplast transformation, conjugation, and electroporation. Thus, the present invention provides recombinant DNA molecules and vectors comprising those recombinant DNA molecules that encode at least a portion of the jerangolid PKS and that, when transformed into a host cell and the host cell is cultured under conditions that lead to the expression of said jerangolid PKS enzymes, results in the production of polyketides including but not limited to jerangolid and/or analogs or derivatives thereof in useful quantities. The present invention also provides recombinant host cells comprising those recombinant vectors.

Suitable culture conditions for production of polyketides using the cells of the invention will vary according to the host cell and the nature of the polyketide being produced, but will be know to those of skill in the art. See, for example, the examples below and WO 98/27203 "Production of Polyketides in Bacteria and Yeast" and WO 01/83803 "Overproduction Hosts For Biosynthesis of Polyketides."

The polyketide product produced by host cells of the invention can be recovered (i.e., separated from the producing cells and at least partially purified) using routine techniques (e.g., extraction from broth followed by chromatography).

The compositions, cells and methods of the invention may be directed to the preparation of an individual polyketide or a number of polyketides. The polyketide may or may not be novel, but the method of preparation permits a more convenient or alternative method of preparing it.

The following Examples are intended to illustrate, but not limit, the scope of the invention.

EXAMPLE 1

Isolation of Jerangolid PKS Cosmids

Genomic DNA was isolated from *Sorangium cellulosum* Soce307, the producer of jerangolid using an established protocol (Jaoua, S., Neff, S., and Schupp, T. "Transfer of mobilizable plasmids to *Sorangium cellulosum* and evidence for their integration into the chromosome," 1992 Plasmid 28:157-165). The DNA was partially digested with Sau3AI using a serial dilution method and libraries were constructed in SuperKOS (a smaller derivative of SuperCos-1) using the protocol for SuperCos-1 from Stratagene. Colonies were picked, cosmid DNA was isolated on the Qiagen robot, and the DNA was submitted for end sequencing. The data was analyzed by BLAST and all PKS positive cosmids were prepared in larger amounts for further analysis.

End sequencing of cosmid and fosmid libraries of the Soce307 genome gave 13 cosmids with PKS sequence on at least one end. Five of these cosmid/fosmid end sequences were highly similar (>92% identity at the nucleotide level) to sequence from the ambruticin PKS, disclosed in co-pending U.S. application Ser. No. 60/551,103, filed 2 Mar. 2004 and incorporated herein by reference in its entirety, indicating they probably contain the jerangolid cluster.

All publications and patent documents cited herein are incorporated herein by reference as if each such publication or document was specifically and individually indicated to be incorporated herein by reference.

Although the present invention has been described in detail with reference to specific embodiments, those of skill in the art will recognize that modifications and improvements are within the scope and spirit of the invention. Citation of publications and patent documents is not intended as an admission that any such document is pertinent prior art, nor does it constitute any admission as to the contents or date of the same. The invention having now been described by way of written description, those of skill in the art will recognize that the invention can be practiced in a variety of embodiments and that the foregoing description are for purposes of illustration and not limitation of the following claims.

What is claimed is:

1. A purified or recombinant polypeptide comprising an amino acid sequence that is at least 95% identical to SEQ ID NO: 27, wherein said polypeptide is capable of producing jerangolid A in the presence of the polypeptide jerA of SEQ ID NO: 23, JerB of SEQ ID NO: 24, JerC of SEQ ID NO: 25, JerD of SEQ ID NO:26, and JerF of SEQ ID NO: 28.

2. The polypeptide of claim 1 comprising SEQ ID No:27.

* * * * *

SEQUENCE LISTING

```
<160> NUMBER OF SEQ ID NOS: 43

<210> SEQ ID NO 1
<211> LENGTH: 67323
<212> TYPE: DNA
```

-continued

<213> ORGANISM: Sorangium cellulosum

<400> SEQUENCE: 1

```
gatcgtcctg ggcgacacgc tggagcaggt ggcgacgcgg ctgctcgagg aggacctcgc     60
ggcgtgccac acgaccggcg aggcggcgga cgtgctgctg aacggggtgc tcgcgtcgag    120
cgcccgcgcc gtggccgcgg cgctgcgcgc gtgcgacgag ttcgccgcgg gcgacagcga    180
tctgccgtcg ctggcccggg cgtgccgcgc gttcgcgggg ctcgcgtcgt tcgggtcgtc    240
gcggtcgctg tcgtcgctcg gcgacggggt gatcgcgccg atgctggaga agacgttcgc    300
gcgcgcggtc ctgcgcgtcc acgggggctg cacgggcagc gacgaggcgg tcgccgccgc    360
caaggaggcg ctgcgcacgc tgcacgacgt ggcgctgtcg cagccgatcg tcgaccgcgg    420
ggcgtggctc gacgcggcgc gggggctcgt ggacagcgag gtggtgaacc cgacggcgtc    480
cggcctcgcg tgcgggctgc tctacctggc gcaggcgatc gacgacgccg aggtggcgcg    540
ggtcgtcggc ctgcggctcg gggcgcggc cgagcccgag gcggcggcgt cgttcctggc    600
cgggttcctc gaggtgaacg cgctggtgct ggtgaagagc cggcccgtgg tcgaggcgct    660
ggacgcgttc ctccgggcga tcgcgccgga gcgcttcaag gacacgctgc cggtccttcg    720
gcgcgcgttc gctgggctcg gcgcgacgga gcggcggtac ctgctcgaga acgtgctcgc    780
ggcgcggaag ctgggggaca aggcgcgcgc ggcgcaggcg gtgctcctgg agaaggaccg    840
ggagaagctg aaggagatga gcgaggacct ctcacaggcg atggacgacc tggacgagtt    900
gctctgacac gacccgtgag acgacccgtg agacgacgac ctggacgacc tggacgacct    960
gaaccaggtt gcggacgacc tggacgaccc ggacgacccg aaccaggttg agttctaggt   1020
tgttctaggt tcacggtaca gaacggttcc cgccggtcaa gcatagcccc ccgacaacac   1080
ggcttctgtt ccgcttcttg cacgctcacc acggcatgac gcatgcgtac ccactctcgt   1140
gatgccgcat ggaggatcta ccagttgctc ggcctcctga aggcacacgc tcgcctgaga   1200
gcacgtccat gtcgtcgccc acccctcgat ccttctggcc atcccacgat cccgctcccg   1260
caggcggctc tacaccacaa gcaccacgtc attcacgctg accccgtgaa acattcgcat   1320
ccaccatgtc cccaccggga atacggcgct gcgtacaccg gcacgccagc gttcgagcgc   1380
cgcgcggtac gtcgcgcgga acgcccgcac ggacgcggca gcggtttgcc acgctcctcc   1440
ctgctcgcgg cccaccgcaa aggtaggatt gcggccaagc agcgcctcga agctcgtggc   1500
acgctggtaa ggcgagacgt tgctggctcg ctcggcacca aagaagcgga gtccttgccg   1560
ctccacctcg gcatgggcca gcgcctcctg tcgttcgagc tcggccaaga tctcgcggcg   1620
gaatgcctcc gcggcgtcct gctcgatgat aggcggtagt gcgagcggca gcgttgcttc   1680
ctggggccac tgtggatttt ccgggtcgag gtatgccgag ggacgagccg cgcgcagcat   1740
ggcgtgaccg atctcaccca catctacctt gacaccgggc cattctctcg aattacggac   1800
gagaccggca gcaacagggt ttgcaaggac ataggcaatc ttttccacaa ccgccgcgcg   1860
agtcagcagc cgtaccacgc tcgtggcttc atggtcccat accgggccct cccacttgcg   1920
cagcaccttc gtgccgagcg cgacgattcg atggaagaac tgcaagaagc gcggcaggac   1980
gccccgcaca tcggtcacga cgaggtgcag atgcgtcgac atcgcgcaaa gggcatgaac   2040
ctcgacgccg tagcggtggg ccgcgacagc gagggcatag accaagaact ggttcatggc   2100
cgcatcgggg cgaaacagga aatgtcggcg cagaacgcga cgggtgatca ggtacgtggc   2160
gccgggagcg atctcgcgag gctggctcat ggccggatca catagacaaa cgctgcgcca   2220
tcaagcgatg tgcatcattt caatgactta ccccgccgcg gggggtggcg gccgccgatt   2280
```

-continued

```
tccgccaatt tccgccacgc tgggccgccg cttgtcacgc gaccagctgg tgtcggaccg   2340
cctcggatta cccccgccgg tagacctccg ccgatagacc tcaacccggg tcgggtcggc   2400
cccccagagt tgggtcgggt cgggtcgaca acctgggtcg gccaacctgg gtcgggttca   2460
ccaaccggcc aacctgggtc aggttgcggc accaaccggc caacctgggt cgggtcgcgg   2520
cggggttgcg gcaggctgca ccccaaccgg ccaacctggg tcgggtcgcg ccgggctcac   2580
tcctcctggc cggcccgcga ccagccgccg agcttgacgc ccggcgtctg cgccaggaag   2640
gcctgcaccg ccggcggcgg cgacgcccac gccgcgaggc gccccgggct ccgcgggatc   2700
ggcgtcgtcg ccgagcgcga gtaggagctc cacgcgccgt cgctgcaggc atagcaggtc   2760
gagcgcgcga gctgcgcggt gagccggagc gacccccgcg cgtcgtaggc cggcgcgatc   2820
ttcacgagct gcggggggtc cttctctcgc cgcgcggcct ccggatcctc ctcgatgtcg   2880
tcgagcgtcg cctcggccgc gcgctgcagc gacggcacgc cggacacctc ggcgagcagg   2940
tcgaccgccg cgccgcgctc ggcgtcccac acagtgaacg cggccccctc ggagccgtgc   3000
gcgccgcaga gatcgctgta cgtgcgctcc tcgatgaaca ggtacggccc cacgctgccg   3060
atcagcgcgg cgctgtgctg gaacacgttg ctctcgtcct gctccggcac cgtgatcacc   3120
gcctggcgct cgccgtcccc gcgcagcacg agcgccgcgt cggtcgccgt gccctcgccc   3180
ggctcgcgcg tgtccccgtc ccagagctcg cacggcgtcg tctcgacctc cttcgcgcgc   3240
gcctcccagc gccactcccc gcgccgggtc gccacgacga tcccgggctc ctcgcggatc   3300
accgcgccgc cctcggcgac gtgccacgtc ctcggcgtcc cctcgcccgt gctgccccag   3360
acgaggacca ccccgtcggc agcaacgttc ccggccgact cggcctcggg cgggcgcggg   3420
gcgggcgcga gctggatgtc ggtggaggcg gccggcgcag gcccgggccg cgcggcacag   3480
ccggagatca gcgccagcga gacgatcaac gcagcaggtc gggagcgcag catgcggagc   3540
cgaaagagca tggtgtgtgc cgcggcccac ggccagggaa gcccgcgccc cgcgcgccgg   3600
aggtgtagcc gcgcgcccac gccgcgtggc acgagcgccc cgtcaccggc gtcgggaccc   3660
gacgatcgag ctccgacgcg ggcagcggca cgaacggcgc gtcgcccgcg tcggcgagcg   3720
cgccgtcctc aggtgccgga acgcgagcgc gcccggcgca ggagcgcccg ctgcgcggcg   3780
ttcagccgga tcccgggcct gcgctgccgg atccgggcct ccatcgcgtc gacgtcggcg   3840
gcgagctcgc gctccagcag cagcgcggcc gcgagggtcg ccgatcggcc gcggcccgag   3900
gcgcagtgca ggtacatgcc gtccacgccc cgcagccgct cgaggagctc caggagccgc   3960
tccacctcgg gccccgtgcc gtcgagcgtc ggcacgcaga ggtagccggg gtggcgccgc   4020
accgcggcgg ccgccggaaa ctcggccgtc atgtccacga cgagccgcac gcccgccggc   4080
agctcgtggg cgagcggccg ccggccgacc cagagcccgg gcgccacctc gttggcgcag   4140
tccgcccgcc cgagcgcccg ctccgcgcgc cataccgccc aggtcaggag gaagtacgga   4200
ccgagcagga cgagcgccca cgcggcctgc gtgccgtctg gccgcttgcc cagcagcgcg   4260
ggccggcgcg cgaggtacgc ggcgccgacc aggccgaagc tcagcgccgg ccagagcagg   4320
gcgagcgcag ccccgccggc caggacggcg agcgcggcga gcgaggcgct caggacgagg   4380
aaggtcaggc cgtatcgcat ggatcggaga ggcgtctgct cggccatgct ctcacatcgg   4440
gcgctcctcg atgaagtcga gcagccgctc gctcgcgtcg aacgcctcgc tcttccggcc   4500
gaacaccggc ggcagatccc ctccgcccgg ccacgtgcgc ccgcccccca cgacagcgca   4560
gcgctcgacc tcggcctcgt cggcgcagcg cgaccgcgcc gtgcacgtcg tgtcgccgtg   4620
```

-continued

```
cgcgtacgtg atgtgggaga cgtcagcgca gccgtcgcga tcgcgccaga tcggagagag   4680
gacagtgcga tgggccggac atcatcacag ctctctcttt cgggatctcg agggccatcc   4740
ggaggtgcgc tgccggcgcg gacagcgtct cacacgcccg gcaaagctgg cctcgagtcc   4800
accgcgaccg ccctctggat ggcgtcgcgg agccacccgt ggccctcgtc gtgctcggag   4860
cgctccggcc agacgagcgt cagcgtgtag ccctcgagcg cgaacgggca cggccgcacc   4920
acgagatcga gcctccgggc cagggccgcg gcgacgcgcg cggacacggt gagcagcagg   4980
tcggaaccgg agacgatgaa cggcgcgaca aggaaatggg acacggtcag cgtcacccgc   5040
cggcgtgttc cctgctccgc cagcgcccga tcgatggcgc cgtggtcctc tccgtgcggc   5100
gagaccatca ggtgctcgca agcagcgtag cgcgccgcgg tgagcggcct ccgggacgcc   5160
gggtgtccgc ggcgcatcac acagacgatc tcctcggccg cgagcagcgt ggagcgacag   5220
ccgtcgggca ccggtccgcc gcgcccgagc ttgccgtcga gctcgccgcg gcgcaggagc   5280
tcggcgaagt cggccgggat gttccggcag cgcaggttga cgcgcggcgc ctcgacggcg   5340
agcagcgcgg tcagcgccgg gagcacgagc agctcgaggt tgtcggtcgc gacaagccgg   5400
aacgtgcgct gcgaccgccg cgggtcgaac cgctcgaccg ggcggaagac ctgctcgagc   5460
cgctcgacgg cctcggccgc ccgcggggcc aggtcccgcg cccgctcgct cagcgtcatc   5520
tgcctgccga cctggatgag cagcgggtcc gcgaaatggg cgcgcagccg cgcgagcgcg   5580
tggctcatcg agggctgcgt cacgcccacg cggcgcgcgg cgcgcgtgac gctcttctcc   5640
tggagcaggg cgtgcaacgc cacgacgagg tgggtgtcga ccgactgcag ccgcatggtc   5700
gatggatacc acgtcgatcc atcgacggcg tctatggatc gccgcgccga ctgccgattc   5760
gacgcccggg gccgtgggtg cctatctctc ctctccggac ggcgcatgcc gccgcgcggc   5820
gcgcgcctac cccccagccg aggagagcaa ccccatgatc atcgagtacg ttcgctacac   5880
gatccccgcg gagcaagaga aggagttcct ggccgcctac cgcgacgccg ccgcggagct   5940
gcgcgggtcg gagcattgcc tcgactacga gatctcccgc tgcgtcgagg atccgacgag   6000
ctacgtcgtc cgcatctgct gggactcgct gcaaggccat ctccagggct tccgcaaggc   6060
ggcggcgttc ccgtcgttct tcgccaaggt gaagccgttc tacgagcgta tccaggagat   6120
gaggcactac gccttgaccg acgtcgccgc gcggcaggcg gggacggccg cgacgggctg   6180
aagggtagac cctgcggccc tccgaacgtc gaggccgcct gcgccggcct cggctgctcc   6240
ccgccagcct gtccgcgcct cacatcgagc cccttgcagg cccagcgcgc ccggtgaggt   6300
gcggagtgac gccgcgatcc cggaaagccg ctggggagac cgcgcgggga aagcgatgcg   6360
ccgcttccgc cgcggtgcgg gcgggtgcag gatgcggcca tgggaatgcc tccggcgctc   6420
gaccgagacc accgccgccg cgccccgcgc gcgcccgccg ccgcgctcat cgcgctcctc   6480
gcagccggcg ccgcgctcgc ggcctgctcc aggagcacag gcgggccgaa gcaccgcgag   6540
gcggcgccgg agcgcgacag cgcctgcacc gatccagcga agcccagggc gtacttctat   6600
cctgcggaga accggacgga ctacgcgcct gacgatccct ggaaggacgg ctgcgccatg   6660
ctggtgccgg atcacctgtt ctgctgtccg gagaaggcct ccaccggctc gccctgatcc   6720
gcgccgcccc gccccgccgc gcgcgcacat gccgctcgtc cggagcgcag ccgccccgcg   6780
cgcgagcgcc acacaggccg caaacgtccc acacgctgcg cctgcaggcc gagcgcaggg   6840
cgccctgcgg agcgccgcgc gcccacctcg ggcgccgtcg cgcggcgacc gacgcggccg   6900
tcgcgcggcg atcgacgcgc gggcagcgcg cttcacggcg cgcgtgggga taccctggcc   6960
tggccgtgga tctgttgagc tacgccgggg cgaacctgca ggaccgcggg ccgagctcgc   7020
```

-continued

```
tgcgcgttcg cttccccgca gcctgaagcg ggcgagcgcg gcgccgcggc gggacggccg   7080
acacgggtgc cgcacaacgc ggcatgtcgc attctgcggc ggcgtcgagc ggatggctgg   7140
acgcgcgcac ctgcgcgcgc cacctgcgct aggacgccgg acatgaagct cgcgcgcaag   7200
ctgacgctcg ccctcgtgtt cggggtattc ctcgtgctcg cgctgagcgc ctacgcccag   7260
atccgcagag aggccaggat cttcgagaac gacgtccagc gcgaccatca cacgatggcc   7320
cgcgcgctcg cggccgcggt catggaggtg tggcgctccg agggaaccgc gcgggcgctg   7380
cgcctcgtgg aggacgccaa cgagcgggaa cagcaggcga acatccgctg ggtctggctc   7440
gatggccagg ccgacgagcc ccatcgcccc cggctggcgc cggagctgct cgcccccgtc   7500
gccgaggggc gcgcggtcgt gcgccggatc ccccagaaag acgcggatct gctcgtgacc   7560
tgcgtgccgg tgtccgtgcc cggcgaccgc gccggcgcgc tcgagctctc cgagtcgctc   7620
gcgggcgcgc gccggtacat ccggagcatg atcctgagca cggcgatcac cacagccgcg   7680
ctgacgctgg tatgtgggtt gcttacaacg ggcctcggag tctggctggt gggacgcccc   7740
atgcgcacgt tgatcgacca ggcgcggcgg atcggcgccg gcgatctctc cgggcggctg   7800
tcgctgcgcc aggaagacga gatcggcgag ctcgggcgcg agatgaacgc catgtgcgat   7860
cgcctcgccg cggcgaacca gaagctcgag tccgaggccg ccgcgcggat cgccgcgctc   7920
cagcagctcc gtcacgccga gcggctcgcg accgtcggca agctcgcgtc cggcatcgcg   7980
cacgagctgg gcgcgcccct ccaggtcgtc acggggcgcg cgcggatgct cgtcgacggc   8040
gacgtgtcgg gcgatgaggt gccgatcaat ggacagatca tcctcgagca gtcgcagcgg   8100
atgacccaga tcatccgcca gctgctcgac ttcgcccggc gccgcagcgc cgagaagcag   8160
gagaccgcgc tccgcggcgt catccgcggc acgttcacga tgctgaagcc gctggcggac   8220
aagcagggtg tcacgatcgt cgaggaggga gacacgccgg atcgggtggt ccacgccgac   8280
gccgaccagc tccagcaggc gctcacgaac gtcgtcgtca acgcgatcca ggccatgccg   8340
tccggcggca cgatcacggt gggcgtccgg accgtccgcg ccagcccccc gcccgaccag   8400
ggaggggccg agggcgacta catcgcgctg tcggtgcgcg acgagggaca gggcatgacg   8460
gccgacgtcc tcgagcacgt cttcgagccg ttcttcacga ccaagcccgt cggcgagggg   8520
accgggctcg gcctgccggt cgcctacggc atcatcaagg agcacggcgg ctggatcgac   8580
gtcgacagcc gccccggctc cgggagccag ttcacgatgt acctgccgca ggagaagcca   8640
tgaccggacg cgtcctgatc gtcgacgatg agcgaggcgt ctgcgagctc ctcgacgccg   8700
ggctgaagaa gcggggattc caggcggcgt ggcgcacgtc ggccgccgag gcgctcgagc   8760
tcctcggcgc ggaggacttc gacgtcgtcg tcaccgacat gaccatgcgc ggcatgaacg   8820
gcctcgagct ctgcgagcgc atcgcccaga accggcccga tctgccggtc atcgtcatca   8880
ccgcgttcgg gagcctcgac accgccacgt cggcgatccg cgccggcgcc tacgacttcg   8940
tgaccaagcc gttcgagctc gacgcgctcc ggctcaccgt cgagcgcgcc ctgcgccacc   9000
gcgccctccg cgaggaggtg cgccggctgc ggcgcgccgt ggacgactcc caccgttacg   9060
agcagatcct cggcggcagc ccggcgatga agggcgtctt cgatctgctc gaccgggtcg   9120
ccgactcgga cacctcgatc ctcatcaccg gcgagagcgg caccggcaag gagctcgtcg   9180
cgcgcgccgt gcaccagcgc agccggcgcg gccagggcgc gttcatcgcg gtgaactgcg   9240
cggcggtccc ggacgccctg ctcgagaccg agctgttcgg ccacgcgcgg ggcgccttca   9300
ccgacgccaa gggggcgagg agcggcctgt tcgcgcgggc ccacggcggc accctgttcc   9360
```

-continued

```
tcgacgagat cggcgagctg ccggtcgggc tccagccgaa gctcctgcgc gccctccagg    9420
agcgcgtcgt ccggcccgtc ggcgcggacg aggaggtccc cgtggacgtg cggctcatcg    9480
cggcgaccaa ccgcgacctg gagaccgcga tcgaggagcg ccgcttccgc gaggacctct    9540
attaccggat caacgtggtc cacgtcgatc tgccgccgct ccgctcccgc ggcgccgacg    9600
tgctgctgct cgcgcagcgc ttcctcgagc acttcgcgac cgtcaaggag cggcccatca    9660
agggcctctc ggcgcccgcg gccgagaagc tcgtcgccta cgcgtggccc ggcaacgtcc    9720
gcgagctcca gaactgcatc gagcgggccg tcgcgctcgc gcggtacgat cagatcacgg    9780
tcgacgatct ccccgagaag atacggagtt accggcgctc ccacgtcctt gtctcgagcg    9840
acgacccgac cgagctcgtc cccatggagg aggtcgagcg gcgctacatc ctgcgcgtcc    9900
tggaggtggt cggcggaaac aagagccagg cagcccaggt cctgggcttc gatcgagcga    9960
ccctgtaccg gaagctcgag cggtacggcc tgcgcgccgg gcgcgcgggc gacccgaggc   10020
cgtgatccgc ccggcgccgc gccggaggtg attccaggag cgcctcgcgg cggcggcgcc   10080
gctcgtcctc acgctgttgc agaacgcgac actcgcggcg tcgcgcgatc ggcagcgccg   10140
cgcgcgggcg cgcgcgatct gcgctggtgg catgagagct gcctgaaagc agggcgcgaa   10200
catgagccac acaacggcgg cgtctgctgc tccggaccgg agagtgccag tcgactggat   10260
cgcgctcgcg aacgcgttcg acaacatcgc tcgaggcgtg cgccatttcc ttcacctcga   10320
cacgggcgcc gtgctccggc tgaacgagcg gctcgtcgat cccgccacgc gcgcgcgcat   10380
cgaggaagac ccggggtgcg tgctcatcga ggccatcgcc gctcgggatc agtatcgatg   10440
gctggaggcg ttcattccca cggtggaaga cctggagttc cggctggcgc tcctgcacag   10500
catgcagggc ccaggatcgt tccggcggtt caaggccgcg ctctcggcca ggccggagca   10560
gctccgccgc tggcgcgcct tccggcagga gcagatccgg gtcgcgatcc tccggtggtt   10620
tcacgcccgc ggactgacgc ccgtcgcgct cgagctctcc tcgccggacg cgagctccga   10680
gccgccgagc tcccgcgccg tcgactcggc tcgccagcag ctttactccg cggcggacgg   10740
cctctgtccg agcgacctcc aggcgctgac gtcgctcgcg gagtacctgc gcgcggcgcg   10800
ctcggcgctg cggatccccg ccgattcatc catgggagac gccgcgcggg ccgtccgcct   10860
ggtcccttga cgacgagcgc ggcagctcga tccggaagac cgagccggcg ccgggacggc   10920
tctcgacgaa gaggcggccg ccgtgcgcct cgacgatgcg cttcgccacc gcgaggccga   10980
ggcccgtgcc cgggatggat ccagacgtgg acttgagccg ccggaacggc tcgaagaggt   11040
gcgccagatc ctcgggctcg atcccgagcc cgcgatcgcg aacggcgatc tcggccccct   11100
cgccgccggc gcggaccgcc acgtcgacct gcccccggc gggggagtac ttgagcgcgt   11160
tcgacaggag gttgttcagc acctgctcga tccgggtcgc gtcgcagcgg acgagcaccg   11220
gtgtctcggg gagcgagagc tcgatggggt gctccggcga gacagggcga tagaggtcca   11280
ccgcctcctg cgcgagatcg cgcaggtcgc gctcctccac ccggagatcg agcttgcagg   11340
cctcgatctg cgacgcgtcg aggaggtccc cgaccatgcg atcgagccgg tcgacctgcc   11400
gcccgacgag cgccatggtc cggcgcacgc tcgactccag gggccggttg tcggcgtcga   11460
ggacgtgcac ggacagccgg agcgccgaca gcgggttcct gaggtcgtgg gccacgccgc   11520
cgaggaacgc gaactgcgcc tcgcgctggc gctccagcga ctctgccatg tcgttgaagg   11580
cgcgcgcgat ctccccgagc tcgcgcggcc cgatcagcgg cgcgcgcgcg gcgcggtcgc   11640
ccgcgccgta gcgcccgatg gcctcctgga tcgcgacgat ggggcggtag atgagccgcc   11700
gcgcgctgag gaggatcgtg gacgcgcccg cgaggaagaa caccaccgcc gcgaggccgg   11760
```

-continued

```
cgccggtcgt gcgccgggtc aggtgcgcga cgagcgcctc cgacgcgcgg gcctgctcga  11820

ggttgatctc gaccaggtga tcgagcgccc tgaacgcctc gtcgagcgcg gggtcgtgca  11880

cgccgagcag cgcgggatcg tgcgcgccag gcgccgacgg gagctcgtgg gcgtcggcgg  11940

cgcggcgccg ggcgaggtag tcctccacgc gccgctccgc gtgctcgagg atcctgccct  12000

cctccgggct gctcacgtgg tcgcgcgccg ccgcgaggcc gctcctcagg ccttgctccc  12060

acgccgccag ggagggggcc agctccccgc ggccggagcc gaccgcgcgg ctgctctggt  12120

gcgcgtcgag caggaggtcg atctccagcc tctccacgag ccggacgctc tcgaccgtgg  12180

cgccgaggat ccgggtggtc tgttgcatgg tcgtcgacgc gaccatcagc gcgcccgcga  12240

caacgatggc cacgctcgtg agaagaagcg tggcggcccc gaggagcgcg ctcaggcgca  12300

cgggccgcgg aagacggggc cagctcaggc cctgcggagt tggctgtcgc atcttcctgc  12360

gttggttcgg atccgcgacg gatgcaacgt cgcctcgatg gagagattga actgcagagg  12420

cacagagcac atcgaggcag ggagcgataa gcgcgctgcg cccgcggcgc tccccgcccc  12480

tccgcgccgg cctcaccggc ctctcgcgcc tcgatcagct cggtcctctg gacggtgatc  12540

cccgtttcct cgacactgcg cgagatgccc gcccgcaccc cccgcaagcc cccgccgccc  12600

gcctcgcccg ctggtcccgc cggcgcgccg gacgacctca ccgacagcga tcgcgacgcg  12660

ctgctgcgct ggcggctcgc gctcgggccc gaggccgagc gggtcgaccc gcgcctctcc  12720

ctcggcgggc tcgggggcgc ggcgcccgcg ctcgacgtcg acgcgcggcg gctcggcgac  12780

ctcgacaagg cgctctcgtt catctacgac gagcgcgccg gcggcctcgg cggctcgcgg  12840

ccctacgtgc ccgagtggct ctccgccgtg cgcgagttct tcagccacga ggtcgtcgcc  12900

ctcgtccaga aggacgccat cgagcgaaag gggctgacgc agctcctctt cgagcccgag  12960

acgctgccgt tcctcgagaa gaacgtcgag ctcgtcgcca cgctcatgag cgccaagggc  13020

ctcatcccgg acgccgcgcg ggacaccgcc cggcagatcg tgcgcgaggt cgtcgaggag  13080

gtgcggcgcg cgctcgaggc cgaggtccgc accgccgtcc tcggcgcgct gcgccggaac  13140

acgacgagcc cgctgcgcgt cctcaggaac ctcgactgga agcgcaccat ccgcaagaac  13200

ctgaaggggt gggacgcgga gcggcgccgc ctcgtccccg acaagctcta tttctgggcg  13260

aaccagacgc gacggcacga gtgggacgtc gccatcctcg tcgaccagtc gggctcgatg  13320

ggcgagagcg tcgtctacag ctccatcatg gccgcgatct tcgcgtcgct cgacgtcctc  13380

cgcacccggc tcctcttctt cgacaccgag gtcgtcgacg tgactccgat gctcgtcgat  13440

ccggtcgacg tgctgttcac ggcgcagctc ggcggcggca ccgacatcaa ccgcgccgtg  13500

gcctacgccc aggcgaactt catcgagcgg cccgagaaga cgctgctcat cctgatcacc  13560

gacctgttcg agggcggcaa cgccgaggag ctcgtcgcgc gcatgcgcca gctcgccgac  13620

agcaaggtga agtcgatctg cctgctcgcg ctgtcggacg gcggaaagcc ctcgtacgac  13680

cacgagatgg cgcagaagct cgccgcgctc gggaccccgt gcttcggctg cacgccgaag  13740

ctcctcgtca aggtggtgga gcggctcatg cgaggtcagg acctcggccc gctgctcggc  13800

gccgaggcgc ggtgagcgcc ccgcgcggcg cgggatcacg gaagcacaga ggacgcagag  13860

gcacttgtct ctcctctgcg tcctctgcgc ctccatggcc gcccgtcagg ggccccgaaa  13920

ccgactggcg cggctcgcga acctcgtcga cgtcagcgaa ggcgcgccct ggacatccgc  13980

ggccgcgcag gccgcgtcag cgcgcgcgac ggatcggctt ggcggcgcgc tcgtccgccc  14040

gccgggcggc ggcgcgcttt cgcgacgtgg cgccgtgggc agcgctcgcg gagacgcgac  14100
```

-continued

```
ggcgggcgcc ggccgcgcga accaccgctt cgagcgaggg tgactggccc acgagaggac  14160
cagtgctgat cgaggggccg actaggctga tagaaagttt cacttgaact accgatgtgg  14220
tggcggaccg atcacgtcgc tcagcggagg gctcgtcgac ctataaactg ttttgatcgt  14280
ttgcgcagcg tcacgatgcg gagatcacga cccctgagcg cccgtccgga cgtgaacttg  14340
tccccccggg ggatccacac gccttccgcc tctcacgacg gacgtacgca cacaccacgg  14400
aggcacgaag gcacggttgt gggttcgctc cgtgccttcg tgtctccgcg gtgcttggcg  14460
agggactgcc cccggaggtt gcaccgggcg ctctgtcacg agctggttgc acgatgcagg  14520
ccaacgatgg ccggatgccg gcgtcgcccg ttttccgggg atggccatgg tccgcctttc  14580
atggttgaaa ccactggttg caaccatggc ggaacggagc ggcgtcgctg cccccgcggc  14640
gcctggcgcc ccggggagag cgcctctcgg cccgcaggac cggtcagcgg ggatccaggg  14700
cgctggccca gcggccccga cgatccagcc gcgcggggcg ggagcggcag cgtggatcac  14760
tgcggacttg ccgtcgatcg aggtccgcat ctggatcggc tcgccgcgac cgtatccgat  14820
ggcgttcatg agcgggctgg cgagcaccgg gtcgacgcgt aggcggcccc accgaccgat  14880
cgccgaggtc gagcgcctgg gcgacgttcc ccggcgagca cgcgacgcgc aggccgggac  14940
gcccgctcgt cagcaccccg ccgccgctgc ccacgccgag acgagctcct gcaggcgatc  15000
tcgggttcac cctcgcgcga ggacctgtgc tccgcggtga gcccgataga cgctgcccgg  15060
gcctccccc tactccgtac ctgcccgaca aaggaccagc ccacgcgcgc tgtcattcgg  15120
ttgagcaccc gccttctgtt cgcagggcgc gccttgaaga gtcggacagg tcgccttccg  15180
gaaaggcagt ggcctggtat ccgccatgtt tccggtgtgc ttcgctgcta tccggtggcc  15240
tggtgtccac catgtttccg gtgtgcttcg ctgctatccg gtggcctggt gtccgccatg  15300
tttccggtgt gcttcgctgc tatccggtgg cctggtgtcc gccatgtttc cggtgtgcct  15360
ctctgctcga gccacgggcc acctctaccc gagcaactcg acctgatgca atgtagttga  15420
gcccgcctgg ctggcagcgg tgccatcccc gtcctgcctc tgacagcagc ggatcgcaga  15480
cccgcctgcg atgccggtag cgggacatcg gcacagatga ctgttcaccg tgcgggcagt  15540
gttcctggct ggaagaataa tcccgtatca attcaataag atgccctggc ggcgccaagc  15600
tcaccacagc ctactcggcg caaccactca gccctcacga caactatgta atttttctca  15660
caacatgagc acttgattga aagattggaa aagtgaacga cgaaaggttg cgtagattac  15720
cgtaggtgct agcctggcgc gcactttcct atgcccgaca cgtcgtcgtc gagccccgta  15780
atggcgatgg ggctatcgga ctcgaaagcc cggtccgtgg aggatgcacg gcctgcctcg  15840
gggcttcctc gtccacccgc gggcatcgct gtggtgggaa tgggatgtcg cttccccggc  15900
ggcatcgatt cgcccggatc cttgtgggcg gccctatctc aagggcgcga ccttatcagc  15960
gaggtcccgc cggaccggtg ggatgtcaat gcccactacg acgccgacgc aagcgtcccc  16020
gggaagattg cgacccgcca tggcggcttc ctcgccgggg tcgcggcgtt cgacgcgcct  16080
ttcttcgacc tctcgccgcg cgaagcgaag catatggatc cgcagcagcg cctcggcctc  16140
gagacggcgt gggaggcgct ggaggacgca ggcctggacg cgaggagctt gcggggcagc  16200
cgggcagggg tgttcgtcgg ctcgatgtgg gcggagtacg acgtgctcgc gtcgcgacat  16260
cccgaatcca tctcgccgca cggggccacg gggagcgacc cggggatgat cgctgcgcgc  16320
atcgcctaca ccttcggcct tcgtgggccg gccttgtcgg tgaatacggc gtcgtcgtcc  16380
tccctcgtgg cggtgcatct cgcattgcag agcttgcaga gcggagagtg cgagctcgcg  16440
ctggccggcg gcgcgaacct catcctgacc ccatacaaca cgatcaagat gacgaagctc  16500
```

-continued

```
gggacgatgt cgcccgacgg ccggtgcaag gcgttcgacc accgcgccaa cggctacgtg  16560
cgcgccgagg gcgtcgggtt cgtggtcctg aagccgctgt cgcgagcgac cgcggacggg  16620
gatcggatct atgcggtcgt gcgtggctcg gccgtgaaca acgacgggct caccgacggg  16680
ctgaccgcgc cgagcgggga ggcgcaggag gccgtgctgc gagaggcgta tgcgcgcgcc  16740
ggggtgtctc ccgccgaggt ggactacgtc gaggcgcatg ggacgggaac gccgctcggc  16800
gaccgcgtgg aggcgacggc gctgggacgg gtgctcggcg caggacgcgc ggcggatcgc  16860
gcgctgcggg tcggttcggt caagacaaac ctcggtcacg cggaggcagc cgccggggtc  16920
atcggtctga tgaagacagc gctgtcgctg cgtcacgggt cgcttccggc gagcctgcac  16980
gtcgagcgcc cgaaccccga gataccccte gaatcgctgg gcctccggct ccagacggcg  17040
cacggcgtgt ggccggaggt cgatcggccc cggcgagcag gcgtgagctc attcggcttc  17100
ggcggcacga actgccatgt ggtgatcgag gagtggcgcg gggcctccca gcagagcgcc  17160
gccgaggcgg gcagcgaccc cggcgccgcc gtaccgccgc ctggccttcc ccttgtgctg  17220
tcggcgaggg accacggggc gctgcgggcg caggcgggcc ggtgggcggc gtggctcacg  17280
gagcaccgcg aggcgcgctg ggcggacgtc gtccacacgg cggcagtgcg gcggacgcac  17340
ctgggcgctc gggccgcggt gatggcggcg ggcgtggccg aggccgtcga tgcgctgaag  17400
gccctggccg acgggcgcgc ccacggggcc gtgacggtcg gcgaggcgcg cgagcggggc  17460
aaggtggtct tcgtgtttcc gggccagggc agccagtggc cggcgatggg gcgagcgctc  17520
ctgtccgcgt cgaaggtgtt cgccgaggcc gtcgaggcgt gcgacgcggc gctgaggccg  17580
ctgacgggct ggtcggtgct ctcgttgctg cgcggcgacg ccggggaggc agcgccgtcg  17640
ctcgaccgcg tcgacgcggt gcagccggcc ctgttcgcga tggctgtcgg cctggccgct  17700
gtctttcgcg cgtggggcct cgatccttcg gccgtggtgg gccacagcca gggcgaggtc  17760
ccggcggcgt acgtcgcggg ggcgctctcg ctcgacgacg cggcgcgggt cgtggcggtc  17820
cgaagcgcgc tcgtgcggcg gctcgcgggc gcaggggcga tggcggcggt ggagctgccg  17880
gccggcgagg tggagcgccg cctggcgccg ttcggggggg ctctggccat tgcggtggtc  17940
aacacgtcga gctcgacggc cgtttctgga gacgccgagg cggtggacag gctggtcgcg  18000
cagctcgagg ccgaaggcat cttctgccga aaggtgaacg tcgattacgc atcccacagc  18060
gcgcacgtgg acgtcgtgct accagagctc ctggagcgcc tggcgccggt ccggccaggg  18120
gccacgagga tccccttcta ttcgacagtg accggcggtg tgctggaggg gacggcgctc  18180
gacggggcgt actggtgccg caacctgcgc cagccggtgc ggctggaccg cgcgctcgcc  18240
cggctgctgg acgacgggca tggcgtcttc gtggaggtca gtgcgcaccc ggtgctggcg  18300
tcgccgctga ccgcggcgtg cgccgagcgc gagggcgtgg ttgtcggcag cttgcagcgc  18360
gacgacggcg ggctcgcgcg gctgctcggc tcgctgggcg cgctgcatgt gcagggccag  18420
ccggtcgact ggcgcgcggt gctggcgccg ttcggcggca gcctggtgga cctgccgacc  18480
tatgcattcc agcgccagcg ttactggttc gatacggatg agagcgtcgc cctcgcagcg  18540
gcgtccagcg tcgcggaaga gtcgtggtca gaaaagctgg ccgggctgtc ttccgcgcga  18600
cgggaagaac ggctgctcga atgggtgcgc gcagagattg cagcggtgct cgggctggag  18660
gcgccggcgg tgccgccaga cgtcttgctg cgggatctcg gattgaaatc gccgatcgcc  18720
gtggagctgg ggagccggct gggacgcagg acacgccgga agctgcccgt gaccttcgtt  18780
tacaaccacc cgacgccacg agcgatcgct cgcgccctcc tggagggaat gttttcctcg  18840
```

-continued

```
atcaaggact ctgcttcgag cgccgctgac gaccgccgcc cgccgggggt gctcgaagac  18900
gttgcccccc cacaggcgct cgagacgtcc gagatgtccg acgatgagct gttccagtcc  18960
atcgatgcgc tcgtctaggg agaccgcgct ctcgtcgaag aaggttgttc aacgctgcgg  19020
gtcgaggatt gctcgtggat cgaagcgata aactgcgtgc gtatctggag aagaccacgg  19080
cctcgctggt cgaggcgaag ggccggatcc gggagctgga agcgcgttcg cgcgagccga  19140
tcgcgatcgt ggcgatggcg tgccggtttc cgggcggcgt cgacagcccc gagaagctct  19200
gggccctgct ggacgaggag agggacgcca tcaccgaggt gccgccctcg cgatgggacc  19260
tcgagcgctt ctatgacccc gatccggacg ccgcgggcaa gacctacagc cgctggggcg  19320
gcttcgttgg cgatctggac cgtttcgacg cggcgttttt cgggatcagc cccgcgagg  19380
cccggagcat cgacccgcaa gagcgctggc tgctggagac cacgtgggag gccctcgagc  19440
gggccggcgt gcgcgcagac acgctggaag ggaccctggg gggcgtttac atcggcctgt  19500
ccggctcgga gtaccagacg gaggcattcc acgatgcgga gcgcatcgac gcctattcgc  19560
tgaccggcgc ttcgccgagc acgaccgtgg ggcgcctcgc ctactggctc gggctacgag  19620
gccccgcggt cgccgtggac accgcgtgca gctcctcgct cgtcgcggtg cacctggcct  19680
gccaggcgct gcggaacggg gagtgcgatt ttgcgctggc aggcggcgtc aatgcgctcc  19740
tggcccccga gagctatgtt gccttctgcc gcctcagggc gctgtccccc accgggcggt  19800
gccagacctt ctccgcggac gccgatggct acgtgcgcgc ggaagggtgc ggggtgctgc  19860
tgctcaagcg tctgtcgcac gcgcagcggg atggagaccg tgtgctcgcg gtcatccggg  19920
gcaatgccat caaccaggac ggccgcagcc aagggttgac ggcgccgaac gggctcgcgc  19980
aggaggacgt catccgcagg gcgctgtcgc aagccgccgt ggagccgacg accgtcgatg  20040
tggtcgaatg ccacgggacc ggcacggcgc tcggcgatcc gatcgaggtc caggcgctcg  20100
gggctgttta cggcgatggg cgccccggag acaggccgct cgtgatcggc tccgtcaaga  20160
cgaacatcgg tcataccgag gcggccgcgg gcatggccgg cctcatcaag gccgtccttt  20220
cgctgcagca cgcccaggtc cctcgatcgc tgcacttcgc ggcgccgagc ccttacatcc  20280
cctgggatac cctccccgtc cgcgtggccg cgcagcgcgt cgcatgggag cggcgcgagc  20340
acccgcggcg cgccgggatc tcctcgttcg ggatcagcgg caccaacgcg cacgtgatcc  20400
tcgaggaggc gccggaagcg ccggcgacgg cgccggaggc ggcggcggtg acgtcgacgc  20460
tgccgttgct tgtgtcgggg cgggatgagg cggcgctcag ggcgcaggcg gagcggtggg  20520
cggcgtggct cgcggcgcac ccggaggcgc gctgggcgga cgtggtgcac acggccgccg  20580
tgcggcgcac gcacctggag gcgcgcgcgg cggtggccgc ggggaacgcc gccgacgccg  20640
ccgcggcgct gggggcgctg gccgccgggc agccgcacaa ggcggtgtcc ctgggcgagg  20700
cgcgcgcgcg cggcgatgtc gtgttcgtgg ttccgggcca ggggagccaa tggccggcga  20760
tggggcgggc gctgctggcc gagtccgagg tgtttgccgc cgctgtcgcg gcctgcgacg  20820
cggcgctgcg gccgttcacg ggctggtcgg tgctctcggt gttgcgcggg gagcagggcg  20880
aggcggtgcc gcccgccgac cgcgtggacg tggtgcagcc ggcgctgttc gcgatggccg  20940
tggggctctc ggcggtctgg cgggcgtggg gcatcgagcc ctcggcggtg gtcggccaca  21000
gccagggcga ggtcgcggcg gcgtacgtcg ccggggcgct gacgctcgag gacgcggcgc  21060
gggtggtggc gctgcgcagc cagctcgtgc ggcgcatcgc cggcggcggc gcgatggccg  21120
tgatcgagcg ccccgtcggc gaggtggagc agcggctttc tcggttcgga gggcagctct  21180
cggtggcggc ggtgaacacg ccgggctcga cggtggtgtc cggggacgcc gcagcggtcg  21240
```

-continued

```
atcgtttgct ggccgagctg gagaccgcgc gggtgttcgc gcggcggatc aaggtcgatt  21300
acgcgtcgca cagcgcgcac gtggacgcga tcctgccgga gctcgaggcc tgcctggcct  21360
cggtcgagcc ccgtacctgc gccatcccgc tgtactcgac ggtgacggga gaagtgctcg  21420
ccggcccgga gctcggcgcg acatactggt gccgcaacct gcgcgagccg gtgcggctcg  21480
accgggcgct ctcgcggctg ctggcggacg ggcacggggt gttcgtggag gtcagcgcgc  21540
atccggtgct ggccatgccg ctgtcggccg cgagcgccga gcgcggcggc gtggtggtgg  21600
gcagcctgca gcgcgacgac ggcggtctgg ggcggctgac gtcgatgctt ggcgcgctgc  21660
acgtgcacgg ccacgccgtg agctggcagc gggtgctggc gccgtacggc ggggcgctcg  21720
tgggcctgcc gacgtacgcg ttccagcgcc agcgccactg gctcgaggcg ccgcggtacg  21780
cggcggagga tacggacggc gcggcgcggc gcgacccgct gtaccgggtc acgtggatcg  21840
aggcggcgct ggaagaagcg ccgtgggcgc ccgagcgcca cgtcgtgctc ggcgggggcg  21900
gcgcgctggc ggcggggctg gggcgctcg cgctggcggg gctgccggag ctgctcgagg  21960
cgctggagaa cagggcggcg gcgcccgagc ggctggtgct ggacctgacg gagggccgcc  22020
caggcgcggt ggcggagtcc gtgcacgcca cgacgcgcga cgcgctcgcg ctggtccagg  22080
catggcttgc ggcgccgcgg ctctcgggca ccgagctggt cgtggtgacg cgggaggcgg  22140
tggcggccgg cccggacgag ggcgtggcgg cgctgggccc cgccgctgtc tgggggctgc  22200
tgcgcacggc ccgcgtcgag caccccgagc gcgcggtgcg cgcggtggat ctggggcgcg  22260
agccgctgga cgtcgcggtc ttgcggcggg cgctgggggc ggtggccgag ccggagctcg  22320
cgctgcgcgc gggcggggcg cgggctgcgc gcctgcgcgc tgtcgacgcc ggcgcgggcg  22380
ccagggagcc ggcggctgcg ctggacccgc agggcacggt gtggatcacg ggcggcaccg  22440
gggagctggg gcggcagatc gcgcggcacc tggtcgcggc gcacggcgtg cggcacctcc  22500
tgctgacgtc gcggcggggc gcggccgcgc cggacgccga ggcgctcgtc gagcagctgc  22560
gggccgacgg cgccgagacg gtcgaggtcg tggcgtgcga cgtgacggac ggcgcggcgc  22620
tttcggcagc agtccaggcg gctgcggcaa ggcacccgct gacggccgtg gtgcacaccg  22680
ccggggagct ggcggacggg gtgctcacgg ggctgacggc ggagcagctc gcgcgggtgc  22740
tggcgccgaa ggtcgacggg gcgtgccacg tgtacgccgc cgcgcaggac cagccgctcg  22800
cggccttcgt gctgttctcc tcgatcgtgg gcacgctggg caacgcgggc caggcgaact  22860
acggggccgc caatgcgttc ctggacgcgt tcgcggcgca gcttcgcgcg cgcggcgtgc  22920
cggcgacgag cctcgcgtgg ggcttctggg agcaggcagg gctcggcatg acgtcgcacc  22980
tcggcgcggc cgacctggcg cgcctcaggc ggcagggcct tgcgccgctg tcggtcgcgc  23040
agggcctgcg cctgctcgac cgggcgctcg cgcgcgcgga ggcgacgctg gtgccggcgg  23100
cgctcgatct tccggcgctc cagcgtgcgg cgagcgacgc cggacgggtg cctccactgc  23160
tgcgcgggct ggtgcgcacg agtcccggcc gccccacggc gaccgcgacc cccgaggccg  23220
ggccggcggc gtcggcgctg cgcgcacggc tctcggcgtt gcccgaggcc gagcggccgg  23280
gcgcgctgct ggatctggtg cgcacggagg tggcggtcgt gctgcagctg gcagggccgg  23340
cgcaggtgcc cgcggacaag ccgctgaagg agctggggct cgattcgctc acggccgtcg  23400
agctgaggaa ccgcctcggc gcgcgcgccg agacggtgct gccgacgacc ctcgcgttcg  23460
accatccgac gccgcgcgcg atcgcggatc tgctgcttca gcgtgcgttc tcggagctcg  23520
cggcggcgaa ggcgacgcgc gcgcggggag cgcacgacga gccgatcgcg atcgtgtcga  23580
```

-continued

```
tggcgtgccg gctcccgggc agcgtcgata cccccgcggc gctgtggaag ctcctggcgg  23640
aggggcggga cgcgatcggg ccgttccccg aggggcgcgg ctgggacgtg gcggggctgt  23700
acgatccgga cccggatgtg ccgggcaagt cgatcaccac gcaaggcggc ttcctctacg  23760
acgccgaccg cttcgatccg acgttcttcg gcatcagccc gcgcgaggcc gagcgcatgg  23820
acccgcagca gcgtctgctg ctcgagtgcg cctgggaggc gctcgagcgc gcgggcctgg  23880
cgccccacgc gctcgaggcg agcgccaccg gcgtcttcgt cggctcgct cacggtgact  23940
acggcgggcg gctcttgcag cagctcgagt ccttcgacgg ccacgtcctc accggcaact  24000
tcctcagcgt cggctcgggg cgcatcgcgt acacgctggg gctccgcggc cctgcgatga  24060
ccgtcgacac ggcgtgctcg tcgtcgctcg tggcggtcca cctcgcgtgc atgtcgctcc  24120
gcgcgggcga gtgcgacatg gcgctcgccg gcggcgccac cgtgatggcc acgccgatga  24180
tcttcgtcga gttcagccgc cagcgcggca cggcgctgga cggtcgttgc aaggcgttcg  24240
gcgccggggc cgatggcgcc ggctggtcgg aggggtgcgg gatcctggcg ctgaagcggc  24300
tgtcggacgc gcagcgcgac ggcgaccgcg tcctggcggt gatccgcggc tccgccgtca  24360
accaggacgg ccgcagccag gggctcaccg cccccaacgg cccggcccag caggacgtca  24420
tccgccaggc cctggccgcg gcggggctca cgcccgccga cgtcgacgcc gtcgaggcgc  24480
acggcaccgg cacgcgcctc ggtgacccca tcgaggcgca ggcgctgctg gcgacctacg  24540
gcgccgcgca cacagcggag cggccgctct ggctcggctc gctcaagtcg aacctcgggc  24600
acacgcaggt cgccgcgggc gtgtcggggc tgatgaagct cgtgctggcc ttgcagcacg  24660
cagagctgcc gaggacgctg cacgccgacc cgccctcgcc gcacgtcgac tggtcgcagg  24720
ggcacgtcaa gctcctgaac gagcccgtgc cgtggccgcg caccgacagg ccgcggcgcg  24780
cggcggtctc gtccttcggc atcagcggca ccaacgcgca cgtcatcgtc gaggaggcgc  24840
cggccgaagc gccggcgaca gcggcggacg caaagtcggt ggaggcgctt ccgatcctgc  24900
cgctgctggt ctcggggtcc gacgagccgg cgctgcgcgc gcaggtgcgg cggctggtgg  24960
agcacctgcg gtcgcacccg gacgagcggc tgctggacgt ggcagcgagc cttgcgacca  25020
cgcgcgcgca tctcgcgatg cggctcgcgc tgcccgtctc ggcaggggcg ccccgggatg  25080
cgtgggtgga tgagctggag gcatttgcca ggggaggagc ggctccgacg caggcatcgc  25140
agacccccgc cgagagcagc gcgggcaagg tcgcggtgct cttcaccggc cagggcagcc  25200
agcgcgccgc catggggcgc gccctgtacg ccacccaccc cgtcttccgc gccgcgctcg  25260
acgccgcatg cgccgagctc gaccgccacc tcgacaggcc cctccacagc gtcctcttcg  25320
cagacgccgg caccgaggcc gccgcgctgc tcgaccagac aggatgggca cagcccgccc  25380
tgttcgctct cgaggtcgcg ctctaccgac agtgggaggc ctggggtctg cgccccgagc  25440
tgctgctcgg ccacagcatc ggcgagctcg ccgccgccca cgtcgccggc gtgctcgacc  25500
tccccgacgc ctccgccctg gtcgccgccc gcggacggct catgcaggcc ctccccccacg  25560
gcggcgccat ggcctccatc gaggccaccg agcacgagct cctacccctg ctcgaccagc  25620
acaccggacg cctctcgctc gccgccctca acgctccacg ccagtcggtc gtcagcggcg  25680
acctgcacgc cgtcgaccag gtctgcgccc acttcatcgc cctcggccga cgcgccaagc  25740
ggctcgacgt cagccacgcc ttccactcgg cgcacatgca gcccatgctc gacgccttcg  25800
ccagcgtcgc ccgcggcctg accttccacc cgccacggct gcccatcgtc agcagcgtca  25860
ccggcgcacg cgccaccacc gaccagctca cctcgcccga ctactgggtg cagcaggtgc  25920
gcgagcccgt gcgcttcctc gacgccatgc gctccctgca cgccgccggc gccgccacct  25980
```

-continued

```
tcgtcgagtg cgggccgcac ggcgtgctca ccgccgcagg cgccgagtgc ctcgctcccg  26040
agggcgctcg cgacgccggc ttcgtcacca gcctccgcaa ggaccgcgac gaggccctcg  26100
ccctggtcca cgccgcctgc gccgtccatg tccgcgggca cgccctcgac tggctccgct  26160
tcttcgacgc caccggcgct cgccgcgtcg agctgcccac ctacgccttc cagcgacagc  26220
gctactggct cgaggcgcca aggcctcgcc ccagcctcga gggcgtcggc ctcaccgccg  26280
caaaccaccc atggctcggc gccgccgtgc gcctcgcaga ccgcgatggc tacgtcctca  26340
gcggccgcct ctccaccatc gaccacccgt gggtcctcga ccacgtggtg ctgggcacgg  26400
cgctgctccc gggcacgggc ttcgtcgagc tggcgtgggc ggcggcagag gcggtcgggc  26460
tgcccggggt atcggagctg gcgatcgagg cgccgctggc gctcccggcg cgcggggcgg  26520
tggcgctgca gatcgcgatc gaggcgccgg acccggcggg gcgccgcggc gtcgcgatct  26580
acagccgccc cgacggcgca gccgacgcgc cctggacagc gcacgcgcgc ggcgtgctgg  26640
gcgccgcggc gcccgacagg gacgcggcgt gggcacaggg cgcgtggccg ccgccggggg  26700
ccgtgcctgt cgatgtgacg cagcggatcg agatcgtgga cgcgtgggtc ggcccggcgt  26760
tccggggcgt caccgcgctg tggcgcgtcg ggcggacgat ctacgccgac gttgcgctgc  26820
cggacggtgt ggcgagcacg gcgcaggact tcgggctgca tccggccttg ctcgatgtgg  26880
cgctacgcgc gttcctgaga gcggagctcg gcgccgatcc ctcgccacgg gagggcacgg  26940
tggtgccgtt cgcgtggtcg gacgtggtgc tcgaggcgcg tgggacggcg gcgctgcggg  27000
tgcgcgtgga ggtggcggcc gatggggacg gcgacgcgat cacggcgtcg atccagctgg  27060
ccgacgggca gggccgcccc gtcgcgcggg tgggcgcgct ccagatgcgg tggacgacgg  27120
ccgagcgggt gcgcgcggcc gcgggcgcgg cggagcgcga tctgtaccgc gtcgcgtgga  27180
cggacgtggc gctggacgac gcggcgtttg cgccggagga gcacgtcgtg gtcggcggcg  27240
acggcgcgct ggcggcggcg ctcggtgcac gcgtggtggc ggggctgccc gagctgctcg  27300
cgtcgctgcc ggacggcgcg gcggcgccac gccggctggt ggtggacctc acggcggacg  27360
ccgcgggcgc ggtcgtcgac gccgtgcacg ccgcagcgcg cgacgcgctg tccctggtgc  27420
agggatggct ggcggcgccg cagctggcgg cgacggagct cgtggtcgtg acgcgcggcg  27480
cggtggcggt cgcgcgggac gagggcgtgg cggcgctggg ccccgcggcg gtctgggggc  27540
tgctccgcgc gacgcgcgtc gagcatgcgg atcgcacggt ccgcgtgctc gatctggggt  27600
ccgcggcgcc ggacatgacg ctcttgcgcc gggcgctcac ggcggccgag gagccagagc  27660
tcgcgctgcg cgcgggcggg gcgcgggcgc cgcgcctcga cgcggccagc gagaccgaag  27720
gagagctggc gccgcccggc ggggcgcgct ctcttcgcct gtccatccgg acgaagggct  27780
cgttcgacgc gctccacctc gcggacgctc ccgatgcgct gcgcccgctc gggccggggc  27840
aggtccggct cgctgtccgc gccacggggc tcaacttccg cgatgtcttg aacgtcctgg  27900
ggacgtaccg cggcgaagcg gggcctctcg gtctggaggg ggctggggtg gtgctggacg  27960
tgggcgaggg agtcaccgcc cttcgacccg gcgaccgggt gatgggcatg ctgcacgcgg  28020
gcatggcgac ccatgcggtc gtcgacgccc ggctgctgac gcacatcccg cgggggcttt  28080
ccttcgtgga agcggcgacg attccagcgg ccttcctcac cgctctgtac gggctgcgcg  28140
acctcggcgc gctgaaggcg gggcagcgcg tgctggtgca cgccgccgcc ggcggggtgg  28200
gcatggcggc ggtccagctt gcgcgcctct ggggagccga ggtgttcgcg acggcgagcg  28260
agggcaagtg gccggcgctg cgtcggatgg ggatcgacca ggcccatatc gcctcgtcgc  28320
```

-continued

```
ggaccctcca cttcaggaaa gccttcctcg atgcaacgca gggacagggc gtcgacgtgg  28380
tgctcgacgc gctcgcgggc gagttcgtcg acgcttcgct cgacctgctc ccgcgcgggg  28440
gcgcgttcgt ggagatgggc aagagcgatg tgcgggatcc cgagcgcgtc gccaaggacc  28500
acccccgcgt tcgctacacg gccttcgatc tgctcgacgc ggggccagac cacatccagg  28560
cgatgctgcg ggagctcgtc ccgctgttcg aggagggcgt cctcgctccc cttccctccg  28620
tggcctacga cctgcgtcgc gccccgcacg ccttccgctc catggccaac gcacgccaca  28680
taggcaagct cgtgctggtg ccgcccgcga cgctcgaccc tgacggcacg gcgttgatca  28740
cgggcggcac gggagagctc gggcggcaga tcgcgcggca cctggtggcg gcgcacggcg  28800
tgcgccacct ggtgctgacg tcacggcgcg gcatggacgc gcccgacgcc gcagcgctgg  28860
tggaatcgct gcgcgcggcg ggcgccgcga cggtggaggt cgcggcgtgc gatgtgacgg  28920
accgtgacgc gctggcggcc atcgtgcagg cgatccccgc ggcgcgcccg ctgaccgccg  28980
tcgtgcacac ggccgccgtg ctggacgacg gcaccgtggc ggggctctcg gccgagcagc  29040
tcgcgcgcgt gctgcggccg aaggtcgacg gcgcctggca gctctacgag gcgacgaggg  29100
acgcgccgct cgcggcgttc atgctcttct cgtcggtcgc cggcacgctg ggcagctcgg  29160
ggcaggcgaa ctacgccgcc gcgaacgcgt tcctcgacgg gctggcggca gagctccgcg  29220
cgcgcggcgt gccggcgatg agcctcgcgt ggggcttctg ggagcagggc gggatcggga  29280
tgacggcgca cctcggcgcc gccgatctgg cgcggctgaa gcggcagggc atcgtgccga  29340
tgacggtcgc gcacggcctg cggctgctcg accgcgccct cgagcgcccg gacgcggcgc  29400
tggtgcccgc ctccctggac atggcggtga tccagcggac ggcgagcgac caccgtcagg  29460
tgccgcccat gctgcgcggg ctggtccgcg tcgcgccgcg gcaggcggca ggggcagcca  29520
gcggcaggag ccatgaggcc tcgaccctgc ggcagcagct cgccgcgctg cccgaaccgg  29580
agcggcagcg agcgttgctc gatctggtcc ggaccgaggc agccgccgtc cttgtgctgc  29640
gcgggccgga cgctgtcccc gccgacaagc cgctcaggga gctcgggctc gactcgctca  29700
cggcagtgga gctcaggaat cggctcagga cccgtgcgca gaccgatctc ccatcgaccc  29760
tcgccttcga ctacccgacg ccgaaagcgg tcgccgtgta tctggcccag gagctcgacc  29820
ttcacgacgt catgacggag atgcgcggac cgagcttgcg ctctgacgac gagctcaagt  29880
cggccatcgc gagcatccgg atctcgacgc tacgccaggc ggggctgctc gacagcctgc  29940
ttcggctcgc cgccagcgaa gccgtctcca catccagcga cacgacacct gaaaccgacg  30000
agctgacgct gcagcatgtt ggagacgatg agctggcacg gcttgtcttc gacctcgccg  30060
gaggagcgca atgaaagaag agatctccgc ccgtcaagct ctcgagaaga gcttcattga  30120
acttcgccgt atcaagcggg agctcgatca gctcaaggcg aagtcgagcg agccgatcgc  30180
gatcgtgtcg atggcgtgcc ggctcccggg cggcgtcgat acccccgcgg cgctgtggca  30240
gctgctctcg gaggggcggg acgcgatcgg gccgttcccc gaggggcgcg agtgggacgt  30300
ggcggggctg tacgacccgg acccggacgc gccgggcaag tcgatcactg cgcaaggcgg  30360
cttcctctac gacgccgacc gcttcgatcc ggcgttcttc gccatcagcc cgcgcgaggc  30420
cgagcggatg gacccgcagc agcggctgct gctcgagtgc gcctgggagg cgctcgagcg  30480
cgcgggcctg gcgccccacg cgctcgaggc gagcgccacg ggcgtcttcg tcggctgtc  30540
ggtcacggac tacggcgggc ggctgctgca cgatcccgag gccctcgacg gctacatcgc  30600
caccggcacc ctgcccagcg tcggctcggg gcgcatcgcc tacacgctgg ggctccgcgg  30660
ccccgcgatg accgtcgaca cggcgtgctc gtcgtcgctc gtgtcgctcc acctcgcgtg  30720
```

-continued

```
catgtcgctc cgcgcgggcg agtgcgacat ggcgctcgcc ggcggcgcca ccgtgatggc  30780
cacgccgatg gccttcatcg agttcagccg ccagcgcggc acggcgctgg acggtcgttg  30840
caaggcgttc ggcgccgggg ccgatggcgc cggctggtcg gaggggtgcg ggatcctggc  30900
gctgaagcgg ctgtcggacg cgcagcgcga cggcgaccgc gtcctggcgg tgatccgcgg  30960
ctccgccgtc aaccaggacg gccgcagcca ggggctcacc gcccccaacg gcccggccca  31020
gcaggacgtc atccgccagg ccctggccgc ggcggggctc acgcccgccg acgtcgacgc  31080
cgtcgaggcg cacggcaccg gcacgcgcct cggcgacccc atcgaggcgc aggcgctgct  31140
ggcgacctac ggcgccgcgc acacagcgga gcggccgctc tggctcggct cgctcaagtc  31200
gaacctcggg cacacgcagg ccgccgcggg cgtgtcgggg ctgatgaagc tcgtgctggc  31260
cttgcagcac gcggagctgc cgaggacgct gcacgccgac ccgccctcgc cgcacgtcga  31320
ctggtcgcgg gggcacgtca agctcctgaa cgagcccgtg ccgtggccgc gcaccgacag  31380
gccgcggcgc gcggcggtct cgtccttcgg cttcagcggc accaacgcgc acatcatcat  31440
cgaggaggcg ccggcggcct ccgccgaggc gacgagccgc ggggagaaga cgtccgcggc  31500
cgcgccgccg tcgatgatgc cgctgctggt ctcgggggtg gacgaggcgg cgctacgagc  31560
gcaggcgggg cggtgggcgg cgtggatcga ggcgcacccg gaggcaggct gggcggacgt  31620
tgtgtacacc gcggcagcgc ggcggacgca cctgggggcc cgtgcggcgc tgacggcggc  31680
ggacgcggcc ggcgctgtcg cggcgctgac ggcgctctcg caagggcagc cgcacgccgc  31740
gctcgccgtg ggcgaggcgc gcgctcgggg gaaggtcgcc ttcgtgtttc cgggccaggg  31800
cagccagtgg ccggcgatgg ggcgggcgct gctctcgcag tcggaggtgt tcgccgcggc  31860
ggtcacggcg tgcgacgcgg cgctgcggcc gttcaccggc tggtcggtgc tctcggtgct  31920
gcgcggcgac tcgggcgcgg aggtgccgcc gctggagcgc gtcgacgtcg tgcagccggc  31980
gctgttcgcg atggcggtgg ggctcgccgc tgtgtggcgc gcgtggggcc tcgagccgtc  32040
ggcggtggtg ggccacagcc aggggggaggt cccggcggcg tacgtcgcgg gggcgctgtc  32100
gctcgaggac gcggcgcgga tcgtggcgct gcgcagccag ctcgtgcggc gcctgtccgg  32160
ggctggcgcg atggccgtga tcgagcgccc ggtaggcgag gtcgagcagc ggctctcgcg  32220
gttcggcggc gcgctgtcgg tggcggcggt caacacgccg cgctcgacgg tggtgtcggg  32280
agatatcgag gcggtcgacc gcctgctggc ggagttcgag ggcgagcagg tcttcgcgcg  32340
gaaggtcaac gtcgactacg cgtcgcacag ccgacacatc gacgggctgc tgccggagct  32400
ggagaacggc ctgggcgcgg tgcggccgcg cgcgagcacg atcccgttct actcgacggt  32460
gaccgggacg gtgctgacgg gcgcggagct ggacgccgcg tactggtgtc gcaacctgcg  32520
cgagccggtg cggctcgacc gggcgctctc gtggctcctg gacgacgggc acggcctgtt  32580
cgtcgaggtc agcgcgcacc cggtgctgac gctgccgctc acaggagcga gcgcggcgag  32640
cggcggtgtg gttgtcggca gcctgcagcg cgacgacggc gggctcggc ggctcctggg  32700
ggtgctggcc gcgctgcacg tgcacggcca cgacgtcgac tggcgcgcgg tgctggctcc  32760
gtggggcgga ggcgtggcgg acttgccgac ctacgcgttc cagcggcagc gctactggct  32820
cgaggcaccg cgcggccggg cagggctgga gagcggaggg ctcctggccg tgaatcaccc  32880
gtggctcagc gcggcggtgc ggctggccga ccgcgacggc tatgtgctga gcggacggct  32940
gtcgacggtc gagcacgcgt gggtcctgga ccacgtggtg ctgggcacgg tgatcctccc  33000
gggcacggcg ttcgtcgagc tggcgctcgc ggcggccgat gcggtcggac tgccctcggt  33060
```

-continued

```
gtcagagctc acgatcgagg cgccgctggc gctgccggcg cgaggggcgg tggcgctgca  33120
ggtgacggtc gaggcgccgg acgcgacggg gcggcggggc ttcgcggtct acagccggcc  33180
cgacggcgcg cacgacgcgc cgtggacggc gcacgcgcgc ggcgtgctcg gcgcagcgcc  33240
cgcggcggcc acgacggcgt gggcggcggg cgcgtggccg ccggcggggg ccgagccggt  33300
cgacgtcacg cggtgggtcg aggcgctgga cgcgtgggtc ggcccggcgt tccggggcgt  33360
gacggcggcg tggcgcgtgg ggcggtcgat ctacgccgac ctggcgttgc ccgagggggt  33420
ctcggagcgg gcgcaggact tcggcctgca tccggccttg ctcgatgcag cgctccaggc  33480
cctcctgagg gcggagctcg gcgcaggcgc gtcgccgcgg gagggcatcc cgatgccctt  33540
cgcgtggtcg gacgtggcgc tcgaggcgcg gggggcagcg gcgctgcggg cgcgcgtgga  33600
ggtcgaggac gccagcgatg gggaccagct cgcggcgtcg atcgagctgg ccgacgcgca  33660
ggggcagccg gtcgcgcgcg cagggacgtt ccgggcgcgg tgggcgacgg cggagcacgt  33720
gcgcatggct gcggcgggct cgagcgagcg tgacctgtac cgggtcacgt gggcggacgt  33780
ggtgctggaa gaagcggcgt gggcgccgga ggagcacgtc gtgctcggcg gcgacggcgc  33840
gctcgcggcg gcgctgggcg cgcgcacggc ggcgctgccg gagctcatcg cggcgctgcc  33900
ggagggcgcg gccgcgccgc gccggctggt gatcgacgcg gccgcgggcg accccggcga  33960
cggcctggtc gcggcggcgc acgcggcggc gcagcgggtc ctgtcgctgg tgcaggggtg  34020
gctctcggag gcgcggctcg cggacagcga gctggtggtg gtgacgcgcg gcgctgtggc  34080
cgccgggccc gacgacggcg tcgcggcgtt gagccacgcg ccgctgtggg gactcgtgcg  34140
cacggcgcgc caggagaacc ccggccgggc ggtgcgcctc gtggacctgg ggcccgagcc  34200
gctggacgga gcgctcctgc gccgggtggt ggcggcggcc gaggagccgg agctcgcgct  34260
gcgcggggc gcggcgcgcg cgccacgcct gcgcgaggtg cgcgcgggcg cggccgacgc  34320
ggcgcggccg acgcggctgg atcccggcgg gacggtgctg atcacgggcg gcaccgggga  34380
gctcgggcgg caggtcgcgc ggcacctcgt ggcgtcgcac ggcgtgcggc acctcgtgct  34440
cacgtcgcgg cgcgggatgg gtgcgccgga cgccgcggcg ctggtggacg agctgcgcgc  34500
cgcgggcgcc gcgacggtcg acgtcgcggc gtgcgacgtc gccgacggcg cggcgctggg  34560
ggcggtcatc gcggcgatcc cggctgcaca ccccctcacg gcggtcgtgc acatggcggg  34620
cgtgctggac gacgtcatcg tgacgaagct ctcggccgag cagctcacgc gcgtgctgcg  34680
gccgaagatc gacggcggct ggcacctggc cgcggcgacg cgaggccatc ggctcgcggc  34740
cttcgtgctg ttctcgtcgg cggccggcac gctgggcagc ccggggcagg cgaactacgc  34800
cgcggccaac acgttccttg acgcgctcgc ggcgcagctc cgcgcgcgcg gcgtgcccgc  34860
gatgagcctc gcgtggggct tctgggagca ggcagggctc ggcatgacgg cgcacctcgg  34920
cgcggccgac ctggcacgcc tcaggcggca gggcatcgcg ccgatcgcgc tcgcgcaggg  34980
catgcagctg ctggaccggg cgctcgcgcg cccggaggcg gcgctggtgc cggcggcgct  35040
cgaccttccg gcgctccagc gtgcggcgag cgacgccggg caggtgccgg cgctgctgcg  35100
cgggctcgtg cgcccggcgg tcgggcggcg cgcggcggcg cctgcggccg ccgcgaccgg  35160
agcggcggcg ctgcgcgcgc ggctcgcgcc gctgcccgag gccgagcggc acgacgtggt  35220
gctcgacctg gtgcgcgccg aggcggcggc cgtgctgcag ctggcggggc cggcgcaggt  35280
ccccgcggac aagccgctga aggagctggg gctcacctcg ctcacggcgg tcgagctgag  35340
gaaccgcctc ggcgcgcgcg ccgagacggc gctgccggcg accctcgcgt tcgaccatcc  35400
gacgccgcgc gcgatcgcgg gtctgctgct tcagcgtgcg ttctcggagc tcgcggcggc  35460
```

-continued

```
ggtggcgacg cgcgcacagg cgccacgcgc gcagggggcg cacgacgagc cgatcgcgat  35520
cgtgtcgatg gcgtgccggc tcccgggcgg cgtcgatacg cccgcccgga tgtggcagct  35580
cctggcggag gggcgggacg cgatcgggcc gttccccgag gggcgcggct gggacgtggc  35640
ggggctgtac gaccccgacc cggacgcgcc gggcaagtcg gtcaccaacc tgggcggctt  35700
cctctacgac gccgaccact tcgatccgac gttcttcggc atcagcccgc gcgaggccga  35760
gcgcatcgac ccgcagcagc ggctgctgct cgagtgcgcc tgggaggcgc tcgagcgcgc  35820
gggcctggcg ccccacacgc tcgaggcgag cgccaccggc gtctttgtcg ggctggtgta  35880
cagcgactac ggcgggcggt tgctggagca cctcgagtcc ttcgacggct acatcgccac  35940
cggcagcttt cccagcgtcg gctcggggcg catcgcctac acgctggggc tccgcggccc  36000
tgcgatgacc gtcgacacgg cgtgctcgtc gtcgctcgtg tcgctccacc tcgcgtgcat  36060
gtcgctccgc gcgggcgagt gcgacatggc gctcgccggc ggcgccaccg tgatggccac  36120
gccgatggcc ttcatcgagt tcagccgcca gcgcggcatg gcccccgacg cacggtgcaa  36180
ggccttcggg gcggaggcga acggcatcgg ccccgcggag ggctgcggga tcctggtgct  36240
caagcggctg tcggacgcgc ggcgcgacgg cgaccgcgtc ctggcggtga tccgcggctc  36300
cgccgtcaac caggacggcc gcagccaggg gctcaccgcc cccaacggcc cggcccagca  36360
ggacgtcatc cgccaggccc tggccgcggc ggggctcacg cccgccgacg tcgacgccgt  36420
cgaggcgcac ggcaccggca cgcgcctcgg cgatcccatc gaggcgcagg cgttgctggc  36480
gacctacggc accgcgcaca cagcggagcg gccgctctgg ctcggctcga tcaagtcgaa  36540
cctcgggcac acgcaggccg ccgcgggggt tgtggggctg atgaagctcg tgctggcgat  36600
gcagcacgcg gagctgccga ggacgctgta tgcggagccc cgatcgccgc acatcgactg  36660
gtcgcagggg cacatcaacc tcctgaacga gcccgtgccg tggccgcgca ccgacaggcc  36720
gcggcgcgcg gcggtctcgt ccttcggcat cagcggcacc aacgcgcacg tcatcatcga  36780
ggaggcgccg gccgaagcgc cggcgacagc ggcggacgca aagtcggtgg aggcgcttcc  36840
gatcctgccg ctgctcctgt cgggtcgcga cgagccggcg ctgcgcgccc aggccgggcg  36900
gctcgccgag cacctgcgcg cccacccggg cgagcggctg ctcgacatcg ccgcgggcct  36960
ggccacgacg cgcacgcacc tcgccacgcg gctcgcgctg ccggtcgccg cggacgcagc  37020
cgcggaggag ctgggcgccc gccttgcgca gttcgccgcc ggcggcccgg cgcccagcgg  37080
cgccgccgtg accgcgccgg ggcagccgcc cggcaaggtc gcggtgctct tcaccggcca  37140
gggcagccag cgcgccggca tggggcgcgc cctgtacgcc acccaccccg tcttccgcgc  37200
cgcgctcgac gccgcatgcg ccgagctcga ccgccacctc gacaggcccc tccacagcgt  37260
cctcttcgca gacgccggca ccgaggccgc cgcgctgctc gaccagacag gatgggcgca  37320
gcccgccctg ttcgctctcg aggtcgcgct ctaccgacag tgggaggcct ggggtctgcg  37380
ccccgagctg ctgctcggcc acagcatcgg cgagctcgcc gccgcccacg tcgccggcgt  37440
gctcgacctc cccgacgcct ccgccctggt cgccgcccgc ggacggctca tgcaggccct  37500
cccccacggc ggcgccatgg cctccatcga ggccaccgag cacgagctcc tacccctgct  37560
cgaccagcac acggggcgcc tctcgctcgc cgccctcaac gctccacgcc agtcggtcgt  37620
cagcggcgac cagcccgccg tcgaccatgt ctgcgctcac ttcatcgccc tcggccgacg  37680
cgccaagcgg ctcgacgtca gccacgcctt ccactcggcg cacatgcaac ccatgctcga  37740
cgccttcgcc agcgtcgccc gcggcctgac cttccacccg ccacggctgc ccatcgtcag  37800
```

-continued

```
cagcgtcacc ggcgcacgcg ccaccaccga ccagctcacc tcgcccgact actgggtgca   37860
gcaggtgcgc gagcccgtgc gcttcctcga cgccatgcgc tccctgcacg ccgccggcgc   37920
cgccaccttc gtcgagtgcg ggccgcacgg cgtgctcacc gccgcaggcg ccgagtgcct   37980
cgctcccgag ggcgctcgcg acgccggctt cgtcaccagc ctccgcaagg accgcgacga   38040
ggccctcgcc ctggtccacg ccgcctgcgc cgtccatgtc cgcgggcacg ccctcgactg   38100
gctccgcttc ttcgacgcca ccggcgctcg ccgcgtcgag ctgcccacct acgccttcca   38160
gcgacagcgc tactggctcg aggcgccaag gcctcgcccc agcctcgagg gtgtcggcct   38220
caccgccgca aaccacccat ggctcggcgc cgccgtgcgc ctcgcagacc gcgatggcta   38280
cgtcctcagc ggccgcctct ccaccatcga ccacccgtgg gtcctcgacc acgtggtggc   38340
aggcacagtg atcttgccag gaacggcgtt cgtcgagctg gcgtgggcgg cggccgaggt   38400
ggtgggcgcc gccgcggtgt ccgaggtgac cttcacgacg ccgctcgtgc tgccgccgcg   38460
cagcgtggtg gagctgcagg tgaggatcgg cgagccggac gcgtccgggc ggcggacgtt   38520
cgccgcgtac agccgcgcgg acgcggcgat cgaggcggag tggacgcaac acgcgaccgg   38580
cgtgctgagc gcgcaggcgg cggccggggc cgacgtggcg gacctttcgg tgtggccacc   38640
gccgggcgcc gaggtggtgg cgctcgacgg cggctacgcc tggctggcgg cgcagggcta   38700
cggctacggc ccggcgttcc aggcgctgcg cgaggtgtgg cgcgcgggca cgacgctgta   38760
cgcgcgggtc gcgctgccgg acgcggtggc ggacacggcg cggggcttcg ggatccatcc   38820
ggcgctgctc gacgcggtgc tgcactcgtt gctggcgccg tcggcgcagg aggaggcgtc   38880
cgacgacgac aaggtgctgc tggcgttcgc gttctcggac gtggtgatcg aggcgcgcgg   38940
ggcagcggag gtgcgcgtcc gcctgaacaa gcaggccgga gacgacgggg agggggtcac   39000
ggcgtcgatt cacctcgccg acgcgcaggg gcggccggtc gcgcgcgtgg gggcgttcca   39060
ggcgcgggcg acgaccacgg agcgggtgcg cgcgctcgcg ggcgcgagcg agcgcgacct   39120
gcaccgggtc acgtggacgg acgtgacgct ggaagagacg ccgtgggcgc acgaggacag   39180
cgtcgtggtc ggcggcgacg gcgcgctggc ggcggcgctg ggcgtgcgcg cggtggccgg   39240
gctgcccgag ctgctcgcgg gcggcgcggc ggcgccgcgt cgtctggtga tcgacgcgac   39300
cgcgggcgac cccggcgacg gcctggtcgc ggcgacgcac gcggcgacgc agcggggcct   39360
cgcgctcttg cagggatggc tctcggaggc gcggctcgcg gcgacggagc tggtgctcgt   39420
gacgcgcggc gcggcggcgg ccgagccgga cgagggtgtg gcggcgctga gccacgcgcc   39480
gctctggggg ctcgtgcgcg cggcgcgcga agagcacccg gcgcgcgcgc tgcgccttgt   39540
cgacctgggg cgcgaggcgc cggacggggc gatcctgcgc cgggcgatcg cggcggacga   39600
cgagccggag ctcgtggtcc gccgcggggc gctgcgggcc gcgcgcctga gcctcgccca   39660
cgctggcccg gacaccgcgg ggcaagcgac gcggctggcc cccggcggga cggtgctgat   39720
cacgggcggc acgggagagc tcggacggca ggtcgcgcgg cacctggtgg cggcgcacgg   39780
cgttcgccac ctggtgctga cgtcacggcg cggaatggac gcgcccgacg ccgcggcgct   39840
ggtggagtcg ctgcgcgcgg cgggcgccgc gacggtggag atcgcggcgt gcgacgtggc   39900
ggacgggcat gcgctggcgg cggtgctccg gaccatcccg gcggagcatc cgctgaccgc   39960
ggtcgtgcac acggcgggcg tgctcgaaga cggcgtcgtg accgggctct cggccgagca   40020
gctcgcgcgc gtgctgcggc cgaaggtcga cggcgcctgg cagctctacg aggcgacgaa   40080
ggacgcgccg ctcgcggcgt tcatgctctt ctcgtcggcg gcgggcacgc tgggcagcgc   40140
ggggcaggcg aactacgccg ctgcgaacgc gttcctcgat gcgctggcgg cagagctccg   40200
```

-continued

```
cgcgcgcggc gtgccggcga tgagcctggc ctggggcttc tgggagcaag gcgggatcgg  40260
catgacggcg cacctcggcg ccgccgacat ggcgcgggtc aagcggcagg gcatcgtacc  40320
gatgacggtc gcgcacggcc tgcggctgct cgaccgcgcg ctggagcggc ccgaggcgac  40380
gctggtgccc ctatcgctcg acgtggcggc gcttcagcgc gcggcgagcg acgccggacg  40440
ggtgccggcg ctgctgcgtg gcctggtgcg cccggcggcc gcccggcgca cggcggcgcc  40500
ggcggccgcg gcgacagggc tccgcgcgcg gctcttgccg ttgtccgagg ccgagcgcca  40560
ggacgtcttg ctcgatctgg tgcgcacgga gatcgcggat atcctcgcgc tgtccgggcc  40620
agcggcggtg cctcccgatc aacccatcag ggagctgggg ctcgattcgc tcacggcggt  40680
ggacgttcgg agccggcttg tgcagaggag cgagatcgac ctcgccgtga ccctcgcgta  40740
cgattacccg accgcgcgag cgatcgcggg acatctgagc gagcagatgg gactcgaagg  40800
agcgccggaa gatcgtgagt cggcgctcga cgagagccag atccgcgccc tgctcatgca  40860
gattcctatc cccacgttgc gccagtcggg gctgctcgga gacctggttc gcctggcctc  40920
cccgcaagcg cccccgcgcg aagaaggtga gagcgagacg ttgagcttcg atcaccttgg  40980
aaatgaagag ttcctcagcc tcgcgtcgaa gctcattgca gaggagggat catgaaccaa  41040
gagactgttc ttcggcagac actcgagaag agtctccaca agatccagca cctcaatcgg  41100
gagctcgagc gtctcaaggc gaagtcgagc gagccgatcg cgatcgtgtc gatggcgtgc  41160
cgctacccgg gcggcgtcga cggtcccgca cggctgtggg agctgctctc ggaggggcgg  41220
gacgcgatcg ggccgttccc cgaggggcgc ggctgggacg tggcggggct gtacgacccc  41280
gacccggacg cgccgggcaa gtcggtcacc acgcagggcg gcttcctcta cgacgccgac  41340
cgcttcgatc cgacgttctt cggcatcagc ccgcgcgagg ccgagcggat ggacccgcag  41400
cagcggctgc tgctcgagtg cgcctgggag gcgctcgagc gcgcgggcgt cgcgccccac  41460
acgctcgagg cgagcgccac cggcgtcttc gtcgggctgg tgtacagcga ctacggcggg  41520
cggctgctgg agcacctcga ggtcttcgac ggctacgtcg ccaccggcag ctttcccagc  41580
gtcggctcgg ggcgcatcgc ctatacgctg gggctccgcg gccctgcggt gaccgtcgac  41640
acggcgtgct cgtcgtcgct cgtgtcgctc cacctcgcgt gcatgtcgct ccgcgcgggc  41700
gagtgcgaca tggcgctcgc cggcggcgcc accgtgatgg ccacgccgat ggccttcatc  41760
gagttcagcc gccagcgcgg catggccccg gacgcacggt gcaaggcctt cggggcggcg  41820
gcgaacggca tcggccccgc ggagggctgc gggatcctgg tgctcaagcg gctgtcggac  41880
gcgcggcgcg acggcgaccg cgtcctggca gtgatccgcg gctccgccgt caaccaggac  41940
ggccgcagcc aggggctcac cgcccccaac ggcccggccc agcaggacgt catccgccag  42000
gccctggccg cggcggggct cacgcccgcc gacgtcgacg ccgtcgaggc gcacggcacc  42060
ggcacgcccc tcggcgatcc catcgaggcg caggcgctgc tggcgaccta cggcaagacg  42120
cacacagcgg agcggccgct ctggctcggc tcgatcaagt ccaacttcgg gcacacgcag  42180
gccgccgcag gggtggcggg catcatcaag ctggtgctgg cgatgcagca cgcggagctg  42240
ccgaggacgc tgtatgcgga gccccgatcg ccgcacgtcg actggtcgca ggggcacgtc  42300
aagctcctca acgagcccgt gccgtggccg cgcaccgaca ggccgcggcg cgcggcggtc  42360
tcgtccttcg gcgtcagcgg caccaacgcg cacgtcatcc tcgaggaggc gccggccgaa  42420
gcgcccgcgg ccgcgcaaac agcggcgggg gtgccgtcga cgctgccgct gctcctgtcg  42480
ggtcgcgacg agccggcgct gcgcgcccag gccgggcggc tcgccgagca cctgcgcgcc  42540
```

-continued

```
cacccggacg agcggctgct cgacatcgcc gcgggcctgg ccacgacgcg cacgcacctc  42600
gccacgcggc tcgcgctgcc ggtcgccgcg gacgcagccg cggaggagct gagcgcccgc  42660
cttgcgcagt tcgccgccgg cggcccggcg cccagcggcg ccgccgtgac cgcgccgggg  42720
cagccgcccg gcaaggtcgc ggtgctcttc accggccagg gcagccagcg cgccgccatg  42780
gggcgcgccc tgtacgccac ccaccccgtc ttccgcgccg cgctcgacgc cgcatgcgcc  42840
gagctcgacc gccacctcga caggcccctc cacagcgtcc tcttcgcaga cgccggcacc  42900
gaggccgccg cgctgctcga ccagacaggc tgggcacagc ccgccctgtt cgctctcgag  42960
gtcgcgctct accgacagtg ggaggcctgg ggcctgcgcg cccacgcgct gctcggccac  43020
agcctcggcg agatcgtcgc cgcccacatc gccggcgtgc tcgacctccc cgacgcctcc  43080
gccctggtcg ccgcccgcgg acggctcatg caggccctcc cccacggcgg cgccatggcc  43140
tccatcgagg ccaccgagca cgagctccta cccctgctcg accagcacac cggacgcctc  43200
tcgctcgccg ccctcaacgc tccacgccag tcggtcgtca gcggcgacca gcccgccgtc  43260
gaccatgtct gcgctcactt caaggccctc ggccggcgcg ccaagcggct cgacgtcagc  43320
cacgccttcc actcggcccg catggaaccc atgctcgacg ccttcgcccg cgtcgcccgc  43380
ggcctgacct accgcgcccc gcgcctgccc gtcgtgagca atgtcaccgg ccgcatggcc  43440
accgccgacg agctcacctc gcccgactac tgggtgcgcc acgtgcgcga gcccgtgcgc  43500
ttcgtcgccg gcgtgcgcgc gctgcacgcc accggcgtcg ccacctacct cgagtgcggg  43560
cccgatccgg tgctcggcgg catggccgca gactgcctca cctccgacga gagccgcgac  43620
ccaggcctga tccccagcct ccgcaaggac cgcgacgagg ccctcgccat cgcccaggcc  43680
gcctgcgccc tgcacgtccg cggacacgcc ctcgactggc cccgcctctt cgacgccacc  43740
ggcgctcgcc gcgtcgagct gccaacctac gccttccagc ggcagcgcta ctggatcgat  43800
gcgccgcggc gcgcggcggg gctcgaaagc gtcggcctca cggccgcaga ccacccctgg  43860
ctgggcgcgg cggtgcggct cgccgaccgg gacgtctacg tgctgagcgg gcggctgtcg  43920
acggtcgacc acccgtggat cctggaccac gtggtgacgg gcacggcgct gatgccagga  43980
acggggttcg tcgagctggc gtgggcgacg gcccaggcgg tgaacgccgc cgcgatcgcg  44040
gagctcaccc tgacgactcc actcgtgttg ccggcgcgcg gcgcggtgca gctccaggtg  44100
acggtcgacg aggccgacgc ggatggccgg cgggcattcg cgatccacag ccggccgcat  44160
gggcccgtcg acctcgagtg gacgcaacac gcgaccggcg tgctgagcgc ggaggcgccg  44220
gcgggagccg acgaggcggc ggggctctcg gagtggccgc cgccgggcgc ggaggcggtg  44280
gcgctcgacg gcgggtatga gcagctgtcc gagcacggct acggccatgg cccggcgttc  44340
caggggctcc gcgggctctg gcgcgcggac cagacgctgt acgcgcacgt cgcgctgccg  44400
gacgctgtcg cgggcacgga gcagggcttc gggctccatc cggcgctctt cgatgcggcg  44460
ctgcagtcgc tggcgcggct gtcgcgcgag gaggcggccg ctggcgaccc ggtgctggtg  44520
ccgttcgcgt ggacggacgt ggcgctgtac gcggccggcg cgaccgagct gcgggcgcgc  44580
atcgcgctgg agcaggcgga gggcggcgcg ccggcggtgg cgtcgctgct gctggccgac  44640
gcgcacggac gaaccgtggc gacgacaggg cgggtgcgcg gggcgagcgc ggcgcagacg  44700
cggtccgccg cgagccgtgc ggagccgatg tacagggtcg cgtggacgga cgtggcgctg  44760
gaggcggcgg cgtgggcgcc cgaagagcac gtcgtgctcg gcggtgacgg tgcgctggcg  44820
tcggcgctgg gcgtgcgcgc ggcggccggg ctgccggagc tgctcgaggc gctggcggac  44880
ggcgcggccg cgccgcggcg gcttgtcgtg gacctgacgg cgggcgacgc gggcgctgtc  44940
```

-continued

```
gtcgcggccg tgcacgccgc ggcgcgcggc gcgctggccc tggtgcaggg atggctcgcc  45000
gcgccgcagc tgacggcgac ggagctcctc gtggtgacgc gctgcgccgt ggcgacaggg  45060
ccggacgagg gcgttgacgc gctggggccg gcggccgtct gggggctgct gcgggccacg  45120
cgcgccgagc accccgaccg cgcggtccgg gtgctggacc tggggcgcga gccgctggac  45180
ggggcgctcc tgcgcagggc gctggccgcg gtggcggagc cggagctgtc gttgcgccgc  45240
ggcgaggcgc gcgcgcctcg cctgcgcgag gcaaagcccg ccgcggcgcc ggcgacacgg  45300
ctggaccctg aagggacggt gctggtcacg ggcggcaccg gggagctggg gcggcaggtc  45360
gcccggcacc tggtggcggc gcacggcgtg cggcacctcg tgctgacgtc gcggcgcggg  45420
atggacgcgc ccgacgccgc ggcgctggta gaagagctgc gcgcggcggg cgcggcgacg  45480
gtcgacgtcg ccgcgtgcga cgtcgccgct ggcccggccc tggcggcggt cgtggaggcg  45540
atcccggcgg cgcatcccct gaccgcggtc gtgcacatgg cgggcgtgct ggacgacggc  45600
atcgtgacga agctctcggc cgagcagctc acgcgcgtgc tgcggccgaa ggtcgacggc  45660
gccattcatc tccacgagct cacgaagcac gcgccgctcg cggccttcgt gatgttctcg  45720
tccgcggcgg gcacgctggg cagcccgggg caggcgaact acacggcggc caacgtgttc  45780
ctggacgcgc tggcggcgcg actgcgcgcg cgcggcgtgc ccgcgatgag cctggcgtgg  45840
ggcttctggg agcaaggcgg gatcggcatg acggcgcacc tcggcgccgc cgatcgggcg  45900
cggatgaagc gacacggcgt cgtggcgatg tcggtcgcgc agggcctgcg gctgctcgat  45960
cgcgcgctcg cgcaccccga ggcggcgctg gtgccgctcg cgctcgacct ctcgtcgctg  46020
cacgcggggg ccagcggcgc cggaccggtg ccgccgctgc tgcgcgggct ggtacgcgcg  46080
cccgccggcc ggcgcacggc ggcgtccgcg gcccggacga acgggaaggg cacggcattg  46140
gcggcgctcc gcgcgcggct cttgccgttg ccgcaggccg agcgcgagga cctcttgctc  46200
gagctcgtgt gcaccgaggt cgcggaggtg ctgcagttgc cggggccggc gcacgtcccg  46260
gcggatcagc cgctccgcga cctggggctc gactcgctca tgaccgtgga gctgcgcaac  46320
cgtctcggcg cgcgcgccga gacgacgctg cccaccacgc tcgcgttcga ctacccgacg  46380
cccagggccc ttgcgtccta tctggagacg ttgctcggca tctccgacga gaacgggcat  46440
tcgggtgagt tgctgcacgt tccgcagaac gaggacgaga tccgctccgc gatagcgcgc  46500
atcccgatag cgaccctgcg cgaggcgggg ctcctccaga gcttgctgcg gctcgccccc  46560
ggcaaggcgg tggccggtga cgtcacgcac ccggtcgatg agctgctggt cgagcacatc  46620
gaggatgaag agctgcttcg actcgctttc gaggccaccg gaggtatcaa gtgaaagacg  46680
aggctctctc gtttcgccga gccctggaga agacggtcgt cgagatccgc cgtctcaatc  46740
gggagatcga cgacctgcgg gcgaagtcga gcgagcccat cgcgatcgtg tcgatggcgt  46800
gccggttccc cggcggcgtc gagaaccccg aggcattgtg gcggctggtc tccgaggggc  46860
aggacgcgat cgggccgttc cccgaggggc gcggctggga cgtggcgggg ctgtacgacc  46920
ccgacccgga tgtgccgggc aagtcgatca ccgcgcgggg cggcttcctc tacgacgccg  46980
atcgcttcga tccggagttc ttcggcatca gcccgcgcga ggccgagcgc atcgatccgc  47040
agcagcggct gctgctcgag tgcgcctggg aggcgctcga gcgcgcgggc gtcgcgcccc  47100
acacgaagga ggcgagcgcc accggcgtct tcgtcgggct gatgtacacg gactacggcc  47160
tgcggctgct gaaccacccc gaggccctcg acggctacat cggcatcggc agcacgggga  47220
gcacgggctc ggggcgcatc gcctacacgc tgggcctgca gggacctgcg atcacggtgg  47280
```

-continued

```
acacggcgtg ctcgtcatcg ctcgtggcgc tccacatggc ctgcgcgtcc ctgcgcgggg  47340
gagagtgcaa cctggcgctt gtcggaggcg tcgccgtgat gacgacgccg acaacgttca  47400
tcgagttcag ccggcagcgg ggcctctcgc tcgacggccg gtgcaagtca ttcggtgccg  47460
aggccgaggg cgtcggctgg ggcgaaggct gcggaatcct ggcgctgaag cggctgtcgg  47520
acgcgcggcg cgacggcgac cgcgtgctcg cgatcatccg cggctccgcc gtcaaccagg  47580
acggccgcag ccaggggttc accgccccca acggcccgag ccagagggcg gtcatccagc  47640
gggcgctggc ggcggcgggg ctgaccgcgg cggacgtcga cgccgtcgag gggcacggca  47700
ccggcacgcg cctcggcgac cccatcgagg cgcaggcgct gctggcgacc tacggcaagg  47760
cgcacacagc ggagcggccg ctctggctcg gctcgatcaa gtccaacttc gggcacacgc  47820
aggccgccgc aggggtggcg ggcatcatca agctggtgct ggcgatgcag cacgcggagc  47880
tcccgaggac gctgcacgcc gacacgccct cgccgcacgt cgactggtcg caggggcacg  47940
tcaagctcct caacgagccc gtgccgtggc cgcgcaccga caggccgcgg cgcgcggcgg  48000
tctcgtcctt cggcatcagc ggcaccaacg cgcacgtcat cctcgaggag gcgccggccg  48060
aagcgcccgc ggccgcgcaa acaccagcgg cggcgggggt gccgtcaacg ctgccgctgc  48120
tcctgtcggg tcgcgacgag ccggcgctgc gcgcccaggc cgggcggctc gccgagcacc  48180
tgcgcgccca cccgggcgag cggctgctcg acatcgccgc gggcctggcc acgacgcgca  48240
cgcacctcgc cacgcggctc gcgctgccgg tcgccgcgga cgcagccgcg gaggagctga  48300
gcgcccgcct tgcgcagttc gccgccggcg gcccggcgcc cagcggcgcc gccgtgaccg  48360
cgccggggca gccgcccggc aaggtcgcgg tgctcttcac cggccagggc agccagcgcg  48420
ccgccatggg gcgcgccctg tacgccaccc accccgtctt ccgcgccgcg ctcgacgccg  48480
catgcgccga gctcgaccgc cacctcgaca ggcccctcca cagcgtcctc ttcgcagacg  48540
ccggcaccga ggccgccgcg ctgctcgacc agacaggctg ggcacagccc gccctgttcg  48600
ctctcgaggt cgcgctctac cgacagtggg aggcctgggg cctgcgcgcc cacgcgctgc  48660
tcggccacag cctcggcgag atcgtcgccg cccacatcgc cggcgtgttc gacctccccg  48720
acgcctccgc cctggtcgcc gcccgcggac ggctcatgca ggccctcccc cacggcggcg  48780
ccatggcctc catcgaggcc accgagcacg agctcctacc cctgctcgac cagcacaccg  48840
gacgcctctc gctcgccgcc ctcaacgctc cacgccagtc ggtcgtcagc ggcgaccagc  48900
ccgccgtcga ccaggtctgc gcccacttca aggccctcgg ccggcgcgcc aagcggctcg  48960
acgtcagcca cgccttccac tcggcccgca tggaacccat gctcgacgcc ttcgcccgcg  49020
tcgcccgcgg cctgacctac cgcgccccgc gcctgcccgt cgtgagcaat gtcaccggcc  49080
gcatggccac cgccgacgag ctcacctcgc ccgactactg ggtgcgccac gtgcgcgagc  49140
ccgtgcgctt cgtcgccggc gtgcgcgcgc tgcacgccac cggcgtcgcc acctacctcg  49200
agtgcgggcc cgatccggtg ctcggcggca tggccgcaga ctgcctcacc tccgacgaga  49260
gccgcgaccc aggcctgatc cccagcctcc gcaaggaccg cgacgaggcc ctcgccatcg  49320
cccaggccgc ctgcgccctg cacgtccgcg gacacgccct cgactggccc cgcctcttcg  49380
acgccaccgg cgctcgccgc gtcgagctgc caacctacgc cttccagcgg cagcgctact  49440
ggctcgagac gccccagacg ccgggcgccg acggggcctc caacctatct tcgcccgccg  49500
aaagccgctt ctgggaggct gtcgagagag cggacatcat ccccctcgcc gaggcgctgc  49560
gcctcgagga tgaggcgcaa cgcgcttcgc tggcgaccct gctgcccgcg ctctcgacct  49620
ggcgccgccg acgccacgag cagagcaccg ccgacgcctg gcgttaccgc gttgcctgga  49680
```

-continued

```
aaccccttgc catcgacgcc cggagcgatc tctcgggggt ctggctgttc ctcgcgcctc  49740
cggatcacgc gaaggacgac ctcgcgcgcg cggtccttcg cgcgctcgcc gagagcggcg  49800
cgacggtcgt ccctgtgctg gtggccgagg gcgacgtcga ccgcgccctc ctgagcgcgc  49860
ggctgcgcga gcaggtcggc gacggcggcg cgatccgcgg cgtgatctcg ctcctcgccc  49920
tggacgagac ctcgctgccg cagcacgacg ggctgccccg gggcctcgcc ttcacgctcg  49980
cgctcgtcca ggccctggga gacacggcga tcgcagcgcc tctatggctg ctcacccgtg  50040
gcgccgtctc cgtgggtcgt tccgaccgcc tcgagcgccc gctgcaggcg ctgacgtggg  50100
gcctcgggcg cgtggtggcg ctggagcacc ccgagcgctg ggtggactc atcgatctcg  50160
ccggcgcgct cgacgaaaag gcgctcaagc ggctcgtcgc cgccctcggt ggtcgcgacg  50220
ccgaggatca gctcgccctg cgcccctccg gactcttcgc gcgacggctg gtcagagcgc  50280
ccctgggtga agcgaccgcg gttcgcgcct ggaaggcgcg cggcaccgcg ctcgtcaccg  50340
gcggcacggg ggacctgggc gcccacgtcg cccggtggct cgcccagaat ggcgccgagc  50400
acctcgtcct caccagccgc cgcggacagg acgcccccgg agcggccgag ctcacggccg  50460
agctcacggc gctcggcgcc cgcgtcacca tcgccgcctg cgactcgtcc gaccgacagg  50520
cgctcgcggc cctgctccag cgcctgaggg ccgaaggccc cccctccgc gccgtcgtcc  50580
acgctgcggg tgtcgaccag gtcaccccgc tggccaggac cagcctggcc gagttcgcag  50640
gcatcgcctc cggcaaggtc gcaggtgctc ggcacctcga cgacttgctc ggcaatgccc  50700
ccctcgacgc cttcatcctc ttctcctcgg tcgcaggcgt ctgggggagc ggctttcagg  50760
gcgcttacgc ggcggccaac gccttcctgg acgcgctggc cgagcagcgc cgcgccctgg  50820
gctcgacggc cacgtcgatc gcctggggcc tctggggcgg caaaagcatg gccgacgacg  50880
ccgccaaaga tcatctcagc aagcgcggcg tgtccccgat gccgccccag ctcgcgatcg  50940
cggccctgca gcgggcgctc gaccacgacg agaccacact caccctcgcc gacgtcaact  51000
ggtcacgctt tgccccggcc tttgccgccg cccgcccgcg cccgttgctg cacgatctcc  51060
cggaagcccg gagcgctctc gagtccccct cgccggcgcc ccgcgaggcc gagctgctca  51120
cccggctcca gggcctctcc agcaccgagc gcgtccgcca cctcgtctcc ctcgtgctgg  51180
cggagaccgc cgtcgtcctc ggccatcctg acgcctcccg cctcgaccct cacacaggct  51240
tcgcggatct cggcctcgac tcgctgatgg ccgtcgagat gcgccggcgg ctccagcagg  51300
caacgggggt gagcctgccg gcgaccctga ccttcgacca cccctcgccc caccacatcg  51360
cgaccttcct cctcgacgag gtcttcgcgc cggccctcgg ccaggccccc ggcgccgagg  51420
aagacgaagc gatcgcccag gccgggctcg cctcgggcga cgagcccgtc gccctcatcg  51480
gcgtggggct gcgtctcccc ggcggagcca ccgacctcga cgggctctgg cgccttctgg  51540
agcaggggat cgacgttgtc ggccccgtcc ctgaagaccg cggctggagc atggacgagc  51600
tctacgatcc cgaccccgac tccctcggca agagctacgt gcgcgaagcg gctttcctcg  51660
atcgcatcga cctcttcgac gcgggcttct tcggcatcag cccccgcgag gcgagccacg  51720
tggacccgca gcaccgcctc ctgctcgagg ccgcgtggca ggccctcgag cacgcaggca  51780
tcgtcccggc ctcgctccag gactcccaga ccggcgtctt cgtgggctca ggcccgagcg  51840
actacgcctt gctccacaac ccggcccagg aggatgaagc ctacaggctt acggggacgc  51900
agccctcgtt cgcgccaggc cggctctcgt tcagcctggg attgcaggga ccggcgctct  51960
ccgtggacac cgcctgctcc tcctcgctcg tcgcgctcca cctcgccgcc caggccctgc  52020
```

-continued

```
gccgcggcga gtgcgggctc gccctcgtcg gcagcgcgca ggtgatggct gctcccgacg  52080
ccttcgtgac gctctcccgc gctcgcgcca tcgctcccga cggccgctcg aagaccttct  52140
ccgcccaggc cgatggctac ggccgcggcg agggggtcat cgtcttcgtc ctcgagcgcc  52200
tgagcgacgc ccgcgcgaga gggcgcgacg tcctcgcggt cctccgcggc agcgccgtca  52260
accacgacgg cgccagcagc ggcatcaccg cgccgaacgg cacctcccag cagaaggtgc  52320
ttcgtgccgc gctccacgat gcgcggctca cgccagcgga cgtcgacgtg gtggagtgcc  52380
acggcacggg cacttccctc ggcgacccca tcgaggtgca agccctggcc gccgtctacg  52440
gaaaggagcg ctccgccgat cggccgctga tgctcggcgc gctcaagacc aacgtcggcc  52500
acctcgaggc cgcgtccggt ctcgccggcg tcgcgaaggt cgtcgcggcg ttgcgccacg  52560
aggcgctgcc ggcgacgctg cacaccgccg cgcgcaaccc tcatatccag tgggatacgc  52620
tgcccgtcca ggtcgtcgac accttgcgtc cctggccgcg gcgcgaggac ggcacccccc  52680
gccgcgccgg cgtgtcggcg ttcgggctct ccggcaccaa cgcccacgtc ctcctcgagg  52740
aagctccgcc tgtccagccg agcacacagg cggagcagcc tgccgcgccg ccgtggttgc  52800
cgctgctcct gtcgggcaag acggacgcgg ccctgcgagc gcaggccgag cggctgcggg  52860
cgcacctcga cgcccatgcc gacctcgggc ttgccgacgt cgcctattcc ctcgccacga  52920
cgcggacgca tttcgcgcat cgggcggtgg tcgtcgcgga cgctggcgcg accctcttcg  52980
aagggctgga cgccatcgcg cgcggcaacg ccgcttccca cgtggtggtc gacgaggcca  53040
agatcgacgg caagaccgtc ttcgtcttcc cgggacaggg ctcgcagtgg gcccagatgg  53100
cgcagccgct gctcgagacc tccgagctct ttcgcgagcg tatcgaggcg tgcgcgcacg  53160
ccctcgcgcc tcacgtcgac tggtcgctgc tcgccgtcct ccgcggcgaa gaaggcgccc  53220
cctcactgga gcgggtcgac gtggtgcagc cggtgctctt cgccgtgatg gtctcgctcg  53280
ctgccctctg gcgctcgatg ggcgtcgagc cggacgccgt cgtcggccat agccagggcg  53340
agatcgccgc cgcctgcgtg gcgggcgcgc tgtcgctcgc ggacgccgcc aaggtggtgg  53400
cgctgcgcag ccgcgcgctc gcgcggctcg ccggccgggg cgccatggcc gtcgtggagc  53460
tccccgccgc cgagctcgcc gagcgcatga agcgctgggg cgagcggctg tccatcgcag  53520
cgctcaacag ccctcgttcc accgtgatct ccggcgatcc ggacgccgtc gacgcgctgc  53580
tccgggagct cgactcggcg gagatcttcg cccgcaaggt gcgcgtcgac tacgcctccc  53640
actgctccca tgtggaggcg attcgccacc agctcctggc cgagctcgcg ggcatcgagc  53700
cgctcccgtc cacgctcccg ctctactcca cggtgagcgg ggacaagctc gatggcgtcg  53760
cgctcgacgc ctcgtactgg taccggaacc tccggcagac cgtccgcttc tcggacgcca  53820
cgcagcggct cgtctccgcg ggacatcgct tcttcgtcga ggtcagcccg catccggtgc  53880
tgacgttcgc cgtgcaggat gtcctcgatg ccgagggggt gcccgccgct gtcgtcggct  53940
cgctacggcg cggcgagggc gacctgcggc ggttccttgt gtcgctgtcc gagctcttca  54000
cccgcggcct cgccctggat tggtccaggg ttctgcccag cggccggcgc gtatcgctgc  54060
ccacctacgc cttccagcgc gagcgctact ggctcggggc tcacagggct cgcggcaccg  54120
acgcgacatc cgccggcctg gcatcggacg agcccacgcg cggcgcgtcg atgccagtgc  54180
ggctctcgtt gcgggacgtg ccgcccgagg agcgccaggg agcgctggag cggttcgtcc  54240
gggagcagct cgcggccgtc ctgcgcatgg atgcggcgcg gatcgagggg cagacgacga  54300
tcaagacgct cgggatcgac tcgctcatgg cgctcgagat ccgcaaacgg ctggaagccg  54360
gactggccgt gaccttgcca tcgacgctca tctggcagtt cccgcacgcc gaagggctcg  54420
```

-continued

```
cacggcacct catgacgcgg ctccccgcgg gggacggaga aggatctgcc gtggtccagc  54480
ccgtggagca gccgcgcgcg ccgaaggagg tgcccgtatc catggatccc tcggcgtggg  54540
tgcaccgccc gcgccccagg gccgacgcgc gcgttcgact gttctgcctt ccctacgccg  54600
gcgcgggcgc ctcgcgcttc cgggcgtggc cagagctgct cccctcctgg gtggaggtct  54660
gcccgatcca gctccccggc agggaagagc gcctccacga gccggccttc gagacgatgg  54720
acgcgctcgt cgacgcgctc gttcccgccg tcgaggcgca catcgatcgg ccctttgcgc  54780
tgttcggctg cagcatgggt gccctcctgg ccttcgagct cgcccgggcg cttcaatccc  54840
gtcatcgctt ggtggcgcgg catctgttcg gcgcggcgag ctcctcacct cggcgcgtga  54900
gcccggtacg ggagcagctc tccgcggtgg tctcccctgg aacggtgcga tcggacgcga  54960
tggcctcgct gcgccagctc ggtctgctgt cgtcctcgtc cctccaggac gaagagatgc  55020
tggacgaggt gtggcccgcg ttccgtgcgg atctatccct gacgctgaag tacacgtgca  55080
gggacgcaac ccccctcgac gcccccatct cggtcttcgg gggcaccgag gaccggaccg  55140
tagggcgcga ggatctcgtc gcctggcata cgctgacgaa ggacgcgttc caggtcgcca  55200
tgctgcccgg gggtcacctg ttcatggacg cgacgccgaa gcggctcttc catcacatcg  55260
agcacgcgct ccagctctag tggaccgtcc gacaggccct tcgacatcgt cctcggcgga  55320
gggcggcgac tccgcgcgga gagcgagccg cgatcgcgcg gcgccgtcca cgatcttcct  55380
gggatttttt ttggacagtt caccagaagc tgcgggatac caaacagaag cgaccatggg  55440
aagcaacgaa gggagtatcg cttgacgatc aacgacgagg tgcggaccag cgacgccgtg  55500
tgggctggtg ccgcgggcta taccagggcg cgtcttcagg tctatgactt cttcatctac  55560
ggcttcaaca gccctgtcgc atggaagtgc ccgggcgagg agctcctcga gaactacaat  55620
cggcacgtct cgggcaatca cctcgacgtc ggcgtgggga cggggtacct gctcgaccgc  55680
tgccgcttcc ccaccgccaa gccgcgtgtg tttctgatgg atctgaaccc ggacgctctg  55740
caggtgacgg cgcagcgact gcaccgcttt cagcctcaga ccttgcggcg gaacgtcctt  55800
gatcccatcc gcttcgacgg agagcccttc gactccatcg ggatgaacta cctcatgcac  55860
tgcgtccctg gatccatccc ggagaaggcc gtgatgttcg accacctgag cgccttgctg  55920
aagccgggcg gcgtgatctt cggcagcacg gtgctctcgg agggcgtgga caaggggatc  55980
gtggcgcgag ccatcatgga ccgcttcaac aagaagggga tcttctcgaa cacccgagac  56040
gccgcctccg atctgacgcg agcgctggag gagcgcttcg acgacgtctc ggtccgcgtc  56100
gtcggctgcg tcgggctgtt ctcagccagg aagcgtacct gcgcgggaac cgagtcgccg  56160
gcgtgaggtg agcggggacg gcgctcaggg cgcggcgagc ggcagcctgc gtgccgggcg  56220
cgcggcctcg tgtccgtccc ccgcctcggc cacccgcccg cggtagatgc gatcgatccg  56280
atcgcgcgcg atgaccaggg gcttgtcgaa ccggccaagc acgttgccct tcaggatccc  56340
gcgcttgtcc gtcaagcggt ccagcaaccg catatcgagg cgcagctcga tgttcatggc  56400
cacctgcatg gcgggccaga ggacggcgcc ggccccgaac ttgctccagg gcgccaggct  56460
cgcgaagaga aacgtataca tctccgacga ctccgggccc accgggttga agaagaccgc  56520
tgaccggagc gggaaggtga cgggctgatt ggtcttcgga tccctgaggg agtggttgta  56580
gatcgtgtag accggcgaga agtaggatgt ccagtccacc acgaatatcg catcctccgg  56640
gatgccgagc agcttctcca tcgcccgcgg catgggccgc ctcggacccg aatgcacgac  56700
ccggatcgtt tcgtcggtca gggtcacccg cgcctcgacc tctggcatcc gctcgagcgg  56760
```

-continued

```
gtagccgagc atgaagtgga cgaagggcgt gtgctcgatc tcgatgaaat tgtcgagcgc  56820
cagctcgaac ggcacggtcg cgcggtggcg gaggagaccg cgcggcacat atccctcgcc  56880
ctcgaggcgc gggaacgctg cctgcgaccc cgcccgcttc acccagatgg caccgtaccg  56940
ctccacggcc tcgaacatgt cctcgcgccg cgcgcacggc cgcgccgccg gggtagccgg  57000
gatctcgccg cggccgtcca cggcccaacg ccagccatgg taggcgcaca ccagccgatc  57060
gccctcgacc cacccctcgc tcaggcgcat gctgcggtgg gggcaacgat ccgtgaatgc  57120
accgaggccg cccgacgagg tccgaaacac cacgatctca tgccccgcga gccgcacatt  57180
gcggggcttg cggcggagct cgtggctcag cagtacaggg tgccagtggt cgagctcagc  57240
catgatcagt tcaccccttg gatgtgccgc gcaatccgcg gcgcctcggc tgcgatgtcg  57300
cggatctgcc ccgtgatggg attgcggaag ccgatgaaga acagcccagg cgccggcgtc  57360
ggcgcgccgt gccaccgcgg gcagccgtgc tcgtccgtgt agcgcgttgc attctcgaga  57420
aaatcatcga gcccgggccg gtaccccgtg gcgagcacca cgacgtcgaa gggcagccca  57480
cggccgtccg tgaacgtcac gcccgtttcc gtgaatgccc gcgggccggg caccaccttg  57540
atcttgccct gctggatcag cgccaccgtg ccgatgtcga tcaacggcat gcggccttcc  57600
ttcaacgccc gggtaccggg gccgaccgcg ggccgacgga tcccccagcg cgacagatcc  57660
cccacggcgc gagacaggat cgcggtcgcg aggcgatccc cgacggccag cgggaggcgc  57720
tcgaagaggg caagggcgtt gaactgcgca ggcagcttga acagctcgcg gggggatcacg  57780
tggttgccgc tgcggaccga gagggtcgtc tccgcgcaat gctcccacag atccagcgcg  57840
atctcgctgg cggagttgcc ggcgcccacc acgagcacgc gctggccccg gaattccgca  57900
ccagatcggt aggcagagct atgaaggatg cgaccgcgga agcgctcctg gtcgggccag  57960
gtggggacgt tgggatgacg gctgtagccg gtggccacga cgagcgcctg gctcctgagc  58020
tcccccgcgt gcgttcgggt cacccaccgc gatccgtcgt ggtacgcgcg ctccacctcg  58080
acacccaggc gcggctccag gcggaatcgc tcggcgtaac gctcgaggta atcgaccatc  58140
tccacccggg agggatacgg cgcagaatac tcgggccagg gctgcccggg cagcgcggag  58200
agctgcttga tcgtgttgag gtgcagccgg tcgtagtggc gccgccacgt ggcgccgacg  58260
gcctccgact tctcgaggag aacgaacggg attccctgct cgcgcaggca tgcgcccacc  58320
gctagcccag acggaccagc gccgacgata accacatggc actcttcaac gtgcacgcat  58380
gaagtctaac caaaattcgc cccggatgcc aactccactt gtgcgggcgt cgcttccggc  58440
aactcgtatg ctggtgagcg gcttcggatc gtgatggaaa gctctgagct cgcccgcagc  58500
tccggagatc ccccgcgtct tcgcgaggag cctggcggac gcgcgcgccc cgcgagcgga  58560
cacggcgacg ctacagcgcg cggacgtcac gcactcgcat gcccgacgcc cgtgccttct  58620
gcctcgcccc gcgtctcgcc gaagtagatg gagcgcatca ggcggtggtt gtgcacgagc  58680
gtcgcgtcgt atttgttgag ccgcatccct ttcatctcga agggcgtatc ggccacgtgc  58740
gggatgaact tcacatcgtc gcggatctcc ttccaggaga gcgctatcgc cgccgatttg  58800
acgaccggaa gcagcggacg gaagcgggga tcggtgatct tgacgaacag gaacgcgcgc  58860
acgaacgtgg tgcgctccgt ctctggcacg aagaagatgc cggcgcgcgc cacgacagga  58920
cgctccatcc cgttctgcgc cgtccaccag gacgtgtaca cggtgtagac ggggctgaag  58980
cgggtcaccc actggttgtg aaatgtgtcg cctggctgga gcagcatcag ccgcgcgagc  59040
gtcgaggggc gctgcggcgc cgagtacttg acctcggtgc ggtcctcgaa gacgtcgcac  59100
gagaagtcga tgcgcgccgc gtcctcgggc gtccagccga ggcggccgtg aacgaacggc  59160
```

-continued

```
gtgtgctcgt cctcggagga attgtcgaag atgacgtgca ggggcgccgg cgcgaggtgc  59220
gagaaggtgc cggcatattc gaagccatcg ctgctgaagt cgagctcggg cagcgccgag  59280
cgcggcgtat cccggtgggc tagccacagg tatccaagct gctcgacgag ctgaaaggag  59340
cgtgtatcgc atcgggtgag cgacggttgc gaggggcagg ctccccgccc ctcggcgtcg  59400
aaatgccacc cgtgataggg gcattccagg cgcccgtccg gccggacacg cccctgcgat  59460
agcggcgcga gccggtgggg gcacgcatcg gcgagcgcgg cggggcggcc ctgctcatcg  59520
cggaagagag cgtaagcatt gcccgcaagg acaacgcgaa ccggcttccg gccgagtttc  59580
gaggccggca agacggggtg aaaatggcgg atgaggtcgc gagcaggcgc ggcgtgcatt  59640
gcgagaccat aacacatccg cgacgccggt tggaaggagc tcccgcgcgc gcgcgacgcc  59700
gatccgcttc cgaaacctcc tgcgcgatgg cgtcgagcga ccgaagtacg aggatctcct  59760
atcggtaggc gacgatgcca ccgaacggcc acttcgcgtg gtcctcgggc gccggataga  59820
cctcccattc ggagaacccg gccgcgcgga gcgacagctc ccactcttgc agcgtcaggt  59880
aaccgacatg ctggcggcga ggcggatcga gcttggcctt gctgtaggtg tgcagcatcg  59940
actgaaaaaa ttcattgggg aagaacaccc cgggccgatc gcggaacgac atggtgaacg  60000
cgagctgacc gcccggcttc agcatcgtgt ggaacgcctg gagggtggcg tgaagatcgc  60060
gcacgtcgta gagcacgtgc tcgaggacga tcagatcgac cgacgcggcc cgggcgaacg  60120
tgctgccagc ggagggcagc gtgtccaggt ccaggcgctg gaaatgaatg cgctgaaaca  60180
cgtcggccgg cgcgtgggtc cgcagccact gcttccccgt ctccatcaac agggcgctga  60240
tgtcggtgta atcgtagcgg gcgaggttct tgctcagcgg gaggaaccgc ggatcggaca  60300
acgcctgccg cagcaccacg ccgagccccg cgccccctc gaatacagag atccccggcc  60360
cctctgcgag cttggccatc agcgcccgcg ccagcatcac gttgcatggc ttcttggcgg  60420
gaaggctgat catcgagtat tcccagaatt tcagcgaggc ctgcatcccg tactggagat  60480
ccatggtggc cagcgcgtcc ttgcccgcca gcaccggccc ggccaggccc cgatagcgct  60540
ggaggaactc gaccatctcg cccaggatcg cgcggtctgc gagcgcgatg gactccttct  60600
cggcgacgcg ctttcgcacc gcctcgctgg gcaccagccg cccgctgggg tcctgggtga  60660
ggtctccctt gtcgctgaag tagtcgagca gcttcctgcg aaactgatag gcggtgaccg  60720
acggagccga ctccggacga tcgtcgagcc cccggacagc gccgctcggg tcgacgaggt  60780
gctcgagcag gatctcgctg gcaacaagct cggtctgacg acggaatgct tctatgtaag  60840
cggtgtaagc gtcgttgtag agatcggtca cgtccaatcg ttgtcgcatg caggtcctcg  60900
cgggtgtggc gcccatcctg cgcagcgcag ggacgaagca ggtcatggaa tggtccagct  60960
cgcccgggaa cgcaaggacg gaccgtccgc tgccggcggg cgccgcgcct ccgagcgcct  61020
cgcgcgccgc gcgtcacctg gagctcagcg cctgcccgtc gttcccgcgg ttcttgtgca  61080
caatggcgta caggatgagc atgtaggcga agagccggaa caggtacagg taatggatgg  61140
cgtcttcctc gacgcgattc agggcgacgg cgatgcggcc cagcatcatc agccagaacg  61200
ccgccgagaa cttcgcgaac agccggtcgc ccgtcttctt ccagaagcgg aggaagaaga  61260
gcgcgacggt cgcgtacccg aacgtcatcg aaccgatcag gaagtcgttc aaaggtccta  61320
cctcgcctct acgcgcgttt actcgcgcag gtcccagatg aggccataaa ggagcagggc  61380
cagcccgatg agcgcggtga ggtggcgcag cgatgataga tcgacgctcc ggatcacgac  61440
gaggtccacg aagagcagga tgttgttcgc tgcgagcgcg gcgaagcaga gcccgctcca  61500
```

-continued

```
caagaggaga cggaccttgc gctgcgcgta tccgcgcagg agcagcacgg cgcacgcgat  61560
gctggtcagg gcgcagagga tgtagaccgc cgctgccatg gctagccgcc ctttcccttc  61620
ttcgtgatca ggaatgcgtc cgagaagctc tggatgtcgc tcggcggggg cgtggcgtag  61680
atgtgattga tcacgctcag ccggcgctcc ttgtacgcct gcgccaggtc gtcgatcgtc  61740
cggcgggtct catcgtctgc cggggcgtac cggtagaaga tgtcctcccc gtcctcccgg  61800
gccacgatca ggcccctgct ggccaggcct ccgaaccggt cctggatcga catcatgctg  61860
gaccctatct cgcgcgccat cgcggccgcg ctccactcgc gctccgccgt gcgacgcatg  61920
agcagaagca cttcgagttg ctcgatcgag gagatgtgcg cgccgaggaa gcgctggacc  61980
cggtcgggga gcccgctaga cacgagctcc tcgccggccg agggtccctc cggtcaccgg  62040
tgcaaccata gccgcagcat agcgagcagg tgctcgggat ccaccggctt cgagatgtaa  62100
tcgttcgcgc ccgcctcgaa gcacttctcc cggtcgccct tcatcgcctt ggccgtgacc  62160
gcgatgatgg gcagcgcatg gtgctcgggc ttcgcgcgga tggcacggat cgtgtcgtag  62220
ccgtccatct ctggcatcat gatgtccatg agcacgatct cgatgtccgg cgtccgctgc  62280
agcatctcga tcgccgctct gcccgtctcc acgtagaccg tcttcatctg ctgggcgtcg  62340
aggatggtcg tcatcgcgaa gatgttccgg acgtcgtcgt cgacgaccag caccttcttg  62400
cccgcgagca ccttgttcga ctggtgcagc tcctggaggg tctgccgctg tcgctcggag  62460
agcgccgcca cagggcggtg caggaacagg gagacgtcgt cgaagagccg ctccttggag  62520
cggacgtgct tgagcaccat cagctggctg aagcggctca gctgcgcctc gtccgcggcc  62580
gagatctcct ccggcgcgta gaccaggacg ggcagctccg tcggcccgct gccctgcgcg  62640
agctgcccga tcagatcgaa gcagcgcatg tcgggcaggt cgaggtgcag gatgaggaca  62700
tcggccccct cggtgaggag cgcgtcgagc gcctcctccc cggaggccac gctccggatc  62760
gtgacgtcgt cgccgccgag gagctcgacg agctcctggc gctcggcctc gtccggctcg  62820
gcgagcacga ccgtccgccg gcgcgacacc atgaactgcg agaggcgcct gaaggtctcg  62880
tcgagcgcgt cccgggtctt gagcggcttg cagagcaccc ccgtcgcgcc catccggagc  62940
gcgcgctcgc gctcctcgtc cgtcgtgatc acctggacgg ggatgtgccg cgtcgcgagg  63000
tcgcgcttca cccggtcgag cacgcgccag ccgtccatgt ccggcaggtt gatgtcgagc  63060
gtgatcgcgt tcacccgccg ctcgcggacg atggagagcg ccgccccgcc gcggtaggcg  63120
aggatcgcct tgaacccgtg gtcgtgcgcg acatccatga cgaagtgcgc gaagctcgcg  63180
tcgttctcga cgatgagcac cacggagtcg ctgggctgga ggctcgcgct gtcgtcgacg  63240
ctctggttga gcaggtgcgg cggcggctcg gccgccgacc gcggcgcgac gtcgcccgag  63300
acgagggccg gcggcgccga gggcacctcc gcggcctgct ccttcctgcg cgggcgcgcc  63360
ggcgtgtacg tgagcggcag gtaaagcgtg aaggtgctcc cgctccccgg cctgctcgag  63420
agcttgatct cgccgccgag catccacgcg atctcgcggc tgatcgcgag cccgaggccg  63480
gtgccgccgt acttccggct cgtcgagccg tccgcctgct ggaaggcctc gaagatgatc  63540
tgctgcttgt cgtgcgggat gccgatgccc gtgtcccgca ccgacatggc gatcgccgcg  63600
ccggcgcgcg agaggccctc gttctcgatg gtccaccccg aggtgaccag atcgacgtcg  63660
agcgcgacgc tgccgcgctc cgtgaacttg aaggagttcg agagcaggtt cttgagcacc  63720
tgctgtacgc gcttcgcgtc cgtgtagatg acctgcggca ggttctgcgc gaagttgagc  63780
tcgaactcga gcctcttcga ctcggcgacg tgctggaacg tgcgctcgac gtagtcttgc  63840
aggtcgctga acgacagctc gcccacgtcg acgatcacgg tccccgactc gatcttggac  63900
```

-continued

```
aggtccagga tgtcgttgat cagcgcgagc aggtcgttgc ccgacgagtg gatcgtcttg  63960
gcgaactcga cctgccgccc cgtgaggttg cggtcggtgt tcttcgagag ctgatcggac  64020
aggatgagga ggctgttcag cggcgtccgg agctcgtgcg acatgttcgc gaggaactcc  64080
gacttgtact tggaggtgat ggcgagctgc cgcgccttct cctcgagcgc ctgccgcgcc  64140
tgctcgacct cgcggttctt ccgctcgacc tcgacgttct gctgggcgag caggcgagcc  64200
ttctccccga gctcggcgtt cgtctgctgc agctcctcct gctggctctg gagctcgcgc  64260
gcgagggact gcgactgctt gagcaggtcc tctgtgcgca tgttcgcctc gatcgtgttg  64320
agcacgatcc cgatcgactc cgtgagctgg tcgaggaacg cctggtgggt cgggctgaat  64380
cgctcgaacg acgcgagctc gatgaccgcc ttgacctgcc cctcgaagag cacggggatg  64440
acgatgatgt tgaccggcgg cgcctcgccg agcccgctcg tgatgcggat gtagtcgggg  64500
ggcgcgttga cgaggaggat cttctccttc tcgagcgcgc attgcccgac gagcccttcg  64560
ccgagcttga aatggttgtc gacgtgcttc cgcaccttgt acgcgtagct cgcgaggagc  64620
ttgaggatcg gctcctcctt cgccacgtcc atcgtgaaga acacgccctg ctgcgcgccg  64680
acgaccgggg ccagctcgga caggatgagc cgaccgacag tgagcagatc cttctgcccc  64740
tggagcatgc gcgagaactt ggcgaggttg gtcttgagcc agtcctgctc gctgttcttc  64800
agcgtcgtgt ccttgaggtt ccggatcatc tcattgatgg tgtccttgag cgccgcgacc  64860
tccccctgcg cctcgacctt gatggaccgg gtgaggtcgc ccttggtcac ggcggtggcg  64920
acctcggcga tcgcgcgcac ctgcgtggtg aggttcgcgg cgagccggtt cacgttgtcg  64980
gtcaggtcct tccacgtgcc ggccgcgccg gggacgctcg cctgaccgcc gagcttgccc  65040
tcgacgccga cctcgcgcgc caccgttgtc acctggtcgg cgaaggtcgc gagcgtctcg  65100
atcacgccgt tgatcgtgtc cgccagcgcc gcgatctcgc ccttcgcgtc gaaggccagc  65160
ttgcgcttca ggtcgccgtt cgcgaccgcg gtcacgacct tggcgatgcc gcgcacctgg  65220
ttcgtcaggt tgccggccat gaagttcacg ttgtcggtca ggtccttcca cgtgccggcg  65280
acgccgggga cgctggcctg cccgccgagc ttgccctcgg tgcccacctc gcgcgccacg  65340
cgcgtcacct ccgacgcgaa cgcgttgagc tggtccacca tcgtgtagtt gatggtgttc  65400
ttcagctcca ggatctcgcc gcggacatcg acggtgatct tcttcgacag gtcgccgttg  65460
gccacggccg ttgtgacggc ggcgatgttg cgcacctgcg cggtcaggtt cgacgccatc  65520
gagttgacgg agtcggtcag gtccttccac gtgccggcga cgccggggac gctggcctgg  65580
ccgccgagct tgccctcggt gcccacctcg cgcgccacgc gcgtcacctc cgacgcgaac  65640
gagcggagct gatccaccat cgtgttgaag gtgtccttca gctccaggat ctcgccgcgg  65700
acatcgacgg tgatcttctt cgacaggtcg ccgttggcca cggccgttgt gacggcggcg  65760
atgttgcgca cctgcgcggt caggttcgac gccatcgagt tgacggagtc ggtcaggtcc  65820
ttccacgtgc cggcgacgcc cttcacctcg gcctgcccgc cgagcttgcc ctcggtgcct  65880
acctcgcgcg cgacgcgcgt cacctcggcc gcgaaggagc tgagctgatc caccatcgtg  65940
ttgaaggtgt tcttcagctc caggatctcg cccttgacgt cgacggtgat cttcttcgac  66000
aggtcgccgc gggccacggc cgtggtcacg tcggcgatgt tgcgcacctg cgcggtcagg  66060
ttcgacgcca tcgaattgac ggagtcggtc aggtccttcc acgtgccggc gacgccgggg  66120
acgctggcct ggccgccgag ctttccctcg gtgcccacct cgcgcgccac gcgcgtcacc  66180
tccgacgcga acgagcggag ctgatccacc atcgtgttga aggtgtcctt cagctccagg  66240
```

```
atctcgccgc ggacatcgac ggtgatcttc ttcgacaggt cgccgttggc gacggccgtg  66300
gtgacggcgg cgatgttgcg cacctgcgcg gtcaggttcg acgccatcga gttgacggag  66360
tcggtcaggt ccttccacgt gccggcgacg ccggggacgc tggcctggcc gccgagcttg  66420
ccctcggtgc ccacctcgcg cgccacgcgc gtcacctccg acgcgaacga gcggagctga  66480
tccaccatcg tgttgaaggt gtccttcagc tccaggatct tcttcgacag gtcgccgttg  66540
gccacggccg ttgtgacggc ggcgatgttg cgcacctgcg cggtcaggtt cgacgccatc  66600
gagttgacgg agtcggtcag gtccttccac gtgccggcga cgcccttcac ctcggcctgc  66660
ccgccgagct tgccctcggt gcctacctcg cgcgcgacgc gcgtcacctc ggccgcgaag  66720
gagctgagct gatccaccat cgtgttgaag gtgttcttca gctccaggat ctcgcccttg  66780
acgtcgacgg tgatcttctt cgacaggtcg ccgcgggcca cggccgtggt cacgtcggcg  66840
atgttgcgca cctgcgcggt caggttcgac gccatcgaat tgacggagtc ggtcaggtcc  66900
ttccacgtgc cggcgacgcc ggggacgctg gcctggccgc cgagctttcc ctcggtgccc  66960
acctcgcgcg ccacgcgcgt cacctccgac gcgaacgagc ggagctgatc caccatcgtg  67020
ttgaaggtgt ccttcagctc caggatctcg ccgcggacat cgacggtgat cttcttcgac  67080
aggtcgccgt tggcgacggc cgtggtgacg tcggcgatgt tgcggacctg cgcggtcagg  67140
ttcgacgcca tcgagttgac ggagtcggtc aggtccttcc acgtgccggc gacgcctgtc  67200
acctcggcct gcccgccgag cttgccctcg gtgcctacct cgcgcgccac gcgcgtcacc  67260
tgggccgcga aggagcggag ctgatccacc atcgtgttga aggtgttctt cagctccagg  67320
atc                                                                67323
```

```
<210> SEQ ID NO 2
<211> LENGTH: 3228
<212> TYPE: DNA
<213> ORGANISM: Sorangium cellulosum

<400> SEQUENCE: 2

atgcccgaca cgtcgtcgtc gagccccgta atggcgatgg ggctatcgga ctcgaaagcc    60
cggtccgtgg aggatgcacg gcctgcctcg gggcttcctc gtccacccgc gggcatcgct   120
gtggtgggaa tgggatgtcg cttccccggc ggcatcgatt cgcccggatc cttgtgggcg   180
gccctatctc aagggcgcga ccttatcagc gaggtcccgc cggaccggtg ggatgtcaat   240
gcccactacg acgccgacgc aagcgtcccc gggaagattg cgacccgcca tggcggcttc   300
ctcgccgggg tcgcggcgtt cgacgcgcct ttcttcgacc tctcgccgcg cgaagcgaag   360
catatggatc cgcagcagcg cctcggcctc gagacggcgt gggaggcgct ggaggacgca   420
ggcctggacg cgaggagctt gcggggcagc cgggcagggg tgttcgtcgg ctcgatgtgg   480
gcggagtacg acgtgctcgc gtcgcgacat cccgaatcca tctcgccgca cggggccacg   540
gggagcgacc cggggatgat cgctgcgcgc atcgcctaca ccttcggcct tcgtgggccg   600
gccttgtcgg tgaatacggc gtcgtcgtcc tccctcgtgg cggtgcatct cgcattgcag   660
agcttgcaga gcggagagtg cgagctcgcg ctggccggcg gcgcgaacct catcctgacc   720
ccatacaaca cgatcaagat gacgaagctc gggacgatgt cgcccgacgg ccggtgcaag   780
gcgttcgacc accgcgccaa cggctacgtg cgcgccgagg gcgtcgggtt cgtggtcctg   840
aagccgctgt cgcgagcgac cgcggacggg gatcggatct atgcggtcgt gcgtggctcg   900
gccgtgaaca acgacgggct caccgacggg ctgaccgcgc cgagcgggga ggcgcaggag   960
gccgtgctgc gagaggcgta tgcgcgcgcc ggggtgtctc ccgccgaggt ggactacgtc  1020
```

-continued

```
gaggcgcatg ggacgggaac gccgctcggc gaccgcgtgg aggcgacggc gctgggacgg   1080

gtgctcggcg caggacgcgc ggcggatcgc gcgctgcggg tcggttcggt caagacaaac   1140

ctcggtcacg cggaggcagc cgccggggtc atcggtctga tgaagacagc gctgtcgctg   1200

cgtcacgggt cgcttccggc gagcctgcac gtcgagcgcc cgaaccccga gataccccctc   1260

gaatcgctgg gcctccggct ccagacggcg cacggcgtgt ggccggaggt cgatcggccc   1320

cggcgagcag gcgtgagctc attcggcttc ggcggcacga actgccatgt ggtgatcgag   1380

gagtggcgcg gggcctcca gcagagcgcc gccgaggcgg gcagcgaccc cggcgccgcc   1440

gtaccgccgc ctggccttcc ccttgtgctg tcggcgaggg accacggggc gctgcgggcg   1500

caggcgggcc ggtgggcggc gtggctcacg gagcaccgcg aggcgcgctg ggcggacgtc   1560

gtccacacgg cggcagtgcg gcggacgcac ctgggcgctc gggccgcggt gatggcggcg   1620

ggcgtggccg aggccgtcga tgcgctgaag gccctggccg acgggcgcgc ccacggggcc   1680

gtgacggtcg gcgaggcgcg cgagcggggc aaggtggtct tcgtgtttcc gggccagggc   1740

agccagtggc cggcgatggg gcgagcgctc ctgtccgcgt cgaaggtgtt cgccgaggcc   1800

gtcgaggcgt gcgacgcggc gctgaggccg ctgacgggct ggtcggtgct ctcgttgctg   1860

cgcggcgacg ccggggaggc agcgccgtcg ctcgaccgcg tcgacgcggt gcagccggcc   1920

ctgttcgcga tggctgtcgg cctggccgct gtctttcgcg cgtggggcct cgatccttcg   1980

gccgtggtgg gccacagcca gggcgaggtc ccggcggcgt acgtcgcggg ggcgctctcg   2040

ctcgacgacg cggcgcgggt cgtggcggtc cgaagcgcgc tcgtgcggcg gctcgcgggc   2100

gcaggggcga tggcggcggt ggagctgccg gccggcgagg tggagcgccg cctggcgccg   2160

ttcgggggggg ctctggccat tgcggtggtc aacacgtcga gctcgacggc cgtttctgga   2220

gacgccgagg cggtggacag gctggtcgcg cagctcgagg ccgaaggcat cttctgccga   2280

aaggtgaacg tcgattacgc atcccacagc gcgcacgtgg acgtcgtgct accagagctc   2340

ctggagcgcc tggcgccggt ccggccaggg gccacgagga tccccttcta ttcgacagtg   2400

accggcggtg tgctggaggg gacggcgctc gacggggcgt actggtgccg caacctgcgc   2460

cagccggtgc ggctggaccg cgcgctcgcc cggctgctgg acgacgggca tggcgtcttc   2520

gtggaggtca gtgcgcaccc ggtgctggcg tcgccgctga ccgcggcgtg cgccgagcgc   2580

gagggcgtgg ttgtcggcag cttgcagcgc gacgacggcg ggctcgcgcg gctgctcggc   2640

tcgctgggcg cgctgcatgt gcagggccag ccggtcgact ggcgcgcggt gctggcgccg   2700

ttcggcggca gcctggtgga cctgccgacc tatgcattcc agcgccagcg ttactggttc   2760

gatacggatg agagcgtcgc cctcgcagcg gcgtccagcg tcgcggaaga gtcgtggtca   2820

gaaaagctgg ccgggctgtc ttccgcgcga cgggaagaac ggctgctcga atgggtgcgc   2880

gcagagattg cagcggtgct cgggctggag gcgccggcgg tgccgccaga cgtcttgctg   2940

cgggatctcg gattgaaatc gccgatcgcc gtggagctgg ggagccggct gggacgcagg   3000

acacgccgga agctgcccgt gaccttcgtt tacaaccacc cgacgccacg agcgatcgct   3060

cgcgccctcc tggagggaat gttttcctcg atcaaggact ctgcttcgag cgccgctgac   3120

gaccgccgcc cgccggggggt gctcgaagac gttgcccccc cacaggcgct cgagacgtcc   3180

gagatgtccg acgatgagct gttccagtcc atcgatgcgc tcgtctag                 3228
```

<210> SEQ ID NO 3
<211> LENGTH: 11040
<212> TYPE: DNA

<213> ORGANISM: Sorangium cellulosum

<400> SEQUENCE: 3

```
gtggatcgaa gcgataaact gcgtgcgtat ctggagaaga ccacggcctc gctggtcgag      60
gcgaagggcc ggatccggga gctggaagcg cgttcgcgcg agccgatcgc gatcgtggcg     120
atggcgtgcc ggtttccggg cggcgtcgac agccccgaga agctctgggc cctgctggac     180
gaggagaggg acgccatcac cgaggtgccg ccctcgcgat gggacctcga gcgcttctat     240
gaccccgatc cggacgccgc gggcaagacc tacagccgct ggggcggctt cgttggcgat     300
ctggaccgtt tcgacgcggc gtttttcggg atcagccccc gcgaggcccg gagcatcgac     360
ccgcaagagc gctggctgct ggagaccacg tgggaggccc tcgagcgggc cggcgtgcgc     420
gcagacacgc tggaagggac cctgggggc  gtttacatcg gcctgtccgg ctcggagtac     480
cagacggagg cattccacga tgcggagcgc atcgacgcct attcgctgac cggcgcttcg     540
ccgagcacga ccgtggggcg cctcgcctac tggctcgggc tacgaggccc cgcggtcgcc     600
gtggacaccg cgtgcagctc ctcgctcgtc gcggtgcacc tggcctgcca ggcgctgcgg     660
aacggggagt gcgattttgc gctggcaggc ggcgtcaatg cgctcctggc ccccgagagc     720
tatgttgcct tctgccgcct cagggcgctg tcccccaccg ggcggtgcca gaccttctcc     780
gcggacgccg atggctacgt gcgcgcggaa gggtgcgggg tgctgctgct caagcgtctg     840
tcgcacgcgc agcgggatgg agaccgtgtg ctcgcggtca tccggggcaa tgccatcaac     900
caggacggcc gcagccaagg gttgacggcg ccgaacgggc tcgcgcagga ggacgtcatc     960
cgcagggcgc tgtcgcaagc cgccgtggag ccgacgaccg tcgatgtggt cgaatgccac    1020
gggaccggca cggcgctcgg cgatccgatc gaggtccagg cgctcggggc tgtttacggc    1080
gatgggcgcc ccggagacag gccgctcgtg atcggctccg tcaagacgaa catcggtcat    1140
accgaggcgg ccgcgggcat ggccggcctc atcaaggccg tcctttcgct gcagcacgcc    1200
caggtccctc gatcgctgca cttcgcggcg ccgagccctt acatcccctg ggataccctc    1260
cccgtccgcg tggccgcgca gcgcgtcgca tgggagcggc gcgagcaccc gcggcgcgcc    1320
gggatctcct cgttcgggat cagcggcacc aacgcgcacg tgatcctcga ggaggcgccg    1380
gaagcgccgg cgacggcgcc ggaggcggcg gcggtgacgt cgacgctgcc gttgcttgtg    1440
tcggggcggg atgaggcggc gctcagggcg caggcggagc ggtgggcggc gtggctcgcg    1500
gcgcacccgg aggcgcgctg ggcggacgtg gtgcacacgg ccgccgtgcg gcgcacgcac    1560
ctggaggcgc gcgcggcggt ggccgcgggg aacgccgccg acgccgccgc ggcgctgggg    1620
gcgctggccg ccgggcagcc gcacaaggcg gtgtccctgg gcgaggcgcg cgcgcgcggc    1680
gatgtcgtgt tcgtggttcc gggccagggg agccaatggc cggcgatggg gcgggcgctg    1740
ctggccgagt ccgaggtgtt tgccgccgct gtcgcggcct gcgacgcggc gctgcggccg    1800
ttcacgggct ggtcggtgct ctcggtgttg cgcggggagc agggcgaggc ggtgccgccc    1860
gccgaccgcg tggacgtggt gcagccggcg ctgttcgcga tggccgtggg gctctcggcg    1920
gtctggcggg cgtggggcat cgagccctcg gcggtggtcg gccacagcca gggcgaggtc    1980
gcggcggcgt acgtcgccgg ggcgctgacg ctcgaggacg cggcgcgggt ggtggcgctg    2040
cgcagccagc tcgtgcggcg catcgccggc ggcggcgcga tggccgtgat cgagcgcccc    2100
gtcggcgagg tggagcagcg gctttctcgg ttcggagggc agctctcggt ggcggcggtg    2160
aacacgccgg gctcgacggt ggtgtccggg gacgccgcag cggtcgatcg tttgctggcc    2220
gagctggaga ccgcgcgggt gttcgcgcgg cggatcaagg tcgattacgc gtcgcacagc    2280
```

-continued

```
gcgcacgtgg acgcgatcct gccggagctc gaggcctgcc tggcctcggt cgagccccgt   2340
acctgcgcca tcccgctgta ctcgacggtg acgggagaag tgctcgccgg cccggagctc   2400
ggcgcgacat actggtgccg caacctgcgc gagccggtgc ggctcgaccg ggcgctctcg   2460
cggctgctgg cggacgggca cggggtgttc gtggaggtca gcgcgcatcc ggtgctggcc   2520
atgccgctgt cggccgcgag cgccgagcgc ggcggcgtgg tggtgggcag cctgcagcgc   2580
gacgacggcg gtctggggcg gctgacgtcg atgcttggcg cgctgcacgt gcacggccac   2640
gccgtgagct ggcagcgggt gctggcgccg tacggcgggg cgctcgtggg cctgccgacg   2700
tacgcgttcc agcgccagcg ccactggctc gaggcgccgc ggtacgcggc ggaggatacg   2760
gacggcgcgg cgcggcgcga cccgctgtac cgggtcacgt ggatcgaggc ggcgctggaa   2820
gaagcgccgt gggcgcccga gcgccacgtc gtgctcggcg ggggcggcgc gctggcggcg   2880
gggctggggg cgctcgcgct ggcggggctg ccggagctgc tcgaggcgct ggagaacagg   2940
gcggcggcgc ccgagcggct ggtgctggac ctgacggagg gccgcccagg cgcggtggcg   3000
gagtccgtgc acgccacgac gcgcgacgcg ctcgcgctgg tccaggcatg gcttgcggcg   3060
ccgcggctct cgggcaccga gctggtcgtg gtgacgcggg aggcggtggc ggccggcccg   3120
gacgagggcg tggcggcgct gggccccgcc gctgtctggg ggctgctgcg cacggcccgc   3180
gtcgagcacc ccgagcgcgc ggtgcgcgcg gtggatctgg ggcgcgagcc gctggacgtc   3240
gcggtcttgc ggcgggcgct gggggcggtg gccgagccgg agctcgcgct gcgcgcgggc   3300
ggggcgcggg ctgcgcgcct gcgcgctgtc gacgccggcg cgggcgccag ggagccggcg   3360
gctgcgctgg acccgcaggg cacggtgtgg atcacgggcg gcaccgggga gctggggcgg   3420
cagatcgcgc ggcacctggt cgcggcgcac ggcgtgcggc acctcctgct gacgtcgcgg   3480
cggggcgcgg ccgcgccgga cgccgaggcg ctcgtcgagc agctgcgggc cgacggcgcc   3540
gagacggtcg aggtcgtggc gtgcgacgtg acggacggcg cggcgctttc ggcagcagtc   3600
caggcggctg cggcaaggca cccgctgacg gccgtggtgc acaccgccgg ggagctggcg   3660
gacggggtgc tcacggggct gacggcggag cagctcgcgc gggtgctggc gccgaaggtc   3720
gacggggcgt gccacgtgta cgccgccgcg caggaccagc cgctcgcggc cttcgtgctg   3780
ttctcctcga tcgtgggcac gctgggcaac gcgggccagg cgaactacgg ggccgccaat   3840
gcgttcctgg acgcgttcgc ggcgcagctt cgcgcgcgcg gcgtgccggc gacgagcctc   3900
gcgtggggct tctgggagca ggcagggctc ggcatgacgt cgcacctcgg cgcggccgac   3960
ctggcgcgcc tcaggcggca gggccttgcg ccgctgtcgg tcgcgcaggg cctgcgcctg   4020
ctcgaccggg cgctcgcgcg cgcggaggcg acgctggtgc cggcggcgct cgatcttccg   4080
gcgctccagc gtgcggcgag cgacgccgga cgggtgcctc cactgctgcg cgggctggtg   4140
cgcacgagtc ccggccgccc cacggcgacc gcgacccccg aggccgggcc ggcggcgtcg   4200
gcgctgcgcg cacggctctc ggcgttgccc gaggccgagc ggccgggcgc gctgctggat   4260
ctggtgcgca cggaggtggc ggtcgtgctg cagctggcag ggccggcgca ggtgcccgcg   4320
gacaagccgc tgaaggagct ggggctcgat tcgctcacgg ccgtcgagct gaggaaccgc   4380
ctcggcgcgc gcgccgagac ggtgctgccg acgaccctcg cgttcgacca tccgacgccg   4440
cgcgcgatcg cggatctgct gcttcagcgt gcgttctcgg agctcgcggc ggcgaaggcg   4500
acgcgcgcgc ggggagcgca cgacgagccg atcgcgatcg tgtcgatggc gtgccggctc   4560
ccgggcagcg tcgatacccc cgcggcgctg tggaagctcc tggcggaggg gcgggacgcg   4620
```

-continued

```
atcgggccgt tccccgaggg gcgcggctgg gacgtggcgg ggctgtacga tccggacccg   4680
gatgtgccgg gcaagtcgat caccacgcaa ggcggcttcc tctacgacgc cgaccgcttc   4740
gatccgacgt tcttcggcat cagcccgcgc gaggccgagc gcatggaccc gcagcagcgt   4800
ctgctgctcg agtgcgcctg ggaggcgctc gagcgcgcgg gcctggcgcc ccacgcgctc   4860
gaggcgagcg ccaccggcgt cttcgtcggg ctcgctcacg gtgactacgg cgggcggctc   4920
ttgcagcagc tcgagtcctt cgacggccac gtcctcaccg gcaacttcct cagcgtcggc   4980
tcggggcgca tcgcgtacac gctggggctc cgcggccctg cgatgaccgt cgacacggcg   5040
tgctcgtcgt cgctcgtggc ggtccacctc gcgtgcatgt cgctccgcgc gggcgagtgc   5100
gacatggcgc tcgccggcgg cgccaccgtg atggccacgc cgatgatctt cgtcgagttc   5160
agccgccagc gcggcacggc gctggacggt cgttgcaagg cgttcggcgc cggggccgat   5220
ggcgccggct ggtcggaggg gtgcgggatc ctggcgctga agcggctgtc ggacgcgcag   5280
cgcgacggcg accgcgtcct ggcggtgatc cgcggctccg ccgtcaacca ggacggccgc   5340
agccaggggc tcaccgcccc caacggcccg gcccagcagg acgtcatccg ccaggccctg   5400
gccgcggcgg ggctcacgcc cgccgacgtc gacgccgtcg aggcgcacgg caccggcacg   5460
cgcctcggtg accccatcga ggcgcaggcg ctgctggcga cctacggcgc cgcgcacaca   5520
gcggagcggc cgctctggct cggctcgctc aagtcgaacc tcgggcacac gcaggtcgcc   5580
gcgggcgtgt cggggctgat gaagctcgtg ctggccttgc agcacgcaga gctgccgagg   5640
acgctgcacg ccgacccgcc ctcgccgcac gtcgactggt cgcaggggca cgtcaagctc   5700
ctgaacgagc ccgtgccgtg gccgcgcacc gacaggccgc ggcgcgcggc ggtctcgtcc   5760
ttcggcatca gcggcaccaa cgcgcacgtc atcgtcgagg aggcgccggc cgaagcgccg   5820
gcgacagcgg cggacgcaaa gtcggtggag gcgcttccga tcctgccgct gctggtctcg   5880
gggtccgacg agccggcgct gcgcgcgcag gtgcggcggc tggtggagca cctgcggtcg   5940
cacccggacg agcggctgct ggacgtggca gcgagccttg cgaccacgcg cgcgcatctc   6000
gcgatgcggc tcgcgctgcc cgtctcggca ggggcgcccc gggatgcgtg ggtggatgag   6060
ctggaggcat ttgccagggg aggagcggct ccgacgcagg catcgcagac cccgccgag    6120
agcagcgcgg gcaaggtcgc ggtgctcttc accggccagg gcagccagcg cgccgccatg   6180
gggcgcgccc tgtacgccac ccaccccgtc ttccgcgccg cgctcgacgc cgcatgcgcc   6240
gagctcgacc gccacctcga caggcccctc cacagcgtcc tcttcgcaga cgccggcacc   6300
gaggccgccg cgctgctcga ccagacagga tgggcacagc ccgccctgtt cgctctcgag   6360
gtcgcgctct accgacagtg ggaggcctgg ggtctgcgcc ccgagctgct gctcggccac   6420
agcatcggcg agctcgccgc cgcccacgtc gccggcgtgc tcgacctccc cgacgcctcc   6480
gccctggtcg ccgcccgcgg acggctcatg caggccctcc cccacggcgg cgccatggcc   6540
tccatcgagg ccaccgagca cgagctccta cccctgctcg accagcacac cggacgcctc   6600
tcgctcgccg ccctcaacgc tccacgccag tcggtcgtca gcggcgacct gcacgccgtc   6660
gaccaggtct gcgcccactt catcgccctc ggccgacgcg ccaagcggct cgacgtcagc   6720
cacgccttcc actcggcgca catgcagccc atgctcgacg ccttcgccag cgtcgcccgc   6780
ggcctgacct tccacccgcc acggctgccc atcgtcagca gcgtcaccgg cgcacgcgcc   6840
accaccgacc agctcacctc gcccgactac tgggtgcagc aggtgcgcga gcccgtgcgc   6900
ttcctcgacg ccatgcgctc cctgcacgcc gccggcgccg ccaccttcgt cgagtgcggg   6960
ccgcacggcg tgctcaccgc cgcaggcgcc gagtgcctcg ctcccgaggg cgctcgcgac   7020
```

-continued

```
gccggcttcg tcaccagcct ccgcaaggac cgcgacgagg ccctcgccct ggtccacgcc   7080
gcctgcgccg tccatgtccg cgggcacgcc ctcgactggc tccgcttctt cgacgccacc   7140
ggcgctcgcc gcgtcgagct gcccacctac gccttccagc gacagcgcta ctggctcgag   7200
gcgccaaggc ctcgccccag cctcgagggc gtcggcctca ccgccgcaaa ccacccatgg   7260
ctcggcgccg ccgtgcgcct cgcagaccgc gatggctacg tcctcagcgg ccgcctctcc   7320
accatcgacc acccgtgggt cctcgaccac gtggtgctgg gcacggcgct gctcccgggc   7380
acgggcttcg tcgagctggc gtgggcggcg gcagaggcgg tcgggctgcc cggggtatcg   7440
gagctggcga tcgaggcgcc gctggcgctc ccggcgcgcg gggcggtggc gctgcagatc   7500
gcgatcgagg cgccggaccc ggcggggcgc cgcggcgtcg cgatctacag ccgccccgac   7560
ggcgcagccg acgcgccctg gacagcgcac gcgcgcggcg tgctgggcgc cgcggcgccc   7620
gacagggacg cggcgtgggc acagggcgcg tggccgccgc cgggggccgt gcctgtcgat   7680
gtgacgcagc ggatcgagat cgtggacgcg tgggtcggcc cggcgttccg gggcgtcacc   7740
gcgctgtggc gcgtcgggcg gacgatctac gccgacgttg cgctgccgga cggtgtggcg   7800
agcacggcgc aggacttcgg gctgcatccg gccttgctcg atgtggcgct acgcgcgttc   7860
ctgagagcgg agctcggcgc cgatccctcg ccacgggagg gcacggtggt gccgttcgcg   7920
tggtcggacg tggtgctcga ggcgcgtggg acggcggcgc tgcgggtgcg cgtggaggtg   7980
gcggccgatg gggacggcga cgcgatcacg gcgtcgatcc agctggccga cgggcagggc   8040
cgccccgtcg cgcgggtggg cgcgctccag atgcggtgga cgacggccga gcgggtgcgc   8100
gcggccgcgg gcgcggcgga gcgcgatctg taccgcgtcg cgtggacgga cgtggcgctg   8160
gacgacgcgg cgtttgcgcc ggaggagcac gtcgtggtcg gcggcgacgg cgcgctggcg   8220
gcggcgctcg gtgcacgcgt ggtggcgggg ctgcccgagc tgctcgcgtc gctgccggac   8280
ggcgcggcgg cgccacgccg gctggtggtg gacctcacgg cggacgccgc gggcgcggtc   8340
gtcgacgccg tgcacgccgc agcgcgcgac gcgctgtccc tggtgcaggg atggctggcg   8400
gcgccgcagc tggcggcgac ggagctcgtg gtcgtgacgc gcggcgcggt ggcggtcgcg   8460
ccggacgagg gcgtggcggc gctgggcccc gcggcggtct gggggctgct ccgcgcgacg   8520
cgcgtcgagc atgcggatcg cacggtccgc gtgctcgatc tggggtccgc ggcgccggac   8580
atgacgctct tgcgccgggc gctcacggcg gccgaggagc cagagctcgc gctgcgcgcg   8640
ggcggggcgc gggcgccgcg cctcgacgcg gccagcgaga ccgaaggaga gctggcgccg   8700
cccggcgggg cgcgctctct tcgcctgtcc atccggacga agggctcgtt cgacgcgctc   8760
cacctcgcgg acgctcccga tgcgctgcgc ccgctcgggc cggggcaggt ccggctcgct   8820
gtccgcgcca cggggctcaa cttccgcgat gtcttgaacg tcctggggac gtaccgcggc   8880
gaagcggggc ctctcggtct ggaggggggct ggggtggtgc tggacgtggg cgagggagtc   8940
accgcccttc gacccggcga ccgggtgatg ggcatgctgc acgcgggcat ggcgacccat   9000
gcggtcgtcg acgcccggct gctgacgcac atcccgcggg ggctttcctt cgtggaagcg   9060
gcgacgattc cagcggcctt cctcaccgct ctgtacgggc tgcgcgacct cggcgcgctg   9120
aaggcggggc agcgcgtgct ggtgcacgcc gccgccggcg gggtgggcat ggcggcggtc   9180
cagcttgcgc gcctctgggg agccgaggtg ttcgcgacgg cgagcgaggg caagtggccg   9240
gcgctgcgtc ggatggggat cgaccaggcc catatcgcct cgtcgcggac cctccacttc   9300
aggaaagcct tcctcgatgc aacgcaggga cagggcgtcg acgtggtgct cgacgcgctc   9360
```

gcgggcgagt tcgtcgacgc ttcgctcgac ctgctcccgc gcgggggcgc gttcgtggag 9420
atgggcaaga gcgatgtgcg ggatcccgag cgcgtcgcca aggaccaccc ccgcgttcgc 9480
tacacggcct tcgatctgct cgacgcgggg ccagaccaca tccaggcgat gctgcgggag 9540
ctcgtcccgc tgttcgagga gggcgtcctc gctccccttc cctccgtggc ctacgacctg 9600
cgtcgcgccc cgcacgcctt ccgctccatg gccaacgcac gccacatagg caagctcgtg 9660
ctggtgccgc ccgcgacgct cgaccctgac ggcacggcgt tgatcacggg cggcacggga 9720
gagctcgggc ggcagatcgc gcggcacctg gtggcggcgc acggcgtgcg ccacctggtg 9780
ctgacgtcac ggcgcggcat ggacgcgccc gacgccgcag cgctggtgga atcgctgcgc 9840
gcggcgggcg ccgcgacggt ggaggtcgcg gcgtgcgatg tgacggaccg tgacgcgctg 9900
gcggccatcg tgcaggcgat ccccgcggcg cgcccgctga ccgccgtcgt gcacacggcc 9960
gccgtgctgg acgacggcac cgtggcgggg ctctcggccg agcagctcgc gcgcgtgctg 10020
cggccgaagg tcgacggcgc ctggcagctc tacgaggcga cgagggacgc gccgctcgcg 10080
gcgttcatgc tcttctcgtc ggtcgccggc acgctgggca gctcggggca ggcgaactac 10140
gccgccgcga acgcgttcct cgacgggctg gcggcagagc tccgcgcgcg cggcgtgccg 10200
gcgatgagcc tcgcgtgggg cttctgggag cagggcggga tcgggatgac ggcgcacctc 10260
ggcgccgccg atctggcgcg gctgaagcgg cagggcatcg tgccgatgac ggtcgcgcac 10320
ggcctgcggc tgctcgaccg cgccctcgag cgcccggacg cggcgctggt gcccgcctcc 10380
ctggacatgg cggtgatcca gcggacggcg agcgaccacc gtcaggtgcc gcccatgctg 10440
cgcgggctgg tccgcgtcgc gccgcggcag gcggcagggg cagccagcgg caggagccat 10500
gaggcctcga ccctgcggca gcagctcgcc gcgctgcccg aaccggagcg gcagcgagcg 10560
ttgctcgatc tggtccggac cgaggcagcc gccgtccttg tgctgcgcgg gccggacgct 10620
gtccccgccg acaagccgct cagggagctc gggctcgact cgctcacggc agtggagctc 10680
aggaatcggc tcaggacccg tgcgcagacc gatctcccat cgaccctcgc cttcgactac 10740
ccgacgccga aagcggtcgc cgtgtatctg gcccaggagc tcgaccttca cgacgtcatg 10800
acggagatgc gcggaccgag cttgcgctct gacgacgagc tcaagtcggc catcgcgagc 10860
atccggatct cgacgctacg ccaggcgggg ctgctcgaca gcctgcttcg gctcgccgcc 10920
agcgaagccg tctccacatc cagcgacacg acacctgaaa ccgacgagct gacgctgcag 10980
catgttggag acgatgagct ggcacggctt gtcttcgacc tcgccggagg agcgcaatga 11040

<210> SEQ ID NO 4
<211> LENGTH: 10965
<212> TYPE: DNA
<213> ORGANISM: Sorangium cellulosum

<400> SEQUENCE: 4
atgaaagaag agatctccgc ccgtcaagct ctcgagaaga gcttcattga acttcgccgt 60
atcaagcggg agctcgatca gctcaaggcg aagtcgagcg agccgatcgc gatcgtgtcg 120
atggcgtgcc ggctcccggg cggcgtcgat acccccgcgg cgctgtggca gctgctctcg 180
gaggggcggg acgcgatcgg gccgttcccc gaggggcgcg agtgggacgt ggcggggctg 240
tacgacccgg acccggacgc gccgggcaag tcgatcactg cgcaaggcgg cttcctctac 300
gacgccgacc gcttcgatcc ggcgttcttc gccatcagcc cgcgcgaggc cgagcggatg 360
gacccgcagc agcggctgct gctcgagtgc gcctgggagg cgctcgagcg cgcgggcctg 420
gcgccccacg cgctcgaggc gagcgccacg ggcgtcttcg tcgggctgtc ggtcacggac 480

-continued

```
tacggcgggc ggctgctgca cgatcccgag gccctcgacg gctacatcgc caccggcacc    540
ctgcccagcg tcggctcggg gcgcatcgcc tacacgctgg ggctccgcgg ccccgcgatg    600
accgtcgaca cggcgtgctc gtcgtcgctc gtgtcgctcc acctcgcgtg catgtcgctc    660
cgcgcgggcg agtgcgacat ggcgctcgcc ggcggcgcca ccgtgatggc cacgccgatg    720
gccttcatcg agttcagccg ccagcgcggc acggcgctgg acggtcgttg caaggcgttc    780
ggcgccgggg ccgatggcgc cggctggtcg gaggggtgcg ggatcctggc gctgaagcgg    840
ctgtcggacg cgcagcgcga cggcgaccgc gtcctggcgg tgatccgcgg ctccgccgtc    900
aaccaggacg gccgcagcca ggggctcacc gcccccaacg gcccggccca gcaggacgtc    960
atccgccagg ccctggccgc ggcggggctc acgcccgccg acgtcgacgc cgtcgaggcg   1020
cacggcaccg gcacgcgcct cggcgacccc atcgaggcgc aggcgctgct ggcgacctac   1080
ggcgccgcgc acacagcgga gcggccgctc tggctcggct cgctcaagtc gaacctcggg   1140
cacacgcagg ccgccgcggg cgtgtcgggg ctgatgaagc tcgtgctggc cttgcagcac   1200
gcggagctgc cgaggacgct gcacgccgac ccgccctcgc cgcacgtcga ctggtcgcgg   1260
gggcacgtca agctcctgaa cgagcccgtg ccgtggccgc gcaccgacag gccgcggcgc   1320
gcggcggtct cgtccttcgg cttcagcggc accaacgcgc acatcatcat cgaggaggcg   1380
ccggcggcct ccgccgaggc gacgagccgc ggggagaaga cgtccgcggc cgcgccgccg   1440
tcgatgatgc cgctgctggt ctcgggggtg gacgaggcgg cgctacgagc gcaggcgggg   1500
cggtgggcgg cgtggatcga ggcgcacccg gaggcaggct gggcggacgt tgtgtacacc   1560
gcggcagcgc ggcggacgca cctgggggcc cgtgcggcgc tgacggcggc ggacgcggcc   1620
ggcgctgtcg cggcgctgac ggcgctctcg caagggcagc cgcacgccgc gctcgccgtg   1680
ggcgaggcgc gcgctcgggg gaaggtcgcc ttcgtgtttc cgggccaggg cagccagtgg   1740
ccggcgatgg ggcgggcgct gctctcgcag tcggaggtgt tcgccgcggc ggtcacggcg   1800
tgcgacgcgg cgctgcggcc gttcaccggc tggtcggtgc tctcggtgct gcgcggcgac   1860
tcgggcgcgg aggtgccgcc gctggagcgc gtcgacgtcg tgcagccggc gctgttcgcg   1920
atggcggtgg ggctcgccgc tgtgtggcgc gcgtggggcc tcgagccgtc ggcggtggtg   1980
ggccacagcc agggggaggt cccggcggcg tacgtcgcgg gggcgctgtc gctcgaggac   2040
gcggcgcgga tcgtggcgct gcgcagccag ctcgtgcggc gcctgtccgg ggctggcgcg   2100
atggccgtga tcgagcgccc ggtaggcgag gtcgagcagc ggctctcgcg gttcggcggc   2160
gcgctgtcgg tggcggcggt caacacgccg cgctcgacgg tggtgtcggg agatatcgag   2220
gcggtcgacc gcctgctggc ggagttcgag ggcgagcagg tcttcgcgcg gaaggtcaac   2280
gtcgactacg cgtcgcacag ccgacacatc gacgggctgc tgccggagct ggagaacggc   2340
ctgggcgcgg tgcggccgcg cgcgagcacg atcccgttct actcgacggt gaccgggacg   2400
gtgctgacgg gcgcggagct ggacgccgcg tactggtgtc gcaacctgcg cgagccggtg   2460
cggctcgacc gggcgctctc gtggctcctg gacgacgggc acggcctgtt cgtcgaggtc   2520
agcgcgcacc cggtgctgac gctgccgctc acaggagcga gcgcggcgag cggcggtgtg   2580
gttgtcggca gcctgcagcg cgacgacggc gggctcgggc ggctcctggg ggtgctggcc   2640
gcgctgcacg tgcacggcca cgacgtcgac tggcgcgcgg tgctggctcc gtggggcgga   2700
ggcgtggcgg acttgccgac ctacgcgttc cagcggcagc gctactggct cgaggcaccg   2760
cgcggccggg cagggctgga gagcggaggg ctcctggccg tgaatcaccc gtggctcagc   2820
```

-continued

```
gcggcggtgc ggctggccga ccgcgacggc tatgtgctga gcggacggct gtcgacggtc   2880
gagcacgcgt gggtcctgga ccacgtggtg ctgggcacgg tgatcctccc gggcacggcg   2940
ttcgtcgagc tggcgctcgc ggcggccgat gcggtcggac tgccctcggt gtcagagctc   3000
acgatcgagg cgccgctggc gctgccggcg cgaggggcgg tggcgctgca ggtgacggtc   3060
gaggcgccgg acgcgacggg gcggcggggc ttcgcggtct acagccggcc cgacggcgcg   3120
cacgacgcgc cgtggacggc gcacgcgcgc ggcgtgctcg gcgcagcgcc cgcggcggcc   3180
acgacggcgt gggcggcggg cgcgtggccg ccggcggggg ccgagccggt cgacgtcacg   3240
cggtgggtcg aggcgctgga cgcgtgggtc ggcccggcgt tccggggcgt gacggcggcg   3300
tggcgcgtgg ggcggtcgat ctacgccgac ctggcgttgc ccgagggggt ctcggagcgg   3360
gcgcaggact tcggcctgca tccggccttg ctcgatgcag cgctccaggc cctcctgagg   3420
gcggagctcg gcgcaggcgc gtcgccgcgg gagggcatcc cgatgccctt cgcgtggtcg   3480
gacgtggcgc tcgaggcgcg gggggcagcg gcgctgcggg cgcgcgtgga ggtcgaggac   3540
gccagcgatg gggaccagct cgcggcgtcg atcgagctgg ccgacgcgca ggggcagccg   3600
gtcgcgcgcg cagggacgtt ccgggcgcgg tgggcgacgg cggagcacgt gcgcatggct   3660
gcggcgggct cgagcgagcg tgacctgtac cgggtcacgt gggcggacgt ggtgctggaa   3720
gaagcggcgt gggcgccgga ggagcacgtc gtgctcggcg gcgacggcgc gctcgcggcg   3780
gcgctgggcg cgcgcacggc ggcgctgccg gagctcatcg cggcgctgcc ggagggcgcg   3840
gccgcgccgc gccggctggt gatcgacgcg gccgcgggcg accccggcga cggcctggtc   3900
gcggcggcgc acgcggcggc gcagcgggtc ctgtcgctgg tgcaggggtg gctctcggag   3960
gcgcggctcg cggacagcga gctggtggtg gtgacgcgcg gcgctgtggc cgccgggccc   4020
gacgacggcg tcgcggcgtt gagccacgcg ccgctgtggg gactcgtgcg cacggcgcgc   4080
caggagaacc ccggccgggc ggtgcgcctc gtggacctgg ggcccgagcc gctggacgga   4140
gcgctcctgc gccgggtggt ggcggcggcc gaggagccgg agctcgcgct gcgcgggggc   4200
gcggcgcgcg cgccacgcct gcgcgaggtg cgcgcgggcg cggccgacgc ggcgcggccg   4260
acgcggctgg atcccggcgg gacggtgctg atcacgggcg gcaccgggga gctcgggcgg   4320
caggtcgcgc ggcacctcgt ggcgtcgcac ggcgtgcggc acctcgtgct cacgtcgcgg   4380
cgcgggatgg gtgcgccgga cgccgcggcg ctggtggacg agctgcgcgc cgcgggcgcc   4440
gcgacggtcg acgtcgcggc gtgcgacgtc gccgacggcg cggcgctggg ggcggtcatc   4500
gcggcgatcc cggctgcaca ccccctcacg gcggtcgtgc acatggcggg cgtgctggac   4560
gacgtcatcg tgacgaagct ctcggccgag cagctcacgc gcgtgctgcg gccgaagatc   4620
gacggcggct ggcacctggc cgcggcgacg cgaggccatc ggctcgcggc cttcgtgctg   4680
ttctcgtcgg cggccggcac gctgggcagc ccggggcagg cgaactacgc cgcggccaac   4740
acgttccttg acgcgctcgc ggcgcagctc cgcgcgcgcg gcgtgcccgc gatgagcctc   4800
gcgtggggct tctgggagca ggcagggctc ggcatgacgg cgcacctcgg cgcggccgac   4860
ctggcacgcc tcaggcggca gggcatcgcg ccgatcgcgc tcgcgcaggg catgcagctg   4920
ctggaccggg cgctcgcgcg cccggaggcg gcgctggtgc cggcggcgct cgaccttccg   4980
gcgctccagc gtgcggcgag cgacgccggg caggtgccgg cgctgctgcg cgggctcgtg   5040
cgcccggcgg tcgggcggcg cgcggcggcg cctgcggccg ccgcgaccgg agcggcggcg   5100
ctgcgcgcgc ggctcgcgcc gctgcccgag gccgagcggc acgacgtggt gctcgacctg   5160
gtgcgcgccg aggcggcggc cgtgctgcag ctggcggggc cggcgcaggt ccccgcggac   5220
```

-continued

```
aagccgctga aggagctggg gctcacctcg ctcacggcgg tcgagctgag gaaccgcctc   5280
ggcgcgcgcg ccgagacggc gctgccggcg accctcgcgt tcgaccatcc gacgccgcgc   5340
gcgatcgcgg gtctgctgct tcagcgtgcg ttctcggagc tcgcggcggc ggtggcgacg   5400
cgcgcacagg cgccacgcgc gcagggggcg cacgacgagc cgatcgcgat cgtgtcgatg   5460
gcgtgccggc tcccgggcgg cgtcgatacg cccgcccgga tgtggcagct cctggcggag   5520
gggcgggacg cgatcgggcc gttccccgag gggcgcggct gggacgtggc ggggctgtac   5580
gaccccgacc cggacgcgcc gggcaagtcg gtcaccaacc tgggcggctt cctctacgac   5640
gccgaccact tcgatccgac gttcttcggc atcagcccgc gcgaggccga gcgcatcgac   5700
ccgcagcagc ggctgctgct cgagtgcgcc tgggaggcgc tcgagcgcgc gggcctggcg   5760
ccccacacgc tcgaggcgag cgccaccggc gtctttgtcg ggctggtgta cagcgactac   5820
ggcgggcggt tgctggagca cctcgagtcc ttcgacggct acatcgccac cggcagcttt   5880
cccagcgtcg gctcggggcg catcgcctac acgctggggc tccgcggccc tgcgatgacc   5940
gtcgacacgg cgtgctcgtc gtcgctcgtg tcgctccacc tcgcgtgcat gtcgctccgc   6000
gcgggcgagt gcgacatggc gctcgccggc ggcgccaccg tgatggccac gccgatggcc   6060
ttcatcgagt tcagccgcca gcgcggcatg gcccccgacg cacggtgcaa ggccttcggg   6120
gcggaggcga acggcatcgg ccccgcggag ggctgcggga tcctggtgct caagcggctg   6180
tcggacgcgc ggcgcgacgg cgaccgcgtc ctggcggtga tccgcggctc cgccgtcaac   6240
caggacggcc gcagccaggg gctcaccgcc cccaacggcc cggcccagca ggacgtcatc   6300
cgccaggccc tggccgcggc ggggctcacg cccgccgacg tcgacgccgt cgaggcgcac   6360
ggcaccggca cgcgcctcgg cgatcccatc gaggcgcagg cgttgctggc gacctacggc   6420
accgcgcaca cagcggagcg gccgctctgg ctcggctcga tcaagtcgaa cctcgggcac   6480
acgcaggccg ccgcgggggt tgtggggctg atgaagctcg tgctggcgat gcagcacgcg   6540
gagctgccga ggacgctgta tgcggagccc cgatcgccgc acatcgactg gtcgcagggg   6600
cacatcaacc tcctgaacga gcccgtgccg tggccgcgca ccgacaggcc gcggcgcgcg   6660
gcggtctcgt ccttcggcat cagcggcacc aacgcgcacg tcatcatcga ggaggcgccg   6720
gccgaagcgc cggcgacagc ggcggacgca aagtcggtgg aggcgcttcc gatcctgccg   6780
ctgctcctgt cgggtcgcga cgagccggcg ctgcgcgccc aggccgggcg gctcgccgag   6840
cacctgcgcg cccacccggg cgagcggctg ctcgacatcg ccgcgggcct ggccacgacg   6900
cgcacgcacc tcgccacgcg gctcgcgctg ccggtcgccg cggacgcagc cgcggaggag   6960
ctgggcgccc gccttgcgca gttcgccgcc ggcggcccgg cgcccagcgg cgccgccgtg   7020
accgcgccgg ggcagccgcc cggcaaggtc gcggtgctct tcaccggcca gggcagccag   7080
cgcgccggca tggggcgcgc cctgtacgcc acccaccccg tcttccgcgc cgcgctcgac   7140
gccgcatgcg ccgagctcga ccgccacctc gacaggcccc tccacagcgt cctcttcgca   7200
gacgccggca ccgaggccgc cgcgctgctc gaccagacag gatgggcgca gcccgccctg   7260
ttcgctctcg aggtcgcgct ctaccgacag tgggaggcct ggggtctgcg ccccgagctg   7320
ctgctcggcc acagcatcgg cgagctcgcc gccgcccacg tcgccggcgt gctcgacctc   7380
cccgacgcct ccgccctggt cgccgcccgc ggacggctca tgcaggccct cccccacggc   7440
ggcgccatgg cctccatcga ggccaccgag cacgagctcc tacccctgct cgaccagcac   7500
acggggcgcc tctcgctcgc cgccctcaac gctccacgcc agtcggtcgt cagcggcgac   7560
```

-continued

```
cagcccgccg tcgaccatgt ctgcgctcac ttcatcgccc tcggccgacg cgccaagcgg   7620
ctcgacgtca gccacgcctt ccactcggcg cacatgcaac ccatgctcga cgccttcgcc   7680
agcgtcgccc gcggcctgac cttccacccg ccacggctgc ccatcgtcag cagcgtcacc   7740
ggcgcacgcg ccaccaccga ccagctcacc tcgcccgact actgggtgca gcaggtgcgc   7800
gagcccgtgc gcttcctcga cgccatgcgc tccctgcacg ccgccggcgc cgccaccttc   7860
gtcgagtgcg ggccgcacgg cgtgctcacc gccgcaggcg ccgagtgcct cgctcccgag   7920
ggcgctcgcg acgccggctt cgtcaccagc ctccgcaagg accgcgacga ggccctcgcc   7980
ctggtccacg ccgcctgcgc cgtccatgtc cgcgggcacg ccctcgactg gctccgcttc   8040
ttcgacgcca ccggcgctcg ccgcgtcgag ctgcccacct acgccttcca gcgacagcgc   8100
tactggctcg aggcgccaag gcctcgcccc agcctcgagg gtgtcggcct caccgccgca   8160
aaccacccat ggctcggcgc cgccgtgcgc ctcgcagacc gcgatggcta cgtcctcagc   8220
ggccgcctct ccaccatcga ccacccgtgg gtcctcgacc acgtggtggc aggcacagtg   8280
atcttgccag gaacggcgtt cgtcgagctg gcgtgggcgg cggccgaggt ggtgggcgcc   8340
gccgcggtgt ccgaggtgac cttcacgacg ccgctcgtgc tgccgccgcg cagcgtggtg   8400
gagctgcagg tgaggatcgg cgagccggac gcgtccgggc ggcggacgtt cgccgcgtac   8460
agccgcgcgg acgcggcgat cgaggcggag tggacgcaac acgcgaccgg cgtgctgagc   8520
gcgcaggcgg cggccggggc cgacgtggcg gacctttcgg tgtggccacc gccgggcgcc   8580
gaggtggtgg cgctcgacgg cggctacgcc tggctggcgg cgcagggcta cggctacggc   8640
ccggcgttcc aggcgctgcg cgaggtgtgg cgcgcgggca cgacgctgta cgcgcgggtc   8700
gcgctgccgg acgcggtggc ggacacggcg cggggcttcg ggatccatcc ggcgctgctc   8760
gacgcggtgc tgcactcgtt gctggcgccg tcggcgcagg aggaggcgtc cgacgacgac   8820
aaggtgctgc tggcgttcgc gttctcggac gtggtgatcg aggcgcgcgg ggcagcggag   8880
gtgcgcgtcc gcctgaacaa gcaggccgga gacgacgggg aggggggtcac ggcgtcgatt   8940
cacctcgccg acgcgcaggg gcggccggtc gcgcgcgtgg gggcgttcca ggcgcgggcg   9000
acgaccacgg agcgggtgcg cgcgctcgcg ggcgcgagcg agcgcgacct gcaccgggtc   9060
acgtggacgg acgtgacgct ggaagagacg ccgtgggcgc acgaggacag cgtcgtggtc   9120
ggcggcgacg gcgcgctggc ggcggcgctg ggcgtgcgcg cggtggccgg gctgcccgag   9180
ctgctcgcgg gcggcgcggc ggcgccgcgt cgtctggtga tcgacgcgac cgcgggcgac   9240
cccggcgacg gcctggtcgc ggcgacgcac gcggcgacgc agcggggcct cgcgctcttg   9300
cagggatggc tctcggaggc gcggctcgcg gcgacggagc tggtgctcgt gacgcgcggc   9360
gcggcggcgg ccgagccgga cgagggtgtg gcggcgctga gccacgcgcc gctctggggg   9420
ctcgtgcgcg cggcgcgcga agagcacccg gcgcgcgcgc tgcgccttgt cgacctgggg   9480
cgcgaggcgc cggacggggc gatcctgcgc cgggcgatcg cggcggacga cgagccggag   9540
ctcgtggtcc gccgcggggc gctgcgggcc gcgcgcctga gcctcgccca cgctggcccg   9600
gacaccgcgg ggcaagcgac gcggctggcc cccggcggga cggtgctgat cacgggcggc   9660
acgggagagc tcggacggca ggtcgcgcgg cacctggtgg cggcgcacgg cgttcgccac   9720
ctggtgctga cgtcacggcg cggaatggac gcgcccgacg ccgcggcgct ggtggagtcg   9780
ctgcgcgcgg cgggcgccgc gacggtggag atcgcggcgt gcgacgtggc ggacgggcat   9840
gcgctggcgg cggtgctccg gaccatcccg gcggagcatc cgctgaccgc ggtcgtgcac   9900
acggcgggcg tgctcgaaga cggcgtcgtg accgggctct cggccgagca gctcgcgcgc   9960
```

-continued

```
gtgctgcggc cgaaggtcga cggcgcctgg cagctctacg aggcgacgaa ggacgcgccg  10020
ctcgcggcgt tcatgctctt ctcgtcggcg gcgggcacgc tgggcagcgc ggggcaggcg  10080
aactacgccg ctgcgaacgc gttcctcgat gcgctggcgg cagagctccg cgcgcgcggc  10140
gtgccggcga tgagcctggc ctggggcttc tgggagcaag gcgggatcgg catgacggcg  10200
cacctcggcg ccgccgacat ggcgcgggtc aagcggcagg gcatcgtacc gatgacggtc  10260
gcgcacggcc tgcggctgct cgaccgcgcg ctggagcggc ccgaggcgac gctggtgccc  10320
ctatcgctcg acgtggcggc gcttcagcgc gcggcgagcg acgccggacg ggtgccggcg  10380
ctgctgcgtg gcctggtgcg cccggcggcc gcccggcgca cggcggcgcc ggcggccgcg  10440
gcgacagggc tccgcgcgcg gctcttgccg ttgtccgagg ccgagcgcca ggacgtcttg  10500
ctcgatctgg tgcgcacgga gatcgcggat atcctcgcgc tgtccgggcc agcggcggtg  10560
cctcccgatc aacccatcag ggagctgggg ctcgattcgc tcacggcggt ggacgttcgg  10620
agccggcttg tgcagaggag cgagatcgac ctcgccgtga ccctcgcgta cgattacccg  10680
accgcgcgag cgatcgcggg acatctgagc gagcagatgg gactcgaagg agcgccggaa  10740
gatcgtgagt cggcgctcga cgagagccag atccgcgccc tgctcatgca gattcctatc  10800
cccacgttgc gccagtcggg gctgctcgga gacctggttc gcctggcctc cccgcaagcg  10860
cccccgcgcg aagaaggtga gagcgagacg ttgagcttcg atcaccttgg aaatgaagag  10920
ttcctcagcc tcgcgtcgaa gctcattgca gaggagggat catga                 10965
```

```
<210> SEQ ID NO 5
<211> LENGTH: 5643
<212> TYPE: DNA
<213> ORGANISM: Sorangium cellulosum

<400> SEQUENCE: 5

atgaaccaag agactgttct tcggcagaca ctcgagaaga gtctccacaa gatccagcac     60
ctcaatcggg agctcgagcg tctcaaggcg aagtcgagcg agccgatcgc gatcgtgtcg    120
atggcgtgcc gctacccggg cggcgtcgac ggtcccgcac ggctgtggga gctgctctcg    180
gaggggcggg acgcgatcgg gccgttcccc gaggggcgcg gctgggacgt ggcggggctg    240
tacgaccccg acccggacgc gccgggcaag tcggtcacca cgcagggcgg cttcctctac    300
gacgccgacc gcttcgatcc gacgttcttc ggcatcagcc cgcgcgaggc cgagcggatg    360
gacccgcagc agcggctgct gctcgagtgc gcctgggagg cgctcgagcg cgcgggcgtc    420
gcgccccaca cgctcgaggc gagcgccacc ggcgtcttcg tcgggctggt gtacagcgac    480
tacggcgggc ggctgctgga gcacctcgag gtcttcgacg gctacgtcgc caccggcagc    540
tttcccagcg tcggctcggg gcgcatcgcc tatacgctgg ggctccgcgg ccctgcggtg    600
accgtcgaca cggcgtgctc gtcgtcgctc gtgtcgctcc acctcgcgtg catgtcgctc    660
cgcgcgggcg agtgcgacat ggcgctcgcc ggcggcgcca ccgtgatggc cacgccgatg    720
gccttcatcg agttcagccg ccagcgcggc atggccccgg acgcacggtg caaggccttc    780
ggggcggcgg cgaacggcat cggccccgcg gagggctgcg ggatcctggt gctcaagcgg    840
ctgtcggacg cgcggcgcga cggcgaccgc gtcctggcag tgatccgcgg ctccgccgtc    900
aaccaggacg gccgcagcca ggggctcacc gcccccaacg gcccggccca gcaggacgtc    960
atccgccagg ccctggccgc ggcggggctc acgcccgccg acgtcgacgc cgtcgaggcg   1020
cacggcaccg gcacgcccct cggcgatccc atcgaggcgc aggcgctgct ggcgacctac   1080
```

-continued

```
ggcaagacgc acacagcgga gcggccgctc tggctcggct cgatcaagtc caacttcggg   1140

cacacgcagg ccgccgcagg ggtggcgggc atcatcaagc tggtgctggc gatgcagcac   1200

gcggagctgc cgaggacgct gtatgcggag ccccgatcgc cgcacgtcga ctggtcgcag   1260

gggcacgtca agctcctcaa cgagcccgtg ccgtggccgc gcaccgacag gccgcggcgc   1320

gcggcggtct cgtccttcgg cgtcagcggc accaacgcgc acgtcatcct cgaggaggcg   1380

ccggccgaag cgcccgcggc cgcgcaaaca gcggcggggg tgccgtcgac gctgccgctg   1440

ctcctgtcgg gtcgcgacga gccggcgctg cgcgcccagg ccgggcggct cgccgagcac   1500

ctgcgcgccc acccggacga gcggctgctc gacatcgccg cgggcctggc cacgacgcgc   1560

acgcacctcg ccacgcggct cgcgctgccg gtcgccgcgg acgcagccgc ggaggagctg   1620

agcgcccgcc ttgcgcagtt cgccgccggc ggcccggcgc ccagcggcgc cgccgtgacc   1680

gcgccggggc agccgcccgg caaggtcgcg gtgctcttca ccggccaggg cagccagcgc   1740

gccgccatgg ggcgcgccct gtacgccacc caccccgtct tccgcgccgc gctcgacgcc   1800

gcatgcgccg agctcgaccg ccacctcgac aggcccctcc acagcgtcct cttcgcagac   1860

gccggcaccg aggccgccgc gctgctcgac cagacaggct gggcacagcc cgccctgttc   1920

gctctcgagg tcgcgctcta ccgacagtgg gaggcctggg gcctgcgcgc ccacgcgctg   1980

ctcggccaca gcctcggcga gatcgtcgcc gcccacatcg ccggcgtgct cgacctcccc   2040

gacgcctccg ccctggtcgc cgcccgcgga cggctcatgc aggccctccc ccacggcggc   2100

gccatggcct ccatcgaggc caccgagcac gagctcctac ccctgctcga ccagcacacc   2160

ggacgcctct cgctcgccgc cctcaacgct ccacgccagt cggtcgtcag cggcgaccag   2220

cccgccgtcg accatgtctg cgctcacttc aaggccctcg gccggcgcgc caagcggctc   2280

gacgtcagcc acgccttcca ctcggcccgc atggaaccca tgctcgacgc cttcgcccgc   2340

gtcgcccgcg gcctgaccta ccgcgccccg cgcctgcccg tcgtgagcaa tgtcaccggc   2400

cgcatggcca ccgccgacga gctcacctcg cccgactact gggtgcgcca cgtgcgcgag   2460

cccgtgcgct tcgtcgccgg cgtgcgcgcg ctgcacgcca ccggcgtcgc cacctacctc   2520

gagtgcgggc ccgatccggt gctcggcggc atggccgcag actgcctcac ctccgacgag   2580

agccgcgacc caggcctgat ccccagcctc cgcaaggacc gcgacgaggc cctcgccatc   2640

gcccaggccg cctgcgccct gcacgtccgc ggacacgccc tcgactggcc ccgcctcttc   2700

gacgccaccg gcgctcgccg cgtcgagctg ccaacctacg ccttccagcg gcagcgctac   2760

tggatcgatg cgccgcggcg cgcggcgggg ctcgaaagcg tcggcctcac ggccgcagac   2820

caccccctggc tgggcgcggc ggtgcggctc gccgaccggg acgtctacgt gctgagcggg   2880

cggctgtcga cggtcgacca cccgtggatc ctggaccacg tggtgacggg cacggcgctg   2940

atgccaggaa cggggttcgt cgagctggcg tgggcgacgg cccaggcggt gaacgccgcc   3000

gcgatcgcgg agctcaccct gacgactcca ctcgtgttgc cggcgcgcgg cgcggtgcag   3060

ctccaggtga cggtcgacga ggccgacgcg gatggccggc gggcattcgc gatccacagc   3120

cggccgcatg ggcccgtcga cctcgagtgg acgcaacacg cgaccggcgt gctgagcgcg   3180

gaggcgccgg cgggagccga cgaggcggcg gggctctcgg agtggccgcc gccgggcgcg   3240

gaggcggtgg cgctcgacgg cgggtatgag cagctgtccg agcacggcta cggccatggc   3300

ccggcgttcc aggggctccg cgggctctgg cgcgcggacc agacgctgta cgcgcacgtc   3360

gcgctgccgg acgctgtcgc gggcacggag cagggcttcg ggctccatcc ggcgctcttc   3420

gatgcggcgc tgcagtcgct ggcgcggctg tcgcgcgagg aggcggccgc tggcgacccg   3480
```

-continued

```
gtgctggtgc cgttcgcgtg gacggacgtg gcgctgtacg cggccggcgc gaccgagctg   3540
cgggcgcgca tcgcgctgga gcaggcggag ggcggcgcgc cggcggtggc gtcgctgctg   3600
ctggccgacg cgcacggacg aaccgtggcg acgacagggc gggtgcgcgg ggcgagcgcg   3660
gcgcagacgc ggtccgccgc gagccgtgcg gagccgatgt acagggtcgc gtggacggac   3720
gtggcgctgg aggcggcggc gtgggcgccc gaagagcacg tcgtgctcgg cggtgacggt   3780
gcgctggcgt cggcgctggg cgtgcgcgcg gcggccgggc tgccggagct gctcgaggcg   3840
ctggcggacg gcgcggccgc gccgcggcgg cttgtcgtgg acctgacggc gggcgacgcg   3900
ggcgctgtcg tcgcggccgt gcacgccgcg gcgcgcggcg cgctggccct ggtgcaggga   3960
tggctcgccg cgccgcagct gacggcgacg gagctcctcg tggtgacgcg ctgcgccgtg   4020
gcgacagggc cggacgaggg cgttgacgcg ctggggccgg cggccgtctg ggggctgctg   4080
cgggccacgc gcgccgagca ccccgaccgc gcggtccggg tgctggacct ggggcgcgag   4140
ccgctggacg gggcgctcct gcgcagggcg ctggccgcgg tggcggagcc ggagctgtcg   4200
ttgcgccgcg gcgaggcgcg cgcgcctcgc ctgcgcgagg caaagcccgc cgcggcgccg   4260
gcgacacggc tggaccctga agggacggtg ctggtcacgg gcggcaccgg ggagctgggg   4320
cggcaggtcg cccggcacct ggtggcggcg cacggcgtgc ggcacctcgt gctgacgtcg   4380
cggcgcggga tggacgcgcc cgacgccgcg gcgctggtag aagagctgcg cgcggcgggc   4440
gcggcgacgg tcgacgtcgc cgcgtgcgac gtcgccgctg gcccggccct ggcggcggtc   4500
gtggaggcga tcccggcggc gcatcccctg accgcggtcg tgcacatggc gggcgtgctg   4560
gacgacggca tcgtgacgaa gctctcggcc gagcagctca cgcgcgtgct gcggccgaag   4620
gtcgacggcg ccattcatct ccacgagctc acgaagcacg cgccgctcgc ggccttcgtg   4680
atgttctcgt ccgcggcggg cacgctgggc agcccggggc aggcgaacta cacggcggcc   4740
aacgtgttcc tggacgcgct ggcggcgcga ctgcgcgcgc gcggcgtgcc cgcgatgagc   4800
ctggcgtggg gcttctggga gcaaggcggg atcggcatga cggcgcacct cggcgccgcc   4860
gatcgggcgc ggatgaagcg acacggcgtc gtggcgatgt cggtcgcgca gggcctgcgg   4920
ctgctcgatc gcgcgctcgc gcaccccgag gcggcgctgg tgccgctcgc gctcgacctc   4980
tcgtcgctgc acgcgggggc cagcggcgcc ggaccggtgc cgccgctgct gcgcgggctg   5040
gtacgcgcgc ccgccggccg gcgcacggcg gcgtccgcgg cccggacgaa cgggaagggc   5100
acggcattgg cggcgctccg cgcgcggctc ttgccgttgc cgcaggccga gcgcgaggac   5160
ctcttgctcg agctcgtgtg caccgaggtc gcggaggtgc tgcagttgcc ggggccggcg   5220
cacgtcccgg cggatcagcc gctccgcgac ctggggctcg actcgctcat gaccgtggag   5280
ctgcgcaacc gtctcggcgc gcgcgccgag acgacgctgc ccaccacgct cgcgttcgac   5340
tacccgacgc ccagggccct tgcgtcctat ctggagacgt tgctcggcat ctccgacgag   5400
aacgggcatt cgggtgagtt gctgcacgtt ccgcagaacg aggacgagat ccgctccgcg   5460
atagcgcgca tcccgatagc gaccctgcgc gaggcggggc tcctccagag cttgctgcgg   5520
ctcgcccccg gcaaggcggt ggccggtgac gtcacgcacc cggtcgatga gctgctggtc   5580
gagcacatcg aggatgaaga gctgcttcga ctcgctttcg aggccaccgg aggtatcaag   5640
tga                                                                 5643
```

<210> SEQ ID NO 6
<211> LENGTH: 8610
<212> TYPE: DNA

<213> ORGANISM: Sorangium cellulosum

<400> SEQUENCE: 6

```
gtgaaagacg aggctctctc gtttcgccga gccctggaga agacggtcgt cgagatccgc     60
cgtctcaatc gggagatcga cgacctgcgg gcgaagtcga gcgagcccat cgcgatcgtg    120
tcgatggcgt gccggttccc cggcggcgtc gagaaccccg aggcattgtg gcggctggtc    180
tccgaggggc aggacgcgat cggccgttc cccgaggggc gcggctggga cgtggcgggg     240
ctgtacgacc ccgacccgga tgtgccgggc aagtcgatca ccgcgcgggg cggcttcctc    300
tacgacgccg atcgcttcga tccggagttc ttcggcatca gcccgcgcga ggccgagcgc    360
atcgatccgc agcagcggct gctgctcgag tgcgcctggg aggcgctcga gcgcgcgggc    420
gtcgcgcccc acacgaagga ggcgagcgcc accggcgtct tcgtcgggct gatgtacacg    480
gactacggcc tgcggctgct gaaccacccc gaggccctcg acggctacat cggcatcggc    540
agcacgggga gcacgggctc ggggcgcatc gcctacacgc tgggcctgca gggacctgcg    600
atcacggtgg acacggcgtg ctcgtcatcg ctcgtggcgc tccacatggc ctgcgcgtcc    660
ctgcgcgggg gagagtgcaa cctggcgctt gtcggaggcg tcgccgtgat gacgacgccg    720
acaacgttca tcgagttcag ccggcagcgg ggcctctcgc tcgacggccg gtgcaagtca    780
ttcggtgccg aggccgaggg cgtcggctgg ggcgaaggct gcggaatcct ggcgctgaag    840
cggctgtcgg acgcgcggcg cgacggcgac cgcgtgctcg cgatcatccg cggctccgcc    900
gtcaaccagg acggccgcag ccaggggttc accgccccca acggcccgag ccagagggcg    960
gtcatccagc gggcgctggc ggcggcgggg ctgaccgcgg cggacgtcga cgccgtcgag   1020
gggcacggca ccggcacgcg cctcggcgac cccatcgagg cgcaggcgct gctggcgacc   1080
tacggcaagg cgcacacagc ggagcggccg ctctggctcg gctcgatcaa gtccaacttc   1140
gggcacacgc aggccgccgc aggggtggcg ggcatcatca agctggtgct ggcgatgcag   1200
cacgcggagc tcccgaggac gctgcacgcc gacacgccct cgccgcacgt cgactggtcg   1260
caggggcacg tcaagctcct caacgagccc gtgccgtggc cgcgcaccga caggccgcgg   1320
cgcgcggcgg tctcgtcctt cggcatcagc ggcaccaacg cgcacgtcat cctcgaggag   1380
gcgccggccg aagcgcccgc ggccgcgcaa acaccagcgg cggcgggggt gccgtcaacg   1440
ctgccgctgc tcctgtcggg tcgcgacgag ccggcgctgc gcgcccaggc cgggcggctc   1500
gccgagcacc tgcgcgccca cccgggcgag cggctgctcg acatcgccgc gggcctggcc   1560
acgacgcgca cgcacctcgc cacgcggctc gcgctgccgg tcgccgcgga cgcagccgcg   1620
gaggagctga gcgcccgcct tgcgcagttc gccgccggcg gcccggcgcc cagcggcgcc   1680
gccgtgaccg cgccggggca gccgcccggc aaggtcgcgg tgctcttcac cggccagggc   1740
agccagcgcg ccgccatggg gcgcgccctg tacgccaccc accccgtctt ccgcgccgcg   1800
ctcgacgccg catgcgccga gctcgaccgc cacctcgaca ggcccctcca cagcgtcctc   1860
ttcgcagacg ccggcaccga ggccgccgcg ctgctcgacc agacaggctg ggcacagccc   1920
gccctgttcg ctctcgaggt cgcgctctac cgacagtggg aggcctgggg cctgcgcgcc   1980
cacgcgctgc tcggccacag cctcggcgag atcgtcgccg cccacatcgc cggcgtgttc   2040
gacctccccg acgcctccgc cctggtcgcc gcccgcggac ggctcatgca ggccctcccc   2100
cacggcggcg ccatggcctc catcgaggcc accgagcacg agctcctacc cctgctcgac   2160
cagcacaccg gacgcctctc gctcgccgcc ctcaacgctc cacgccagtc ggtcgtcagc   2220
ggcgaccagc ccgccgtcga ccaggtctgc gcccacttca aggccctcgg ccggcgcgcc   2280
```

```
aagcggctcg acgtcagcca cgccttccac tcggcccgca tggaacccat gctcgacgcc   2340

ttcgcccgcg tcgcccgcgg cctgacctac cgcgccccgc gcctgcccgt cgtgagcaat   2400

gtcaccggcc gcatggccac cgccgacgag ctcacctcgc ccgactactg ggtgcgccac   2460

gtgcgcgagc ccgtgcgctt cgtcgccggc gtgcgcgcgc tgcacgccac cggcgtcgcc   2520

acctacctcg agtgcgggcc cgatccggtg ctcggcggca tggccgcaga ctgcctcacc   2580

tccgacgaga gccgcgaccc aggcctgatc cccagcctcc gcaaggaccg cgacgaggcc   2640

ctcgccatcg cccaggccgc ctgcgccctg cacgtccgcg gacacgccct cgactggccc   2700

cgcctcttcg acgccaccgg cgctcgccgc gtcgagctgc caacctacgc cttccagcgg   2760

cagcgctact ggctcgagac gccccagacg ccgggcgccg acggggcctc caacctatct   2820

tcgcccgccg aaagccgctt ctgggaggct gtcgagagag cggacatcat ccccctcgcc   2880

gaggcgctgc gcctcgagga tgaggcgcaa cgcgcttcgc tggcgaccct gctgcccgcg   2940

ctctcgacct ggcgccgccg acgccacgag cagagcaccg ccgacgcctg gcgttaccgc   3000

gttgcctgga accccttgcc catcgacgcc cggagcgatc tctcggggt ctggctgttc    3060

ctcgcgcctc cggatcacgc gaaggacgac ctcgcgcgcg cggtccttcg cgcgctcgcc   3120

gagagcggcg cgacggtcgt ccctgtgctg gtggccgagg gcgacgtcga ccgcgccctc   3180

ctgagcgcgc ggctgcgcga gcaggtcggc gacggcggcg cgatccgcgg cgtgatctcg   3240

ctcctcgccc tggacgagac ctcgctgccg cagcacgacg ggctgccccg gggcctcgcc   3300

ttcacgctcg cgctcgtcca ggccctggga gacacggcga tcgcagcgcc tctatggctg   3360

ctcacccgtg gcgccgtctc cgtgggtcgt tccgaccgcc tcgagcgccc gctgcaggcg   3420

ctgacgtggg gcctcgggcg cgtggtggcg ctggagcacc ccgagcgctg ggtggactc    3480

atcgatctcg ccggcgcgct cgacgaaaag gcgctcaagc ggctcgtcgc cgccctcggt   3540

ggtcgcgacg ccgaggatca gctcgccctg cgcccctccg gactcttcgc gcgacggctg   3600

gtcagagcgc ccctgggtga agcgaccgcg gttcgcgcct ggaaggcgcg cggcaccgcg   3660

ctcgtcaccg gcggcacggg ggacctgggc gcccacgtcg cccggtggct cgcccagaat   3720

ggcgccgagc acctcgtcct caccagccgc cgcggacagg acgcccccgg agcggccgag   3780

ctcacggccg agctcacggc gctcggcgcc cgcgtcacca tcgccgcctg cgactcgtcc   3840

gaccgacagg cgctcgcggc cctgctccag cgcctgaggg ccgaaggccc cccctccgc    3900

gccgtcgtcc acgctgcggg tgtcgaccag gtcaccccgc tggccaggac cagcctggcc   3960

gagttcgcag gcatcgcctc cggcaaggtc gcaggtgctc ggcacctcga cgacttgctc   4020

ggcaatgccc ccctcgacgc cttcatcctc ttctcctcgg tcgcaggcgt ctgggggagc   4080

ggctttcagg gcgcttacgc ggcggccaac gccttcctgg acgcgctggc cgagcagcgc   4140

cgcgccctgg gctcgacggc cacgtcgatc gcctggggcc tctggggcgg caaaagcatg   4200

gccgacgacg ccgccaaaga tcatctcagc aagcgcggcg tgtccccgat gccgccccag   4260

ctcgcgatcg cggccctgca gcgggcgctc gaccacgacg agaccacact caccctcgcc   4320

gacgtcaact ggtcacgctt tgccccggcc tttgccgccg cccgcccgcg cccgttgctg   4380

cacgatctcc cggaagcccg gagcgctctc gagtccccct cgccggcgcc ccgcgaggcc   4440

gagctgctca cccggctcca gggcctctcc agcaccgagc gcgtccgcca cctcgtctcc   4500

ctcgtgctgg cggagaccgc cgtcgtcctc ggccatcctg acgcctcccg cctcgaccct   4560

cacacaggct tcgcggatct cggcctcgac tcgctgatgg ccgtcgagat gcgccggcgg   4620
```

-continued

```
ctccagcagg caacgggggt gagcctgccg gcgaccctga ccttcgacca cccctcgccc   4680
caccacatcg cgaccttcct cctcgacgag gtcttcgcgc cggccctcgg ccaggccccc   4740
ggcgccgagg aagacgaagc gatcgcccag gccgggctcg cctcgggcga cgagcccgtc   4800
gccctcatcg gcgtggggct gcgtctcccc ggcggagcca ccgacctcga cgggctctgg   4860
cgccttctgg agcaggggat cgacgttgtc ggccccgtcc ctgaagaccg cggctggagc   4920
atggacgagc tctacgatcc cgaccccgac tccctcggca agagctacgt gcgcgaagcg   4980
gctttcctcg atcgcatcga cctcttcgac gcgggcttct tcggcatcag cccccgcgag   5040
gcgagccacg tggacccgca gcaccgcctc ctgctcgagg ccgcgtggca ggccctcgag   5100
cacgcaggca tcgtcccggc ctcgctccag gactcccaga ccggcgtctt cgtgggctca   5160
ggcccgagcg actacgcctt gctccacaac ccggcccagg aggatgaagc ctacaggctt   5220
acggggacgc agccctcgtt cgcgccaggc cggctctcgt tcagcctggg attgcaggga   5280
ccggcgctct ccgtggacac cgcctgctcc tcctcgctcg tcgcgctcca cctcgccgcc   5340
caggccctgc gccgcggcga gtgcgggctc gccctcgtcg gcagcgcgca ggtgatggct   5400
gctcccgacg ccttcgtgac gctctcccgc gctcgcgcca tcgctcccga cggccgctcg   5460
aagaccttct ccgcccaggc cgatggctac ggccgcggcg aggggggtcat cgtcttcgtc   5520
ctcgagcgcc tgagcgacgc ccgcgcgaga gggcgcgacg tcctcgcggt cctccgcggc   5580
agcgccgtca accacgacgg cgccagcagc ggcatcaccg cgccgaacgg cacctcccag   5640
cagaaggtgc ttcgtgccgc gctccacgat gcgcggctca cgccagcgga cgtcgacgtg   5700
gtggagtgcc acggcacggg cacttccctc ggcgacccca tcgaggtgca agccctggcc   5760
gccgtctacg gaaaggagcg ctccgccgat cggccgctga tgctcggcgc gctcaagacc   5820
aacgtcggcc acctcgaggc cgcgtccggt ctcgccggcg tcgcgaaggt cgtcgcggcg   5880
ttgcgccacg aggcgctgcc ggcgacgctg cacaccgccg cgcgcaaccc tcatatccag   5940
tgggatacgc tgcccgtcca ggtcgtcgac accttgcgtc cctggccgcg gcgcgaggac   6000
ggcacccccc gccgcgccgg cgtgtcggcg ttcgggctct ccggcaccaa cgcccacgtc   6060
ctcctcgagg aagctccgcc tgtccagccg agcacacagg cggagcagcc tgccgcgccg   6120
ccgtggttgc cgctgctcct gtcgggcaag acggacgcgg ccctgcgagc gcaggccgag   6180
cggctgcggg cgcacctcga cgcccatgcc gacctcgggc ttgccgacgt cgcctattcc   6240
ctcgccacga cgcggacgca tttcgcgcat cgggcggtgg tcgtcgcgga cgctggcgcg   6300
accctcttcg aagggctgga cgccatcgcg cgcggcaacg ccgcttccca cgtggtggtc   6360
gacgaggcca agatcgacgg caagaccgtc ttcgtcttcc cgggacaggg ctcgcagtgg   6420
gcccagatgg cgcagccgct gctcgagacc tccgagctct ttcgcgagcg tatcgaggcg   6480
tgcgcgcacg ccctcgcgcc tcacgtcgac tggtcgctgc tcgccgtcct ccgcggcgaa   6540
gaaggcgccc cctcactgga gcgggtcgac gtggtgcagc cggtgctctt cgccgtgatg   6600
gtctcgctcg ctgccctctg gcgctcgatg ggcgtcgagc cggacgccgt cgtcggccat   6660
agccagggcg agatcgccgc cgcctgcgtg gcgggcgcgc tgtcgctcgc ggacgccgcc   6720
aaggtggtgg cgctgcgcag ccgcgcgctc gcgcggctcg ccggccgggg cgccatggcc   6780
gtcgtggagc tccccgccgc cgagctcgcc gagcgcatga agcgctgggg cgagcggctg   6840
tccatcgcag cgctcaacag ccctcgttcc accgtgatct ccggcgatcc ggacgccgtc   6900
gacgcgctgc tccgggagct cgactcggcg gagatcttcg cccgcaaggt gcgcgtcgac   6960
tacgcctccc actgctccca tgtggaggcg attcgccacc agctcctggc cgagctcgcg   7020
```

```
ggcatcgagc cgctcccgtc cacgctcccg ctctactcca cggtgagcgg ggacaagctc   7080
gatggcgtcg cgctcgacgc ctcgtactgg taccggaacc tccggcagac cgtccgcttc   7140
tcggacgcca cgcagcggct cgtctccgcg ggacatcgct tcttcgtcga ggtcagcccg   7200
catccggtgc tgacgttcgc cgtgcaggat gtcctcgatg ccgagggggt gcccgccgct   7260
gtcgtcggct cgctacggcg cggcgagggc gacctgcggc ggttccttgt gtcgctgtcc   7320
gagctcttca cccgcggcct cgccctggat tggtccaggg ttctgcccag cggccggcgc   7380
gtatcgctgc ccacctacgc cttccagcgc gagcgctact ggctcggggc tcacagggct   7440
cgcggcaccg acgcgacatc cgccggcctg gcatcggacg agcccacgcg cggcgcgtcg   7500
atgccagtgc ggctctcgtt gcgggacgtg ccgcccgagg agcgccaggg agcgctggag   7560
cggttcgtcc gggagcagct cgcggccgtc ctgcgcatgg atgcggcgcg gatcgagggg   7620
cagacgacga tcaagacgct cgggatcgac tcgctcatgg cgctcgagat ccgcaaacgg   7680
ctggaagccg gactggccgt gaccttgcca tcgacgctca tctggcagtt cccgcacgcc   7740
gaagggctcg cacggcacct catgacgcgg ctccccgcgg gggacggaga aggatctgcc   7800
gtggtccagc ccgtggagca gccgcgcgcg ccgaaggagg tgcccgtatc catggatccc   7860
tcggcgtggg tgcaccgccc gcgccccagg gccgacgcgc gcgttcgact gttctgcctt   7920
ccctacgccg gcgcgggcgc ctcgcgcttc cgggcgtggc cagagctgct cccctcctgg   7980
gtggaggtct gcccgatcca gctccccggc agggaagagc gcctccacga gccggccttc   8040
gagacgatgg acgcgctcgt cgacgcgctc gttcccgccg tcgaggcgca catcgatcgg   8100
ccctttgcgc tgttcggctg cagcatgggt gccctcctgg ccttcgagct cgcccgggcg   8160
cttcaatccc gtcatcgctt ggtggcgcgg catctgttcg gcgcggcgag ctcctcacct   8220
cggcgcgtga gcccggtacg ggagcagctc tccgcggtgg tctcccctgg aacggtgcga   8280
tcggacgcga tggcctcgct gcgccagctc ggtctgctgt cgtcctcgtc cctccaggac   8340
gaagagatgc tggacgaggt gtggcccgcg ttccgtgcgg atctatccct gacgctgaag   8400
tacacgtgca gggacgcaac ccccctcgac gcccccatct cggtcttcgg gggcaccgag   8460
gaccggaccg tagggcgcga ggatctcgtc gcctggcata cgctgacgaa ggacgcgttc   8520
caggtcgcca tgctgcccgg gggtcacctg ttcatggacg cgacgccgaa gcggctcttc   8580
catcacatcg agcacgcgct ccagctctag                                    8610
```

<210> SEQ ID NO 7
<211> LENGTH: 687
<212> TYPE: DNA
<213> ORGANISM: Sorangium cellulosum

<400> SEQUENCE: 7

```
gtgcggacca gcgacgccgt gtgggctggt gccgcgggct ataccagggc gcgtcttcag     60
gtctatgact tcttcatcta cggcttcaac agccctgtcg catggaagtg cccgggcgag    120
gagctcctcg agaactacaa tcggcacgtc tcgggcaatc acctcgacgt cggcgtgggg    180
acggggtacc tgctcgaccg ctgccgcttc cccaccgcca agccgcgtgt gtttctgatg    240
gatctgaacc cggacgctct gcaggtgacg gcgcagcgac tgcaccgctt tcagcctcag    300
accttgcggc ggaacgtcct tgatcccatc cgcttcgacg gagagccctt cgactccatc    360
gggatgaact acctcatgca ctgcgtccct ggatccatcc cggagaaggc cgtgatgttc    420
gaccacctga gcgccttgct gaagccgggc ggcgtgatct tcggcagcac ggtgctctcg    480
```

-continued

```
gagggcgtgg acaaggggat cgtggcgcga gccatcatgg accgcttcaa caagaagggg    540

atcttctcga acacccgaga cgccgcctcc gatctgacgc gagcgctgga ggagcgcttc    600

gacgacgtct cggtccgcgt cgtcggctgc gtcgggctgt tctcagccag gaagcgtacc    660

tgcgcgggaa ccgagtcgcc ggcgtga                                        687
```

<210> SEQ ID NO 8
<211> LENGTH: 906
<212> TYPE: DNA
<213> ORGANISM: Sorangium cellulosum

<400> SEQUENCE: 8

```
atcgtcctgg gcgacacgct ggagcaggtg gcgacgcggc tgctcgagga ggacctcgcg     60

gcgtgccaca cgaccggcga ggcggcggac gtgctgctga acggggtgct cgcgtcgagc    120

gcccgcgccg tggccgcggc gctgcgcgcg tgcgacgagt tcgccgcggg cgacagcgat    180

ctgccgtcgc tggcccgggc gtgccgcgcg ttcgcggggc tcgcgtcgtt cgggtcgtcg    240

cggtcgctgt cgtcgctcgg cgacggggtg atcgcgccga tgctggagaa gacgttcgcg    300

cgcgcggtcc tgcgcgtcca cggggctgc acgggcagcg acgaggcggt cgccgccgcc    360

aaggaggcgc tgcgcacgct gcacgacgtg gcgctgtcgc agccgatcgt cgaccgcggg    420

gcgtggctcg acgcggcgcg gggctcgtg gacagcgagg tggtgaaccc gacggcgtcc    480

ggcctcgcgt gcgggctgct ctacctggcg caggcgatcg acgacgccga ggtggcgcgg    540

gtcgtcggcc tgcggctcgg gggcgcggcc gagcccgagg cggcggcgtc gttcctggcc    600

gggttcctcg aggtgaacgc gctggtgctg gtgaagagcc ggcccgtggt cgaggcgctg    660

gacgcgttcc tccgggcgat cgcgccggag cgcttcaagg acacgctgcc ggtccttcgg    720

cgcgcgttcg ctgggctcgg cgcgacggag cggcggtacc tgctcgagaa cgtgctcgcg    780

gcgcggaagc tgggggacaa ggcgcgcgcg gcgcaggcgg tgctcctgga gaaggaccgg    840

gagaagctga aggagatgag cgaggacctc tcacaggcga tggacgacct ggacgagttg    900

ctctga                                                               906
```

<210> SEQ ID NO 9
<211> LENGTH: 1038
<212> TYPE: DNA
<213> ORGANISM: Sorangium cellulosum

<400> SEQUENCE: 9

```
tcacacgccc ggcaaagctg gcctcgagtc caccgcgacc gccctctgga tggcgtcgcg     60

gagccacccg tggccctcgt cgtgctcgga gcgctccggc cagacgagcg tcagcgtgta    120

gccctcgagc gcgaacgggc acggccgcac cacgagatcg agcctccggg ccagggccgc    180

ggcgacgcgc gcggacacgg tgagcagcag gtcggaaccg gagacgatga acggcgcgac    240

aaggaaatgg gacacggtca gcgtcacccg ccggcgtgtt ccctgctccg ccagcgcccg    300

atcgatggcg ccgtggtcct ctccgtgcgg cgagaccatc aggtgctcgc aagcagcgta    360

gcgcgccgcg gtgagcggcc tccgggacgc cgggtgtccg cggcgcatca cacagacgat    420

ctcctcggcc gcgagcagcg tggagcgaca gccgtcgggc accggtccgc cgcgcccgag    480

cttgccgtcg agctcgccgc ggcgcaggag ctcggcgaag tcggccggga tgttccggca    540

gcgcaggttg acgcgcggcg cctcgacggc gagcagcgcg gtcagcgccg ggagcacgag    600

cagctcgagg ttgtcggtcg cgacaagccg gaacgtgcgc tgcgaccgcc gcgggtcgaa    660

ccgctcgacc gggcggaaga cctgctcgag ccgctcgacg gcctcggccg cccgcggggc    720
```

```
caggtcccgc gcccgctcgc tcagcgtcat ctgcctgccg acctggatga gcagcgggtc     780

cgcgaaatgg gcgcgcagcc gcgcgagcgc gtggctcatc gagggctgcg tcacgcccac     840

gcggcgcgcg gcgcgcgtga cgctcttctc ctggagcagg gcgtgcaacg ccacgacgag     900

gtgggtgtcg accgactgca gccgcatggt cgatggatac cacgtcgatc catcgacggc     960

gtctatggat cgccgcgccg actgccgatt cgacgcccgg ggccgtgggt gcctatctct    1020

cctctccgga cggcgcat                                                  1038
```

<210> SEQ ID NO 10
<211> LENGTH: 327
<212> TYPE: DNA
<213> ORGANISM: Sorangium cellulosum

<400> SEQUENCE: 10

```
atgatcatcg agtacgttcg ctacacgatc cccgcggagc aagagaagga gttcctggcc      60

gcctaccgcg acgccgccgc ggagctgcgc gggtcggagc attgcctcga ctacgagatc     120

tcccgctgcg tcgaggatcc gacgagctac gtcgtccgca tctgctggga ctcgctgcaa     180

ggccatctcc agggcttccg caaggcggcg gcgttcccgt cgttcttcgc caaggtgaag     240

ccgttctacg agcgtatcca ggagatgagg cactacgcct tgaccgacgt cgccgcgcgg     300

caggcgggga cggccgcgac gggctga                                         327
```

<210> SEQ ID NO 11
<211> LENGTH: 1461
<212> TYPE: DNA
<213> ORGANISM: Sorangium cellulosum

<400> SEQUENCE: 11

```
atgaagctcg cgcgcaagct gacgctcgcc ctcgtgttcg gggtattcct cgtgctcgcg      60

ctgagcgcct acgcccagat ccgcagagag gccaggatct tcgagaacga cgtccagcgc     120

gaccatcaca cgatggcccg cgcgctcgcg gccgcggtca tggaggtgtg gcgctccgag     180

ggaaccgcgc gggcgctgcg cctcgtggag gacgccaacg agcgggaaca gcaggcgaac     240

atccgctggg tctggctcga tggccaggcc gacgagcccc atcgcccccg gctggcgccg     300

gagctgctcg cccccgtcgc cgaggggcgc gcggtcgtgc gccggatccc ccagaaagac     360

gcggatctgc tcgtgacctg cgtgccggtg tccgtgcccg gcgaccgcgc cggcgcgctc     420

gagctctccg agtcgctcgc gggcgcgcgc cggtacatcc ggagcatgat cctgagcacg     480

gcgatcacca cagccgcgct gacgctggta tgtgggttgc ttacaacggg cctcggagtc     540

tggctggtgg gacgccccat gcgcacgttg atcgaccagg cgcggcggat cggcgccggc     600

gatctctccg ggcggctgtc gctgcgccag gaagacgaga tcggcgagct cgggcgcgag     660

atgaacgcca tgtgcgatcg cctcgccgcg gcgaaccaga agctcgagtc cgaggccgcc     720

gcgcggatcg ccgcgctcca gcagctccgt cacgccgagc ggctcgcgac cgtcggcaag     780

ctcgcgtccg gcatcgcgca cgagctgggc gcgcccctcc aggtcgtcac ggggcgcgcg     840

cggatgctcg tcgacggcga cgtgtcgggc gatgaggtgc cgatcaatgg acagatcatc     900

ctcgagcagt cgcagcggat gacccagatc atccgccagc tgctcgactt cgcccggcgc     960

cgcagcgccg agaagcagga gaccgcgctc cgcggcgtca tccgcggcac gttcacgatg    1020

ctgaagccgc tggcggacaa gcagggtgtc acgatcgtcg aggagggaga cacgccggat    1080

cgggtggtcc acgccgacgc cgaccagctc cagcaggcgc tcacgaacgt cgtcgtcaac    1140
```

-continued

```
gcgatccagg ccatgccgtc cggcggcacg atcacggtgg gcgtccggac cgtccgcgcc   1200

agccccccgc ccgaccaggg aggggccgag ggcgactaca tcgcgctgtc ggtgcgcgac   1260

gagggacagg gcatgacggc cgacgtcctc gagcacgtct tcgagccgtt cttcacgacc   1320

aagcccgtcg gcgaggggac cgggctcggc ctgccggtcg cctacggcat catcaaggag   1380

cacggcggct ggatcgacgt cgacagccgc cccggctccg ggagccagtt cacgatgtac   1440

ctgccgcagg agaagccatg a                                             1461
```

<210> SEQ ID NO 12
<211> LENGTH: 1386
<212> TYPE: DNA
<213> ORGANISM: Sorangium cellulosum

<400> SEQUENCE: 12

```
atgaccggac gcgtcctgat cgtcgacgat gagcgaggcg tctgcgagct cctcgacgcc     60

gggctgaaga agcggggatt ccaggcggcg tggcgcacgt cggccgccga ggcgctcgag    120

ctcctcggcg cggaggactt cgacgtcgtc gtcaccgaca tgaccatgcg cggcatgaac    180

ggcctcgagc tctgcgagcg catcgcccag aaccggcccg atctgccggt catcgtcatc    240

accgcgttcg ggagcctcga caccgccacg tcggcgatcc gcgccggcgc ctacgacttc    300

gtgaccaagc cgttcgagct cgacgcgctc cggctcaccg tcgagcgcgc cctgcgccac    360

cgcgccctcc gcgaggaggt gcgccggctg cggcgcgccg tggacgactc ccaccgttac    420

gagcagatcc tcggcggcag cccggcgatg aagggcgtct tcgatctgct cgaccgggtc    480

gccgactcgg acacctcgat cctcatcacc ggcgagagcg gcaccggcaa ggagctcgtc    540

gcgcgcgccg tgcaccagcg cagccggcgc ggccagggcg cgttcatcgc ggtgaactgc    600

gcggcggtcc cggacgccct gctcgagacc gagctgttcg gccacgcgcg gggcgccttc    660

accgacgcca agggggcgag gagcggcctg ttcgcgcggg cccacggcgg caccctgttc    720

ctcgacgaga tcggcgagct gccggtcggg ctccagccga agctcctgcg cgccctccag    780

gagcgcgtcg tccggcccgt cggcgcggac gaggaggtcc ccgtggacgt gcggctcatc    840

gcggcgacca accgcgacct ggagaccgcg atcgaggagc gccgcttccg cgaggacctc    900

tattaccgga tcaacgtggt ccacgtcgat ctgccgccgc tccgctcccg cggcgccgac    960

gtgctgctgc tcgcgcagcg cttcctcgag cacttcgcga ccgtcaagga gcggcccatc   1020

aagggcctct cggcgcccgc ggccgagaag ctcgtcgcct acgcgtggcc cggcaacgtc   1080

cgcgagctcc agaactgcat cgagcgggcc gtcgcgctcg cgcggtacga tcagatcacg   1140

gtcgacgatc tccccgagaa gatacggagt taccggcgct cccacgtcct tgtctcgagc   1200

gacgacccga ccgagctcgt ccccatggag gaggtcgagc ggcgctacat cctgcgcgtc   1260

ctggaggtgg tcggcggaaa caagagccag gcagcccagg tcctgggctt cgatcgagcg   1320

accctgtacc ggaagctcga gcggtacggc ctgcgcgccg ggcgcgcggg cgacccgagg   1380

ccgtga                                                              1386
```

<210> SEQ ID NO 13
<211> LENGTH: 1527
<212> TYPE: DNA
<213> ORGANISM: Sorangium cellulosum

<400> SEQUENCE: 13

```
tcatccatgg gagacgccgc gcgggccgtc cgcctggtcc cttgacgacg agcgcggcag     60

ctcgatccgg aagaccgagc cggcgccggg acggctctcg acgaagaggc ggccgccgtg    120
```

-continued

```
cgcctcgacg atgcgcttcg ccaccgcgag gccgaggccc gtgcccggga tggatccaga    180
cgtggacttg agccgccgga acggctcgaa gaggtgcgcc agatcctcgg gctcgatccc    240
gagcccgcga tcgcgaacgg cgatctcggc cccctcgccg ccggcgcgga ccgccacgtc    300
gacctgcccc ccggcggggg agtacttgag cgcgttcgac aggaggttgt tcagcacctg    360
ctcgatccgg gtcgcgtcgc agcggacgag caccggtgtc tcggggagcg agagctcgat    420
ggggtgctcc ggcgagacag ggcgatagag gtccaccgcc tcctgcgcga gatcgcgcag    480
gtcgcgctcc tccacccgga gatcgagctt gcaggcctcg atctgcgacg cgtcgaggag    540
gtccccgacc atgcgatcga gccggtcgac ctgccgcccg acgagcgcca tggtccggcg    600
cacgctcgac tccaggggcc ggttgtcggc gtcgaggacg tgcacggaca gccggagcgc    660
cgacagcggg ttcctgaggt cgtgggccac gccgccgagg aacgcgaact gcgcctcgcg    720
ctggcgctcc agcgactctg ccatgtcgtt gaaggcgcgc gcgatctccc cgagctcgcg    780
cggcccgatc agcggcgcgc gcgcggcgcg gtcgcccgcg ccgtagcgcc cgatggcctc    840
ctggatcgcg acgatggggc ggtagatgag ccgccgcgcg ctgaggagga tcgtggacgc    900
gcccgcgagg aagaacacca ccgccgcgag gccggcgccg gtcgtgcgcc gggtcaggtg    960
cgcgacgagc gcctccgacg cgcgggcctg ctcgaggttg atctcgacca ggtgatcgag   1020
cgccctgaac gcctcgtcga gcgcggggtc gtgcacgccg agcagcgcgg gatcgtgcgc   1080
gccaggcgcc gacgggagct cgtgggcgtc ggcggcgcgg cgccgggcga ggtagtcctc   1140
cacgcgccgc tccgcgtgct cgaggatcct gccctcctcc gggctgctca cgtggtcgcg   1200
cgccgccgcg aggccgctcc tcaggccttg ctcccacgcc gccagggagg gggccagctc   1260
cccgcggccg gagccgaccg cgcggctgct ctggtgcgcg tcgagcagga ggtcgatctc   1320
cagcctctcc acgagccgga cgctctcgac cgtggcgccg aggatccggg tggtctgttg   1380
catggtcgtc gacgcgacca tcagcgcgcc cgcgacaacg atggccacgc tcgtgagaag   1440
aagcgtggcg gccccgagga gcgcgctcag gcgcacgggc cgcggaagac ggggccagct   1500
caggccctgc ggagttggct gtcgcat                                       1527
```

<210> SEQ ID NO 14
<211> LENGTH: 1251
<212> TYPE: DNA
<213> ORGANISM: Sorangium cellulosum

<400> SEQUENCE: 14

```
atgcccgccc gcaccccccg caagcccccg ccgcccgcct cgcccgctgg tcccgccggc     60
gcgccggacg acctcaccga cagcgatcgc gacgcgctgc tgcgctggcg gctcgcgctc    120
gggcccgagg ccgagcgggt cgacccgcgc ctctccctcg gcgggctcgg gggcgcggcg    180
cccgcgctcg acgtcgacgc gcggcggctc ggcgacctcg acaaggcgct ctcgttcatc    240
tacgacgagc gcgccggcgg cctcggcggc tcgcggccct acgtgcccga gtggctctcc    300
gccgtgcgcg agttcttcag ccacgaggtc gtcgccctcg tccagaagga cgccatcgag    360
cgaaaggggc tgacgcagct cctcttcgag cccgagacgc tgccgttcct cgagaagaac    420
gtcgagctcg tcgccacgct catgagcgcc aagggcctca tcccggacgc cgcgcgggac    480
accgcccggc agatcgtgcg cgaggtcgtc gaggaggtgc ggcgcgcgct cgaggccgag    540
gtccgcaccg ccgtcctcgg cgcgctgcgc cggaacacga cgagcccgct gcgcgtcctc    600
aggaacctcg actggaagcg caccatccgc aagaacctga aggggtggga cgcggagcgg    660
```

```
cgccgcctcg tccccgacaa gctctatttc tgggcgaacc agacgcgacg gcacgagtgg    720

gacgtcgcca tcctcgtcga ccagtcgggc tcgatgggcg agagcgtcgt ctacagctcc    780

atcatggccg cgatcttcgc gtcgctcgac gtcctccgca cccggctcct cttcttcgac    840

accgaggtcg tcgacgtgac tccgatgctc gtcgatccgg tcgacgtgct gttcacggcg    900

cagctcggcg gcggcaccga catcaaccgc gccgtggcct acgcccaggc gaacttcatc    960

gagcggcccg agaagacgct gctcatcctg atcaccgacc tgttcgaggg cggcaacgcc   1020

gaggagctcg tcgcgcgcat gcgccagctc gccgacagca aggtgaagtc gatctgcctg   1080

ctcgcgctgt cggacggcgg aaagccctcg tacgaccacg agatggcgca gaagctcgcc   1140

gcgctcggga ccccgtgctt cggctgcacg ccgaagctcc tcgtcaaggt ggtggagcgg   1200

ctcatgcgag gtcaggacct cggcccgctg ctcggcgccg aggcgcggtg a            1251
```

<210> SEQ ID NO 15
<211> LENGTH: 1059
<212> TYPE: DNA
<213> ORGANISM: Sorangium cellulosum

<400> SEQUENCE: 15

```
tcagggcgcg gcgagcggca gcctgcgtgc cgggcgcgcg gcctcgtgtc cgtcccccgc     60

ctcggccacc cgcccgcggt agatgcgatc gatccgatcg cgcgcgatga ccaggggctt    120

gtcgaaccgg ccaagcacgt tgcccttcag gatcccgcgc ttgtccgtca agcggtccag    180

caaccgcata tcgaggcgca gctcgatgtt catggccacc tgcatggcgg gccagaggac    240

ggcgccggcc ccgaacttgc tccagggcgc caggctcgcg aagagaaacg tatacatctc    300

cgacgactcc gggcccaccg ggttgaagaa gaccgctgac cggagcggga aggtgacggg    360

ctgattggtc ttcggatccc tgagggagtg gttgtagatc gtgtagaccg gcgagaagta    420

ggatgtccag tccaccacga atatcgcatc ctccgggatg ccgagcagct tctccatcgc    480

ccgcggcatg ggccgcctcg gacccgaatg cacgacccgg atcgtttcgt cggtcagggt    540

cacccgcgcc tcgacctctg gcatccgctc gagcgggtag ccgagcatga agtggacgaa    600

gggcgtgtgc tcgatctcga tgaaattgtc gagcgccagc tcgaacggca cggtcgcgcg    660

gtggcggagg agaccgcgcg gcacatatcc ctcgccctcg aggcgcggga acgctgcctg    720

cgaccccgcc cgcttcaccc agatggcacc gtaccgctcc acggcctcga acatgtcctc    780

gcgccgcgcg cacggccgcg ccgccggggt agccgggatc tcgccgcggc cgtccacggc    840

ccaacgccag ccatggtagg cgcacaccag ccgatcgccc tcgacccacc cctcgctcag    900

gcgcatgctg cggtggggc aacgatccgt gaatgcaccg aggccgcccg acgaggtccg     960

aaacaccacg atctcatgcc ccgcgagccg cacattgcgg ggcttgcggc ggagctcgtg   1020

gctcagcagt acagggtgcc agtggtcgag ctcagccat                          1059
```

<210> SEQ ID NO 16
<211> LENGTH: 1131
<212> TYPE: DNA
<213> ORGANISM: Sorangium cellulosum

<400> SEQUENCE: 16

```
tcagttcacc ccttggatgt gccgcgcaat ccgcggcgcc tcggctgcga tgtcgcggat     60

ctgccccgtg atgggattgc ggaagccgat gaagaacagc ccaggcgccg gcgtcggcgc    120

gccgtgccac cgcgggcagc cgtgctcgtc cgtgtagcgc gttgcattct cgagaaaatc    180

atcgagcccg ggccggtacc ccgtggcgag caccacgacg tcgaagggca gcccacggcc    240
```

-continued

```
gtccgtgaac gtcacgcccg tttccgtgaa tgcccgcggg ccgggcacca ccttgatctt    300
gccctgctgg atcagcgcca ccgtgccgat gtcgatcaac ggcatgcggc cttccttcaa    360
cgcccgggta ccggggccga ccgcgggccg acggatcccc cagcgcgaca gatcccccac    420
ggcgcgagac aggatcgcgg tcgcgaggcg atccccgacg gccagcggga ggcgctcgaa    480
gagggcaagg gcgttgaact gcgcaggcag cttgaacagc tcgcggggga tcacgtggtt    540
gccgctgcgg accgagaggg tcgtctccgc gcaatgctcc cacagatcca gcgcgatctc    600
gctggcggag ttgccggcgc ccaccacgag cacgcgctgg ccccggaatt ccgcaccaga    660
tcggtaggca gagctatgaa ggatgcgacc gcggaagcgc tcctggtcgg gccaggtggg    720
gacgttggga tgacggctgt agccggtggc cacgacgagc gcctggctcc tgagctcccc    780
cgcgtgcgtt cgggtcaccc accgcgatcc gtcgtggtac gcgcgctcca cctcgacacc    840
caggcgcggc tccaggcgga atcgctcggc gtaacgctcg aggtaatcga ccatctccac    900
ccgggaggga tacggcgcag aatactcggg ccagggctgc ccgggcagcg cggagagctg    960
cttgatcgtg ttgaggtgca gccggtcgta gtggcgccgc cacgtggcgc cgacggcctc   1020
cgacttctcg aggagaacga acgggattcc ctgctcgcgc aggcatgcgc ccaccgctag   1080
cccagacgga ccagcgccga cgataaccac atggcactct tcaacgtgca c            1131
```

<210> SEQ ID NO 17
<211> LENGTH: 1071
<212> TYPE: DNA
<213> ORGANISM: Sorangium cellulosum

<400> SEQUENCE: 17

```
tcacgcactc gcatgcccga cgcccgtgcc ttctgcctcg ccccgcgtct cgccgaagta     60
gatggagcgc atcaggcggt ggttgtgcac gagcgtcgcg tcgtatttgt tgagccgcat    120
ccctttcatc tcgaagggcg tatcggccac gtgcgggatg aacttcacat cgtcgcggat    180
ctccttccag gagagcgcta tcgccgccga tttgacgacc ggaagcagcg gacggaagcg    240
gggatcggtg atcttgacga acaggaacgc gcgcacgaac gtggtgcgct ccgtctctgg    300
cacgaagaag atgccggcgc gcgccacgac aggacgctcc atcccgttct gcgccgtcca    360
ccaggacgtg tacacggtgt agacggggct gaagcgggtc acccactggt tgtgaaatgt    420
gtcgcctggc tggagcagca tcagccgcgc gagcgtcgag ggcgctgcg gcgccgagta     480
cttgacctcg gtgcggtcct cgaagacgtc gcacgagaag tcgatgcgcg ccgcgtcctc    540
gggcgtccag ccgaggcggc cgtgaacgaa cggcgtgtgc tcgtcctcgg aggaattgtc    600
gaagatgacg tgcaggggcg ccggcgcgag gtgcgagaag gtgccggcat attcgaagcc    660
atcgctgctg aagtcgagct cgggcagcgc cgagcgcggc gtatcccggt gggctagcca    720
caggtatcca agctgctcga cgagctgaaa ggagcgtgta tcgcatcggg tgagcgacgg    780
ttgcgagggg caggctcccc gcccctcggc gtcgaaatgc cacccgtgat aggggcattc    840
caggcgcccg tccggccgga cacgcccctg cgatagcggc gcgagccggt gggggcacgc    900
atcggcgagc gcggcggggc ggccctgctc atcgcggaag agagcgtaag cattgcccgc    960
aaggacaacg cgaaccggct tccggccgag tttcgaggcc ggcaagacgg ggtgaaaatg   1020
gcggatgagg tcgcgagcag gcgcggcgtg cattgcgaga ccataacaca t            1071
```

<210> SEQ ID NO 18
<211> LENGTH: 1188
<212> TYPE: DNA

<213> ORGANISM: Sorangium cellulosum

<400> SEQUENCE: 18

```
ctatcggtag gcgacgatgc caccgaacgg ccacttcgcg tggtcctcgg gcgccggata     60
gacctcccat tcggagaacc cggccgcgcg gagcgacagc tcccactctt gcagcgtcag    120
gtaaccgaca tgctggcggc gaggcggatc gagcttggcc ttgctgtagg tgtgcagcat    180
cgactgaaaa aattcattgg ggaagaacac cccgggccga tcgcggaacg acatggtgaa    240
cgcgagctga ccgcccggct tcagcatcgt gtggaacgcc tggagggtgg cgtgaagatc    300
gcgcacgtcg tagagcacgt gctcgaggac gatcagatcg accgacgcgg cccgggcgaa    360
cgtgctgcca gcggagggca gcgtgtccag gtccaggcgc tggaaatgaa tgcgctgaaa    420
cacgtcggcc ggcgcgtggg tccgcagcca ctgcttcccc gtctccatca acagggcgct    480
gatgtcggtg taatcgtagc gggcgaggtt cttgctcagc gggaggaacc gcggatcgga    540
caacgcctgc cgcagcacca cgccgagccc cgcgcccccc tcgaatacag agatccccgg    600
cccctctgcg agcttggcca tcagcgcccg cgccagcatc acgttgcatg gcttcttggc    660
gggaaggctg atcatcgagt attcccagaa tttcagcgag gcctgcatcc cgtactggag    720
atccatggtg gccagcgcgt ccttgcccgc cagcaccggc ccggccaggc cccgatagcg    780
ctggaggaac tcgaccatct cgcccaggat cgcgcggtct gcgagcgcga tggactcctt    840
ctcggcgacg cgctttcgca ccgcctcgct gggcaccagc cgcccgctgg ggtcctgggt    900
gaggtctccc ttgtcgctga agtagtcgag cagcttcctg cgaaactgat aggcggtgac    960
cgacggagcc gactccggac gatcgtcgag cccccggaca gcgccgctcg ggtcgacgag   1020
gtgctcgagc aggatctcgc tggcaacaag ctcggtctga cgacggaatg cttctatgta   1080
agcggtgtaa gcgtcgttgt agagatcggt cacgtccaat cgttgtcgca tgcaggtcct   1140
cgcgggtgtg gcgcccatcc tgcgcagcgc agggacgaag caggtcat                1188
```

<210> SEQ ID NO 19
<211> LENGTH: 255
<212> TYPE: DNA
<213> ORGANISM: Sorangium cellulosum

<400> SEQUENCE: 19

```
tcacctggag ctcagcgcct gcccgtcgtt cccgcggttc ttgtgcacaa tggcgtacag     60
gatgagcatg taggcgaaga gccggaacag gtacaggtaa tggatggcgt cttcctcgac    120
gcgattcagg gcgacggcga tgcggcccag catcatcagc cagaacgccg ccgagaactt    180
cgcgaacagc cggtcgcccg tcttcttcca gaagcggagg aagaagagcg cgacggtcgc    240
gtacccgaac gtcat                                                     255
```

<210> SEQ ID NO 20
<211> LENGTH: 261
<212> TYPE: DNA
<213> ORGANISM: Sorangium cellulosum

<400> SEQUENCE: 20

```
ttactcgcgc aggtcccaga tgaggccata aaggagcagg gccagcccga tgagcgcggt     60
gaggtggcgc agcgatgata gatcgacgct ccggatcacg acgaggtcca cgaagagcag    120
gatgttgttc gctgcgagcg cggcgaagca gagcccgctc cacaagagga gacggacctt    180
gcgctgcgcg tatccgcgca ggagcagcac ggcgcacgcg atgctggtca gggcgcagag    240
gatgtagacc gccgctgcca t                                              261
```

<210> SEQ ID NO 21
<211> LENGTH: 402
<212> TYPE: DNA
<213> ORGANISM: Sorangium cellulosum

<400> SEQUENCE: 21
ctagccgccc tttcccttct tcgtgatcag gaatgcgtcc gagaagctct ggatgtcgct 60
cggcgggggc gtggcgtaga tgtgattgat cacgctcagc cggcgctcct tgtacgcctg 120
cgccaggtcg tcgatcgtcc ggcgggtctc atcgtctgcc ggggcgtacc ggtagaagat 180
gtcctccccg tcctcccggg ccacgatcag gcccctgctg gccaggcctc cgaaccggtc 240
ctggatcgac atcatgctgg accctatctc gcgcgccatc gcggccgcgc tccactcgcg 300
ctccgccgtg cgacgcatga gcagaagcac ttcgagttgc tcgatcgagg agatgtgcgc 360
gccgaggaag cgctggaccc ggtcggggag cccgctagac ac 402

<210> SEQ ID NO 22
<211> LENGTH: 5289
<212> TYPE: DNA
<213> ORGANISM: Sorangium cellulosum

<400> SEQUENCE: 22
tcaccggtgc aaccatagcc gcagcatagc gagcaggtgc tcgggatcca ccggcttcga 60
gatgtaatcg ttcgcgcccg cctcgaagca cttctcccgg tcgcccttca tcgccttggc 120
cgtgaccgcg atgatgggca gcgcatggtg ctcgggcttc gcgcggatgg cacggatcgt 180
gtcgtagccg tccatctctg gcatcatgat gtccatgagc acgatctcga tgtccggcgt 240
ccgctgcagc atctcgatcg ccgctctgcc cgtctccacg tagaccgtct tcatctgctg 300
ggcgtcgagg atggtcgtca tcgcgaagat gttccggacg tcgtcgtcga cgaccagcac 360
cttcttgccc gcgagcacct tgttcgactg gtgcagctcc tggagggtct gccgctgtcg 420
ctcggagagc gccgccacag ggcggtgcag gaacagggag acgtcgtcga agagccgctc 480
cttggagcgg acgtgcttga gcaccatcag ctggctgaag cggctcagct gcgcctcgtc 540
cgcggccgag atctcctccg gcgcgtagac caggacgggc agctccgtcg gcccgctgcc 600
ctgcgcgagc tgcccgatca gatcgaagca gcgcatgtcg ggcaggtcga ggtgcaggat 660
gaggacatcg gccccctcgg tgaggagcgc gtcgagcgcc tcctccccgg aggccacgct 720
ccggatcgtg acgtcgtcgc cgccgaggag ctcgacgagc tcctggcgct cggcctcgtc 780
cggctcggcg agcacgaccg tccgccggcg cgacaccatg aactgcgaga ggcgcctgaa 840
ggtctcgtcg agcgcgtccc gggtcttgag cggcttgcag agcacccccg tcgcgcccat 900
ccggagcgcg cgctcgcgct cctcgtccgt cgtgatcacc tggacgggga tgtgccgcgt 960
cgcgaggtcg cgcttcaccc ggtcgagcac gcgccagccg tccatgtccg gcaggttgat 1020
gtcgagcgtg atcgcgttca cccgccgctc gcggacgatg gagagcgccg ccccgccgcg 1080
gtaggcgagg atcgccttga acccgtggtc gtgcgcgaca tccatgacga agtgcgcgaa 1140
gctcgcgtcg ttctcgacga tgagcaccac ggagtcgctg ggctggaggc tcgcgctgtc 1200
gtcgacgctc tggttgagca ggtgcggcgg cggctcggcc gccgaccgcg gcgcgacgtc 1260
gcccgagacg agggccggcg gcgccgaggg cacctccgcg gcctgctcct tcctgcgcgg 1320
gcgcgccggc gtgtacgtga gcggcaggta aagcgtgaag gtgctcccgc tccccggcct 1380
gctcgagagc ttgatctcgc cgccgagcat ccacgcgatc tcgcggctga tcgcgagccc 1440

-continued

```
gaggccggtg ccgccgtact tccggctcgt cgagccgtcc gcctgctgga aggcctcgaa   1500
gatgatctgc tgcttgtcgt gcgggatgcc gatgcccgtg tcccgcaccg acatggcgat   1560
cgccgcgccg gcgcgcgaga ggccctcgtt ctcgatggtc caccccgagg tgaccagatc   1620
gacgtcgagc gcgacgctgc cgcgctccgt gaacttgaag gagttcgaga gcaggttctt   1680
gagcacctgc tgtacgcgct tcgcgtccgt gtagatgacc tgcggcaggt tctgcgcgaa   1740
gttgagctcg aactcgagcc tcttcgactc ggcgacgtgc tggaacgtgc gctcgacgta   1800
gtcttgcagg tcgctgaacg acagctcgcc cacgtcgacg atcacggtcc ccgactcgat   1860
cttggacagg tccaggatgt cgttgatcag cgcgagcagg tcgttgcccg acgagtggat   1920
cgtcttggcg aactcgacct gccgccccgt gaggttgcgg tcggtgttct tcgagagctg   1980
atcggacagg atgaggaggc tgttcagcgg cgtccggagc tcgtgcgaca tgttcgcgag   2040
gaactccgac ttgtacttgg aggtgatggc gagctgccgc gccttctcct cgagcgcctg   2100
ccgcgcctgc tcgacctcgc ggttcttccg ctcgacctcg acgttctgct gggcgagcag   2160
gcgagccttc tccccgagct cggcgttcgt ctgctgcagc tcctcctgct ggctctggag   2220
ctcgcgcgcg agggactgcg actgcttgag caggtcctct gtgcgcatgt tcgcctcgat   2280
cgtgttgagc acgatcccga tcgactccgt gagctggtcg aggaacgcct ggtgggtcgg   2340
gctgaatcgc tcgaacgacg cgagctcgat gaccgccttg acctgcccct cgaagagcac   2400
ggggatgacg atgatgttga ccggcggcgc ctcgccgagc ccgctcgtga tgcggatgta   2460
gtcgggggc gcgttgacga ggaggatctt ctccttctcg agcgcgcatt gcccgacgag   2520
cccttcgccg agcttgaaat ggttgtcgac gtgcttccgc accttgtacg cgtagctcgc   2580
gaggagcttg aggatcggct cctccttcgc cacgtccatc gtgaagaaca cgccctgctg   2640
cgcgccgacg accggggcca gctcggacag gatgagccga ccgacagtga gcagatcctt   2700
ctgcccctgg agcatgcgcg agaacttggc gaggttggtc ttgagccagt cctgctcgct   2760
gttcttcagc gtcgtgtcct tgaggttccg gatcatctca ttgatggtgt ccttgagcgc   2820
cgcgacctcc ccctgcgcct cgaccttgat ggaccgggtg aggtcgccct tggtcacggc   2880
ggtggcgacc tcggcgatcg cgcgcacctg cgtggtgagg ttcgcggcga gccggttcac   2940
gttgtcggtc aggtccttcc acgtgccggc cgcgccgggg acgctcgcct gaccgccgag   3000
cttgccctcg acgccgacct cgcgcgccac cgttgtcacc tggtcggcga aggtcgcgag   3060
cgtctcgatc acgccgttga tcgtgtccgc cagcgccgcg atctcgccct tcgcgtcgaa   3120
ggccagcttg cgcttcaggt cgccgttcgc gaccgcggtc acgaccttgg cgatgccgcg   3180
cacctggttc gtcaggttgc cggccatgaa gttcacgttg tcggtcaggt ccttccacgt   3240
gccggcgacg ccggggacgc tggcctgccc gccgagcttg ccctcggtgc ccacctcgcg   3300
cgccacgcgc gtcacctccg acgcgaacgc gttgagctgg tccaccatcg tgtagttgat   3360
ggtgttcttc agctccagga tctcgccgcg gacatcgacg gtgatcttct tcgacaggtc   3420
gccgttggcc acggccgttg tgacggcggc gatgttgcgc acctgcgcgg tcaggttcga   3480
cgccatcgag ttgacggagt cggtcaggtc cttccacgtg ccggcgacgc cggggacgct   3540
ggcctggccg ccgagcttgc cctcggtgcc cacctcgcgc gccacgcgcg tcacctccga   3600
cgcgaacgag cggagctgat ccaccatcgt gttgaaggtg tccttcagct ccaggatctc   3660
gccgcggaca tcgacggtga tcttcttcga caggtcgccg ttggccacgg ccgttgtgac   3720
ggcggcgatg ttgcgcacct gcgcggtcag gttcgacgcc atcgagttga cggagtcggt   3780
caggtccttc cacgtgccgg cgacgccctt cacctcggcc tgcccgccga gcttgccctc   3840
```

```
ggtgcctacc tcgcgcgcga cgcgcgtcac ctcggccgcg aaggagctga gctgatccac   3900

catcgtgttg aaggtgttct tcagctccag gatctcgccc ttgacgtcga cggtgatctt   3960

cttcgacagg tcgccgcggg ccacggccgt ggtcacgtcg gcgatgttgc gcacctgcgc   4020

ggtcaggttc gacgccatcg aattgacgga gtcggtcagg tccttccacg tgccggcgac   4080

gccggggacg ctggcctggc cgccgagctt tccctcggtg cccacctcgc gcgccacgcg   4140

cgtcacctcc gacgcgaacg agcggagctg atccaccatc gtgttgaagg tgtccttcag   4200

ctccaggatc tcgccgcgga catcgacggt gatcttcttc gacaggtcgc cgttggcgac   4260

ggccgtggtg acggcggcga tgttgcgcac ctgcgcggtc aggttcgacg ccatcgagtt   4320

gacggagtcg gtcaggtcct tccacgtgcc ggcgacgccg gggacgctgg cctggccgcc   4380

gagcttgccc tcggtgccca cctcgcgcgc cacgcgcgtc acctccgacg cgaacgagcg   4440

gagctgatcc accatcgtgt tgaaggtgtc cttcagctcc aggatcttct tcgacaggtc   4500

gccgttggcc acggccgttg tgacggcggc gatgttgcgc acctgcgcgg tcaggttcga   4560

cgccatcgag ttgacggagt cggtcaggtc cttccacgtg ccggcgacgc ccttcacctc   4620

ggcctgcccg ccgagcttgc cctcggtgcc tacctcgcgc gcgacgcgcg tcacctcggc   4680

cgcgaaggag ctgagctgat ccaccatcgt gttgaaggtg ttcttcagct ccaggatctc   4740

gcccttgacg tcgacggtga tcttcttcga caggtcgccg cgggccacgg ccgtggtcac   4800

gtcggcgatg ttgcgcacct gcgcggtcag gttcgacgcc atcgaattga cggagtcggt   4860

caggtccttc cacgtgccgg cgacgccggg gacgctggcc tggccgccga gctttccctc   4920

ggtgcccacc tcgcgcgcca cgcgcgtcac ctccgacgcg aacgagcgga gctgatccac   4980

catcgtgttg aaggtgtcct tcagctccag gatctcgccg cggacatcga cggtgatctt   5040

cttcgacagg tcgccgttgg cgacggccgt ggtgacgtcg gcgatgttgc ggacctgcgc   5100

ggtcaggttc gacgccatcg agttgacgga gtcggtcagg tccttccacg tgccggcgac   5160

gcctgtcacc tcggcctgcc cgccgagctt gccctcggtg cctacctcgc gcgccacgcg   5220

cgtcacctgg gccgcgaagg agcggagctg atccaccatc gtgttgaagg tgttcttcag   5280

ctccaggat                                                           5289
```

<210> SEQ ID NO 23
<211> LENGTH: 1075
<212> TYPE: PRT
<213> ORGANISM: Sorangium cellulosum

<400> SEQUENCE: 23

```
Met Pro Asp Thr Ser Ser Ser Ser Pro Val Met Ala Met Gly Leu Ser
1               5                   10                  15

Asp Ser Lys Ala Arg Ser Val Glu Asp Ala Arg Pro Ala Ser Gly Leu
            20                  25                  30

Pro Arg Pro Pro Ala Gly Ile Ala Val Val Gly Met Gly Cys Arg Phe
        35                  40                  45

Pro Gly Gly Ile Asp Ser Pro Gly Ser Leu Trp Ala Ala Leu Ser Gln
    50                  55                  60

Gly Arg Asp Leu Ile Ser Glu Val Pro Pro Asp Arg Trp Asp Val Asn
65                  70                  75                  80

Ala His Tyr Asp Ala Asp Ala Ser Val Pro Gly Lys Ile Ala Thr Arg
                85                  90                  95

His Gly Gly Phe Leu Ala Gly Val Ala Ala Phe Asp Ala Pro Phe Phe
            100                 105                 110
```

-continued

```
Asp Leu Ser Pro Arg Glu Ala Lys His Met Asp Pro Gln Gln Arg Leu
        115                 120                 125

Gly Leu Glu Thr Ala Trp Glu Ala Leu Glu Asp Ala Gly Leu Asp Ala
    130                 135                 140

Arg Ser Leu Arg Gly Ser Arg Ala Gly Val Phe Val Gly Ser Met Trp
145                 150                 155                 160

Ala Glu Tyr Asp Val Leu Ala Ser Arg His Pro Glu Ser Ile Ser Pro
                165                 170                 175

His Gly Ala Thr Gly Ser Asp Pro Gly Met Ile Ala Ala Arg Ile Ala
            180                 185                 190

Tyr Thr Phe Gly Leu Arg Gly Pro Ala Leu Ser Val Asn Thr Ala Ser
        195                 200                 205

Ser Ser Ser Leu Val Ala Val His Leu Ala Leu Gln Ser Leu Gln Ser
    210                 215                 220

Gly Glu Cys Glu Leu Ala Leu Ala Gly Gly Ala Asn Leu Ile Leu Thr
225                 230                 235                 240

Pro Tyr Asn Thr Ile Lys Met Thr Lys Leu Gly Thr Met Ser Pro Asp
                245                 250                 255

Gly Arg Cys Lys Ala Phe Asp His Arg Ala Asn Gly Tyr Val Arg Ala
            260                 265                 270

Glu Gly Val Gly Phe Val Val Leu Lys Pro Leu Ser Arg Ala Thr Ala
        275                 280                 285

Asp Gly Asp Arg Ile Tyr Ala Val Val Arg Gly Ser Ala Val Asn Asn
    290                 295                 300

Asp Gly Leu Thr Asp Gly Leu Thr Ala Pro Ser Gly Glu Ala Gln Glu
305                 310                 315                 320

Ala Val Leu Arg Glu Ala Tyr Ala Arg Ala Gly Val Ser Pro Ala Glu
                325                 330                 335

Val Asp Tyr Val Glu Ala His Gly Thr Gly Thr Pro Leu Gly Asp Arg
            340                 345                 350

Val Glu Ala Thr Ala Leu Gly Arg Val Leu Gly Ala Gly Arg Ala Ala
        355                 360                 365

Asp Arg Ala Leu Arg Val Gly Ser Val Lys Thr Asn Leu Gly His Ala
    370                 375                 380

Glu Ala Ala Ala Gly Val Ile Gly Leu Met Lys Thr Ala Leu Ser Leu
385                 390                 395                 400

Arg His Gly Ser Leu Pro Ala Ser Leu His Val Glu Arg Pro Asn Pro
                405                 410                 415

Glu Ile Pro Leu Glu Ser Leu Gly Leu Arg Leu Gln Thr Ala His Gly
            420                 425                 430

Val Trp Pro Glu Val Asp Arg Pro Arg Arg Ala Gly Val Ser Ser Phe
        435                 440                 445

Gly Phe Gly Gly Thr Asn Cys His Val Val Ile Glu Glu Trp Arg Gly
    450                 455                 460

Gly Leu Gln Gln Ser Ala Ala Glu Ala Gly Ser Asp Pro Gly Ala Ala
465                 470                 475                 480

Val Pro Pro Pro Gly Leu Pro Leu Val Leu Ser Ala Arg Asp His Gly
                485                 490                 495

Ala Leu Arg Ala Gln Ala Gly Arg Trp Ala Ala Trp Leu Thr Glu His
            500                 505                 510

Arg Glu Ala Arg Trp Ala Asp Val Val His Thr Ala Ala Val Arg Arg
        515                 520                 525
```

-continued

```
Thr His Leu Gly Ala Arg Ala Ala Val Met Ala Ala Gly Val Ala Glu
    530                 535                 540

Ala Val Asp Ala Leu Lys Ala Leu Ala Asp Gly Arg Ala His Gly Ala
545                 550                 555                 560

Val Thr Val Gly Glu Ala Arg Glu Arg Gly Lys Val Val Phe Val Phe
                565                 570                 575

Pro Gly Gln Gly Ser Gln Trp Pro Ala Met Gly Arg Ala Leu Leu Ser
            580                 585                 590

Ala Ser Lys Val Phe Ala Glu Ala Val Glu Ala Cys Asp Ala Ala Leu
        595                 600                 605

Arg Pro Leu Thr Gly Trp Ser Val Leu Ser Leu Leu Arg Gly Asp Ala
    610                 615                 620

Gly Glu Ala Ala Pro Ser Leu Asp Arg Val Asp Ala Val Gln Pro Ala
625                 630                 635                 640

Leu Phe Ala Met Ala Val Gly Leu Ala Ala Val Phe Arg Ala Trp Gly
                645                 650                 655

Leu Asp Pro Ser Ala Val Val Gly His Ser Gln Gly Glu Val Pro Ala
            660                 665                 670

Ala Tyr Val Ala Gly Ala Leu Ser Leu Asp Asp Ala Ala Arg Val Val
        675                 680                 685

Ala Val Arg Ser Ala Leu Val Arg Arg Leu Ala Gly Ala Gly Ala Met
    690                 695                 700

Ala Ala Val Glu Leu Pro Ala Gly Glu Val Glu Arg Arg Leu Ala Pro
705                 710                 715                 720

Phe Gly Gly Ala Leu Ala Ile Ala Val Val Asn Thr Ser Ser Ser Thr
                725                 730                 735

Ala Val Ser Gly Asp Ala Glu Ala Val Asp Arg Leu Val Ala Gln Leu
            740                 745                 750

Glu Ala Glu Gly Ile Phe Cys Arg Lys Val Asn Val Asp Tyr Ala Ser
        755                 760                 765

His Ser Ala His Val Asp Val Val Leu Pro Glu Leu Leu Glu Arg Leu
    770                 775                 780

Ala Pro Val Arg Pro Gly Ala Thr Arg Ile Pro Phe Tyr Ser Thr Val
785                 790                 795                 800

Thr Gly Gly Val Leu Glu Gly Thr Ala Leu Asp Gly Ala Tyr Trp Cys
                805                 810                 815

Arg Asn Leu Arg Gln Pro Val Arg Leu Asp Arg Ala Leu Ala Arg Leu
            820                 825                 830

Leu Asp Asp Gly His Gly Val Phe Val Glu Val Ser Ala His Pro Val
        835                 840                 845

Leu Ala Ser Pro Leu Thr Ala Ala Cys Ala Glu Arg Glu Gly Val Val
    850                 855                 860

Val Gly Ser Leu Gln Arg Asp Asp Gly Gly Leu Ala Arg Leu Leu Gly
865                 870                 875                 880

Ser Leu Gly Ala Leu His Val Gln Gly Gln Pro Val Asp Trp Arg Ala
                885                 890                 895

Val Leu Ala Pro Phe Gly Gly Ser Leu Val Asp Leu Pro Thr Tyr Ala
            900                 905                 910

Phe Gln Arg Gln Arg Tyr Trp Phe Asp Thr Asp Glu Ser Val Ala Leu
        915                 920                 925

Ala Ala Ala Ser Ser Val Ala Glu Glu Ser Trp Ser Glu Lys Leu Ala
    930                 935                 940

Gly Leu Ser Ser Ala Arg Arg Glu Glu Arg Leu Leu Glu Trp Val Arg
```

```
945                 950                 955                 960

Ala Glu Ile Ala Ala Val Leu Gly Leu Glu Ala Pro Ala Val Pro Pro
                965                 970                 975

Asp Val Leu Leu Arg Asp Leu Gly Leu Lys Ser Pro Ile Ala Val Glu
            980                 985                 990

Leu Gly Ser Arg Leu Gly Arg Arg  Thr Arg Arg Lys Leu  Pro Val Thr
        995                 1000                 1005

Phe Val  Tyr Asn His Pro Thr  Pro Arg Ala Ile Ala  Arg Ala Leu
    1010                 1015                 1020

Leu Glu  Gly Met Phe Ser Ser  Ile Lys Asp Ser Ala  Ser Ser Ala
    1025                 1030                 1035

Ala Asp  Asp Arg Arg Pro Pro  Gly Val Leu Glu Asp  Val Ala Pro
    1040                 1045                 1050

Pro Gln  Ala Leu Glu Thr Ser  Glu Met Ser Asp Asp  Glu Leu Phe
    1055                 1060                 1065

Gln Ser  Ile Asp Ala Leu Val
    1070                 1075


<210> SEQ ID NO 24
<211> LENGTH: 3679
<212> TYPE: PRT
<213> ORGANISM: Sorangium cellulosum

<400> SEQUENCE: 24

Met Asp Arg Ser Asp Lys Leu Arg Ala Tyr Leu Glu Lys Thr Thr Ala
1               5                   10                  15

Ser Leu Val Glu Ala Lys Gly Arg Ile Arg Glu Leu Glu Ala Arg Ser
            20                  25                  30

Arg Glu Pro Ile Ala Ile Val Ala Met Ala Cys Arg Phe Pro Gly Gly
        35                  40                  45

Val Asp Ser Pro Glu Lys Leu Trp Ala Leu Leu Asp Glu Glu Arg Asp
    50                  55                  60

Ala Ile Thr Glu Val Pro Pro Ser Arg Trp Asp Leu Glu Arg Phe Tyr
65                  70                  75                  80

Asp Pro Asp Pro Asp Ala Ala Gly Lys Thr Tyr Ser Arg Trp Gly Gly
                85                  90                  95

Phe Val Gly Asp Leu Asp Arg Phe Asp Ala Ala Phe Phe Gly Ile Ser
            100                 105                 110

Pro Arg Glu Ala Arg Ser Ile Asp Pro Gln Glu Arg Trp Leu Leu Glu
        115                 120                 125

Thr Thr Trp Glu Ala Leu Glu Arg Ala Gly Val Arg Ala Asp Thr Leu
    130                 135                 140

Glu Gly Thr Leu Gly Gly Val Tyr Ile Gly Leu Ser Gly Ser Glu Tyr
145                 150                 155                 160

Gln Thr Glu Ala Phe His Asp Ala Glu Arg Ile Asp Ala Tyr Ser Leu
                165                 170                 175

Thr Gly Ala Ser Pro Ser Thr Thr Val Gly Arg Leu Ala Tyr Trp Leu
            180                 185                 190

Gly Leu Arg Gly Pro Ala Val Ala Val Asp Thr Ala Cys Ser Ser Ser
        195                 200                 205

Leu Val Ala Val His Leu Ala Cys Gln Ala Leu Arg Asn Gly Glu Cys
    210                 215                 220

Asp Phe Ala Leu Ala Gly Gly Val Asn Ala Leu Leu Ala Pro Glu Ser
225                 230                 235                 240
```

-continued

```
Tyr Val Ala Phe Cys Arg Leu Arg Ala Leu Ser Pro Thr Gly Arg Cys
                245                 250                 255

Gln Thr Phe Ser Ala Asp Ala Asp Gly Tyr Val Arg Ala Glu Gly Cys
            260                 265                 270

Gly Val Leu Leu Leu Lys Arg Leu Ser His Ala Gln Arg Asp Gly Asp
        275                 280                 285

Arg Val Leu Ala Val Ile Arg Gly Asn Ala Ile Asn Gln Asp Gly Arg
    290                 295                 300

Ser Gln Gly Leu Thr Ala Pro Asn Gly Leu Ala Gln Glu Asp Val Ile
305                 310                 315                 320

Arg Arg Ala Leu Ser Gln Ala Ala Val Glu Pro Thr Thr Val Asp Val
                325                 330                 335

Val Glu Cys His Gly Thr Gly Thr Ala Leu Gly Asp Pro Ile Glu Val
            340                 345                 350

Gln Ala Leu Gly Ala Val Tyr Gly Asp Gly Arg Pro Gly Asp Arg Pro
        355                 360                 365

Leu Val Ile Gly Ser Val Lys Thr Asn Ile Gly His Thr Glu Ala Ala
    370                 375                 380

Ala Gly Met Ala Gly Leu Ile Lys Ala Val Leu Ser Leu Gln His Ala
385                 390                 395                 400

Gln Val Pro Arg Ser Leu His Phe Ala Ala Pro Ser Pro Tyr Ile Pro
                405                 410                 415

Trp Asp Thr Leu Pro Val Arg Val Ala Ala Gln Arg Val Ala Trp Glu
            420                 425                 430

Arg Arg Glu His Pro Arg Arg Ala Gly Ile Ser Ser Phe Gly Ile Ser
        435                 440                 445

Gly Thr Asn Ala His Val Ile Leu Glu Glu Ala Pro Glu Ala Pro Ala
    450                 455                 460

Thr Ala Pro Glu Ala Ala Ala Val Thr Ser Thr Leu Pro Leu Leu Val
465                 470                 475                 480

Ser Gly Arg Asp Glu Ala Ala Leu Arg Ala Gln Ala Glu Arg Trp Ala
                485                 490                 495

Ala Trp Leu Ala Ala His Pro Glu Ala Arg Trp Ala Asp Val Val His
            500                 505                 510

Thr Ala Ala Val Arg Arg Thr His Leu Glu Ala Arg Ala Ala Val Ala
        515                 520                 525

Ala Gly Asn Ala Ala Asp Ala Ala Ala Ala Leu Gly Ala Leu Ala Ala
    530                 535                 540

Gly Gln Pro His Lys Ala Val Ser Leu Gly Glu Ala Arg Ala Arg Gly
545                 550                 555                 560

Asp Val Val Phe Val Val Pro Gly Gln Gly Ser Gln Trp Pro Ala Met
                565                 570                 575

Gly Arg Ala Leu Leu Ala Glu Ser Glu Val Phe Ala Ala Ala Val Ala
            580                 585                 590

Ala Cys Asp Ala Ala Leu Arg Pro Phe Thr Gly Trp Ser Val Leu Ser
        595                 600                 605

Val Leu Arg Gly Glu Gln Gly Glu Ala Val Pro Pro Ala Asp Arg Val
    610                 615                 620

Asp Val Val Gln Pro Ala Leu Phe Ala Met Ala Val Gly Leu Ser Ala
625                 630                 635                 640

Val Trp Arg Ala Trp Gly Ile Glu Pro Ser Ala Val Val Gly His Ser
                645                 650                 655

Gln Gly Glu Val Ala Ala Ala Tyr Val Ala Gly Ala Leu Thr Leu Glu
```

-continued

```
            660                 665                 670

Asp Ala Ala Arg Val Val Ala Leu Arg Ser Gln Leu Val Arg Arg Ile
        675                 680                 685

Ala Gly Gly Gly Ala Met Ala Val Ile Glu Arg Pro Val Gly Glu Val
    690                 695                 700

Glu Gln Arg Leu Ser Arg Phe Gly Gly Gln Leu Ser Val Ala Ala Val
705                 710                 715                 720

Asn Thr Pro Gly Ser Thr Val Val Ser Gly Asp Ala Ala Ala Val Asp
                725                 730                 735

Arg Leu Leu Ala Glu Leu Glu Thr Ala Arg Val Phe Ala Arg Arg Ile
            740                 745                 750

Lys Val Asp Tyr Ala Ser His Ser Ala His Val Asp Ala Ile Leu Pro
        755                 760                 765

Glu Leu Glu Ala Cys Leu Ala Ser Val Glu Pro Arg Thr Cys Ala Ile
    770                 775                 780

Pro Leu Tyr Ser Thr Val Thr Gly Glu Val Leu Ala Gly Pro Glu Leu
785                 790                 795                 800

Gly Ala Thr Tyr Trp Cys Arg Asn Leu Arg Glu Pro Val Arg Leu Asp
                805                 810                 815

Arg Ala Leu Ser Arg Leu Leu Ala Asp Gly His Gly Val Phe Val Glu
            820                 825                 830

Val Ser Ala His Pro Val Leu Ala Met Pro Leu Ser Ala Ala Ser Ala
        835                 840                 845

Glu Arg Gly Gly Val Val Val Gly Ser Leu Gln Arg Asp Asp Gly Gly
    850                 855                 860

Leu Gly Arg Leu Thr Ser Met Leu Gly Ala Leu His Val His Gly His
865                 870                 875                 880

Ala Val Ser Trp Gln Arg Val Leu Ala Pro Tyr Gly Gly Ala Leu Val
                885                 890                 895

Gly Leu Pro Thr Tyr Ala Phe Gln Arg Gln Arg His Trp Leu Glu Ala
            900                 905                 910

Pro Arg Tyr Ala Ala Glu Asp Thr Asp Gly Ala Ala Arg Arg Asp Pro
        915                 920                 925

Leu Tyr Arg Val Thr Trp Ile Glu Ala Ala Leu Glu Glu Ala Pro Trp
    930                 935                 940

Ala Pro Glu Arg His Val Val Leu Gly Gly Gly Gly Ala Leu Ala Ala
945                 950                 955                 960

Gly Leu Gly Ala Leu Ala Leu Ala Gly Leu Pro Glu Leu Leu Glu Ala
                965                 970                 975

Leu Glu Asn Arg Ala Ala Ala Pro Glu Arg Leu Val Leu Asp Leu Thr
            980                 985                 990

Glu Gly Arg Pro Gly Ala Val Ala  Glu Ser Val His Ala  Thr Thr Arg
        995                 1000                1005

Asp Ala  Leu Ala Leu Val Gln  Ala Trp Leu Ala Ala  Pro Arg Leu
    1010                1015                1020

Ser Gly  Thr Glu Leu Val Val  Val Thr Arg Glu Ala  Val Ala Ala
    1025                1030                1035

Gly Pro  Asp Glu Gly Val Ala  Ala Leu Gly Pro Ala  Ala Val Trp
    1040                1045                1050

Gly Leu  Leu Arg Thr Ala Arg  Val Glu His Pro Glu  Arg Ala Val
    1055                1060                1065

Arg Ala  Val Asp Leu Gly Arg  Glu Pro Leu Asp Val  Ala Val Leu
    1070                1075                1080
```

```
Arg Arg Ala Leu Gly Ala Val Ala Glu Pro Glu Leu Ala Leu Arg
    1085                1090                1095

Ala Gly Gly Ala Arg Ala Ala Arg Leu Arg Ala Val Asp Ala Gly
    1100                1105                1110

Ala Gly Ala Arg Glu Pro Ala Ala Ala Leu Asp Pro Gln Gly Thr
    1115                1120                1125

Val Trp Ile Thr Gly Gly Thr Gly Glu Leu Gly Arg Gln Ile Ala
    1130                1135                1140

Arg His Leu Val Ala Ala His Gly Val Arg His Leu Leu Leu Thr
    1145                1150                1155

Ser Arg Arg Gly Ala Ala Ala Pro Asp Ala Glu Ala Leu Val Glu
    1160                1165                1170

Gln Leu Arg Ala Asp Gly Ala Glu Thr Val Glu Val Val Ala Cys
    1175                1180                1185

Asp Val Thr Asp Gly Ala Ala Leu Ser Ala Ala Val Gln Ala Ala
    1190                1195                1200

Ala Ala Arg His Pro Leu Thr Ala Val Val His Thr Ala Gly Glu
    1205                1210                1215

Leu Ala Asp Gly Val Leu Thr Gly Leu Thr Ala Glu Gln Leu Ala
    1220                1225                1230

Arg Val Leu Ala Pro Lys Val Asp Gly Ala Cys His Val Tyr Ala
    1235                1240                1245

Ala Ala Gln Asp Gln Pro Leu Ala Ala Phe Val Leu Phe Ser Ser
    1250                1255                1260

Ile Val Gly Thr Leu Gly Asn Ala Gly Gln Ala Asn Tyr Gly Ala
    1265                1270                1275

Ala Asn Ala Phe Leu Asp Ala Phe Ala Ala Gln Leu Arg Ala Arg
    1280                1285                1290

Gly Val Pro Ala Thr Ser Leu Ala Trp Gly Phe Trp Glu Gln Ala
    1295                1300                1305

Gly Leu Gly Met Thr Ser His Leu Gly Ala Ala Asp Leu Ala Arg
    1310                1315                1320

Leu Arg Arg Gln Gly Leu Ala Pro Leu Ser Val Ala Gln Gly Leu
    1325                1330                1335

Arg Leu Leu Asp Arg Ala Leu Ala Arg Ala Glu Ala Thr Leu Val
    1340                1345                1350

Pro Ala Ala Leu Asp Leu Pro Ala Leu Gln Arg Ala Ala Ser Asp
    1355                1360                1365

Ala Gly Arg Val Pro Pro Leu Leu Arg Gly Leu Val Arg Thr Ser
    1370                1375                1380

Pro Gly Arg Pro Thr Ala Thr Ala Thr Pro Glu Ala Gly Pro Ala
    1385                1390                1395

Ala Ser Ala Leu Arg Ala Arg Leu Ser Ala Leu Pro Glu Ala Glu
    1400                1405                1410

Arg Pro Gly Ala Leu Leu Asp Leu Val Arg Thr Glu Val Ala Val
    1415                1420                1425

Val Leu Gln Leu Ala Gly Pro Ala Gln Val Pro Ala Asp Lys Pro
    1430                1435                1440

Leu Lys Glu Leu Gly Leu Asp Ser Leu Thr Ala Val Glu Leu Arg
    1445                1450                1455

Asn Arg Leu Gly Ala Arg Ala Glu Thr Val Leu Pro Thr Thr Leu
    1460                1465                1470
```

-continued

```
Ala Phe  Asp His Pro Thr Pro  Arg Ala Ile Ala Asp  Leu Leu Leu
    1475                 1480                 1485

Gln Arg  Ala Phe Ser Glu Leu  Ala Ala Ala Lys Ala  Thr Arg Ala
    1490                 1495                 1500

Arg Gly  Ala His Asp Glu Pro  Ile Ala Ile Val Ser  Met Ala Cys
    1505                 1510                 1515

Arg Leu  Pro Gly Ser Val Asp  Thr Pro Ala Ala Leu  Trp Lys Leu
    1520                 1525                 1530

Leu Ala  Glu Gly Arg Asp Ala  Ile Gly Pro Phe Pro  Glu Gly Arg
    1535                 1540                 1545

Gly Trp  Asp Val Ala Gly Leu  Tyr Asp Pro Asp Pro  Asp Val Pro
    1550                 1555                 1560

Gly Lys  Ser Ile Thr Thr Gln  Gly Gly Phe Leu Tyr  Asp Ala Asp
    1565                 1570                 1575

Arg Phe  Asp Pro Thr Phe Phe  Gly Ile Ser Pro Arg  Glu Ala Glu
    1580                 1585                 1590

Arg Met  Asp Pro Gln Gln Arg  Leu Leu Leu Glu Cys  Ala Trp Glu
    1595                 1600                 1605

Ala Leu  Glu Arg Ala Gly Leu  Ala Pro His Ala Leu  Glu Ala Ser
    1610                 1615                 1620

Ala Thr  Gly Val Phe Val Gly  Leu Ala His Gly Asp  Tyr Gly Gly
    1625                 1630                 1635

Arg Leu  Leu Gln Gln Leu Glu  Ser Phe Asp Gly His  Val Leu Thr
    1640                 1645                 1650

Gly Asn  Phe Leu Ser Val Gly  Ser Gly Arg Ile Ala  Tyr Thr Leu
    1655                 1660                 1665

Gly Leu  Arg Gly Pro Ala Met  Thr Val Asp Thr Ala  Cys Ser Ser
    1670                 1675                 1680

Ser Leu  Val Ala Val His Leu  Ala Cys Met Ser Leu  Arg Ala Gly
    1685                 1690                 1695

Glu Cys  Asp Met Ala Leu Ala  Gly Gly Ala Thr Val  Met Ala Thr
    1700                 1705                 1710

Pro Met  Ile Phe Val Glu Phe  Ser Arg Gln Arg Gly  Thr Ala Leu
    1715                 1720                 1725

Asp Gly  Arg Cys Lys Ala Phe  Gly Ala Gly Ala Asp  Gly Ala Gly
    1730                 1735                 1740

Trp Ser  Glu Gly Cys Gly Ile  Leu Ala Leu Lys Arg  Leu Ser Asp
    1745                 1750                 1755

Ala Gln  Arg Asp Gly Asp Arg  Val Leu Ala Val Ile  Arg Gly Ser
    1760                 1765                 1770

Ala Val  Asn Gln Asp Gly Arg  Ser Gln Gly Leu Thr  Ala Pro Asn
    1775                 1780                 1785

Gly Pro  Ala Gln Gln Asp Val  Ile Arg Gln Ala Leu  Ala Ala Ala
    1790                 1795                 1800

Gly Leu  Thr Pro Ala Asp Val  Asp Ala Val Glu Ala  His Gly Thr
    1805                 1810                 1815

Gly Thr  Arg Leu Gly Asp Pro  Ile Glu Ala Gln Ala  Leu Leu Ala
    1820                 1825                 1830

Thr Tyr  Gly Ala Ala His Thr  Ala Glu Arg Pro Leu  Trp Leu Gly
    1835                 1840                 1845

Ser Leu  Lys Ser Asn Leu Gly  His Thr Gln Val Ala  Ala Gly Val
    1850                 1855                 1860

Ser Gly  Leu Met Lys Leu Val  Leu Ala Leu Gln His  Ala Glu Leu
```

-continued

```
    1865                1870                1875

Pro Arg  Thr Leu His Ala Asp  Pro Pro Ser Pro His  Val Asp Trp
    1880                1885                1890

Ser Gln  Gly His Val Lys Leu  Leu Asn Glu Pro Val  Pro Trp Pro
    1895                1900                1905

Arg Thr  Asp Arg Pro Arg Arg  Ala Ala Val Ser Ser  Phe Gly Ile
    1910                1915                1920

Ser Gly  Thr Asn Ala His Val  Ile Val Glu Glu Ala  Pro Ala Glu
    1925                1930                1935

Ala Pro  Ala Thr Ala Ala Asp  Ala Lys Ser Val Glu  Ala Leu Pro
    1940                1945                1950

Ile Leu  Pro Leu Leu Val Ser  Gly Ser Asp Glu Pro  Ala Leu Arg
    1955                1960                1965

Ala Gln  Val Arg Arg Leu Val  Glu His Leu Arg Ser  His Pro Asp
    1970                1975                1980

Glu Arg  Leu Leu Asp Val Ala  Ala Ser Leu Ala Thr  Thr Arg Ala
    1985                1990                1995

His Leu  Ala Met Arg Leu Ala  Leu Pro Val Ser Ala  Gly Ala Pro
    2000                2005                2010

Arg Asp  Ala Trp Val Asp Glu  Leu Glu Ala Phe Ala  Arg Gly Gly
    2015                2020                2025

Ala Ala  Pro Thr Gln Ala Ser  Gln Thr Pro Ala Glu  Ser Ser Ala
    2030                2035                2040

Gly Lys  Val Ala Val Leu Phe  Thr Gly Gln Gly Ser  Gln Arg Ala
    2045                2050                2055

Ala Met  Gly Arg Ala Leu Tyr  Ala Thr His Pro Val  Phe Arg Ala
    2060                2065                2070

Ala Leu  Asp Ala Ala Cys Ala  Glu Leu Asp Arg His  Leu Asp Arg
    2075                2080                2085

Pro Leu  His Ser Val Leu Phe  Ala Asp Ala Gly Thr  Glu Ala Ala
    2090                2095                2100

Ala Leu  Leu Asp Gln Thr Gly  Trp Ala Gln Pro Ala  Leu Phe Ala
    2105                2110                2115

Leu Glu  Val Ala Leu Tyr Arg  Gln Trp Glu Ala Trp  Gly Leu Arg
    2120                2125                2130

Pro Glu  Leu Leu Leu Gly His  Ser Ile Gly Glu Leu  Ala Ala Ala
    2135                2140                2145

His Val  Ala Gly Val Leu Asp  Leu Pro Asp Ala Ser  Ala Leu Val
    2150                2155                2160

Ala Ala  Arg Gly Arg Leu Met  Gln Ala Leu Pro His  Gly Gly Ala
    2165                2170                2175

Met Ala  Ser Ile Glu Ala Thr  Glu His Glu Leu Leu  Pro Leu Leu
    2180                2185                2190

Asp Gln  His Thr Gly Arg Leu  Ser Leu Ala Ala Leu  Asn Ala Pro
    2195                2200                2205

Arg Gln  Ser Val Val Ser Gly  Asp Leu His Ala Val  Asp Gln Val
    2210                2215                2220

Cys Ala  His Phe Ile Ala Leu  Gly Arg Arg Ala Lys  Arg Leu Asp
    2225                2230                2235

Val Ser  His Ala Phe His Ser  Ala His Met Gln Pro  Met Leu Asp
    2240                2245                2250

Ala Phe  Ala Ser Val Ala Arg  Gly Leu Thr Phe His  Pro Pro Arg
    2255                2260                2265
```

-continued

```
Leu Pro  Ile Val Ser Ser Val  Thr Gly Ala Arg Ala  Thr Thr Asp
    2270                 2275                 2280

Gln Leu  Thr Ser Pro Asp Tyr  Trp Val Gln Gln Val  Arg Glu Pro
    2285                 2290                 2295

Val Arg  Phe Leu Asp Ala Met  Arg Ser Leu His Ala  Ala Gly Ala
    2300                 2305                 2310

Ala Thr  Phe Val Glu Cys Gly  Pro His Gly Val Leu  Thr Ala Ala
    2315                 2320                 2325

Gly Ala  Glu Cys Leu Ala Pro  Glu Gly Ala Arg Asp  Ala Gly Phe
    2330                 2335                 2340

Val Thr  Ser Leu Arg Lys Asp  Arg Asp Glu Ala Leu  Ala Leu Val
    2345                 2350                 2355

His Ala  Ala Cys Ala Val His  Val Arg Gly His Ala  Leu Asp Trp
    2360                 2365                 2370

Leu Arg  Phe Phe Asp Ala Thr  Gly Ala Arg Arg Val  Glu Leu Pro
    2375                 2380                 2385

Thr Tyr  Ala Phe Gln Arg Gln  Arg Tyr Trp Leu Glu  Ala Pro Arg
    2390                 2395                 2400

Pro Arg  Pro Ser Leu Glu Gly  Val Gly Leu Thr Ala  Ala Asn His
    2405                 2410                 2415

Pro Trp  Leu Gly Ala Ala Val  Arg Leu Ala Asp Arg  Asp Gly Tyr
    2420                 2425                 2430

Val Leu  Ser Gly Arg Leu Ser  Thr Ile Asp His Pro  Trp Val Leu
    2435                 2440                 2445

Asp His  Val Val Leu Gly Thr  Ala Leu Leu Pro Gly  Thr Gly Phe
    2450                 2455                 2460

Val Glu  Leu Ala Trp Ala Ala  Ala Glu Ala Val Gly  Leu Pro Gly
    2465                 2470                 2475

Val Ser  Glu Leu Ala Ile Glu  Ala Pro Leu Ala Leu  Pro Ala Arg
    2480                 2485                 2490

Gly Ala  Val Ala Leu Gln Ile  Ala Ile Glu Ala Pro  Asp Pro Ala
    2495                 2500                 2505

Gly Arg  Arg Gly Val Ala Ile  Tyr Ser Arg Pro Asp  Gly Ala Ala
    2510                 2515                 2520

Asp Ala  Pro Trp Thr Ala His  Ala Arg Gly Val Leu  Gly Ala Ala
    2525                 2530                 2535

Ala Pro  Asp Arg Asp Ala Ala  Trp Ala Gln Gly Ala  Trp Pro Pro
    2540                 2545                 2550

Pro Gly  Ala Val Pro Val Asp  Val Thr Gln Arg Ile  Glu Ile Val
    2555                 2560                 2565

Asp Ala  Trp Val Gly Pro Ala  Phe Arg Gly Val Thr  Ala Leu Trp
    2570                 2575                 2580

Arg Val  Gly Arg Thr Ile Tyr  Ala Asp Val Ala Leu  Pro Asp Gly
    2585                 2590                 2595

Val Ala  Ser Thr Ala Gln Asp  Phe Gly Leu His Pro  Ala Leu Leu
    2600                 2605                 2610

Asp Val  Ala Leu Arg Ala Phe  Leu Arg Ala Glu Leu  Gly Ala Asp
    2615                 2620                 2625

Pro Ser  Pro Arg Glu Gly Thr  Val Val Pro Phe Ala  Trp Ser Asp
    2630                 2635                 2640

Val Val  Leu Glu Ala Arg Gly  Thr Ala Ala Leu Arg  Val Arg Val
    2645                 2650                 2655
```

```
Glu Val  Ala Ala Asp Gly Asp  Gly Asp Ala Ile Thr  Ala Ser Ile
    2660                 2665                 2670

Gln Leu  Ala Asp Gly Gln Gly  Arg Pro Val Ala Arg  Val Gly Ala
    2675                 2680                 2685

Leu Gln  Met Arg Trp Thr Thr  Ala Glu Arg Val Arg  Ala Ala Ala
    2690                 2695                 2700

Gly Ala  Ala Glu Arg Asp Leu  Tyr Arg Val Ala Trp  Thr Asp Val
    2705                 2710                 2715

Ala Leu  Asp Asp Ala Ala Phe  Ala Pro Glu Glu His  Val Val Val
    2720                 2725                 2730

Gly Gly  Asp Gly Ala Leu Ala  Ala Ala Leu Gly Ala  Arg Val Val
    2735                 2740                 2745

Ala Gly  Leu Pro Glu Leu Leu  Ala Ser Leu Pro Asp  Gly Ala Ala
    2750                 2755                 2760

Ala Pro  Arg Arg Leu Val Val  Asp Leu Thr Ala Asp  Ala Ala Gly
    2765                 2770                 2775

Ala Val  Val Asp Ala Val His  Ala Ala Ala Arg Asp  Ala Leu Ser
    2780                 2785                 2790

Leu Val  Gln Gly Trp Leu Ala  Ala Pro Gln Leu Ala  Ala Thr Glu
    2795                 2800                 2805

Leu Val  Val Val Thr Arg Gly  Ala Val Ala Val Ala  Pro Asp Glu
    2810                 2815                 2820

Gly Val  Ala Ala Leu Gly Pro  Ala Ala Val Trp Gly  Leu Leu Arg
    2825                 2830                 2835

Ala Thr  Arg Val Glu His Ala  Asp Arg Thr Val Arg  Val Leu Asp
    2840                 2845                 2850

Leu Gly  Ser Ala Ala Pro Asp  Met Thr Leu Leu Arg  Arg Ala Leu
    2855                 2860                 2865

Thr Ala  Ala Glu Glu Pro Glu  Leu Ala Leu Arg Ala  Gly Gly Ala
    2870                 2875                 2880

Arg Ala  Pro Arg Leu Asp Ala  Ala Ser Glu Thr Glu  Gly Glu Leu
    2885                 2890                 2895

Ala Pro  Pro Gly Gly Ala Arg  Ser Leu Arg Leu Ser  Ile Arg Thr
    2900                 2905                 2910

Lys Gly  Ser Phe Asp Ala Leu  His Leu Ala Asp Ala  Pro Asp Ala
    2915                 2920                 2925

Leu Arg  Pro Leu Gly Pro Gly  Gln Val Arg Leu Ala  Val Arg Ala
    2930                 2935                 2940

Thr Gly  Leu Asn Phe Arg Asp  Val Leu Asn Val Leu  Gly Thr Tyr
    2945                 2950                 2955

Arg Gly  Glu Ala Gly Pro Leu  Gly Leu Glu Gly Ala  Gly Val Val
    2960                 2965                 2970

Leu Asp  Val Gly Glu Gly Val  Thr Ala Leu Arg Pro  Gly Asp Arg
    2975                 2980                 2985

Val Met  Gly Met Leu His Ala  Gly Met Ala Thr His  Ala Val Val
    2990                 2995                 3000

Asp Ala  Arg Leu Leu Thr His  Ile Pro Arg Gly Leu  Ser Phe Val
    3005                 3010                 3015

Glu Ala  Ala Thr Ile Pro Ala  Ala Phe Leu Thr Ala  Leu Tyr Gly
    3020                 3025                 3030

Leu Arg  Asp Leu Gly Ala Leu  Lys Ala Gly Gln Arg  Val Leu Val
    3035                 3040                 3045

His Ala  Ala Ala Gly Gly Val  Gly Met Ala Ala Val  Gln Leu Ala
```

-continued

```
    3050                3055                3060

Arg Leu  Trp Gly Ala Glu Val  Phe Ala Thr Ala Ser  Glu Gly Lys
    3065                3070                3075

Trp Pro  Ala Leu Arg Arg Met  Gly Ile Asp Gln Ala  His Ile Ala
    3080                3085                3090

Ser Ser  Arg Thr Leu His Phe  Arg Lys Ala Phe Leu  Asp Ala Thr
    3095                3100                3105

Gln Gly  Gln Gly Val Asp Val  Val Leu Asp Ala Leu  Ala Gly Glu
    3110                3115                3120

Phe Val  Asp Ala Ser Leu Asp  Leu Leu Pro Arg Gly  Gly Ala Phe
    3125                3130                3135

Val Glu  Met Gly Lys Ser Asp  Val Arg Asp Pro Glu  Arg Val Ala
    3140                3145                3150

Lys Asp  His Pro Arg Val Arg  Tyr Thr Ala Phe Asp  Leu Leu Asp
    3155                3160                3165

Ala Gly  Pro Asp His Ile Gln  Ala Met Leu Arg Glu  Leu Val Pro
    3170                3175                3180

Leu Phe  Glu Glu Gly Val Leu  Ala Pro Leu Pro Ser  Val Ala Tyr
    3185                3190                3195

Asp Leu  Arg Arg Ala Pro His  Ala Phe Arg Ser Met  Ala Asn Ala
    3200                3205                3210

Arg His  Ile Gly Lys Leu Val  Leu Val Pro Pro Ala  Thr Leu Asp
    3215                3220                3225

Pro Asp  Gly Thr Ala Leu Ile  Thr Gly Gly Thr Gly  Glu Leu Gly
    3230                3235                3240

Arg Gln  Ile Ala Arg His Leu  Val Ala Ala His Gly  Val Arg His
    3245                3250                3255

Leu Val  Leu Thr Ser Arg Arg  Gly Met Asp Ala Pro  Asp Ala Ala
    3260                3265                3270

Ala Leu  Val Glu Ser Leu Arg  Ala Ala Gly Ala Ala  Thr Val Glu
    3275                3280                3285

Val Ala  Ala Cys Asp Val Thr  Asp Arg Asp Ala Leu  Ala Ala Ile
    3290                3295                3300

Val Gln  Ala Ile Pro Ala Ala  Arg Pro Leu Thr Ala  Val Val His
    3305                3310                3315

Thr Ala  Ala Val Leu Asp Asp  Gly Thr Val Ala Gly  Leu Ser Ala
    3320                3325                3330

Glu Gln  Leu Ala Arg Val Leu  Arg Pro Lys Val Asp  Gly Ala Trp
    3335                3340                3345

Gln Leu  Tyr Glu Ala Thr Arg  Asp Ala Pro Leu Ala  Ala Phe Met
    3350                3355                3360

Leu Phe  Ser Ser Val Ala Gly  Thr Leu Gly Ser Ser  Gly Gln Ala
    3365                3370                3375

Asn Tyr  Ala Ala Ala Asn Ala  Phe Leu Asp Gly Leu  Ala Ala Glu
    3380                3385                3390

Leu Arg  Ala Arg Gly Val Pro  Ala Met Ser Leu Ala  Trp Gly Phe
    3395                3400                3405

Trp Glu  Gln Gly Gly Ile Gly  Met Thr Ala His Leu  Gly Ala Ala
    3410                3415                3420

Asp Leu  Ala Arg Leu Lys Arg  Gln Gly Ile Val Pro  Met Thr Val
    3425                3430                3435

Ala His  Gly Leu Arg Leu Leu  Asp Arg Ala Leu Glu  Arg Pro Asp
    3440                3445                3450
```

```
Ala Ala  Leu Val Pro Ala Ser  Leu Asp Met Ala Val  Ile Gln Arg
    3455                 3460                 3465

Thr Ala  Ser Asp His Arg Gln  Val Pro Pro Met Leu  Arg Gly Leu
    3470                 3475                 3480

Val Arg  Val Ala Pro Arg Gln  Ala Ala Gly Ala Ala  Ser Gly Arg
    3485                 3490                 3495

Ser His  Glu Ala Ser Thr Leu  Arg Gln Gln Leu Ala  Ala Leu Pro
    3500                 3505                 3510

Glu Pro  Glu Arg Gln Arg Ala  Leu Leu Asp Leu Val  Arg Thr Glu
    3515                 3520                 3525

Ala Ala  Ala Val Leu Val Leu  Arg Gly Pro Asp Ala  Val Pro Ala
    3530                 3535                 3540

Asp Lys  Pro Leu Arg Glu Leu  Gly Leu Asp Ser Leu  Thr Ala Val
    3545                 3550                 3555

Glu Leu  Arg Asn Arg Leu Arg  Thr Arg Ala Gln Thr  Asp Leu Pro
    3560                 3565                 3570

Ser Thr  Leu Ala Phe Asp Tyr  Pro Thr Pro Lys Ala  Val Ala Val
    3575                 3580                 3585

Tyr Leu  Ala Gln Glu Leu Asp  Leu His Asp Val Met  Thr Glu Met
    3590                 3595                 3600

Arg Gly  Pro Ser Leu Arg Ser  Asp Asp Glu Leu Lys  Ser Ala Ile
    3605                 3610                 3615

Ala Ser  Ile Arg Ile Ser Thr  Leu Arg Gln Ala Gly  Leu Leu Asp
    3620                 3625                 3630

Ser Leu  Leu Arg Leu Ala Ala  Ser Glu Ala Val Ser  Thr Ser Ser
    3635                 3640                 3645

Asp Thr  Thr Pro Glu Thr Asp  Glu Leu Thr Leu Gln  His Val Gly
    3650                 3655                 3660

Asp Asp  Glu Leu Ala Arg Leu  Val Phe Asp Leu Ala  Gly Gly Ala
    3665                 3670                 3675

Gln


<210> SEQ ID NO 25
<211> LENGTH: 3654
<212> TYPE: PRT
<213> ORGANISM: Sorangium cellulosum

<400> SEQUENCE: 25

Met Lys Glu Glu Ile Ser Ala Arg Gln Ala Leu Glu Lys Ser Phe Ile
1               5                   10                  15

Glu Leu Arg Arg Ile Lys Arg Glu Leu Asp Gln Leu Lys Ala Lys Ser
            20                  25                  30

Ser Glu Pro Ile Ala Ile Val Ser Met Ala Cys Arg Leu Pro Gly Gly
        35                  40                  45

Val Asp Thr Pro Ala Ala Leu Trp Gln Leu Leu Ser Glu Gly Arg Asp
    50                  55                  60

Ala Ile Gly Pro Phe Pro Glu Gly Arg Glu Trp Asp Val Ala Gly Leu
65                  70                  75                  80

Tyr Asp Pro Asp Pro Asp Ala Pro Gly Lys Ser Ile Thr Ala Gln Gly
                85                  90                  95

Gly Phe Leu Tyr Asp Ala Asp Arg Phe Asp Pro Ala Phe Phe Ala Ile
            100                 105                 110

Ser Pro Arg Glu Ala Glu Arg Met Asp Pro Gln Gln Arg Leu Leu Leu
        115                 120                 125
```

```
Glu Cys Ala Trp Glu Ala Leu Glu Arg Ala Gly Leu Ala Pro His Ala
    130                 135                 140

Leu Glu Ala Ser Ala Thr Gly Val Phe Val Gly Leu Ser Val Thr Asp
145                 150                 155                 160

Tyr Gly Gly Arg Leu Leu His Asp Pro Glu Ala Leu Asp Gly Tyr Ile
                165                 170                 175

Ala Thr Gly Thr Leu Pro Ser Val Gly Ser Gly Arg Ile Ala Tyr Thr
            180                 185                 190

Leu Gly Leu Arg Gly Pro Ala Met Thr Val Asp Thr Ala Cys Ser Ser
        195                 200                 205

Ser Leu Val Ser Leu His Leu Ala Cys Met Ser Leu Arg Ala Gly Glu
    210                 215                 220

Cys Asp Met Ala Leu Ala Gly Gly Ala Thr Val Met Ala Thr Pro Met
225                 230                 235                 240

Ala Phe Ile Glu Phe Ser Arg Gln Arg Gly Thr Ala Leu Asp Gly Arg
                245                 250                 255

Cys Lys Ala Phe Gly Ala Gly Ala Asp Gly Ala Gly Trp Ser Glu Gly
            260                 265                 270

Cys Gly Ile Leu Ala Leu Lys Arg Leu Ser Asp Ala Gln Arg Asp Gly
        275                 280                 285

Asp Arg Val Leu Ala Val Ile Arg Gly Ser Ala Val Asn Gln Asp Gly
    290                 295                 300

Arg Ser Gln Gly Leu Thr Ala Pro Asn Gly Pro Ala Gln Gln Asp Val
305                 310                 315                 320

Ile Arg Gln Ala Leu Ala Ala Ala Gly Leu Thr Pro Ala Asp Val Asp
                325                 330                 335

Ala Val Glu Ala His Gly Thr Gly Thr Arg Leu Gly Asp Pro Ile Glu
            340                 345                 350

Ala Gln Ala Leu Leu Ala Thr Tyr Gly Ala Ala His Thr Ala Glu Arg
        355                 360                 365

Pro Leu Trp Leu Gly Ser Leu Lys Ser Asn Leu Gly His Thr Gln Ala
    370                 375                 380

Ala Ala Gly Val Ser Gly Leu Met Lys Leu Val Leu Ala Leu Gln His
385                 390                 395                 400

Ala Glu Leu Pro Arg Thr Leu His Ala Asp Pro Pro Ser Pro His Val
                405                 410                 415

Asp Trp Ser Arg Gly His Val Lys Leu Leu Asn Glu Pro Val Pro Trp
            420                 425                 430

Pro Arg Thr Asp Arg Pro Arg Arg Ala Ala Val Ser Ser Phe Gly Phe
        435                 440                 445

Ser Gly Thr Asn Ala His Ile Ile Ile Glu Glu Ala Pro Ala Ala Ser
    450                 455                 460

Ala Glu Ala Thr Ser Arg Gly Glu Lys Thr Ser Ala Ala Ala Pro Pro
465                 470                 475                 480

Ser Met Met Pro Leu Leu Val Ser Gly Val Asp Glu Ala Ala Leu Arg
                485                 490                 495

Ala Gln Ala Gly Arg Trp Ala Ala Trp Ile Glu Ala His Pro Glu Ala
            500                 505                 510

Gly Trp Ala Asp Val Val Tyr Thr Ala Ala Ala Arg Arg Thr His Leu
        515                 520                 525

Gly Ala Arg Ala Ala Leu Thr Ala Ala Asp Ala Ala Gly Ala Val Ala
    530                 535                 540
```

-continued

```
Ala Leu Thr Ala Leu Ser Gln Gly Gln Pro His Ala Ala Leu Ala Val
545                 550                 555                 560

Gly Glu Ala Arg Ala Arg Gly Lys Val Ala Phe Val Phe Pro Gly Gln
                565                 570                 575

Gly Ser Gln Trp Pro Ala Met Gly Arg Ala Leu Leu Ser Gln Ser Glu
            580                 585                 590

Val Phe Ala Ala Ala Val Thr Ala Cys Asp Ala Ala Leu Arg Pro Phe
        595                 600                 605

Thr Gly Trp Ser Val Leu Ser Val Leu Arg Gly Asp Ser Gly Ala Glu
    610                 615                 620

Val Pro Pro Leu Glu Arg Val Asp Val Val Gln Pro Ala Leu Phe Ala
625                 630                 635                 640

Met Ala Val Gly Leu Ala Ala Val Trp Arg Ala Trp Gly Leu Glu Pro
                645                 650                 655

Ser Ala Val Val Gly His Ser Gln Gly Glu Val Pro Ala Ala Tyr Val
            660                 665                 670

Ala Gly Ala Leu Ser Leu Glu Asp Ala Ala Arg Ile Val Ala Leu Arg
        675                 680                 685

Ser Gln Leu Val Arg Arg Leu Ser Gly Ala Gly Ala Met Ala Val Ile
    690                 695                 700

Glu Arg Pro Val Gly Glu Val Glu Gln Arg Leu Ser Arg Phe Gly Gly
705                 710                 715                 720

Ala Leu Ser Val Ala Ala Val Asn Thr Pro Arg Ser Thr Val Val Ser
                725                 730                 735

Gly Asp Ile Glu Ala Val Asp Arg Leu Leu Ala Glu Phe Glu Gly Glu
            740                 745                 750

Gln Val Phe Ala Arg Lys Val Asn Val Asp Tyr Ala Ser His Ser Arg
        755                 760                 765

His Ile Asp Gly Leu Leu Pro Glu Leu Glu Asn Gly Leu Gly Ala Val
    770                 775                 780

Arg Pro Arg Ala Ser Thr Ile Pro Phe Tyr Ser Thr Val Thr Gly Thr
785                 790                 795                 800

Val Leu Thr Gly Ala Glu Leu Asp Ala Ala Tyr Trp Cys Arg Asn Leu
                805                 810                 815

Arg Glu Pro Val Arg Leu Asp Arg Ala Leu Ser Trp Leu Leu Asp Asp
            820                 825                 830

Gly His Gly Leu Phe Val Glu Val Ser Ala His Pro Val Leu Thr Leu
        835                 840                 845

Pro Leu Thr Gly Ala Ser Ala Ala Ser Gly Gly Val Val Val Gly Ser
    850                 855                 860

Leu Gln Arg Asp Asp Gly Gly Leu Gly Arg Leu Leu Gly Val Leu Ala
865                 870                 875                 880

Ala Leu His Val His Gly His Asp Val Asp Trp Arg Ala Val Leu Ala
                885                 890                 895

Pro Trp Gly Gly Gly Val Ala Asp Leu Pro Thr Tyr Ala Phe Gln Arg
            900                 905                 910

Gln Arg Tyr Trp Leu Glu Ala Pro Arg Gly Arg Ala Gly Leu Glu Ser
        915                 920                 925

Gly Gly Leu Leu Ala Val Asn His Pro Trp Leu Ser Ala Ala Val Arg
    930                 935                 940

Leu Ala Asp Arg Asp Gly Tyr Val Leu Ser Gly Arg Leu Ser Thr Val
945                 950                 955                 960

Glu His Ala Trp Val Leu Asp His Val Val Leu Gly Thr Val Ile Leu
```

-continued

```
                965                 970                 975

Pro Gly Thr Ala Phe Val Glu Leu Ala Leu Ala Ala Ala Asp Ala Val
            980                 985                 990

Gly Leu Pro Ser Val Ser Glu Leu  Thr Ile Glu Ala Pro  Leu Ala Leu
        995                 1000                1005

Pro Ala  Arg Gly Ala Val Ala  Leu Gln Val Thr Val  Glu Ala Pro
    1010                 1015                1020

Asp Ala  Thr Gly Arg Arg Gly  Phe Ala Val Tyr Ser  Arg Pro Asp
    1025                 1030                1035

Gly Ala  His Asp Ala Pro Trp  Thr Ala His Ala Arg  Gly Val Leu
    1040                 1045                1050

Gly Ala  Ala Pro Ala Ala Ala  Thr Thr Ala Trp Ala  Ala Gly Ala
    1055                 1060                1065

Trp Pro  Pro Ala Gly Ala Glu  Pro Val Asp Val Thr  Arg Trp Val
    1070                 1075                1080

Glu Ala  Leu Asp Ala Trp Val  Gly Pro Ala Phe Arg  Gly Val Thr
    1085                 1090                1095

Ala Ala  Trp Arg Val Gly Arg  Ser Ile Tyr Ala Asp  Leu Ala Leu
    1100                 1105                1110

Pro Glu  Gly Val Ser Glu Arg  Ala Gln Asp Phe Gly  Leu His Pro
    1115                 1120                1125

Ala Leu  Leu Asp Ala Ala Leu  Gln Ala Leu Leu Arg  Ala Glu Leu
    1130                 1135                1140

Gly Ala  Gly Ala Ser Pro Arg  Glu Gly Ile Pro Met  Pro Phe Ala
    1145                 1150                1155

Trp Ser  Asp Val Ala Leu Glu  Ala Arg Gly Ala Ala  Ala Leu Arg
    1160                 1165                1170

Ala Arg  Val Glu Val Glu Asp  Ala Ser Asp Gly Asp  Gln Leu Ala
    1175                 1180                1185

Ala Ser  Ile Glu Leu Ala Asp  Ala Gln Gly Gln Pro  Val Ala Arg
    1190                 1195                1200

Ala Gly  Thr Phe Arg Ala Arg  Trp Ala Thr Ala Glu  His Val Arg
    1205                 1210                1215

Met Ala  Ala Ala Gly Ser Ser  Glu Arg Asp Leu Tyr  Arg Val Thr
    1220                 1225                1230

Trp Ala  Asp Val Val Leu Glu  Glu Ala Ala Trp Ala  Pro Glu Glu
    1235                 1240                1245

His Val  Val Leu Gly Gly Asp  Gly Ala Leu Ala Ala  Ala Leu Gly
    1250                 1255                1260

Ala Arg  Thr Ala Ala Leu Pro  Glu Leu Ile Ala Ala  Leu Pro Glu
    1265                 1270                1275

Gly Ala  Ala Ala Pro Arg Arg  Leu Val Ile Asp Ala  Ala Ala Gly
    1280                 1285                1290

Asp Pro  Gly Asp Gly Leu Val  Ala Ala Ala His Ala  Ala Ala Gln
    1295                 1300                1305

Arg Val  Leu Ser Leu Val Gln  Gly Trp Leu Ser Glu  Ala Arg Leu
    1310                 1315                1320

Ala Asp  Ser Glu Leu Val Val  Val Thr Arg Gly Ala  Val Ala Ala
    1325                 1330                1335

Gly Pro  Asp Asp Gly Val Ala  Ala Leu Ser His Ala  Pro Leu Trp
    1340                 1345                1350

Gly Leu  Val Arg Thr Ala Arg  Gln Glu Asn Pro Gly  Arg Ala Val
    1355                 1360                1365
```

```
Arg Leu  Val Asp Leu Gly Pro  Glu Pro Leu Asp Gly  Ala Leu Leu
    1370                 1375                 1380

Arg Arg  Val Val Ala Ala Ala  Glu Glu Pro Glu Leu  Ala Leu Arg
    1385                 1390                 1395

Gly Gly  Ala Ala Arg Ala Pro  Arg Leu Arg Glu Val  Arg Ala Gly
    1400                 1405                 1410

Ala Ala  Asp Ala Ala Arg Pro  Thr Arg Leu Asp Pro  Gly Gly Thr
    1415                 1420                 1425

Val Leu  Ile Thr Gly Gly Thr  Gly Glu Leu Gly Arg  Gln Val Ala
    1430                 1435                 1440

Arg His  Leu Val Ala Ser His  Gly Val Arg His Leu  Val Leu Thr
    1445                 1450                 1455

Ser Arg  Arg Gly Met Gly Ala  Pro Asp Ala Ala Ala  Leu Val Asp
    1460                 1465                 1470

Glu Leu  Arg Ala Ala Gly Ala  Ala Thr Val Asp Val  Ala Ala Cys
    1475                 1480                 1485

Asp Val  Ala Asp Gly Ala Ala  Leu Gly Ala Val Ile  Ala Ala Ile
    1490                 1495                 1500

Pro Ala  Ala His Pro Leu Thr  Ala Val Val His Met  Ala Gly Val
    1505                 1510                 1515

Leu Asp  Asp Val Ile Val Thr  Lys Leu Ser Ala Glu  Gln Leu Thr
    1520                 1525                 1530

Arg Val  Leu Arg Pro Lys Ile  Asp Gly Gly Trp His  Leu Ala Ala
    1535                 1540                 1545

Ala Thr  Arg Gly His Arg Leu  Ala Ala Phe Val Leu  Phe Ser Ser
    1550                 1555                 1560

Ala Ala  Gly Thr Leu Gly Ser  Pro Gly Gln Ala Asn  Tyr Ala Ala
    1565                 1570                 1575

Ala Asn  Thr Phe Leu Asp Ala  Leu Ala Ala Gln Leu  Arg Ala Arg
    1580                 1585                 1590

Gly Val  Pro Ala Met Ser Leu  Ala Trp Gly Phe Trp  Glu Gln Ala
    1595                 1600                 1605

Gly Leu  Gly Met Thr Ala His  Leu Gly Ala Ala Asp  Leu Ala Arg
    1610                 1615                 1620

Leu Arg  Arg Gln Gly Ile Ala  Pro Ile Ala Leu Ala  Gln Gly Met
    1625                 1630                 1635

Gln Leu  Leu Asp Arg Ala Leu  Ala Arg Pro Glu Ala  Ala Leu Val
    1640                 1645                 1650

Pro Ala  Ala Leu Asp Leu Pro  Ala Leu Gln Arg Ala  Ala Ser Asp
    1655                 1660                 1665

Ala Gly  Gln Val Pro Ala Leu  Leu Arg Gly Leu Val  Arg Pro Ala
    1670                 1675                 1680

Val Gly  Arg Arg Ala Ala Ala  Pro Ala Ala Ala Ala  Thr Gly Ala
    1685                 1690                 1695

Ala Ala  Leu Arg Ala Arg Leu  Ala Pro Leu Pro Glu  Ala Glu Arg
    1700                 1705                 1710

His Asp  Val Val Leu Asp Leu  Val Arg Ala Glu Ala  Ala Ala Val
    1715                 1720                 1725

Leu Gln  Leu Ala Gly Pro Ala  Gln Val Pro Ala Asp  Lys Pro Leu
    1730                 1735                 1740

Lys Glu  Leu Gly Leu Thr Ser  Leu Thr Ala Val Glu  Leu Arg Asn
    1745                 1750                 1755
```

-continued

```
Arg Leu Gly Ala Arg Ala Glu Thr Ala Leu Pro Ala Thr Leu Ala
    1760                1765                1770

Phe Asp His Pro Thr Pro Arg Ala Ile Ala Gly Leu Leu Leu Gln
    1775                1780                1785

Arg Ala Phe Ser Glu Leu Ala Ala Ala Val Ala Thr Arg Ala Gln
    1790                1795                1800

Ala Pro Arg Ala Gln Gly Ala His Asp Glu Pro Ile Ala Ile Val
    1805                1810                1815

Ser Met Ala Cys Arg Leu Pro Gly Gly Val Asp Thr Pro Ala Arg
    1820                1825                1830

Met Trp Gln Leu Leu Ala Glu Gly Arg Asp Ala Ile Gly Pro Phe
    1835                1840                1845

Pro Glu Gly Arg Gly Trp Asp Val Ala Gly Leu Tyr Asp Pro Asp
    1850                1855                1860

Pro Asp Ala Pro Gly Lys Ser Val Thr Asn Leu Gly Gly Phe Leu
    1865                1870                1875

Tyr Asp Ala Asp His Phe Asp Pro Thr Phe Phe Gly Ile Ser Pro
    1880                1885                1890

Arg Glu Ala Glu Arg Ile Asp Pro Gln Gln Arg Leu Leu Leu Glu
    1895                1900                1905

Cys Ala Trp Glu Ala Leu Glu Arg Ala Gly Leu Ala Pro His Thr
    1910                1915                1920

Leu Glu Ala Ser Ala Thr Gly Val Phe Val Gly Leu Val Tyr Ser
    1925                1930                1935

Asp Tyr Gly Gly Arg Leu Leu Glu His Leu Glu Ser Phe Asp Gly
    1940                1945                1950

Tyr Ile Ala Thr Gly Ser Phe Pro Ser Val Gly Ser Gly Arg Ile
    1955                1960                1965

Ala Tyr Thr Leu Gly Leu Arg Gly Pro Ala Met Thr Val Asp Thr
    1970                1975                1980

Ala Cys Ser Ser Ser Leu Val Ser Leu His Leu Ala Cys Met Ser
    1985                1990                1995

Leu Arg Ala Gly Glu Cys Asp Met Ala Leu Ala Gly Gly Ala Thr
    2000                2005                2010

Val Met Ala Thr Pro Met Ala Phe Ile Glu Phe Ser Arg Gln Arg
    2015                2020                2025

Gly Met Ala Pro Asp Ala Arg Cys Lys Ala Phe Gly Ala Glu Ala
    2030                2035                2040

Asn Gly Ile Gly Pro Ala Glu Gly Cys Gly Ile Leu Val Leu Lys
    2045                2050                2055

Arg Leu Ser Asp Ala Arg Arg Asp Gly Asp Arg Val Leu Ala Val
    2060                2065                2070

Ile Arg Gly Ser Ala Val Asn Gln Asp Gly Arg Ser Gln Gly Leu
    2075                2080                2085

Thr Ala Pro Asn Gly Pro Ala Gln Gln Asp Val Ile Arg Gln Ala
    2090                2095                2100

Leu Ala Ala Ala Gly Leu Thr Pro Ala Asp Val Asp Ala Val Glu
    2105                2110                2115

Ala His Gly Thr Gly Thr Arg Leu Gly Asp Pro Ile Glu Ala Gln
    2120                2125                2130

Ala Leu Leu Ala Thr Tyr Gly Thr Ala His Thr Ala Glu Arg Pro
    2135                2140                2145

Leu Trp Leu Gly Ser Ile Lys Ser Asn Leu Gly His Thr Gln Ala
```

-continued

```
    2150                2155                2160

Ala Ala  Gly Val Val Gly Leu  Met Lys Leu Val Leu  Ala Met Gln
    2165                2170                2175

His Ala  Glu Leu Pro Arg Thr  Leu Tyr Ala Glu Pro  Arg Ser Pro
    2180                2185                2190

His Ile  Asp Trp Ser Gln Gly  His Ile Asn Leu Leu  Asn Glu Pro
    2195                2200                2205

Val Pro  Trp Pro Arg Thr Asp  Arg Pro Arg Arg Ala  Ala Val Ser
    2210                2215                2220

Ser Phe  Gly Ile Ser Gly Thr  Asn Ala His Val Ile  Ile Glu Glu
    2225                2230                2235

Ala Pro  Ala Glu Ala Pro Ala  Thr Ala Ala Asp Ala  Lys Ser Val
    2240                2245                2250

Glu Ala  Leu Pro Ile Leu Pro  Leu Leu Leu Ser Gly  Arg Asp Glu
    2255                2260                2265

Pro Ala  Leu Arg Ala Gln Ala  Gly Arg Leu Ala Glu  His Leu Arg
    2270                2275                2280

Ala His  Pro Gly Glu Arg Leu  Leu Asp Ile Ala Ala  Gly Leu Ala
    2285                2290                2295

Thr Thr  Arg Thr His Leu Ala  Thr Arg Leu Ala Leu  Pro Val Ala
    2300                2305                2310

Ala Asp  Ala Ala Ala Glu Glu  Leu Gly Ala Arg Leu  Ala Gln Phe
    2315                2320                2325

Ala Ala  Gly Gly Pro Ala Pro  Ser Gly Ala Ala Val  Thr Ala Pro
    2330                2335                2340

Gly Gln  Pro Pro Gly Lys Val  Ala Val Leu Phe Thr  Gly Gln Gly
    2345                2350                2355

Ser Gln  Arg Ala Gly Met Gly  Arg Ala Leu Tyr Ala  Thr His Pro
    2360                2365                2370

Val Phe  Arg Ala Ala Leu Asp  Ala Ala Cys Ala Glu  Leu Asp Arg
    2375                2380                2385

His Leu  Asp Arg Pro Leu His  Ser Val Leu Phe Ala  Asp Ala Gly
    2390                2395                2400

Thr Glu  Ala Ala Ala Leu Leu  Asp Gln Thr Gly Trp  Ala Gln Pro
    2405                2410                2415

Ala Leu  Phe Ala Leu Glu Val  Ala Leu Tyr Arg Gln  Trp Glu Ala
    2420                2425                2430

Trp Gly  Leu Arg Pro Glu Leu  Leu Leu Gly His Ser  Ile Gly Glu
    2435                2440                2445

Leu Ala  Ala Ala His Val Ala  Gly Val Leu Asp Leu  Pro Asp Ala
    2450                2455                2460

Ser Ala  Leu Val Ala Ala Arg  Gly Arg Leu Met Gln  Ala Leu Pro
    2465                2470                2475

His Gly  Gly Ala Met Ala Ser  Ile Glu Ala Thr Glu  His Glu Leu
    2480                2485                2490

Leu Pro  Leu Leu Asp Gln His  Thr Gly Arg Leu Ser  Leu Ala Ala
    2495                2500                2505

Leu Asn  Ala Pro Arg Gln Ser  Val Val Ser Gly Asp  Gln Pro Ala
    2510                2515                2520

Val Asp  His Val Cys Ala His  Phe Ile Ala Leu Gly  Arg Arg Ala
    2525                2530                2535

Lys Arg  Leu Asp Val Ser His  Ala Phe His Ser Ala  His Met Gln
    2540                2545                2550
```

-continued

```
Pro Met  Leu Asp Ala Phe Ala  Ser Val Ala Arg Gly  Leu Thr Phe
    2555                 2560                 2565

His Pro  Pro Arg Leu Pro Ile  Val Ser Ser Val Thr  Gly Ala Arg
    2570                 2575                 2580

Ala Thr  Thr Asp Gln Leu Thr  Ser Pro Asp Tyr Trp  Val Gln Gln
    2585                 2590                 2595

Val Arg  Glu Pro Val Arg Phe  Leu Asp Ala Met Arg  Ser Leu His
    2600                 2605                 2610

Ala Ala  Gly Ala Ala Thr Phe  Val Glu Cys Gly Pro  His Gly Val
    2615                 2620                 2625

Leu Thr  Ala Ala Gly Ala Glu  Cys Leu Ala Pro Glu  Gly Ala Arg
    2630                 2635                 2640

Asp Ala  Gly Phe Val Thr Ser  Leu Arg Lys Asp Arg  Asp Glu Ala
    2645                 2650                 2655

Leu Ala  Leu Val His Ala Ala  Cys Ala Val His Val  Arg Gly His
    2660                 2665                 2670

Ala Leu  Asp Trp Leu Arg Phe  Phe Asp Ala Thr Gly  Ala Arg Arg
    2675                 2680                 2685

Val Glu  Leu Pro Thr Tyr Ala  Phe Gln Arg Gln Arg  Tyr Trp Leu
    2690                 2695                 2700

Glu Ala  Pro Arg Pro Arg Pro  Ser Leu Glu Gly Val  Gly Leu Thr
    2705                 2710                 2715

Ala Ala  Asn His Pro Trp Leu  Gly Ala Ala Val Arg  Leu Ala Asp
    2720                 2725                 2730

Arg Asp  Gly Tyr Val Leu Ser  Gly Arg Leu Ser Thr  Ile Asp His
    2735                 2740                 2745

Pro Trp  Val Leu Asp His Val  Val Ala Gly Thr Val  Ile Leu Pro
    2750                 2755                 2760

Gly Thr  Ala Phe Val Glu Leu  Ala Trp Ala Ala Ala  Glu Val Val
    2765                 2770                 2775

Gly Ala  Ala Ala Val Ser Glu  Val Thr Phe Thr Thr  Pro Leu Val
    2780                 2785                 2790

Leu Pro  Pro Arg Ser Val Val  Glu Leu Gln Val Arg  Ile Gly Glu
    2795                 2800                 2805

Pro Asp  Ala Ser Gly Arg Arg  Thr Phe Ala Ala Tyr  Ser Arg Ala
    2810                 2815                 2820

Asp Ala  Ala Ile Glu Ala Glu  Trp Thr Gln His Ala  Thr Gly Val
    2825                 2830                 2835

Leu Ser  Ala Gln Ala Ala Ala  Gly Ala Asp Val Ala  Asp Leu Ser
    2840                 2845                 2850

Val Trp  Pro Pro Pro Gly Ala  Glu Val Val Ala Leu  Asp Gly Gly
    2855                 2860                 2865

Tyr Ala  Trp Leu Ala Ala Gln  Gly Tyr Gly Tyr Gly  Pro Ala Phe
    2870                 2875                 2880

Gln Ala  Leu Arg Glu Val Trp  Arg Ala Gly Thr Thr  Leu Tyr Ala
    2885                 2890                 2895

Arg Val  Ala Leu Pro Asp Ala  Val Ala Asp Thr Ala  Arg Gly Phe
    2900                 2905                 2910

Gly Ile  His Pro Ala Leu Leu  Asp Ala Val Leu His  Ser Leu Leu
    2915                 2920                 2925

Ala Pro  Ser Ala Gln Glu Glu  Ala Ser Asp Asp Asp  Lys Val Leu
    2930                 2935                 2940
```

```
Leu Ala  Phe Ala Phe Ser Asp  Val Val Ile Glu Ala  Arg Gly Ala
    2945                 2950                 2955

Ala Glu  Val Arg Val Arg Leu  Asn Lys Gln Ala Gly  Asp Asp Gly
    2960                 2965                 2970

Glu Gly  Val Thr Ala Ser Ile  His Leu Ala Asp Ala  Gln Gly Arg
    2975                 2980                 2985

Pro Val  Ala Arg Val Gly Ala  Phe Gln Ala Arg Ala  Thr Thr Thr
    2990                 2995                 3000

Glu Arg  Val Arg Ala Leu Ala  Gly Ala Ser Glu Arg  Asp Leu His
    3005                 3010                 3015

Arg Val  Thr Trp Thr Asp Val  Thr Leu Glu Glu Thr  Pro Trp Ala
    3020                 3025                 3030

His Glu  Asp Ser Val Val Val  Gly Gly Asp Gly Ala  Leu Ala Ala
    3035                 3040                 3045

Ala Leu  Gly Val Arg Ala Val  Ala Gly Leu Pro Glu  Leu Leu Ala
    3050                 3055                 3060

Gly Gly  Ala Ala Ala Pro Arg  Arg Leu Val Ile Asp  Ala Thr Ala
    3065                 3070                 3075

Gly Asp  Pro Gly Asp Gly Leu  Val Ala Ala Thr His  Ala Ala Thr
    3080                 3085                 3090

Gln Arg  Gly Leu Ala Leu Leu  Gln Gly Trp Leu Ser  Glu Ala Arg
    3095                 3100                 3105

Leu Ala  Ala Thr Glu Leu Val  Leu Val Thr Arg Gly  Ala Ala Ala
    3110                 3115                 3120

Ala Glu  Pro Asp Glu Gly Val  Ala Ala Leu Ser His  Ala Pro Leu
    3125                 3130                 3135

Trp Gly  Leu Val Arg Ala Ala  Arg Glu Glu His Pro  Ala Arg Ala
    3140                 3145                 3150

Leu Arg  Leu Val Asp Leu Gly  Arg Glu Ala Pro Asp  Gly Ala Ile
    3155                 3160                 3165

Leu Arg  Arg Ala Ile Ala Ala  Asp Asp Glu Pro Glu  Leu Val Val
    3170                 3175                 3180

Arg Arg  Gly Ala Leu Arg Ala  Ala Arg Leu Ser Leu  Ala His Ala
    3185                 3190                 3195

Gly Pro  Asp Thr Ala Gly Gln  Ala Thr Arg Leu Ala  Pro Gly Gly
    3200                 3205                 3210

Thr Val  Leu Ile Thr Gly Gly  Thr Gly Glu Leu Gly  Arg Gln Val
    3215                 3220                 3225

Ala Arg  His Leu Val Ala Ala  His Gly Val Arg His  Leu Val Leu
    3230                 3235                 3240

Thr Ser  Arg Arg Gly Met Asp  Ala Pro Asp Ala Ala  Ala Leu Val
    3245                 3250                 3255

Glu Ser  Leu Arg Ala Ala Gly  Ala Ala Thr Val Glu  Ile Ala Ala
    3260                 3265                 3270

Cys Asp  Val Ala Asp Gly His  Ala Leu Ala Ala Val  Leu Arg Thr
    3275                 3280                 3285

Ile Pro  Ala Glu His Pro Leu  Thr Ala Val Val His  Thr Ala Gly
    3290                 3295                 3300

Val Leu  Glu Asp Gly Val Val  Thr Gly Leu Ser Ala  Glu Gln Leu
    3305                 3310                 3315

Ala Arg  Val Leu Arg Pro Lys  Val Asp Gly Ala Trp  Gln Leu Tyr
    3320                 3325                 3330

Glu Ala  Thr Lys Asp Ala Pro  Leu Ala Ala Phe Met  Leu Phe Ser
```

-continued

```
    3335                3340                3345

Ser Ala  Ala Gly Thr Leu Gly  Ser Ala Gly Gln Ala  Asn Tyr Ala
    3350                3355                3360

Ala Ala  Asn Ala Phe Leu Asp  Ala Leu Ala Ala Glu  Leu Arg Ala
    3365                3370                3375

Arg Gly  Val Pro Ala Met Ser  Leu Ala Trp Gly Phe  Trp Glu Gln
    3380                3385                3390

Gly Gly  Ile Gly Met Thr Ala  His Leu Gly Ala Ala  Asp Met Ala
    3395                3400                3405

Arg Val  Lys Arg Gln Gly Ile  Val Pro Met Thr Val  Ala His Gly
    3410                3415                3420

Leu Arg  Leu Leu Asp Arg Ala  Leu Glu Arg Pro Glu  Ala Thr Leu
    3425                3430                3435

Val Pro  Leu Ser Leu Asp Val  Ala Ala Leu Gln Arg  Ala Ala Ser
    3440                3445                3450

Asp Ala  Gly Arg Val Pro Ala  Leu Leu Arg Gly Leu  Val Arg Pro
    3455                3460                3465

Ala Ala  Ala Arg Arg Thr Ala  Ala Pro Ala Ala Ala  Ala Thr Gly
    3470                3475                3480

Leu Arg  Ala Arg Leu Leu Pro  Leu Ser Glu Ala Glu  Arg Gln Asp
    3485                3490                3495

Val Leu  Leu Asp Leu Val Arg  Thr Glu Ile Ala Asp  Ile Leu Ala
    3500                3505                3510

Leu Ser  Gly Pro Ala Ala Val  Pro Pro Asp Gln Pro  Ile Arg Glu
    3515                3520                3525

Leu Gly  Leu Asp Ser Leu Thr  Ala Val Asp Val Arg  Ser Arg Leu
    3530                3535                3540

Val Gln  Arg Ser Glu Ile Asp  Leu Ala Val Thr Leu  Ala Tyr Asp
    3545                3550                3555

Tyr Pro  Thr Ala Arg Ala Ile  Ala Gly His Leu Ser  Glu Gln Met
    3560                3565                3570

Gly Leu  Glu Gly Ala Pro Glu  Asp Arg Glu Ser Ala  Leu Asp Glu
    3575                3580                3585

Ser Gln  Ile Arg Ala Leu Leu  Met Gln Ile Pro Ile  Pro Thr Leu
    3590                3595                3600

Arg Gln  Ser Gly Leu Leu Gly  Asp Leu Val Arg Leu  Ala Ser Pro
    3605                3610                3615

Gln Ala  Pro Pro Arg Glu Glu  Gly Glu Ser Glu Thr  Leu Ser Phe
    3620                3625                3630

Asp His  Leu Gly Asn Glu Glu  Phe Leu Ser Leu Ala  Ser Lys Leu
    3635                3640                3645

Ile Ala  Glu Glu Gly Ser
    3650


<210> SEQ ID NO 26
<211> LENGTH: 1880
<212> TYPE: PRT
<213> ORGANISM: Sorangium cellulosum

<400> SEQUENCE: 26

Met Asn Gln Glu Thr Val Leu Arg Gln Thr Leu Glu Lys Ser Leu His
1               5                   10                  15

Lys Ile Gln His Leu Asn Arg Glu Leu Glu Arg Leu Lys Ala Lys Ser
            20                  25                  30
```

-continued

```
Ser Glu Pro Ile Ala Ile Val Ser Met Ala Cys Arg Tyr Pro Gly Gly
        35                  40                  45

Val Asp Gly Pro Ala Arg Leu Trp Glu Leu Leu Ser Glu Gly Arg Asp
    50                  55                  60

Ala Ile Gly Pro Phe Pro Glu Gly Arg Gly Trp Asp Val Ala Gly Leu
65                  70                  75                  80

Tyr Asp Pro Asp Pro Asp Ala Pro Gly Lys Ser Val Thr Thr Gln Gly
                85                  90                  95

Gly Phe Leu Tyr Asp Ala Asp Arg Phe Asp Pro Thr Phe Phe Gly Ile
            100                 105                 110

Ser Pro Arg Glu Ala Glu Arg Met Asp Pro Gln Gln Arg Leu Leu Leu
        115                 120                 125

Glu Cys Ala Trp Glu Ala Leu Glu Arg Ala Gly Val Ala Pro His Thr
    130                 135                 140

Leu Glu Ala Ser Ala Thr Gly Val Phe Val Gly Leu Val Tyr Ser Asp
145                 150                 155                 160

Tyr Gly Gly Arg Leu Leu Glu His Leu Glu Val Phe Asp Gly Tyr Val
                165                 170                 175

Ala Thr Gly Ser Phe Pro Ser Val Gly Ser Gly Arg Ile Ala Tyr Thr
            180                 185                 190

Leu Gly Leu Arg Gly Pro Ala Val Thr Val Asp Thr Ala Cys Ser Ser
        195                 200                 205

Ser Leu Val Ser Leu His Leu Ala Cys Met Ser Leu Arg Ala Gly Glu
    210                 215                 220

Cys Asp Met Ala Leu Ala Gly Gly Ala Thr Val Met Ala Thr Pro Met
225                 230                 235                 240

Ala Phe Ile Glu Phe Ser Arg Gln Arg Gly Met Ala Pro Asp Ala Arg
                245                 250                 255

Cys Lys Ala Phe Gly Ala Ala Ala Asn Gly Ile Gly Pro Ala Glu Gly
            260                 265                 270

Cys Gly Ile Leu Val Leu Lys Arg Leu Ser Asp Ala Arg Arg Asp Gly
        275                 280                 285

Asp Arg Val Leu Ala Val Ile Arg Gly Ser Ala Val Asn Gln Asp Gly
    290                 295                 300

Arg Ser Gln Gly Leu Thr Ala Pro Asn Gly Pro Ala Gln Gln Asp Val
305                 310                 315                 320

Ile Arg Gln Ala Leu Ala Ala Ala Gly Leu Thr Pro Ala Asp Val Asp
                325                 330                 335

Ala Val Glu Ala His Gly Thr Gly Thr Pro Leu Gly Asp Pro Ile Glu
            340                 345                 350

Ala Gln Ala Leu Leu Ala Thr Tyr Gly Lys Thr His Thr Ala Glu Arg
        355                 360                 365

Pro Leu Trp Leu Gly Ser Ile Lys Ser Asn Phe Gly His Thr Gln Ala
    370                 375                 380

Ala Ala Gly Val Ala Gly Ile Ile Lys Leu Val Leu Ala Met Gln His
385                 390                 395                 400

Ala Glu Leu Pro Arg Thr Leu Tyr Ala Glu Pro Arg Ser Pro His Val
                405                 410                 415

Asp Trp Ser Gln Gly His Val Lys Leu Leu Asn Glu Pro Val Pro Trp
            420                 425                 430

Pro Arg Thr Asp Arg Pro Arg Arg Ala Ala Val Ser Ser Phe Gly Val
        435                 440                 445

Ser Gly Thr Asn Ala His Val Ile Leu Glu Glu Ala Pro Ala Glu Ala
```

-continued

```
    450                 455                 460

Pro Ala Ala Ala Gln Thr Ala Ala Gly Val Pro Ser Thr Leu Pro Leu
465                 470                 475                 480

Leu Leu Ser Gly Arg Asp Glu Pro Ala Leu Arg Ala Gln Ala Gly Arg
                485                 490                 495

Leu Ala Glu His Leu Arg Ala His Pro Asp Glu Arg Leu Leu Asp Ile
            500                 505                 510

Ala Ala Gly Leu Ala Thr Thr Arg Thr His Leu Ala Thr Arg Leu Ala
        515                 520                 525

Leu Pro Val Ala Ala Asp Ala Ala Ala Glu Glu Leu Ser Ala Arg Leu
    530                 535                 540

Ala Gln Phe Ala Ala Gly Gly Pro Ala Pro Ser Gly Ala Ala Val Thr
545                 550                 555                 560

Ala Pro Gly Gln Pro Pro Gly Lys Val Ala Val Leu Phe Thr Gly Gln
                565                 570                 575

Gly Ser Gln Arg Ala Ala Met Gly Arg Ala Leu Tyr Ala Thr His Pro
            580                 585                 590

Val Phe Arg Ala Ala Leu Asp Ala Ala Cys Ala Glu Leu Asp Arg His
        595                 600                 605

Leu Asp Arg Pro Leu His Ser Val Leu Phe Ala Asp Ala Gly Thr Glu
    610                 615                 620

Ala Ala Ala Leu Leu Asp Gln Thr Gly Trp Ala Gln Pro Ala Leu Phe
625                 630                 635                 640

Ala Leu Glu Val Ala Leu Tyr Arg Gln Trp Glu Ala Trp Gly Leu Arg
                645                 650                 655

Ala His Ala Leu Leu Gly His Ser Leu Gly Glu Ile Val Ala Ala His
            660                 665                 670

Ile Ala Gly Val Leu Asp Leu Pro Asp Ala Ser Ala Leu Val Ala Ala
        675                 680                 685

Arg Gly Arg Leu Met Gln Ala Leu Pro His Gly Gly Ala Met Ala Ser
    690                 695                 700

Ile Glu Ala Thr Glu His Glu Leu Leu Pro Leu Leu Asp Gln His Thr
705                 710                 715                 720

Gly Arg Leu Ser Leu Ala Ala Leu Asn Ala Pro Arg Gln Ser Val Val
                725                 730                 735

Ser Gly Asp Gln Pro Ala Val Asp His Val Cys Ala His Phe Lys Ala
            740                 745                 750

Leu Gly Arg Arg Ala Lys Arg Leu Asp Val Ser His Ala Phe His Ser
        755                 760                 765

Ala Arg Met Glu Pro Met Leu Asp Ala Phe Ala Arg Val Ala Arg Gly
    770                 775                 780

Leu Thr Tyr Arg Ala Pro Arg Leu Pro Val Val Ser Asn Val Thr Gly
785                 790                 795                 800

Arg Met Ala Thr Ala Asp Glu Leu Thr Ser Pro Asp Tyr Trp Val Arg
                805                 810                 815

His Val Arg Glu Pro Val Arg Phe Val Ala Gly Val Arg Ala Leu His
            820                 825                 830

Ala Thr Gly Val Ala Thr Tyr Leu Glu Cys Gly Pro Asp Pro Val Leu
        835                 840                 845

Gly Gly Met Ala Ala Asp Cys Leu Thr Ser Asp Glu Ser Arg Asp Pro
    850                 855                 860

Gly Leu Ile Pro Ser Leu Arg Lys Asp Arg Asp Glu Ala Leu Ala Ile
865                 870                 875                 880
```

-continued

```
Ala Gln Ala Ala Cys Ala Leu His Val Arg Gly His Ala Leu Asp Trp
                885                 890                 895

Pro Arg Leu Phe Asp Ala Thr Gly Ala Arg Arg Val Glu Leu Pro Thr
            900                 905                 910

Tyr Ala Phe Gln Arg Gln Arg Tyr Trp Ile Asp Ala Pro Arg Arg Ala
        915                 920                 925

Ala Gly Leu Glu Ser Val Gly Leu Thr Ala Ala Asp His Pro Trp Leu
    930                 935                 940

Gly Ala Ala Val Arg Leu Ala Asp Arg Asp Val Tyr Val Leu Ser Gly
945                 950                 955                 960

Arg Leu Ser Thr Val Asp His Pro Trp Ile Leu Asp His Val Val Thr
                965                 970                 975

Gly Thr Ala Leu Met Pro Gly Thr Gly Phe Val Glu Leu Ala Trp Ala
            980                 985                 990

Thr Ala Gln Ala Val Asn Ala Ala  Ala Ile Ala Glu Leu  Thr Leu Thr
        995                 1000                1005

Thr Pro  Leu Val Leu Pro Ala  Arg Gly Ala Val Gln  Leu Gln Val
    1010                 1015                1020

Thr Val  Asp Glu Ala Asp Ala  Asp Gly Arg Arg Ala  Phe Ala Ile
    1025                 1030                1035

His Ser  Arg Pro His Gly Pro  Val Asp Leu Glu Trp  Thr Gln His
    1040                 1045                1050

Ala Thr  Gly Val Leu Ser Ala  Glu Ala Pro Ala Gly  Ala Asp Glu
    1055                 1060                1065

Ala Ala  Gly Leu Ser Glu Trp  Pro Pro Pro Gly Ala  Glu Ala Val
    1070                 1075                1080

Ala Leu  Asp Gly Gly Tyr Glu  Gln Leu Ser Glu His  Gly Tyr Gly
    1085                 1090                1095

His Gly  Pro Ala Phe Gln Gly  Leu Arg Gly Leu Trp  Arg Ala Asp
    1100                 1105                1110

Gln Thr  Leu Tyr Ala His Val  Ala Leu Pro Asp Ala  Val Ala Gly
    1115                 1120                1125

Thr Glu  Gln Gly Phe Gly Leu  His Pro Ala Leu Phe  Asp Ala Ala
    1130                 1135                1140

Leu Gln  Ser Leu Ala Arg Leu  Ser Arg Glu Glu Ala  Ala Ala Gly
    1145                 1150                1155

Asp Pro  Val Leu Val Pro Phe  Ala Trp Thr Asp Val  Ala Leu Tyr
    1160                 1165                1170

Ala Ala  Gly Ala Thr Glu Leu  Arg Ala Arg Ile Ala  Leu Glu Gln
    1175                 1180                1185

Ala Glu  Gly Gly Ala Pro Ala  Val Ala Ser Leu Leu  Leu Ala Asp
    1190                 1195                1200

Ala His  Gly Arg Thr Val Ala  Thr Thr Gly Arg Val  Arg Gly Ala
    1205                 1210                1215

Ser Ala  Ala Gln Thr Arg Ser  Ala Ala Ser Arg Ala  Glu Pro Met
    1220                 1225                1230

Tyr Arg  Val Ala Trp Thr Asp  Val Ala Leu Glu Ala  Ala Ala Trp
    1235                 1240                1245

Ala Pro  Glu Glu His Val Val  Leu Gly Gly Asp Gly  Ala Leu Ala
    1250                 1255                1260

Ser Ala  Leu Gly Val Arg Ala  Ala Ala Gly Leu Pro  Glu Leu Leu
    1265                 1270                1275
```

-continued

```
Glu Ala  Leu Ala Asp Gly Ala  Ala Ala Pro Arg Arg  Leu Val Val
    1280                 1285                 1290

Asp Leu  Thr Ala Gly Asp Ala  Gly Ala Val Val Ala  Ala Val His
    1295                 1300                 1305

Ala Ala  Ala Arg Gly Ala Leu  Ala Leu Val Gln Gly  Trp Leu Ala
    1310                 1315                 1320

Ala Pro  Gln Leu Thr Ala Thr  Glu Leu Leu Val Val  Thr Arg Cys
    1325                 1330                 1335

Ala Val  Ala Thr Gly Pro Asp  Glu Gly Val Asp Ala  Leu Gly Pro
    1340                 1345                 1350

Ala Ala  Val Trp Gly Leu Leu  Arg Ala Thr Arg Ala  Glu His Pro
    1355                 1360                 1365

Asp Arg  Ala Val Arg Val Leu  Asp Leu Gly Arg Glu  Pro Leu Asp
    1370                 1375                 1380

Gly Ala  Leu Leu Arg Arg Ala  Leu Ala Ala Val Ala  Glu Pro Glu
    1385                 1390                 1395

Leu Ser  Leu Arg Arg Gly Glu  Ala Arg Ala Pro Arg  Leu Arg Glu
    1400                 1405                 1410

Ala Lys  Pro Ala Ala Ala Pro  Ala Thr Arg Leu Asp  Pro Glu Gly
    1415                 1420                 1425

Thr Val  Leu Val Thr Gly Gly  Thr Gly Glu Leu Gly  Arg Gln Val
    1430                 1435                 1440

Ala Arg  His Leu Val Ala Ala  His Gly Val Arg His  Leu Val Leu
    1445                 1450                 1455

Thr Ser  Arg Arg Gly Met Asp  Ala Pro Asp Ala Ala  Ala Leu Val
    1460                 1465                 1470

Glu Glu  Leu Arg Ala Ala Gly  Ala Ala Thr Val Asp  Val Ala Ala
    1475                 1480                 1485

Cys Asp  Val Ala Ala Gly Pro  Ala Leu Ala Ala Val  Val Glu Ala
    1490                 1495                 1500

Ile Pro  Ala Ala His Pro Leu  Thr Ala Val Val His  Met Ala Gly
    1505                 1510                 1515

Val Leu  Asp Asp Gly Ile Val  Thr Lys Leu Ser Ala  Glu Gln Leu
    1520                 1525                 1530

Thr Arg  Val Leu Arg Pro Lys  Val Asp Gly Ala Ile  His Leu His
    1535                 1540                 1545

Glu Leu  Thr Lys His Ala Pro  Leu Ala Ala Phe Val  Met Phe Ser
    1550                 1555                 1560

Ser Ala  Ala Gly Thr Leu Gly  Ser Pro Gly Gln Ala  Asn Tyr Thr
    1565                 1570                 1575

Ala Ala  Asn Val Phe Leu Asp  Ala Leu Ala Ala Arg  Leu Arg Ala
    1580                 1585                 1590

Arg Gly  Val Pro Ala Met Ser  Leu Ala Trp Gly Phe  Trp Glu Gln
    1595                 1600                 1605

Gly Gly  Ile Gly Met Thr Ala  His Leu Gly Ala Ala  Asp Arg Ala
    1610                 1615                 1620

Arg Met  Lys Arg His Gly Val  Val Ala Met Ser Val  Ala Gln Gly
    1625                 1630                 1635

Leu Arg  Leu Leu Asp Arg Ala  Leu Ala His Pro Glu  Ala Ala Leu
    1640                 1645                 1650

Val Pro  Leu Ala Leu Asp Leu  Ser Ser Leu His Ala  Gly Ala Ser
    1655                 1660                 1665

Gly Ala  Gly Pro Val Pro Pro  Leu Leu Arg Gly Leu  Val Arg Ala
```

```
    1670                1675                1680

Pro Ala  Gly Arg Arg Thr Ala  Ala Ser Ala Ala Arg  Thr Asn Gly
    1685                1690                1695

Lys Gly  Thr Ala Leu Ala Ala  Leu Arg Ala Arg Leu  Leu Pro Leu
    1700                1705                1710

Pro Gln  Ala Glu Arg Glu Asp  Leu Leu Leu Glu Leu  Val Cys Thr
    1715                1720                1725

Glu Val  Ala Glu Val Leu Gln  Leu Pro Gly Pro Ala  His Val Pro
    1730                1735                1740

Ala Asp  Gln Pro Leu Arg Asp  Leu Gly Leu Asp Ser  Leu Met Thr
    1745                1750                1755

Val Glu  Leu Arg Asn Arg Leu  Gly Ala Arg Ala Glu  Thr Thr Leu
    1760                1765                1770

Pro Thr  Thr Leu Ala Phe Asp  Tyr Pro Thr Pro Arg  Ala Leu Ala
    1775                1780                1785

Ser Tyr  Leu Glu Thr Leu Leu  Gly Ile Ser Asp Glu  Asn Gly His
    1790                1795                1800

Ser Gly  Glu Leu Leu His Val  Pro Gln Asn Glu Asp  Glu Ile Arg
    1805                1810                1815

Ser Ala  Ile Ala Arg Ile Pro  Ile Ala Thr Leu Arg  Glu Ala Gly
    1820                1825                1830

Leu Leu  Gln Ser Leu Leu Arg  Leu Ala Pro Gly Lys  Ala Val Ala
    1835                1840                1845

Gly Asp  Val Thr His Pro Val  Asp Glu Leu Leu Val  Glu His Ile
    1850                1855                1860

Glu Asp  Glu Glu Leu Leu Arg  Leu Ala Phe Glu Ala  Thr Gly Gly
    1865                1870                1875

Ile Lys
    1880


<210> SEQ ID NO 27
<211> LENGTH: 2869
<212> TYPE: PRT
<213> ORGANISM: Sorangium cellulosum

<400> SEQUENCE: 27

Met Lys Asp Glu Ala Leu Ser Phe Arg Arg Ala Leu Glu Lys Thr Val
1               5                   10                  15

Val Glu Ile Arg Arg Leu Asn Arg Glu Ile Asp Asp Leu Arg Ala Lys
            20                  25                  30

Ser Ser Glu Pro Ile Ala Ile Val Ser Met Ala Cys Arg Phe Pro Gly
        35                  40                  45

Gly Val Glu Asn Pro Glu Ala Leu Trp Arg Leu Val Ser Glu Gly Gln
    50                  55                  60

Asp Ala Ile Gly Pro Phe Pro Glu Gly Arg Gly Trp Asp Val Ala Gly
65                  70                  75                  80

Leu Tyr Asp Pro Asp Pro Asp Val Pro Gly Lys Ser Ile Thr Ala Arg
                85                  90                  95

Gly Gly Phe Leu Tyr Asp Ala Asp Arg Phe Asp Pro Glu Phe Phe Gly
            100                 105                 110

Ile Ser Pro Arg Glu Ala Glu Arg Ile Asp Pro Gln Gln Arg Leu Leu
        115                 120                 125

Leu Glu Cys Ala Trp Glu Ala Leu Glu Arg Ala Gly Val Ala Pro His
    130                 135                 140
```

-continued

```
Thr Lys Glu Ala Ser Ala Thr Gly Val Phe Val Gly Leu Met Tyr Thr
145                 150                 155                 160

Asp Tyr Gly Leu Arg Leu Leu Asn His Pro Glu Ala Leu Asp Gly Tyr
                165                 170                 175

Ile Gly Ile Gly Ser Thr Gly Ser Thr Gly Ser Gly Arg Ile Ala Tyr
            180                 185                 190

Thr Leu Gly Leu Gln Gly Pro Ala Ile Thr Val Asp Thr Ala Cys Ser
        195                 200                 205

Ser Ser Leu Val Ala Leu His Met Ala Cys Ala Ser Leu Arg Gly Gly
    210                 215                 220

Glu Cys Asn Leu Ala Leu Val Gly Gly Val Ala Val Met Thr Thr Pro
225                 230                 235                 240

Thr Thr Phe Ile Glu Phe Ser Arg Gln Arg Gly Leu Ser Leu Asp Gly
                245                 250                 255

Arg Cys Lys Ser Phe Gly Ala Glu Ala Glu Gly Val Gly Trp Gly Glu
            260                 265                 270

Gly Cys Gly Ile Leu Ala Leu Lys Arg Leu Ser Asp Ala Arg Arg Asp
        275                 280                 285

Gly Asp Arg Val Leu Ala Ile Ile Arg Gly Ser Ala Val Asn Gln Asp
    290                 295                 300

Gly Arg Ser Gln Gly Phe Thr Ala Pro Asn Gly Pro Ser Gln Arg Ala
305                 310                 315                 320

Val Ile Gln Arg Ala Leu Ala Ala Ala Gly Leu Thr Ala Ala Asp Val
                325                 330                 335

Asp Ala Val Glu Gly His Gly Thr Gly Thr Arg Leu Gly Asp Pro Ile
            340                 345                 350

Glu Ala Gln Ala Leu Leu Ala Thr Tyr Gly Lys Ala His Thr Ala Glu
        355                 360                 365

Arg Pro Leu Trp Leu Gly Ser Ile Lys Ser Asn Phe Gly His Thr Gln
    370                 375                 380

Ala Ala Ala Gly Val Ala Gly Ile Ile Lys Leu Val Leu Ala Met Gln
385                 390                 395                 400

His Ala Glu Leu Pro Arg Thr Leu His Ala Asp Thr Pro Ser Pro His
                405                 410                 415

Val Asp Trp Ser Gln Gly His Val Lys Leu Leu Asn Glu Pro Val Pro
            420                 425                 430

Trp Pro Arg Thr Asp Arg Pro Arg Arg Ala Ala Val Ser Ser Phe Gly
        435                 440                 445

Ile Ser Gly Thr Asn Ala His Val Ile Leu Glu Glu Ala Pro Ala Glu
    450                 455                 460

Ala Pro Ala Ala Ala Gln Thr Pro Ala Ala Ala Gly Val Pro Ser Thr
465                 470                 475                 480

Leu Pro Leu Leu Leu Ser Gly Arg Asp Glu Pro Ala Leu Arg Ala Gln
                485                 490                 495

Ala Gly Arg Leu Ala Glu His Leu Arg Ala His Pro Gly Glu Arg Leu
            500                 505                 510

Leu Asp Ile Ala Ala Gly Leu Ala Thr Thr Arg Thr His Leu Ala Thr
        515                 520                 525

Arg Leu Ala Leu Pro Val Ala Ala Asp Ala Ala Ala Glu Glu Leu Ser
    530                 535                 540

Ala Arg Leu Ala Gln Phe Ala Ala Gly Gly Pro Ala Pro Ser Gly Ala
545                 550                 555                 560

Ala Val Thr Ala Pro Gly Gln Pro Pro Gly Lys Val Ala Val Leu Phe
```

-continued

```
                565                 570                 575

Thr Gly Gln Gly Ser Gln Arg Ala Ala Met Gly Arg Ala Leu Tyr Ala
            580                 585                 590

Thr His Pro Val Phe Arg Ala Ala Leu Asp Ala Ala Cys Ala Glu Leu
        595                 600                 605

Asp Arg His Leu Asp Arg Pro Leu His Ser Val Leu Phe Ala Asp Ala
    610                 615                 620

Gly Thr Glu Ala Ala Ala Leu Leu Asp Gln Thr Gly Trp Ala Gln Pro
625                 630                 635                 640

Ala Leu Phe Ala Leu Glu Val Ala Leu Tyr Arg Gln Trp Glu Ala Trp
                645                 650                 655

Gly Leu Arg Ala His Ala Leu Leu Gly His Ser Leu Gly Glu Ile Val
            660                 665                 670

Ala Ala His Ile Ala Gly Val Phe Asp Leu Pro Asp Ala Ser Ala Leu
        675                 680                 685

Val Ala Ala Arg Gly Arg Leu Met Gln Ala Leu Pro His Gly Gly Ala
    690                 695                 700

Met Ala Ser Ile Glu Ala Thr Glu His Glu Leu Leu Pro Leu Leu Asp
705                 710                 715                 720

Gln His Thr Gly Arg Leu Ser Leu Ala Ala Leu Asn Ala Pro Arg Gln
                725                 730                 735

Ser Val Val Ser Gly Asp Gln Pro Ala Val Asp Gln Val Cys Ala His
            740                 745                 750

Phe Lys Ala Leu Gly Arg Arg Ala Lys Arg Leu Asp Val Ser His Ala
        755                 760                 765

Phe His Ser Ala Arg Met Glu Pro Met Leu Asp Ala Phe Ala Arg Val
    770                 775                 780

Ala Arg Gly Leu Thr Tyr Arg Ala Pro Arg Leu Pro Val Val Ser Asn
785                 790                 795                 800

Val Thr Gly Arg Met Ala Thr Ala Asp Glu Leu Thr Ser Pro Asp Tyr
                805                 810                 815

Trp Val Arg His Val Arg Glu Pro Val Arg Phe Val Ala Gly Val Arg
            820                 825                 830

Ala Leu His Ala Thr Gly Val Ala Thr Tyr Leu Glu Cys Gly Pro Asp
        835                 840                 845

Pro Val Leu Gly Gly Met Ala Ala Asp Cys Leu Thr Ser Asp Glu Ser
    850                 855                 860

Arg Asp Pro Gly Leu Ile Pro Ser Leu Arg Lys Asp Arg Asp Glu Ala
865                 870                 875                 880

Leu Ala Ile Ala Gln Ala Ala Cys Ala Leu His Val Arg Gly His Ala
                885                 890                 895

Leu Asp Trp Pro Arg Leu Phe Asp Ala Thr Gly Ala Arg Arg Val Glu
            900                 905                 910

Leu Pro Thr Tyr Ala Phe Gln Arg Gln Arg Tyr Trp Leu Glu Thr Pro
        915                 920                 925

Gln Thr Pro Gly Ala Asp Gly Ala Ser Asn Leu Ser Ser Pro Ala Glu
    930                 935                 940

Ser Arg Phe Trp Glu Ala Val Glu Arg Ala Asp Ile Ile Pro Leu Ala
945                 950                 955                 960

Glu Ala Leu Arg Leu Glu Asp Glu Ala Gln Arg Ala Ser Leu Ala Thr
                965                 970                 975

Leu Leu Pro Ala Leu Ser Thr Trp Arg Arg Arg Arg His Glu Gln Ser
            980                 985                 990
```

```
Thr Ala Asp Ala Trp Arg Tyr Arg  Val Ala Trp Lys Pro  Leu Ala Ile
        995                 1000                1005

Asp Ala  Arg Ser Asp Leu Ser  Gly Val Trp Leu Phe  Leu Ala Pro
    1010                 1015                 1020

Pro Asp  His Ala Lys Asp Asp  Leu Ala Arg Ala Val  Leu Arg Ala
    1025                 1030                 1035

Leu Ala  Glu Ser Gly Ala Thr  Val Val Pro Val Leu  Val Ala Glu
    1040                 1045                 1050

Gly Asp  Val Asp Arg Ala Leu  Leu Ser Ala Arg Leu  Arg Glu Gln
    1055                 1060                 1065

Val Gly  Asp Gly Gly Ala Ile  Arg Gly Val Ile Ser  Leu Leu Ala
    1070                 1075                 1080

Leu Asp  Glu Thr Ser Leu Pro  Gln His Asp Gly Leu  Pro Arg Gly
    1085                 1090                 1095

Leu Ala  Phe Thr Leu Ala Leu  Val Gln Ala Leu Gly  Asp Thr Ala
    1100                 1105                 1110

Ile Ala  Ala Pro Leu Trp Leu  Leu Thr Arg Gly Ala  Val Ser Val
    1115                 1120                 1125

Gly Arg  Ser Asp Arg Leu Glu  Arg Pro Leu Gln Ala  Leu Thr Trp
    1130                 1135                 1140

Gly Leu  Gly Arg Val Val Ala  Leu Glu His Pro Glu  Arg Trp Gly
    1145                 1150                 1155

Gly Leu  Ile Asp Leu Ala Gly  Ala Leu Asp Glu Lys  Ala Leu Lys
    1160                 1165                 1170

Arg Leu  Val Ala Ala Leu Gly  Gly Arg Asp Ala Glu  Asp Gln Leu
    1175                 1180                 1185

Ala Leu  Arg Pro Ser Gly Leu  Phe Ala Arg Arg Leu  Val Arg Ala
    1190                 1195                 1200

Pro Leu  Gly Glu Ala Thr Ala  Val Arg Ala Trp Lys  Ala Arg Gly
    1205                 1210                 1215

Thr Ala  Leu Val Thr Gly Gly  Thr Gly Asp Leu Gly  Ala His Val
    1220                 1225                 1230

Ala Arg  Trp Leu Ala Gln Asn  Gly Ala Glu His Leu  Val Leu Thr
    1235                 1240                 1245

Ser Arg  Arg Gly Gln Asp Ala  Pro Gly Ala Ala Glu  Leu Thr Ala
    1250                 1255                 1260

Glu Leu  Thr Ala Leu Gly Ala  Arg Val Thr Ile Ala  Ala Cys Asp
    1265                 1270                 1275

Ser Ser  Asp Arg Gln Ala Leu  Ala Ala Leu Leu Gln  Arg Leu Arg
    1280                 1285                 1290

Ala Glu  Gly Pro Pro Leu Arg  Ala Val Val His Ala  Ala Gly Val
    1295                 1300                 1305

Asp Gln  Val Thr Pro Leu Ala  Arg Thr Ser Leu Ala  Glu Phe Ala
    1310                 1315                 1320

Gly Ile  Ala Ser Gly Lys Val  Ala Gly Ala Arg His  Leu Asp Asp
    1325                 1330                 1335

Leu Leu  Gly Asn Ala Pro Leu  Asp Ala Phe Ile Leu  Phe Ser Ser
    1340                 1345                 1350

Val Ala  Gly Val Trp Gly Ser  Gly Phe Gln Gly Ala  Tyr Ala Ala
    1355                 1360                 1365

Ala Asn  Ala Phe Leu Asp Ala  Leu Ala Glu Gln Arg  Arg Ala Leu
    1370                 1375                 1380
```

-continued

```
Gly Ser  Thr Ala Thr Ser Ile  Ala Trp Gly Leu Trp  Gly Gly Lys
    1385                 1390                 1395

Ser Met  Ala Asp Asp Ala Ala  Lys Asp His Leu Ser  Lys Arg Gly
    1400                 1405                 1410

Val Ser  Pro Met Pro Pro Gln  Leu Ala Ile Ala Ala  Leu Gln Arg
    1415                 1420                 1425

Ala Leu  Asp His Asp Glu Thr  Thr Leu Thr Leu Ala  Asp Val Asn
    1430                 1435                 1440

Trp Ser  Arg Phe Ala Pro Ala  Phe Ala Ala Ala Arg  Pro Arg Pro
    1445                 1450                 1455

Leu Leu  His Asp Leu Pro Glu  Ala Arg Ser Ala Leu  Glu Ser Pro
    1460                 1465                 1470

Ser Pro  Ala Pro Arg Glu Ala  Glu Leu Leu Thr Arg  Leu Gln Gly
    1475                 1480                 1485

Leu Ser  Ser Thr Glu Arg Val  Arg His Leu Val Ser  Leu Val Leu
    1490                 1495                 1500

Ala Glu  Thr Ala Val Val Leu  Gly His Pro Asp Ala  Ser Arg Leu
    1505                 1510                 1515

Asp Pro  His Thr Gly Phe Ala  Asp Leu Gly Leu Asp  Ser Leu Met
    1520                 1525                 1530

Ala Val  Glu Met Arg Arg Arg  Leu Gln Gln Ala Thr  Gly Val Ser
    1535                 1540                 1545

Leu Pro  Ala Thr Leu Thr Phe  Asp His Pro Ser Pro  His His Ile
    1550                 1555                 1560

Ala Thr  Phe Leu Leu Asp Glu  Val Phe Ala Pro Ala  Leu Gly Gln
    1565                 1570                 1575

Ala Pro  Gly Ala Glu Glu Asp  Glu Ala Ile Ala Gln  Ala Gly Leu
    1580                 1585                 1590

Ala Ser  Gly Asp Glu Pro Val  Ala Leu Ile Gly Val  Gly Leu Arg
    1595                 1600                 1605

Leu Pro  Gly Gly Ala Thr Asp  Leu Asp Gly Leu Trp  Arg Leu Leu
    1610                 1615                 1620

Glu Gln  Gly Ile Asp Val Val  Gly Pro Val Pro Glu  Asp Arg Gly
    1625                 1630                 1635

Trp Ser  Met Asp Glu Leu Tyr  Asp Pro Asp Pro Asp  Ser Leu Gly
    1640                 1645                 1650

Lys Ser  Tyr Val Arg Glu Ala  Ala Phe Leu Asp Arg  Ile Asp Leu
    1655                 1660                 1665

Phe Asp  Ala Gly Phe Phe Gly  Ile Ser Pro Arg Glu  Ala Ser His
    1670                 1675                 1680

Val Asp  Pro Gln His Arg Leu  Leu Leu Glu Ala Ala  Trp Gln Ala
    1685                 1690                 1695

Leu Glu  His Ala Gly Ile Val  Pro Ala Ser Leu Gln  Asp Ser Gln
    1700                 1705                 1710

Thr Gly  Val Phe Val Gly Ser  Gly Pro Ser Asp Tyr  Ala Leu Leu
    1715                 1720                 1725

His Asn  Pro Ala Gln Glu Asp  Glu Ala Tyr Arg Leu  Thr Gly Thr
    1730                 1735                 1740

Gln Pro  Ser Phe Ala Pro Gly  Arg Leu Ser Phe Ser  Leu Gly Leu
    1745                 1750                 1755

Gln Gly  Pro Ala Leu Ser Val  Asp Thr Ala Cys Ser  Ser Ser Leu
    1760                 1765                 1770

Val Ala  Leu His Leu Ala Ala  Gln Ala Leu Arg Arg  Gly Glu Cys
```

-continued

```
    1775                1780                1785

Gly Leu  Ala Leu Val Gly Ser  Ala Gln Val Met Ala  Ala Pro Asp
    1790                1795                1800

Ala Phe  Val Thr Leu Ser Arg  Ala Arg Ala Ile Ala  Pro Asp Gly
    1805                1810                1815

Arg Ser  Lys Thr Phe Ser Ala  Gln Ala Asp Gly Tyr  Gly Arg Gly
    1820                1825                1830

Glu Gly  Val Ile Val Phe Val  Leu Glu Arg Leu Ser  Asp Ala Arg
    1835                1840                1845

Ala Arg  Gly Arg Asp Val Leu  Ala Val Leu Arg Gly  Ser Ala Val
    1850                1855                1860

Asn His  Asp Gly Ala Ser Ser  Gly Ile Thr Ala Pro  Asn Gly Thr
    1865                1870                1875

Ser Gln  Gln Lys Val Leu Arg  Ala Ala Leu His Asp  Ala Arg Leu
    1880                1885                1890

Thr Pro  Ala Asp Val Asp Val  Val Glu Cys His Gly  Thr Gly Thr
    1895                1900                1905

Ser Leu  Gly Asp Pro Ile Glu  Val Gln Ala Leu Ala  Ala Val Tyr
    1910                1915                1920

Gly Lys  Glu Arg Ser Ala Asp  Arg Pro Leu Met Leu  Gly Ala Leu
    1925                1930                1935

Lys Thr  Asn Val Gly His Leu  Glu Ala Ala Ser Gly  Leu Ala Gly
    1940                1945                1950

Val Ala  Lys Val Val Ala Ala  Leu Arg His Glu Ala  Leu Pro Ala
    1955                1960                1965

Thr Leu  His Thr Ala Ala Arg  Asn Pro His Ile Gln  Trp Asp Thr
    1970                1975                1980

Leu Pro  Val Gln Val Val Asp  Thr Leu Arg Pro Trp  Pro Arg Arg
    1985                1990                1995

Glu Asp  Gly Thr Pro Arg Arg  Ala Gly Val Ser Ala  Phe Gly Leu
    2000                2005                2010

Ser Gly  Thr Asn Ala His Val  Leu Leu Glu Glu Ala  Pro Pro Val
    2015                2020                2025

Gln Pro  Ser Thr Gln Ala Glu  Gln Pro Ala Ala Pro  Pro Trp Leu
    2030                2035                2040

Pro Leu  Leu Leu Ser Gly Lys  Thr Asp Ala Ala Leu  Arg Ala Gln
    2045                2050                2055

Ala Glu  Arg Leu Arg Ala His  Leu Asp Ala His Ala  Asp Leu Gly
    2060                2065                2070

Leu Ala  Asp Val Ala Tyr Ser  Leu Ala Thr Thr Arg  Thr His Phe
    2075                2080                2085

Ala His  Arg Ala Val Val Val  Ala Asp Ala Gly Ala  Thr Leu Phe
    2090                2095                2100

Glu Gly  Leu Asp Ala Ile Ala  Arg Gly Asn Ala Ala  Ser His Val
    2105                2110                2115

Val Val  Asp Glu Ala Lys Ile  Asp Gly Lys Thr Val  Phe Val Phe
    2120                2125                2130

Pro Gly  Gln Gly Ser Gln Trp  Ala Gln Met Ala Gln  Pro Leu Leu
    2135                2140                2145

Glu Thr  Ser Glu Leu Phe Arg  Glu Arg Ile Glu Ala  Cys Ala His
    2150                2155                2160

Ala Leu  Ala Pro His Val Asp  Trp Ser Leu Leu Ala  Val Leu Arg
    2165                2170                2175
```

-continued

```
Gly Glu  Glu Gly Ala Pro Ser  Leu Glu Arg Val Asp  Val Val Gln
    2180                 2185                 2190

Pro Val  Leu Phe Ala Val Met  Val Ser Leu Ala Ala  Leu Trp Arg
    2195                 2200                 2205

Ser Met  Gly Val Glu Pro Asp  Ala Val Val Gly His  Ser Gln Gly
    2210                 2215                 2220

Glu Ile  Ala Ala Ala Cys Val  Ala Gly Ala Leu Ser  Leu Ala Asp
    2225                 2230                 2235

Ala Ala  Lys Val Val Ala Leu  Arg Ser Arg Ala Leu  Ala Arg Leu
    2240                 2245                 2250

Ala Gly  Arg Gly Ala Met Ala  Val Val Glu Leu Pro  Ala Ala Glu
    2255                 2260                 2265

Leu Ala  Glu Arg Met Lys Arg  Trp Gly Glu Arg Leu  Ser Ile Ala
    2270                 2275                 2280

Ala Leu  Asn Ser Pro Arg Ser  Thr Val Ile Ser Gly  Asp Pro Asp
    2285                 2290                 2295

Ala Val  Asp Ala Leu Leu Arg  Glu Leu Asp Ser Ala  Glu Ile Phe
    2300                 2305                 2310

Ala Arg  Lys Val Arg Val Asp  Tyr Ala Ser His Cys  Ser His Val
    2315                 2320                 2325

Glu Ala  Ile Arg His Gln Leu  Leu Ala Glu Leu Ala  Gly Ile Glu
    2330                 2335                 2340

Pro Leu  Pro Ser Thr Leu Pro  Leu Tyr Ser Thr Val  Ser Gly Asp
    2345                 2350                 2355

Lys Leu  Asp Gly Val Ala Leu  Asp Ala Ser Tyr Trp  Tyr Arg Asn
    2360                 2365                 2370

Leu Arg  Gln Thr Val Arg Phe  Ser Asp Ala Thr Gln  Arg Leu Val
    2375                 2380                 2385

Ser Ala  Gly His Arg Phe Phe  Val Glu Val Ser Pro  His Pro Val
    2390                 2395                 2400

Leu Thr  Phe Ala Val Gln Asp  Val Leu Asp Ala Glu  Gly Val Pro
    2405                 2410                 2415

Ala Ala  Val Val Gly Ser Leu  Arg Arg Gly Glu Gly  Asp Leu Arg
    2420                 2425                 2430

Arg Phe  Leu Val Ser Leu Ser  Glu Leu Phe Thr Arg  Gly Leu Ala
    2435                 2440                 2445

Leu Asp  Trp Ser Arg Val Leu  Pro Ser Gly Arg Arg  Val Ser Leu
    2450                 2455                 2460

Pro Thr  Tyr Ala Phe Gln Arg  Glu Arg Tyr Trp Leu  Gly Ala His
    2465                 2470                 2475

Arg Ala  Arg Gly Thr Asp Ala  Thr Ser Ala Gly Leu  Ala Ser Asp
    2480                 2485                 2490

Glu Pro  Thr Arg Gly Ala Ser  Met Pro Val Arg Leu  Ser Leu Arg
    2495                 2500                 2505

Asp Val  Pro Pro Glu Glu Arg  Gln Gly Ala Leu Glu  Arg Phe Val
    2510                 2515                 2520

Arg Glu  Gln Leu Ala Ala Val  Leu Arg Met Asp Ala  Ala Arg Ile
    2525                 2530                 2535

Glu Gly  Gln Thr Thr Ile Lys  Thr Leu Gly Ile Asp  Ser Leu Met
    2540                 2545                 2550

Ala Leu  Glu Ile Arg Lys Arg  Leu Glu Ala Gly Leu  Ala Val Thr
    2555                 2560                 2565
```

-continued

```
Leu Pro Ser Thr Leu Ile Trp Gln Phe Pro His Ala Glu Gly Leu
    2570                2575                2580

Ala Arg His Leu Met Thr Arg Leu Pro Ala Gly Asp Gly Glu Gly
    2585                2590                2595

Ser Ala Val Val Gln Pro Val Glu Gln Pro Arg Ala Pro Lys Glu
    2600                2605                2610

Val Pro Val Ser Met Asp Pro Ser Ala Trp Val His Arg Pro Arg
    2615                2620                2625

Pro Arg Ala Asp Ala Arg Val Arg Leu Phe Cys Leu Pro Tyr Ala
    2630                2635                2640

Gly Ala Gly Ala Ser Arg Phe Arg Ala Trp Pro Glu Leu Leu Pro
    2645                2650                2655

Ser Trp Val Glu Val Cys Pro Ile Gln Leu Pro Gly Arg Glu Glu
    2660                2665                2670

Arg Leu His Glu Pro Ala Phe Glu Thr Met Asp Ala Leu Val Asp
    2675                2680                2685

Ala Leu Val Pro Ala Val Glu Ala His Ile Asp Arg Pro Phe Ala
    2690                2695                2700

Leu Phe Gly Cys Ser Met Gly Ala Leu Leu Ala Phe Glu Leu Ala
    2705                2710                2715

Arg Ala Leu Gln Ser Arg His Arg Leu Val Ala Arg His Leu Phe
    2720                2725                2730

Gly Ala Ala Ser Ser Ser Pro Arg Arg Val Ser Pro Val Arg Glu
    2735                2740                2745

Gln Leu Ser Ala Val Val Ser Pro Gly Thr Val Arg Ser Asp Ala
    2750                2755                2760

Met Ala Ser Leu Arg Gln Leu Gly Leu Leu Ser Ser Ser Ser Leu
    2765                2770                2775

Gln Asp Glu Glu Met Leu Asp Glu Val Trp Pro Ala Phe Arg Ala
    2780                2785                2790

Asp Leu Ser Leu Thr Leu Lys Tyr Thr Cys Arg Asp Ala Thr Pro
    2795                2800                2805

Leu Asp Ala Pro Ile Ser Val Phe Gly Gly Thr Glu Asp Arg Thr
    2810                2815                2820

Val Gly Arg Glu Asp Leu Val Ala Trp His Thr Leu Thr Lys Asp
    2825                2830                2835

Ala Phe Gln Val Ala Met Leu Pro Gly Gly His Leu Phe Met Asp
    2840                2845                2850

Ala Thr Pro Lys Arg Leu Phe His His Ile Glu His Ala Leu Gln
    2855                2860                2865

Leu
```

<210> SEQ ID NO 28
<211> LENGTH: 228
<212> TYPE: PRT
<213> ORGANISM: Sorangium cellulosum

<400> SEQUENCE: 28

```
Met Arg Thr Ser Asp Ala Val Trp Ala Gly Ala Ala Gly Tyr Thr Arg
1               5                   10                  15

Ala Arg Leu Gln Val Tyr Asp Phe Phe Ile Tyr Gly Phe Asn Ser Pro
            20                  25                  30

Val Ala Trp Lys Cys Pro Gly Glu Glu Leu Leu Glu Asn Tyr Asn Arg
        35                  40                  45
```

-continued

```
His Val Ser Gly Asn His Leu Asp Val Gly Val Gly Thr Gly Tyr Leu
    50                  55                  60

Leu Asp Arg Cys Arg Phe Pro Thr Ala Lys Pro Arg Val Phe Leu Met
65                  70                  75                  80

Asp Leu Asn Pro Asp Ala Leu Gln Val Thr Ala Gln Arg Leu His Arg
                85                  90                  95

Phe Gln Pro Gln Thr Leu Arg Arg Asn Val Leu Asp Pro Ile Arg Phe
            100                 105                 110

Asp Gly Glu Pro Phe Asp Ser Ile Gly Met Asn Tyr Leu Met His Cys
        115                 120                 125

Val Pro Gly Ser Ile Pro Glu Lys Ala Val Met Phe Asp His Leu Ser
    130                 135                 140

Ala Leu Leu Lys Pro Gly Gly Val Ile Phe Gly Ser Thr Val Leu Ser
145                 150                 155                 160

Glu Gly Val Asp Lys Gly Ile Val Ala Arg Ala Ile Met Asp Arg Phe
                165                 170                 175

Asn Lys Lys Gly Ile Phe Ser Asn Thr Arg Asp Ala Ala Ser Asp Leu
            180                 185                 190

Thr Arg Ala Leu Glu Glu Arg Phe Asp Asp Val Ser Val Arg Val Val
        195                 200                 205

Gly Cys Val Gly Leu Phe Ser Ala Arg Lys Arg Thr Cys Ala Gly Thr
    210                 215                 220

Glu Ser Pro Ala
225
```

<210> SEQ ID NO 29
<211> LENGTH: 301
<212> TYPE: PRT
<213> ORGANISM: Sorangium cellulosum

<400> SEQUENCE: 29

```
Ile Val Leu Gly Asp Thr Leu Glu Gln Val Ala Thr Arg Leu Leu Glu
1               5                   10                  15

Glu Asp Leu Ala Ala Cys His Thr Thr Gly Glu Ala Ala Asp Val Leu
            20                  25                  30

Leu Asn Gly Val Leu Ala Ser Ser Ala Arg Ala Val Ala Ala Ala Leu
        35                  40                  45

Arg Ala Cys Asp Glu Phe Ala Ala Gly Asp Ser Asp Leu Pro Ser Leu
    50                  55                  60

Ala Arg Ala Cys Arg Ala Phe Ala Gly Leu Ala Ser Phe Gly Ser Ser
65                  70                  75                  80

Arg Ser Leu Ser Ser Leu Gly Asp Gly Val Ile Ala Pro Met Leu Glu
                85                  90                  95

Lys Thr Phe Ala Arg Ala Val Leu Arg Val His Gly Gly Cys Thr Gly
            100                 105                 110

Ser Asp Glu Ala Val Ala Ala Ala Lys Glu Ala Leu Arg Thr Leu His
        115                 120                 125

Asp Val Ala Leu Ser Gln Pro Ile Val Asp Arg Gly Ala Trp Leu Asp
    130                 135                 140

Ala Ala Arg Gly Leu Val Asp Ser Glu Val Val Asn Pro Thr Ala Ser
145                 150                 155                 160

Gly Leu Ala Cys Gly Leu Leu Tyr Leu Ala Gln Ala Ile Asp Asp Ala
                165                 170                 175

Glu Val Ala Arg Val Val Gly Leu Arg Leu Gly Gly Ala Ala Glu Pro
            180                 185                 190
```

```
Glu Ala Ala Ala Ser Phe Leu Ala Gly Phe Leu Glu Val Asn Ala Leu
        195                 200                 205

Val Leu Val Lys Ser Arg Pro Val Val Glu Ala Leu Asp Ala Phe Leu
    210                 215                 220

Arg Ala Ile Ala Pro Glu Arg Phe Lys Asp Thr Leu Pro Val Leu Arg
225                 230                 235                 240

Arg Ala Phe Ala Gly Leu Gly Ala Thr Glu Arg Arg Tyr Leu Leu Glu
                245                 250                 255

Asn Val Leu Ala Ala Arg Lys Leu Gly Asp Lys Ala Arg Ala Ala Gln
            260                 265                 270

Ala Val Leu Leu Glu Lys Asp Arg Glu Lys Leu Lys Glu Met Ser Glu
        275                 280                 285

Asp Leu Ser Gln Ala Met Asp Asp Leu Asp Glu Leu Leu
    290                 295                 300


<210> SEQ ID NO 30
<211> LENGTH: 345
<212> TYPE: PRT
<213> ORGANISM: Sorangium cellulosum

<400> SEQUENCE: 30

Met Arg Arg Pro Glu Arg Arg Asp Arg His Pro Arg Pro Arg Ala Ser
1               5                   10                  15

Asn Arg Gln Ser Ala Arg Arg Ser Ile Asp Ala Val Asp Gly Ser Thr
            20                  25                  30

Trp Tyr Pro Ser Thr Met Arg Leu Gln Ser Val Asp Thr His Leu Val
        35                  40                  45

Val Ala Leu His Ala Leu Leu Gln Glu Lys Ser Val Thr Arg Ala Ala
    50                  55                  60

Arg Arg Val Gly Val Thr Gln Pro Ser Met Ser His Ala Leu Ala Arg
65                  70                  75                  80

Leu Arg Ala His Phe Ala Asp Pro Leu Leu Ile Gln Val Gly Arg Gln
                85                  90                  95

Met Thr Leu Ser Glu Arg Ala Arg Asp Leu Ala Pro Arg Ala Ala Glu
            100                 105                 110

Ala Val Glu Arg Leu Glu Gln Val Phe Arg Pro Val Glu Arg Phe Asp
        115                 120                 125

Pro Arg Arg Ser Gln Arg Thr Phe Arg Leu Val Ala Thr Asp Asn Leu
    130                 135                 140

Glu Leu Leu Val Leu Pro Ala Leu Thr Ala Leu Leu Ala Val Glu Ala
145                 150                 155                 160

Pro Arg Val Asn Leu Arg Cys Arg Asn Ile Pro Ala Asp Phe Ala Glu
                165                 170                 175

Leu Leu Arg Arg Gly Glu Leu Asp Gly Lys Leu Gly Arg Gly Gly Pro
            180                 185                 190

Val Pro Asp Gly Cys Arg Ser Thr Leu Leu Ala Ala Glu Glu Ile Val
        195                 200                 205

Cys Val Met Arg Arg Gly His Pro Ala Ser Arg Arg Pro Leu Thr Ala
    210                 215                 220

Ala Arg Tyr Ala Ala Cys Glu His Leu Met Val Ser Pro His Gly Glu
225                 230                 235                 240

Asp His Gly Ala Ile Asp Arg Ala Leu Ala Glu Gln Gly Thr Arg Arg
                245                 250                 255

Arg Val Thr Leu Thr Val Ser His Phe Leu Val Ala Pro Phe Ile Val
```

-continued

```
            260                 265                 270

Ser Gly Ser Asp Leu Leu Leu Thr Val Ser Ala Arg Val Ala Ala Ala
        275                 280                 285

Leu Ala Arg Arg Leu Asp Leu Val Val Arg Pro Cys Pro Phe Ala Leu
    290                 295                 300

Glu Gly Tyr Thr Leu Thr Leu Val Trp Pro Glu Arg Ser Glu His Asp
305                 310                 315                 320

Glu Gly His Gly Trp Leu Arg Asp Ala Ile Gln Arg Ala Val Ala Val
                325                 330                 335

Asp Ser Arg Pro Ala Leu Pro Gly Val
            340                 345


<210> SEQ ID NO 31
<211> LENGTH: 108
<212> TYPE: PRT
<213> ORGANISM: Sorangium cellulosum

<400> SEQUENCE: 31

Met Ile Ile Glu Tyr Val Arg Tyr Thr Ile Pro Ala Glu Gln Glu Lys
1               5                   10                  15

Glu Phe Leu Ala Ala Tyr Arg Asp Ala Ala Ala Glu Leu Arg Gly Ser
            20                  25                  30

Glu His Cys Leu Asp Tyr Glu Ile Ser Arg Cys Val Glu Asp Pro Thr
        35                  40                  45

Ser Tyr Val Val Arg Ile Cys Trp Asp Ser Leu Gln Gly His Leu Gln
    50                  55                  60

Gly Phe Arg Lys Ala Ala Ala Phe Pro Ser Phe Phe Ala Lys Val Lys
65                  70                  75                  80

Pro Phe Tyr Glu Arg Ile Gln Glu Met Arg His Tyr Ala Leu Thr Asp
                85                  90                  95

Val Ala Ala Arg Gln Ala Gly Thr Ala Ala Thr Gly
            100                 105


<210> SEQ ID NO 32
<211> LENGTH: 486
<212> TYPE: PRT
<213> ORGANISM: Sorangium cellulosum

<400> SEQUENCE: 32

Met Lys Leu Ala Arg Lys Leu Thr Leu Ala Leu Val Phe Gly Val Phe
1               5                   10                  15

Leu Val Leu Ala Leu Ser Ala Tyr Ala Gln Ile Arg Arg Glu Ala Arg
            20                  25                  30

Ile Phe Glu Asn Asp Val Gln Arg Asp His His Thr Met Ala Arg Ala
        35                  40                  45

Leu Ala Ala Ala Val Met Glu Val Trp Arg Ser Glu Gly Thr Ala Arg
    50                  55                  60

Ala Leu Arg Leu Val Glu Asp Ala Asn Glu Arg Glu Gln Gln Ala Asn
65                  70                  75                  80

Ile Arg Trp Val Trp Leu Asp Gly Gln Ala Asp Glu Pro His Arg Pro
                85                  90                  95

Arg Leu Ala Pro Glu Leu Leu Ala Pro Val Ala Glu Gly Arg Ala Val
            100                 105                 110

Val Arg Arg Ile Pro Gln Lys Asp Ala Asp Leu Leu Val Thr Cys Val
        115                 120                 125

Pro Val Ser Val Pro Gly Asp Arg Ala Gly Ala Leu Glu Leu Ser Glu
```

```
    130                 135                 140

Ser Leu Ala Gly Ala Arg Arg Tyr Ile Arg Ser Met Ile Leu Ser Thr
145                 150                 155                 160

Ala Ile Thr Thr Ala Ala Leu Thr Leu Val Cys Gly Leu Leu Thr Thr
                165                 170                 175

Gly Leu Gly Val Trp Leu Val Gly Arg Pro Met Arg Thr Leu Ile Asp
            180                 185                 190

Gln Ala Arg Arg Ile Gly Ala Gly Asp Leu Ser Gly Arg Leu Ser Leu
        195                 200                 205

Arg Gln Glu Asp Glu Ile Gly Glu Leu Gly Arg Glu Met Asn Ala Met
    210                 215                 220

Cys Asp Arg Leu Ala Ala Ala Asn Gln Lys Leu Glu Ser Glu Ala Ala
225                 230                 235                 240

Ala Arg Ile Ala Ala Leu Gln Gln Leu Arg His Ala Glu Arg Leu Ala
                245                 250                 255

Thr Val Gly Lys Leu Ala Ser Gly Ile Ala His Glu Leu Gly Ala Pro
            260                 265                 270

Leu Gln Val Val Thr Gly Arg Ala Arg Met Leu Val Asp Gly Asp Val
        275                 280                 285

Ser Gly Asp Glu Val Pro Ile Asn Gly Gln Ile Ile Leu Glu Gln Ser
    290                 295                 300

Gln Arg Met Thr Gln Ile Ile Arg Gln Leu Leu Asp Phe Ala Arg Arg
305                 310                 315                 320

Arg Ser Ala Glu Lys Gln Glu Thr Ala Leu Arg Gly Val Ile Arg Gly
                325                 330                 335

Thr Phe Thr Met Leu Lys Pro Leu Ala Asp Lys Gln Gly Val Thr Ile
            340                 345                 350

Val Glu Glu Gly Asp Thr Pro Asp Arg Val Val His Ala Asp Ala Asp
        355                 360                 365

Gln Leu Gln Gln Ala Leu Thr Asn Val Val Val Asn Ala Ile Gln Ala
    370                 375                 380

Met Pro Ser Gly Gly Thr Ile Thr Val Gly Val Arg Thr Val Arg Ala
385                 390                 395                 400

Ser Pro Pro Pro Asp Gln Gly Gly Ala Glu Gly Asp Tyr Ile Ala Leu
                405                 410                 415

Ser Val Arg Asp Glu Gly Gln Gly Met Thr Ala Asp Val Leu Glu His
            420                 425                 430

Val Phe Glu Pro Phe Phe Thr Thr Lys Pro Val Gly Glu Gly Thr Gly
        435                 440                 445

Leu Gly Leu Pro Val Ala Tyr Gly Ile Ile Lys Glu His Gly Gly Trp
    450                 455                 460

Ile Asp Val Asp Ser Arg Pro Gly Ser Gly Ser Gln Phe Thr Met Tyr
465                 470                 475                 480

Leu Pro Gln Glu Lys Pro
                485


<210> SEQ ID NO 33
<211> LENGTH: 461
<212> TYPE: PRT
<213> ORGANISM: Sorangium cellulosum

<400> SEQUENCE: 33

Met Thr Gly Arg Val Leu Ile Val Asp Asp Glu Arg Gly Val Cys Glu
1               5                   10                  15
```

```
Leu Leu Asp Ala Gly Leu Lys Lys Arg Gly Phe Gln Ala Ala Trp Arg
            20                  25                  30

Thr Ser Ala Ala Glu Ala Leu Glu Leu Leu Gly Ala Glu Asp Phe Asp
        35                  40                  45

Val Val Val Thr Asp Met Thr Met Arg Gly Met Asn Gly Leu Glu Leu
    50                  55                  60

Cys Glu Arg Ile Ala Gln Asn Arg Pro Asp Leu Pro Val Ile Val Ile
65                  70                  75                  80

Thr Ala Phe Gly Ser Leu Asp Thr Ala Thr Ser Ala Ile Arg Ala Gly
                85                  90                  95

Ala Tyr Asp Phe Val Thr Lys Pro Phe Glu Leu Asp Ala Leu Arg Leu
            100                 105                 110

Thr Val Glu Arg Ala Leu Arg His Arg Ala Leu Arg Glu Glu Val Arg
        115                 120                 125

Arg Leu Arg Arg Ala Val Asp Asp Ser His Arg Tyr Glu Gln Ile Leu
    130                 135                 140

Gly Gly Ser Pro Ala Met Lys Gly Val Phe Asp Leu Leu Asp Arg Val
145                 150                 155                 160

Ala Asp Ser Asp Thr Ser Ile Leu Ile Thr Gly Glu Ser Gly Thr Gly
                165                 170                 175

Lys Glu Leu Val Ala Arg Ala Val His Gln Arg Ser Arg Arg Gly Gln
            180                 185                 190

Gly Ala Phe Ile Ala Val Asn Cys Ala Ala Val Pro Asp Ala Leu Leu
        195                 200                 205

Glu Thr Glu Leu Phe Gly His Ala Arg Gly Ala Phe Thr Asp Ala Lys
    210                 215                 220

Gly Ala Arg Ser Gly Leu Phe Ala Arg Ala His Gly Gly Thr Leu Phe
225                 230                 235                 240

Leu Asp Glu Ile Gly Glu Leu Pro Val Gly Leu Gln Pro Lys Leu Leu
                245                 250                 255

Arg Ala Leu Gln Glu Arg Val Val Arg Pro Val Gly Ala Asp Glu Glu
            260                 265                 270

Val Pro Val Asp Val Arg Leu Ile Ala Ala Thr Asn Arg Asp Leu Glu
        275                 280                 285

Thr Ala Ile Glu Glu Arg Arg Phe Arg Glu Asp Leu Tyr Tyr Arg Ile
    290                 295                 300

Asn Val Val His Val Asp Leu Pro Pro Leu Arg Ser Arg Gly Ala Asp
305                 310                 315                 320

Val Leu Leu Leu Ala Gln Arg Phe Leu Glu His Phe Ala Thr Val Lys
                325                 330                 335

Glu Arg Pro Ile Lys Gly Leu Ser Ala Pro Ala Ala Glu Lys Leu Val
            340                 345                 350

Ala Tyr Ala Trp Pro Gly Asn Val Arg Glu Leu Gln Asn Cys Ile Glu
        355                 360                 365

Arg Ala Val Ala Leu Ala Arg Tyr Asp Gln Ile Thr Val Asp Asp Leu
    370                 375                 380

Pro Glu Lys Ile Arg Ser Tyr Arg Arg Ser His Val Leu Val Ser Ser
385                 390                 395                 400

Asp Asp Pro Thr Glu Leu Val Pro Met Glu Glu Val Glu Arg Arg Tyr
                405                 410                 415

Ile Leu Arg Val Leu Glu Val Val Gly Gly Asn Lys Ser Gln Ala Ala
            420                 425                 430

Gln Val Leu Gly Phe Asp Arg Ala Thr Leu Tyr Arg Lys Leu Glu Arg
```

-continued

```
        435                 440                 445

Tyr Gly Leu Arg Ala Gly Arg Ala Gly Asp Pro Arg Pro
    450                 455                 460


<210> SEQ ID NO 34
<211> LENGTH: 508
<212> TYPE: PRT
<213> ORGANISM: Sorangium cellulosum

<400> SEQUENCE: 34

Met Arg Gln Pro Thr Pro Gln Gly Leu Ser Trp Pro Arg Leu Pro Arg
1               5                   10                  15

Pro Val Arg Leu Ser Ala Leu Leu Gly Ala Ala Thr Leu Leu Leu Thr
            20                  25                  30

Ser Val Ala Ile Val Val Ala Gly Ala Leu Met Val Ala Ser Thr Thr
        35                  40                  45

Met Gln Gln Thr Thr Arg Ile Leu Gly Ala Thr Val Glu Ser Val Arg
    50                  55                  60

Leu Val Glu Arg Leu Glu Ile Asp Leu Leu Leu Asp Ala His Gln Ser
65                  70                  75                  80

Ser Arg Ala Val Gly Ser Gly Arg Gly Glu Leu Ala Pro Ser Leu Ala
                85                  90                  95

Ala Trp Glu Gln Gly Leu Arg Ser Gly Leu Ala Ala Ala Arg Asp His
            100                 105                 110

Val Ser Ser Pro Glu Glu Gly Arg Ile Leu Glu His Ala Glu Arg Arg
        115                 120                 125

Val Glu Asp Tyr Leu Ala Arg Arg Arg Ala Ala Asp Ala His Glu Leu
    130                 135                 140

Pro Ser Ala Pro Gly Ala His Asp Pro Ala Leu Leu Gly Val His Asp
145                 150                 155                 160

Pro Ala Leu Asp Glu Ala Phe Arg Ala Leu Asp His Leu Val Glu Ile
                165                 170                 175

Asn Leu Glu Gln Ala Arg Ala Ser Glu Ala Leu Val Ala His Leu Thr
            180                 185                 190

Arg Arg Thr Thr Gly Ala Gly Leu Ala Ala Val Val Phe Phe Leu Ala
        195                 200                 205

Gly Ala Ser Thr Ile Leu Leu Ser Ala Arg Arg Leu Ile Tyr Arg Pro
    210                 215                 220

Ile Val Ala Ile Gln Glu Ala Ile Gly Arg Tyr Gly Ala Gly Asp Arg
225                 230                 235                 240

Ala Ala Arg Ala Pro Leu Ile Gly Pro Arg Glu Leu Gly Glu Ile Ala
                245                 250                 255

Arg Ala Phe Asn Asp Met Ala Glu Ser Leu Glu Arg Gln Arg Glu Ala
            260                 265                 270

Gln Phe Ala Phe Leu Gly Gly Val Ala His Asp Leu Arg Asn Pro Leu
        275                 280                 285

Ser Ala Leu Arg Leu Ser Val His Val Leu Asp Ala Asp Asn Arg Pro
    290                 295                 300

Leu Glu Ser Ser Val Arg Arg Thr Met Ala Leu Val Gly Arg Gln Val
305                 310                 315                 320

Asp Arg Leu Asp Arg Met Val Gly Asp Leu Leu Asp Ala Ser Gln Ile
                325                 330                 335

Glu Ala Cys Lys Leu Asp Leu Arg Val Glu Glu Arg Asp Leu Arg Asp
            340                 345                 350
```

-continued

```
Leu Ala Gln Glu Ala Val Asp Leu Tyr Arg Pro Val Ser Pro Glu His
        355                 360                 365

Pro Ile Glu Leu Ser Leu Pro Glu Thr Pro Val Leu Val Arg Cys Asp
    370                 375                 380

Ala Thr Arg Ile Glu Gln Val Leu Asn Asn Leu Leu Ser Asn Ala Leu
385                 390                 395                 400

Lys Tyr Ser Pro Ala Gly Gly Gln Val Asp Val Ala Val Arg Ala Gly
                405                 410                 415

Gly Glu Gly Ala Glu Ile Ala Val Arg Asp Arg Gly Leu Gly Ile Glu
            420                 425                 430

Pro Glu Asp Leu Ala His Leu Phe Glu Pro Phe Arg Arg Leu Lys Ser
        435                 440                 445

Thr Ser Gly Ser Ile Pro Gly Thr Gly Leu Gly Leu Ala Val Ala Lys
    450                 455                 460

Arg Ile Val Glu Ala His Gly Gly Arg Leu Phe Val Glu Ser Arg Pro
465                 470                 475                 480

Gly Ala Gly Ser Val Phe Arg Ile Glu Leu Pro Arg Ser Ser Ser Arg
                485                 490                 495

Asp Gln Ala Asp Gly Pro Arg Gly Val Ser His Gly
            500                 505


<210> SEQ ID NO 35
<211> LENGTH: 416
<212> TYPE: PRT
<213> ORGANISM: Sorangium cellulosum

<400> SEQUENCE: 35

Met Pro Ala Arg Thr Pro Arg Lys Pro Pro Pro Pro Ala Ser Pro Ala
1               5                   10                  15

Gly Pro Ala Gly Ala Pro Asp Asp Leu Thr Asp Ser Asp Arg Asp Ala
            20                  25                  30

Leu Leu Arg Trp Arg Leu Ala Leu Gly Pro Glu Ala Glu Arg Val Asp
        35                  40                  45

Pro Arg Leu Ser Leu Gly Gly Leu Gly Gly Ala Ala Pro Ala Leu Asp
    50                  55                  60

Val Asp Ala Arg Arg Leu Gly Asp Leu Asp Lys Ala Leu Ser Phe Ile
65                  70                  75                  80

Tyr Asp Glu Arg Ala Gly Gly Leu Gly Gly Ser Arg Pro Tyr Val Pro
                85                  90                  95

Glu Trp Leu Ser Ala Val Arg Glu Phe Phe Ser His Glu Val Val Ala
            100                 105                 110

Leu Val Gln Lys Asp Ala Ile Glu Arg Lys Gly Leu Thr Gln Leu Leu
        115                 120                 125

Phe Glu Pro Glu Thr Leu Pro Phe Leu Glu Lys Asn Val Glu Leu Val
    130                 135                 140

Ala Thr Leu Met Ser Ala Lys Gly Leu Ile Pro Asp Ala Ala Arg Asp
145                 150                 155                 160

Thr Ala Arg Gln Ile Val Arg Glu Val Val Glu Glu Val Arg Arg Ala
                165                 170                 175

Leu Glu Ala Glu Val Arg Thr Ala Val Leu Gly Ala Leu Arg Arg Asn
            180                 185                 190

Thr Thr Ser Pro Leu Arg Val Leu Arg Asn Leu Asp Trp Lys Arg Thr
        195                 200                 205

Ile Arg Lys Asn Leu Lys Gly Trp Asp Ala Glu Arg Arg Arg Leu Val
    210                 215                 220
```

```
Pro Asp Lys Leu Tyr Phe Trp Ala Asn Gln Thr Arg Arg His Glu Trp
225                 230                 235                 240

Asp Val Ala Ile Leu Val Asp Gln Ser Gly Ser Met Gly Glu Ser Val
                245                 250                 255

Val Tyr Ser Ser Ile Met Ala Ala Ile Phe Ala Ser Leu Asp Val Leu
            260                 265                 270

Arg Thr Arg Leu Leu Phe Phe Asp Thr Glu Val Val Asp Val Thr Pro
        275                 280                 285

Met Leu Val Asp Pro Val Asp Val Leu Phe Thr Ala Gln Leu Gly Gly
    290                 295                 300

Gly Thr Asp Ile Asn Arg Ala Val Ala Tyr Ala Gln Ala Asn Phe Ile
305                 310                 315                 320

Glu Arg Pro Glu Lys Thr Leu Leu Ile Leu Ile Thr Asp Leu Phe Glu
                325                 330                 335

Gly Gly Asn Ala Glu Glu Leu Val Ala Arg Met Arg Gln Leu Ala Asp
            340                 345                 350

Ser Lys Val Lys Ser Ile Cys Leu Leu Ala Leu Ser Asp Gly Gly Lys
        355                 360                 365

Pro Ser Tyr Asp His Glu Met Ala Gln Lys Leu Ala Ala Leu Gly Thr
    370                 375                 380

Pro Cys Phe Gly Cys Thr Pro Lys Leu Leu Val Lys Val Val Glu Arg
385                 390                 395                 400

Leu Met Arg Gly Gln Asp Leu Gly Pro Leu Leu Gly Ala Glu Ala Arg
                405                 410                 415


<210> SEQ ID NO 36
<211> LENGTH: 352
<212> TYPE: PRT
<213> ORGANISM: Sorangium cellulosum

<400> SEQUENCE: 36

Met Ala Glu Leu Asp His Trp His Pro Val Leu Leu Ser His Glu Leu
1               5                   10                  15

Arg Arg Lys Pro Arg Asn Val Arg Leu Ala Gly His Glu Ile Val Val
            20                  25                  30

Phe Arg Thr Ser Ser Gly Gly Leu Gly Ala Phe Thr Asp Arg Cys Pro
        35                  40                  45

His Arg Ser Met Arg Leu Ser Glu Gly Trp Val Glu Gly Asp Arg Leu
    50                  55                  60

Val Cys Ala Tyr His Gly Trp Arg Trp Ala Val Asp Gly Arg Gly Glu
65                  70                  75                  80

Ile Pro Ala Thr Pro Ala Ala Arg Pro Cys Ala Arg Arg Glu Asp Met
                85                  90                  95

Phe Glu Ala Val Glu Arg Tyr Gly Ala Ile Trp Val Lys Arg Ala Gly
            100                 105                 110

Ser Gln Ala Ala Phe Pro Arg Leu Glu Gly Glu Gly Tyr Val Pro Arg
        115                 120                 125

Gly Leu Leu Arg His Arg Ala Thr Val Pro Phe Glu Leu Ala Leu Asp
    130                 135                 140

Asn Phe Ile Glu Ile Glu His Thr Pro Phe Val His Phe Met Leu Gly
145                 150                 155                 160

Tyr Pro Leu Glu Arg Met Pro Glu Val Glu Ala Arg Val Thr Leu Thr
                165                 170                 175

Asp Glu Thr Ile Arg Val Val His Ser Gly Pro Arg Arg Pro Met Pro
```

-continued

```
            180                 185                 190

Arg Ala Met Glu Lys Leu Leu Gly Ile Pro Glu Asp Ala Ile Phe Val
        195                 200                 205

Val Asp Trp Thr Ser Tyr Phe Ser Pro Val Tyr Thr Ile Tyr Asn His
    210                 215                 220

Ser Leu Arg Asp Pro Lys Thr Asn Gln Pro Val Thr Phe Pro Leu Arg
225                 230                 235                 240

Ser Ala Val Phe Phe Asn Pro Val Gly Pro Glu Ser Ser Glu Met Tyr
                245                 250                 255

Thr Phe Leu Phe Ala Ser Leu Ala Pro Trp Ser Lys Phe Gly Ala Gly
            260                 265                 270

Ala Val Leu Trp Pro Ala Met Gln Val Ala Met Asn Ile Glu Leu Arg
        275                 280                 285

Leu Asp Met Arg Leu Leu Asp Arg Leu Thr Asp Lys Arg Gly Ile Leu
    290                 295                 300

Lys Gly Asn Val Leu Gly Arg Phe Asp Lys Pro Leu Val Ile Ala Arg
305                 310                 315                 320

Asp Arg Ile Asp Arg Ile Tyr Arg Gly Arg Val Ala Glu Ala Gly Asp
                325                 330                 335

Gly His Glu Ala Ala Arg Pro Ala Arg Arg Leu Pro Leu Ala Ala Pro
            340                 345                 350


<210> SEQ ID NO 37
<211> LENGTH: 376
<212> TYPE: PRT
<213> ORGANISM: Sorangium cellulosum

<400> SEQUENCE: 37

Met His Val Glu Glu Cys His Val Val Ile Val Gly Ala Gly Pro Ser
1               5                   10                  15

Gly Leu Ala Val Gly Ala Cys Leu Arg Glu Gln Gly Ile Pro Phe Val
            20                  25                  30

Leu Leu Glu Lys Ser Glu Ala Val Gly Ala Thr Trp Arg Arg His Tyr
        35                  40                  45

Asp Arg Leu His Leu Asn Thr Ile Lys Gln Leu Ser Ala Leu Pro Gly
    50                  55                  60

Gln Pro Trp Pro Glu Tyr Ser Ala Pro Tyr Pro Ser Arg Val Glu Met
65                  70                  75                  80

Val Asp Tyr Leu Glu Arg Tyr Ala Glu Arg Phe Arg Leu Glu Pro Arg
                85                  90                  95

Leu Gly Val Glu Val Glu Arg Ala Tyr His Asp Gly Ser Arg Trp Val
            100                 105                 110

Thr Arg Thr His Ala Gly Glu Leu Arg Ser Gln Ala Leu Val Val Ala
        115                 120                 125

Thr Gly Tyr Ser Arg His Pro Asn Val Pro Thr Trp Pro Asp Gln Glu
    130                 135                 140

Arg Phe Arg Gly Arg Ile Leu His Ser Ser Ala Tyr Arg Ser Gly Ala
145                 150                 155                 160

Glu Phe Arg Gly Gln Arg Val Leu Val Val Gly Ala Gly Asn Ser Ala
                165                 170                 175

Ser Glu Ile Ala Leu Asp Leu Trp Glu His Cys Ala Glu Thr Thr Leu
            180                 185                 190

Ser Val Arg Ser Gly Asn His Val Ile Pro Arg Glu Leu Phe Lys Leu
        195                 200                 205
```

-continued

Pro Ala Gln Phe Asn Ala Leu Ala Leu Phe Glu Arg Leu Pro Leu Ala
210 215 220

Val Gly Asp Arg Leu Ala Thr Ala Ile Leu Ser Arg Ala Val Gly Asp
225 230 235 240

Leu Ser Arg Trp Gly Ile Arg Arg Pro Ala Val Gly Pro Gly Thr Arg
245 250 255

Ala Leu Lys Glu Gly Arg Met Pro Leu Ile Asp Ile Gly Thr Val Ala
260 265 270

Leu Ile Gln Gln Gly Lys Ile Lys Val Val Pro Gly Pro Arg Ala Phe
275 280 285

Thr Glu Thr Gly Val Thr Phe Thr Asp Gly Arg Gly Leu Pro Phe Asp
290 295 300

Val Val Val Leu Ala Thr Gly Tyr Arg Pro Gly Leu Asp Asp Phe Leu
305 310 315 320

Glu Asn Ala Thr Arg Tyr Thr Asp Glu His Gly Cys Pro Arg Trp His
325 330 335

Gly Ala Pro Thr Pro Ala Pro Gly Leu Phe Phe Ile Gly Phe Arg Asn
340 345 350

Pro Ile Thr Gly Gln Ile Arg Asp Ile Ala Ala Glu Ala Pro Arg Ile
355 360 365

Ala Arg His Ile Gln Gly Val Asn
370 375

<210> SEQ ID NO 38
<211> LENGTH: 356
<212> TYPE: PRT
<213> ORGANISM: Sorangium cellulosum

<400> SEQUENCE: 38

Met Cys Tyr Gly Leu Ala Met His Ala Ala Pro Ala Arg Asp Leu Ile
1 5 10 15

Arg His Phe His Pro Val Leu Pro Ala Ser Lys Leu Gly Arg Lys Pro
20 25 30

Val Arg Val Val Leu Ala Gly Asn Ala Tyr Ala Leu Phe Arg Asp Glu
35 40 45

Gln Gly Arg Pro Ala Ala Leu Ala Asp Ala Cys Pro His Arg Leu Ala
50 55 60

Pro Leu Ser Gln Gly Arg Val Arg Pro Asp Gly Arg Leu Glu Cys Pro
65 70 75 80

Tyr His Gly Trp His Phe Asp Ala Glu Gly Arg Gly Ala Cys Pro Ser
85 90 95

Gln Pro Ser Leu Thr Arg Cys Asp Thr Arg Ser Phe Gln Leu Val Glu
100 105 110

Gln Leu Gly Tyr Leu Trp Leu Ala His Arg Asp Thr Pro Arg Ser Ala
115 120 125

Leu Pro Glu Leu Asp Phe Ser Ser Asp Gly Phe Glu Tyr Ala Gly Thr
130 135 140

Phe Ser His Leu Ala Pro Ala Pro Leu His Val Ile Phe Asp Asn Ser
145 150 155 160

Ser Glu Asp Glu His Thr Pro Phe Val His Gly Arg Leu Gly Trp Thr
165 170 175

Pro Glu Asp Ala Ala Arg Ile Asp Phe Ser Cys Asp Val Phe Glu Asp
180 185 190

Arg Thr Glu Val Lys Tyr Ser Ala Pro Gln Arg Pro Ser Thr Leu Ala
195 200 205

```
Arg Leu Met Leu Leu Gln Pro Gly Asp Thr Phe His Asn Gln Trp Val
    210                 215                 220

Thr Arg Phe Ser Pro Val Tyr Thr Val Tyr Thr Ser Trp Trp Thr Ala
225                 230                 235                 240

Gln Asn Gly Met Glu Arg Pro Val Val Ala Arg Ala Gly Ile Phe Phe
                245                 250                 255

Val Pro Glu Thr Glu Arg Thr Thr Phe Val Arg Ala Phe Leu Phe Val
            260                 265                 270

Lys Ile Thr Asp Pro Arg Phe Arg Pro Leu Leu Pro Val Val Lys Ser
        275                 280                 285

Ala Ala Ile Ala Leu Ser Trp Lys Glu Ile Arg Asp Asp Val Lys Phe
    290                 295                 300

Ile Pro His Val Ala Asp Thr Pro Phe Glu Met Lys Gly Met Arg Leu
305                 310                 315                 320

Asn Lys Tyr Asp Ala Thr Leu Val His Asn His Arg Leu Met Arg Ser
                325                 330                 335

Ile Tyr Phe Gly Glu Thr Arg Gly Glu Ala Glu Gly Thr Gly Val Gly
            340                 345                 350

His Ala Ser Ala
        355


<210> SEQ ID NO 39
<211> LENGTH: 395
<212> TYPE: PRT
<213> ORGANISM: Sorangium cellulosum

<400> SEQUENCE: 39

Met Thr Cys Phe Val Pro Ala Leu Arg Arg Met Gly Ala Thr Pro Ala
1               5                   10                  15

Arg Thr Cys Met Arg Gln Arg Leu Asp Val Thr Asp Leu Tyr Asn Asp
            20                  25                  30

Ala Tyr Thr Ala Tyr Ile Glu Ala Phe Arg Arg Gln Thr Glu Leu Val
        35                  40                  45

Ala Ser Glu Ile Leu Leu Glu His Leu Val Asp Pro Ser Gly Ala Val
    50                  55                  60

Arg Gly Leu Asp Asp Arg Pro Glu Ser Ala Pro Ser Val Thr Ala Tyr
65                  70                  75                  80

Gln Phe Arg Arg Lys Leu Leu Asp Tyr Phe Ser Asp Lys Gly Asp Leu
                85                  90                  95

Thr Gln Asp Pro Ser Gly Arg Leu Val Pro Ser Glu Ala Val Arg Lys
            100                 105                 110

Arg Val Ala Glu Lys Glu Ser Ile Ala Leu Ala Asp Arg Ala Ile Leu
        115                 120                 125

Gly Glu Met Val Glu Phe Leu Gln Arg Tyr Arg Gly Leu Ala Gly Pro
    130                 135                 140

Val Leu Ala Gly Lys Asp Ala Leu Ala Thr Met Asp Leu Gln Tyr Gly
145                 150                 155                 160

Met Gln Ala Ser Leu Lys Phe Trp Glu Tyr Ser Met Ile Ser Leu Pro
                165                 170                 175

Ala Lys Lys Pro Cys Asn Val Met Leu Ala Arg Ala Leu Met Ala Lys
            180                 185                 190

Leu Ala Glu Gly Pro Gly Ile Ser Val Phe Glu Gly Gly Ala Gly Leu
        195                 200                 205

Gly Val Val Leu Arg Gln Ala Leu Ser Asp Pro Arg Phe Leu Pro Leu
```

```
    210                 215                 220

Ser Lys Asn Leu Ala Arg Tyr Asp Tyr Thr Asp Ile Ser Ala Leu Leu
225                 230                 235                 240

Met Glu Thr Gly Lys Gln Trp Leu Arg Thr His Ala Pro Ala Asp Val
                245                 250                 255

Phe Gln Arg Ile His Phe Gln Arg Leu Asp Leu Asp Thr Leu Pro Ser
            260                 265                 270

Ala Gly Ser Thr Phe Ala Arg Ala Ala Ser Val Asp Leu Ile Val Leu
        275                 280                 285

Glu His Val Leu Tyr Asp Val Arg Asp Leu His Ala Thr Leu Gln Ala
    290                 295                 300

Phe His Thr Met Leu Lys Pro Gly Gly Gln Leu Ala Phe Thr Met Ser
305                 310                 315                 320

Phe Arg Asp Arg Pro Gly Val Phe Phe Pro Asn Glu Phe Phe Gln Ser
                325                 330                 335

Met Leu His Thr Tyr Ser Lys Ala Lys Leu Asp Pro Pro Arg Arg Gln
            340                 345                 350

His Val Gly Tyr Leu Thr Leu Gln Glu Trp Glu Leu Ser Leu Arg Ala
        355                 360                 365

Ala Gly Phe Ser Glu Trp Glu Val Tyr Pro Ala Pro Glu Asp His Ala
    370                 375                 380

Lys Trp Pro Phe Gly Gly Ile Val Ala Tyr Arg
385                 390                 395


<210> SEQ ID NO 40
<211> LENGTH: 84
<212> TYPE: PRT
<213> ORGANISM: Sorangium cellulosum

<400> SEQUENCE: 40

Met Thr Phe Gly Tyr Ala Thr Val Ala Leu Phe Phe Leu Arg Phe Trp
1               5                   10                  15

Lys Lys Thr Gly Asp Arg Leu Phe Ala Lys Phe Ser Ala Ala Phe Trp
            20                  25                  30

Leu Met Met Leu Gly Arg Ile Ala Val Ala Leu Asn Arg Val Glu Glu
        35                  40                  45

Asp Ala Ile His Tyr Leu Tyr Leu Phe Arg Leu Phe Ala Tyr Met Leu
    50                  55                  60

Ile Leu Tyr Ala Ile Val His Lys Asn Arg Gly Asn Asp Gly Gln Ala
65                  70                  75                  80

Leu Ser Ser Arg


<210> SEQ ID NO 41
<211> LENGTH: 86
<212> TYPE: PRT
<213> ORGANISM: Sorangium cellulosum

<400> SEQUENCE: 41

Met Ala Ala Ala Val Tyr Ile Leu Cys Ala Leu Thr Ser Ile Ala Cys
1               5                   10                  15

Ala Val Leu Leu Leu Arg Gly Tyr Ala Gln Arg Lys Val Arg Leu Leu
            20                  25                  30

Leu Trp Ser Gly Leu Cys Phe Ala Ala Leu Ala Ala Asn Asn Ile Leu
        35                  40                  45

Leu Phe Val Asp Leu Val Val Ile Arg Ser Val Asp Leu Ser Ser Leu
    50                  55                  60
```

-continued

```
Arg His Leu Thr Ala Leu Ile Gly Leu Ala Leu Leu Leu Tyr Gly Leu
65                  70                  75                  80

Ile Trp Asp Leu Arg Glu
                85


<210> SEQ ID NO 42
<211> LENGTH: 125
<212> TYPE: PRT
<213> ORGANISM: Sorangium cellulosum

<400> SEQUENCE: 42

Met Gln Arg Phe Leu Gly Ala His Ile Ser Ser Ile Glu Gln Leu Glu
1               5                   10                  15

Val Leu Leu Leu Met Arg Arg Thr Ala Glu Arg Glu Trp Ser Ala Ala
            20                  25                  30

Ala Met Ala Arg Glu Ile Gly Ser Ser Met Met Ser Ile Gln Asp Arg
        35                  40                  45

Phe Gly Gly Leu Ala Ser Arg Gly Leu Ile Val Ala Arg Glu Asp Gly
    50                  55                  60

Glu Asp Ile Phe Tyr Arg Tyr Ala Pro Ala Asp Asp Glu Thr Arg Arg
65                  70                  75                  80

Thr Ile Asp Asp Leu Ala Gln Ala Tyr Lys Glu Arg Arg Leu Ser Val
                85                  90                  95

Ile Asn His Ile Tyr Ala Thr Pro Pro Pro Ser Asp Ile Gln Ser Phe
            100                 105                 110

Ser Asp Ala Phe Leu Ile Thr Lys Lys Gly Lys Gly Gly
        115                 120                 125


<210> SEQ ID NO 43
<211> LENGTH: 1762
<212> TYPE: PRT
<213> ORGANISM: Sorangium cellulosum

<400> SEQUENCE: 43

Ile Leu Glu Leu Lys Asn Thr Phe Asn Thr Met Val Asp Gln Leu Arg
1               5                   10                  15

Ser Phe Ala Ala Gln Val Thr Arg Val Ala Arg Glu Val Gly Thr Glu
            20                  25                  30

Gly Lys Leu Gly Gly Gln Ala Glu Val Thr Gly Val Ala Gly Thr Trp
        35                  40                  45

Lys Asp Leu Thr Asp Ser Val Asn Ser Met Ala Ser Asn Leu Thr Ala
    50                  55                  60

Gln Val Arg Asn Ile Ala Asp Val Thr Thr Ala Val Ala Asn Gly Asp
65                  70                  75                  80

Leu Ser Lys Lys Ile Thr Val Asp Val Arg Gly Glu Ile Leu Glu Leu
                85                  90                  95

Lys Asp Thr Phe Asn Thr Met Val Asp Gln Leu Arg Ser Phe Ala Ser
            100                 105                 110

Glu Val Thr Arg Val Ala Arg Glu Val Gly Thr Glu Gly Lys Leu Gly
        115                 120                 125

Gly Gln Ala Ser Val Pro Gly Val Ala Gly Thr Trp Lys Asp Leu Thr
    130                 135                 140

Asp Ser Val Asn Ser Met Ala Ser Asn Leu Thr Ala Gln Val Arg Asn
145                 150                 155                 160

Ile Ala Asp Val Thr Thr Ala Val Ala Arg Gly Asp Leu Ser Lys Lys
                165                 170                 175
```

-continued

```
Ile Thr Val Asp Val Lys Gly Glu Ile Leu Glu Leu Lys Asn Thr Phe
            180                 185                 190

Asn Thr Met Val Asp Gln Leu Ser Ser Phe Ala Ala Glu Val Thr Arg
        195                 200                 205

Val Ala Arg Glu Val Gly Thr Glu Gly Lys Leu Gly Gly Gln Ala Glu
    210                 215                 220

Val Lys Gly Val Ala Gly Thr Trp Lys Asp Leu Thr Asp Ser Val Asn
225                 230                 235                 240

Ser Met Ala Ser Asn Leu Thr Ala Gln Val Arg Asn Ile Ala Ala Val
                245                 250                 255

Thr Thr Ala Val Ala Asn Gly Asp Leu Ser Lys Lys Ile Leu Glu Leu
            260                 265                 270

Lys Asp Thr Phe Asn Thr Met Val Asp Gln Leu Arg Ser Phe Ala Ser
        275                 280                 285

Glu Val Thr Arg Val Ala Arg Glu Val Gly Thr Glu Gly Lys Leu Gly
    290                 295                 300

Gly Gln Ala Ser Val Pro Gly Val Ala Gly Thr Trp Lys Asp Leu Thr
305                 310                 315                 320

Asp Ser Val Asn Ser Met Ala Ser Asn Leu Thr Ala Gln Val Arg Asn
                325                 330                 335

Ile Ala Ala Val Thr Thr Ala Val Ala Asn Gly Asp Leu Ser Lys Lys
            340                 345                 350

Ile Thr Val Asp Val Arg Gly Glu Ile Leu Glu Leu Lys Asp Thr Phe
        355                 360                 365

Asn Thr Met Val Asp Gln Leu Arg Ser Phe Ala Ser Glu Val Thr Arg
    370                 375                 380

Val Ala Arg Glu Val Gly Thr Glu Gly Lys Leu Gly Gly Gln Ala Ser
385                 390                 395                 400

Val Pro Gly Val Ala Gly Thr Trp Lys Asp Leu Thr Asp Ser Val Asn
                405                 410                 415

Ser Met Ala Ser Asn Leu Thr Ala Gln Val Arg Asn Ile Ala Asp Val
            420                 425                 430

Thr Thr Ala Val Ala Arg Gly Asp Leu Ser Lys Lys Ile Thr Val Asp
        435                 440                 445

Val Lys Gly Glu Ile Leu Glu Leu Lys Asn Thr Phe Asn Thr Met Val
    450                 455                 460

Asp Gln Leu Ser Ser Phe Ala Ala Glu Val Thr Arg Val Ala Arg Glu
465                 470                 475                 480

Val Gly Thr Glu Gly Lys Leu Gly Gly Gln Ala Glu Val Lys Gly Val
                485                 490                 495

Ala Gly Thr Trp Lys Asp Leu Thr Asp Ser Val Asn Ser Met Ala Ser
            500                 505                 510

Asn Leu Thr Ala Gln Val Arg Asn Ile Ala Ala Val Thr Thr Ala Val
        515                 520                 525

Ala Asn Gly Asp Leu Ser Lys Lys Ile Thr Val Asp Val Arg Gly Glu
    530                 535                 540

Ile Leu Glu Leu Lys Asp Thr Phe Asn Thr Met Val Asp Gln Leu Arg
545                 550                 555                 560

Ser Phe Ala Ser Glu Val Thr Arg Val Ala Arg Glu Val Gly Thr Glu
                565                 570                 575

Gly Lys Leu Gly Gly Gln Ala Ser Val Pro Gly Val Ala Gly Thr Trp
            580                 585                 590
```

-continued

```
Lys Asp Leu Thr Asp Ser Val Asn Ser Met Ala Ser Asn Leu Thr Ala
        595                 600                 605

Gln Val Arg Asn Ile Ala Ala Val Thr Thr Ala Val Ala Asn Gly Asp
    610                 615                 620

Leu Ser Lys Lys Ile Thr Val Asp Val Arg Gly Glu Ile Leu Glu Leu
625                 630                 635                 640

Lys Asn Thr Ile Asn Tyr Thr Met Val Asp Gln Leu Asn Ala Phe Ala
                645                 650                 655

Ser Glu Val Thr Arg Val Ala Arg Glu Val Gly Thr Glu Gly Lys Leu
            660                 665                 670

Gly Gly Gln Ala Ser Val Pro Gly Val Ala Gly Thr Trp Lys Asp Leu
        675                 680                 685

Thr Asp Asn Val Asn Phe Met Ala Gly Asn Leu Thr Asn Gln Val Arg
    690                 695                 700

Gly Ile Ala Lys Val Val Thr Ala Val Ala Asn Gly Asp Leu Lys Arg
705                 710                 715                 720

Lys Leu Ala Phe Asp Ala Lys Gly Glu Ile Ala Ala Leu Ala Asp Thr
                725                 730                 735

Ile Asn Gly Val Ile Glu Thr Leu Ala Thr Phe Ala Asp Gln Val Thr
            740                 745                 750

Thr Val Ala Arg Glu Val Gly Val Glu Gly Lys Leu Gly Gly Gln Ala
        755                 760                 765

Ser Val Pro Gly Ala Ala Gly Thr Trp Lys Asp Leu Thr Asp Asn Val
    770                 775                 780

Asn Arg Leu Ala Ala Asn Leu Thr Thr Gln Val Arg Ala Ile Ala Glu
785                 790                 795                 800

Val Ala Thr Ala Val Thr Lys Gly Asp Leu Thr Arg Ser Ile Lys Val
                805                 810                 815

Glu Ala Gln Gly Glu Val Ala Ala Leu Lys Asp Thr Ile Asn Glu Met
            820                 825                 830

Ile Arg Asn Leu Lys Asp Thr Thr Leu Lys Asn Ser Glu Gln Asp Trp
        835                 840                 845

Leu Lys Thr Asn Leu Ala Lys Phe Ser Arg Met Leu Gln Gly Gln Lys
    850                 855                 860

Asp Leu Leu Thr Val Gly Arg Leu Ile Leu Ser Glu Leu Ala Pro Val
865                 870                 875                 880

Val Gly Ala Gln Gln Gly Val Phe Phe Thr Met Asp Val Ala Lys Glu
                885                 890                 895

Glu Pro Ile Leu Lys Leu Leu Ala Ser Tyr Ala Tyr Lys Val Arg Lys
            900                 905                 910

His Val Asp Asn His Phe Lys Leu Gly Glu Gly Leu Val Gly Gln Cys
        915                 920                 925

Ala Leu Glu Lys Glu Lys Ile Leu Leu Val Asn Ala Pro Pro Asp Tyr
    930                 935                 940

Ile Arg Ile Thr Ser Gly Leu Gly Glu Ala Pro Pro Val Asn Ile Ile
945                 950                 955                 960

Val Ile Pro Val Leu Phe Glu Gly Gln Val Lys Ala Val Ile Glu Leu
                965                 970                 975

Ala Ser Phe Glu Arg Phe Ser Pro Thr His Gln Ala Phe Leu Asp Gln
            980                 985                 990

Leu Thr Glu Ser Ile Gly Ile Val  Leu Asn Thr Ile Glu  Ala Asn Met
        995                 1000                1005

Arg Thr  Glu Asp Leu Leu Lys  Gln Ser Gln Ser Leu  Ala Arg Glu
```

```
    1010                1015                1020

Leu Gln  Ser Gln Gln Glu Glu  Leu Gln Gln Thr Asn  Ala Glu Leu
    1025                1030                1035

Gly Glu  Lys Ala Arg Leu Leu  Ala Gln Gln Asn Val  Glu Val Glu
    1040                1045                1050

Arg Lys  Asn Arg Glu Val Glu  Gln Ala Arg Gln Ala  Leu Glu Glu
    1055                1060                1065

Lys Ala  Arg Gln Leu Ala Ile  Thr Ser Lys Tyr Lys  Ser Glu Phe
    1070                1075                1080

Leu Ala  Asn Met Ser His Glu  Leu Arg Thr Pro Leu  Asn Ser Leu
    1085                1090                1095

Leu Ile  Leu Ser Asp Gln Leu  Ser Lys Asn Thr Asp  Arg Asn Leu
    1100                1105                1110

Thr Gly  Arg Gln Val Glu Phe  Ala Lys Thr Ile His  Ser Ser Gly
    1115                1120                1125

Asn Asp  Leu Leu Ala Leu Ile  Asn Asp Ile Leu Asp  Leu Ser Lys
    1130                1135                1140

Ile Glu  Ser Gly Thr Val Ile  Val Asp Val Gly Glu  Leu Ser Phe
    1145                1150                1155

Ser Asp  Leu Gln Asp Tyr Val  Glu Arg Thr Phe Gln  His Val Ala
    1160                1165                1170

Glu Ser  Lys Arg Leu Glu Phe  Glu Leu Asn Phe Ala  Gln Asn Leu
    1175                1180                1185

Pro Gln  Val Ile Tyr Thr Asp  Ala Lys Arg Val Gln  Gln Val Leu
    1190                1195                1200

Lys Asn  Leu Leu Ser Asn Ser  Phe Lys Phe Thr Glu  Arg Gly Ser
    1205                1210                1215

Val Ala  Leu Asp Val Asp Leu  Val Thr Ser Gly Trp  Thr Ile Glu
    1220                1225                1230

Asn Glu  Gly Leu Ser Arg Ala  Gly Ala Ala Ile Ala  Met Ser Val
    1235                1240                1245

Arg Asp  Thr Gly Ile Gly Ile  Pro His Asp Lys Gln  Gln Ile Ile
    1250                1255                1260

Phe Glu  Ala Phe Gln Gln Ala  Asp Gly Ser Thr Ser  Arg Lys Tyr
    1265                1270                1275

Gly Gly  Thr Gly Leu Gly Leu  Ala Ile Ser Arg Glu  Ile Ala Trp
    1280                1285                1290

Met Leu  Gly Gly Glu Ile Lys  Leu Ser Ser Arg Pro  Gly Ser Gly
    1295                1300                1305

Ser Thr  Phe Thr Leu Tyr Leu  Pro Leu Thr Tyr Thr  Pro Ala Arg
    1310                1315                1320

Pro Arg  Arg Lys Glu Gln Ala  Ala Glu Val Pro Ser  Ala Pro Pro
    1325                1330                1335

Ala Leu  Val Ser Gly Asp Val  Ala Pro Arg Ser Ala  Ala Glu Pro
    1340                1345                1350

Pro Pro  His Leu Leu Asn Gln  Ser Val Asp Asp Ser  Ala Ser Leu
    1355                1360                1365

Gln Pro  Ser Asp Ser Val Val  Leu Ile Val Glu Asn  Asp Ala Ser
    1370                1375                1380

Phe Ala  His Phe Val Met Asp  Val Ala His Asp His  Gly Phe Lys
    1385                1390                1395

Ala Ile  Leu Ala Tyr Arg Gly  Gly Ala Ala Leu Ser  Ile Val Arg
    1400                1405                1410
```

```
Glu Arg  Arg Val Asn Ala Ile  Thr Leu Asp Ile Asn  Leu Pro Asp
    1415                 1420                 1425

Met Asp  Gly Trp Arg Val Leu  Asp Arg Val Lys Arg  Asp Leu Ala
    1430                 1435                 1440

Thr Arg  His Ile Pro Val Gln  Val Ile Thr Thr Asp  Glu Glu Arg
    1445                 1450                 1455

Glu Arg  Ala Leu Arg Met Gly  Ala Thr Gly Val Leu  Cys Lys Pro
    1460                 1465                 1470

Leu Lys  Thr Arg Asp Ala Leu  Asp Glu Thr Phe Arg  Arg Leu Ser
    1475                 1480                 1485

Gln Phe  Met Val Ser Arg Arg  Arg Thr Val Val Leu  Ala Glu Pro
    1490                 1495                 1500

Asp Glu  Ala Glu Arg Gln Glu  Leu Val Glu Leu Leu  Gly Gly Asp
    1505                 1510                 1515

Asp Val  Thr Ile Arg Ser Val  Ala Ser Gly Glu Glu  Ala Leu Asp
    1520                 1525                 1530

Ala Leu  Leu Thr Glu Gly Ala  Asp Val Leu Ile Leu  His Leu Asp
    1535                 1540                 1545

Leu Pro  Asp Met Arg Cys Phe  Asp Leu Ile Gly Gln  Leu Ala Gln
    1550                 1555                 1560

Gly Ser  Gly Pro Thr Glu Leu  Pro Val Leu Val Tyr  Ala Pro Glu
    1565                 1570                 1575

Glu Ile  Ser Ala Ala Asp Glu  Ala Gln Leu Ser Arg  Phe Ser Gln
    1580                 1585                 1590

Leu Met  Val Leu Lys His Val  Arg Ser Lys Glu Arg  Leu Phe Asp
    1595                 1600                 1605

Asp Val  Ser Leu Phe Leu His  Arg Pro Val Ala Ala  Leu Ser Glu
    1610                 1615                 1620

Arg Gln  Arg Gln Thr Leu Gln  Glu Leu His Gln Ser  Asn Lys Val
    1625                 1630                 1635

Leu Ala  Gly Lys Lys Val Leu  Val Val Asp Asp Asp  Val Arg Asn
    1640                 1645                 1650

Ile Phe  Ala Met Thr Thr Ile  Leu Asp Ala Gln Gln  Met Lys Thr
    1655                 1660                 1665

Val Tyr  Val Glu Thr Gly Arg  Ala Ala Ile Glu Met  Leu Gln Arg
    1670                 1675                 1680

Thr Pro  Asp Ile Glu Ile Val  Leu Met Asp Ile Met  Met Pro Glu
    1685                 1690                 1695

Met Asp  Gly Tyr Asp Thr Ile  Arg Ala Ile Arg Ala  Lys Pro Glu
    1700                 1705                 1710

His His  Ala Leu Pro Ile Ile  Ala Val Thr Ala Lys  Ala Met Lys
    1715                 1720                 1725

Gly Asp  Arg Glu Lys Cys Phe  Glu Ala Gly Ala Asn  Asp Tyr Ile
    1730                 1735                 1740

Ser Lys  Pro Val Asp Pro Glu  His Leu Leu Ala Met  Leu Arg Leu
    1745                 1750                 1755

Trp Leu  His Arg
    1760
```